US008847013B2

(12) United States Patent
Herrmann et al.

(10) Patent No.: US 8,847,013 B2
(45) Date of Patent: Sep. 30, 2014

(54) COMPOSITIONS AND METHODS FOR THE SUPPRESSION OF TARGET POLYNUCLEOTIDES FROM LEPIDOPTERA

(75) Inventors: Rafael Herrmann, Wilmington, DE (US); Michael Lassner, Urbandale, IA (US); Albert L. Lu, Newark, DE (US); Mark Nelson, Newark, DE (US); James K. Presnail, Avondale, PA (US); Janet A. Rice, Wilmington, DE (US)

(73) Assignees: Pioneer Hi Bred International Inc, Johnston, IA (US); E I du Pont de Nemours and Company, Wilmington, DE (US)

( * ) Notice: Subject to any disclaimer, the term of this patent is extended or adjusted under 35 U.S.C. 154(b) by 1043 days.

(21) Appl. No.: 12/351,267

(22) Filed: Jan. 9, 2009

(65) Prior Publication Data

US 2009/0265818 A1 Oct. 22, 2009

Related U.S. Application Data

(60) Provisional application No. 61/021,699, filed on Jan. 17, 2008, provisional application No. 61/021,676, filed on Jan. 17, 2008.

(51) Int. Cl.
*A01H 1/00* (2006.01)
*C12N 15/82* (2006.01)
*C07H 21/04* (2006.01)

(52) U.S. Cl.
CPC .................. *C12N 15/8286* (2013.01)
USPC ........... 800/286; 800/285; 800/279; 536/24.5

(58) Field of Classification Search
USPC ....................................................... 800/286
See application file for complete search history.

(56) References Cited

U.S. PATENT DOCUMENTS

| 6,087,559 | A | * | 7/2000 | Nichols ......................... 800/284 |
| 2003/0150017 | A1 | | 8/2003 | Mesa et al. |
| 2005/0095199 | A1 | | 5/2005 | Whyard et al. |
| 2006/0021087 | A1 | | 1/2006 | Baum et al. |
| 2006/0075515 | A1 | | 4/2006 | Luethy et al. |
| 2006/0200878 | A1 | | 9/2006 | Lutfiyya et al. |
| 2006/0272049 | A1 | | 11/2006 | Waterhouse et al. |
| 2007/0199100 | A1 | | 8/2007 | Michaeli et al. |

FOREIGN PATENT DOCUMENTS

| EP | 1 818 405 A3 | 8/2007 |
| WO | WO 01/34815 A | 5/2001 |
| WO | WO 01/37654 A2 | 5/2001 |
| WO | WO 02/00904 A | 1/2002 |
| WO | WO 03/052110 A2 | 6/2003 |
| WO | WO 2005/049841 A1 | 6/2005 |
| WO | WO 2005/077116 A | 8/2005 |
| WO | WO 2005/110068 A2 | 11/2005 |
| WO | WO 2006/044480 A2 | 4/2006 |
| WO | WO 2006/045590 A2 | 5/2006 |
| WO | WO 2006/047495 A | 5/2006 |
| WO | WO 2007/003023 A | 1/2007 |
| WO | WO 2007/087153 A2 | 8/2007 |
| WO | WO 2007/095469 A2 | 8/2007 |

OTHER PUBLICATIONS

Deng et al. Genbank Accession No. DY794087, 2006.*
Agrawal, N., et al., "siRNA-Directed Silencing of Transgene Expressed in Cultured Insect Cells", *Biochemical and Biophysical Research Communications*, 2004, pp. 428-434, vol. 320, No. 2, Elsevier Inc.
Atkinson, H. J., et al., "Engineering Plants for Nematode Resistance," *Ann. Rev. Phytopathol*, 2003, pp. 615-639, vol. 41.
Bakhetia, M., et al., "Rna Interference and Plant Parasitic Nematodes," *Trends in Plant Science*, 2005, pp. 362-367, vol. 10, No. 8, Elsevier Ltd.
Boutla, A., et al., "Induction of RNA Interference in *Caenorhabditis elegans* by RNAs Derived From Plants Exhibiting Post-Transcriptional Gene Silencing", *Nucleic Acids Research*, 2002, pp. 1688-1694, vol. 30, No. 7.
Gao, B., et al., "The Parasitome of the Phytonematode Heterodera Glycines,", *Molecular Plant-Microbe Interactions*, 2003, pp. 720-726, vol. 16, No. 8, APS Press, USA.
Gao, B., et al., "Identification of Putative Parasitism Genes Expressed in the Esophageal Gland Cells of the Soybean Cyst Nematode Heterodera Glycines," *Molecular Plant-Microbe Interactions*, 2001, pp. 1247-1254, vol. 14., No. 10, APS Press, USA.
Urwin, P. E., et al., "Ingeston of Double-Stranded RNA by Preparasitic Juvenile Cyst Nematodes Leads to RNA Interference," *Molecular Plant-Microbe Interactions*, 2002, pp. 747-752, vol. 15, No. 8.
Zhu, Y. C., et al., Enhanced Esterase Gene Expression and Activity in a Malathion-Resistant Strain of the Tarnished Plant Bug, *Lygus Lineolaris*, Insect Biochemistry and Molecular Biolog, 2004, pp. 1175-1186, vol. 34, Elsevier Ltd.
Zhu, Y. C., et al., Comparative Study on Glutathione S-Transferase Activity, cDNA, and Gene Expression Between Malathion Susceptible and Resistant Strains of the Tarnished Plant Bug, *Lygus lineolaris*, 2007, *Pesticide Biochemistry and Physiology*, pp. 62-72, vol. 87, Elsevier Ltd.
Database EMBL [online]: Database Access No. EY786966.

* cited by examiner

*Primary Examiner* — Li Zheng
(74) *Attorney, Agent, or Firm* — Pioneer Hi-Bred Int'l

(57) ABSTRACT

Methods and compositions are provided which employ a silencing element that, when ingested by a pest, such as a Lepidopteran pest, decreases the expression of a target sequence in the pest. In specific embodiments, the decrease in expression of the target sequence controls the pest, thereby limiting damage to a plant. The present invention provides target polynucleotides encoding polypeptides from specific protein families and various target polynucleotides as set forth, or active variants and fragments thereof, wherein a decrease in expression of one or more sequences in the target pest has insecticidal activity. Further provided are silencing elements which when ingested by the pest decrease the level of the target polypeptide and thereby control the pest. In a specific embodiment, the pest is *Spodoptera frugiperda*. Plants, plant parts, bacteria and other host cells comprising the silencing elements or an active variant or fragment thereof of the invention are also provided.

24 Claims, No Drawings

US 8,847,013 B2

COMPOSITIONS AND METHODS FOR THE SUPPRESSION OF TARGET POLYNUCLEOTIDES FROM LEPIDOPTERA

CROSS-REFERENCE TO RELATED APPLICATIONS

This application claims priority to U.S. Provisional Application No. 61/021,699, filed Jan. 17, 2008, and U.S. Provisional Application No. 61/021,676; filed Jan. 17, 2008; both of which are herein incorporated by reference in their entirety.

FIELD OF THE INVENTION

The present invention relates generally to methods of molecular biology and gene silencing to control pests.

REFERENCE TO A SEQUENCE LISTING SUBMITTED AS A TEXT FILE VIA EFS-WEB

The official copy of the sequence listing is submitted concurrently with the specification as a text file via EFS-Web, in compliance with the American Standard Code for Information Interchange (ASCII), with a file name of 366590seqlist-.txt, a creation date of Jan. 9, 2009, and a size of 102 Kb. The sequence listing filed via EFS-Web is part of the specification and is hereby incorporated in its entirety by reference herein.

BACKGROUND OF THE INVENTION

Insect pests are a serious problem in agriculture. They destroy millions of acres of staple crops such as corn, soybeans, peas, and cotton. Yearly, these pests cause over $100 billion dollars in crop damage in the U.S. alone. In an ongoing seasonal battle, farmers must apply billions of gallons of synthetic pesticides to combat these pests. Other methods employed in the past delivered insecticidal activity by microorganisms or genes derived from microorganisms expressed in transgenic plants. For example, certain species of microorganisms of the genus *Bacillus* are known to possess pesticidal activity against a broad range of insect pests including *Lepidoptera, Diptera, Coleoptera, Hemiptera*, and others, In fact, microbial pesticides, particularly those obtained from *Bacillus* strains, have played an important role in agriculture as alternatives to chemical pest control. Agricultural scientists have developed crop plants with enhanced insect resistance by genetically engineering crop plants to produce insecticidal proteins from *Bacillus*. For example, corn and cotton plants genetically engineered to produce Cry toxins (see, e.g., Aronson (2002) *Cell Mol. Life. Sci.* 59(3):417-425; Schnepf et al. (1998) *Microbiol. Mol. Biol. Rev.* 62(3):775-806) are now widely used in American agriculture and have provided the farmer with an alternative to traditional insect-control methods. However, these Bt insecticidal proteins only protect plants from a relatively narrow range of pests. Moreover, these modes of insecticidal activity provided varying levels of specificity and, in some cases, caused significant environmental consequences. Thus, there is an immediate need for alternative methods to control pests.

BRIEF SUMMARY OF THE INVENTION

Methods and compositions are provided which employ a silencing element that, when ingested by a pest, such as a pest from the Lepidoptera order, is capable of decreasing the expression of a target sequence in the pest. In specific embodiments, the decrease in expression of the target sequence controls the pest and thereby the methods and compositions are capable of limiting damage to a plant. The present invention provides various target polynucleotides encoding polypeptides from specific families as disclosed elsewhere herein and various target polynucleotides set forth in SEQ ID NOS:1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 or active variants or fragments thereof, wherein a decrease in expression of one or more the sequences in the target pest controls the pest (i.e., has insecticidal activity). Further provided are silencing elements, which when ingested by the pest, decrease the level of expression of one or more of the target polynucleotides. In specific embodiments, the silencing element comprises at least 15, 20, or 22 consecutive nucleotides of any one of SEQ ID NO:1-50. In specific embodiments, the pest that is controlled is *Spodoptera frugiperda*. Plants, plant parts, plant cells, bacteria and other host cells comprising the silencing elements or an active variant or fragment thereof are also provided.

In another embodiment, a method for controlling a pest, such as a pest from the Lepidoptera order, is provided. The method comprises feeding to a pest a composition comprising a silencing element, wherein the silencing element, when ingested by the pest, reduces the level of a target sequence in the pest and thereby controls the pest. Further provided are methods to protect a plant from a pest. Such methods comprise introducing into the plant or plant part a silencing element of the invention. When the plant expressing the silencing element is ingested by the pest, the level of the target sequence is decreased and the pest is controlled.

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

I. Overview

Methods and compositions are provided which employ a silencing element that, when ingested by a pest, such as a pest from the Lepidoptera order, is capable of decreasing the expression of a target sequence in the pest. In specific embodiments, the decrease in expression of the target sequence controls the pest and thereby the methods and compositions are capable of limiting damage to a plant or plant part. The present invention provides target polynucleotides which encode polypeptides from a variety of protein classes including, for example, a juvenile hormone polypeptide, a vacuolar polypeptide, a cadherin polypeptide, a cuticle polypeptide, a translation initiation factor, a SAR1 polypeptide, an elongation factor, a phosphooligosaccharide, a myosin polypeptide, a potassium channel amino acid transporter, a potassium inwardly rectifier polypeptide, an amino acid transporter, a tubulin polypeptide, a ubiquitin polypeptide, and small nuclear ribonucleoprotein. In other embodiments the target polynucleotides are set forth in SEQ ID NOS: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 or active variants and fragments thereof. Silencing elements designed in view of these target polynucleotides are provided which, when ingested by the pest, decrease the expression of one or more of the target sequences and thereby controls the pest (i.e., has insecticidal activity). See, for example, SEQ ID NOS:51-465.

As used herein, by "controlling a pest" or "controls a pest" is intended any affect on a pest that results in limiting the damage that the pest causes. Controlling a pest includes, but is not limited to, killing the pest, inhibiting development of the pest, altering fertility or growth of the pest in such a manner that the pest provides less damage to the plant, decreasing the number of offspring produced, producing less fit pests, producing pests more susceptible to predator attack, or deterring the pests from eating the plant.

By "disease resistance" is intended that the plants avoid the disease symptoms that are the outcome of plant-pathogen interactions. That is, pathogens are prevented from causing plant diseases and the associated disease symptoms, or alternatively, the disease symptoms caused by the pathogen is minimized or lessened.

Reducing the level of expression of the target polynucleotide or the polypeptide encoded thereby, in the pest results in the suppression, control, and/or killing the invading pathogenic organism. Reducing the level of expression of the target sequence of the pest will reduce the disease symptoms resulting from pathogen challenge by at least about 2% to at least about 6%, at least about 5% to about 50%, at least about 10% to about 60%, at least about 30% to about 70%, at least about 40% to about 80%, or at least about 50% to about 90% or greater. Hence, the methods of the invention can be utilized to protect plants from disease, particularly those diseases that are caused by pests from the Lepidoptera order.

Assays that measure the control of a pest are commonly known in the art, as are methods to quantitate disease resistance in plants following pathogen infection. See, for example, U.S. Pat. No. 5,614,395, herein incorporated by reference. Such techniques include, measuring over time, the average lesion diameter, the pathogen biomass, and the overall percentage of decayed plant tissues. See, for example, Thomma et al. (1998) *Plant Biology* 95:15107-15111, herein incorporated by reference. See, also the examples below.

The invention is drawn to compositions and methods for protecting plants from a plant pest, such as pests from the Lepidoptera order or inducing resistance in a plant to a plant pest, such as pests from the Lepidoptera order. Caterpillars and related forms of lepidopteran insects comprise an important group of plant-feeding agricultural pests, especially during the larvae stage of growth. Feeding methods of Lepidoptera larvae typically include chewing plants or plant parts. As used herein, the term "Lepidoptera" is used to refer to any member of the Lepidoptera order. In particular embodiments, compositions and methods of the invention control Lepidoptera larvae (i.e. caterpillars). Accordingly, the compositions and methods are also useful in protecting plants against any Lepidoptera including, for example, *Pieris rapae, Pectinophora gossypiella, Synanthedon exitiosa, Melittia cucurbitae, Cydia pomonella, Grapholita molesta, Ostrinia nubilalis, Plodia interpunctella, Galleria mellonella, Manduca sexta, Manduca quinquemaculata, Lymantria dispar, Euproctis chrysorrhoea, Trichoplusia ni, Mamestra brassicae, Agrotis ipsilon, Plutella xylostella, Anticarsia gemmatalis, Psuedoplusia includens, Epinotia aporema, Helicoverpa zea, Heliothis virescens, Heliothis armigera, Spodoptera exigua, Scirpophaga incertulus, Sesamia* spp., *Buseolafusca, Cnaphalocrocis medinalis, Chilo suppressalis,* or *Spodoptera littoralis*. In particular embodiments, methods control *Spodoptera frugiperda*.

II. Target Sequences

As used herein, a "target sequence" or "target polynucleotide" comprises any sequence in the pest that one desires to reduce the level of expression. In specific embodiments, decreasing the level of the target sequence in the pest controls the pest. For instance, the target sequence can be essential for growth and development. While the target sequence can be expressed in any tissue of the pest, in specific embodiments of the invention, the sequences targeted for suppression in the pest are expressed in cells of the gut tissue of the pest, cells in the midgut of the pest, and cells lining the gut lumen or the midgut. Such target sequences can be involved in gut cell metabolism, growth or differentiation.

In one embodiment of the invention the target sequence comprises a polypeptide belonging to one or more classes of enzymes such as a juvenile hormone polypeptide, a vacuolar polypeptide, a cadherin polypeptide, a cuticle polypeptide, a translation initiation factor, a SAR1 polypeptide, an elongation factor, a phosphooligosaccharide, a myosin polypeptide, a potassium channel amino acid transporter, a potassium inwardly rectifier, an amino acid transporter, a tubulin polypeptide, a ubiquitin polypeptide, and a small nuclear ribonucleoprotein. Non-limiting examples of target sequences of the invention include a polynucleotide set forth in SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. As exemplified elsewhere herein, decreasing the level of expression of these target sequence or members of the recited enzyme classes in Lepidoptera controls the pest.

III. Silencing Elements

By "silencing element" is intended a polynucleotide which when ingested by a pest, is capable of reducing or eliminating the level or expression of a target polynucleotide or the polypeptide encoded thereby. The silencing element employed can reduce or eliminate the expression level of the target sequence by influencing the level of the target RNA transcript or, alternatively, by influencing translation and thereby affecting the level of the encoded polypeptide. Methods to assay for functional silencing elements that are capable of reducing or eliminating the level of a sequence of interest are disclosed elsewhere herein. A single polynucleotide employed in the methods of the invention can comprises one or more silencing elements to the same or different target polynucleotides.

In specific embodiments, the target sequence is not a plant endogenous gene. In other embodiments, while the silencing element controls pests, preferably the silencing element has no effect on the normal plant or plant part.

As discussed in further detail below, silencing elements can include, but are not limited to, a sense suppression element, an antisense suppression element, a double stranded RNA, a miRNA, or a hairpin suppression element. Non-limiting examples of silencing elements that can be employed to decrease expression of these target Lepidoptera sequences comprise fragments and variants of the sense or antisense sequence or consists of the sense or antisense sequence of the sequence set forth in SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 54, 57, 60, 63, 66, 69, 72, 75, 78, 81, 84, 87, 90, 93, 96, 99, 102, 105, 108, 111, 114, 117, 120, 123, 126, 129, 132, 135, 138, 141, 144, 147, 150, 153, 156, 159, 162, 165, 168, 171, 174, 177, 180, 183, 186, 189, 192, 195, 198, 201, 204, 207, 210, 213, 216, 219, 222, 225, 228, 231, 234, 237, 240, 243, 246, 249, 252, 255, 258, 261, 264, 267, 270, 273, 276, 279, 282, 285, 288, 291, 294, 297, 300, 303, 306, 309, 312, 315, 318, 321, 324, 327, 330, 333, 336, 339, 342, 345, 348, 351, 354, 357, 360, 363, 366, 369, 372, 375, 378, 381, 384, 387, 390, 393, 396, 399, 402, 405, 408, 411, 415, 418, 421, 424, 427, 430, 433, 436, 439, 442, 457, 460, and/or 463 or a biologically active variant or fragment thereof. In specific embodiments, the silencing element comprises or consists of at least one of the sequences set forth in any one of SEQ ID NOS: 51-465. In further embodiments, the silencing elements can comprise at least one thymine residue at the 3' end. This can aid in stabilization. Thus, the silencing elements can have at least 1, 2, 3, 4, 5, 6, 7, 8, 9, 10 or more thymine residues at the 3' end.

In further embodiments, the silencing element comprises SEQ ID NO: 52 and 53; 55 and 56; 58 and 59; 61 and 62; 64 and 65; 67 and 68; 70 and 71; 73 and 74; 76 and 77; 79 and 80; 82 and 83; 85 and 86; 88 and 89; 91 and 92; 94 and 95; 97 and 98; 100 and 101; 103 and 104; 106 and 107; 109 and 110; 112 and 113; 115 and 116; 118 and 119; 121 and 122; 124 and 125; 127 and 128; 130 and 131; 133 and 134; 136 and 137; 139 and 140; 142 and 143; 145 and 146; 148 and 149; 151 and 152; 154 and 155; 157 and 158; 160 and 161; 163 and 164; 166 and 167; 169 and 170; 172 and 173; 175 and 176; 178 and 179; 181 and 182; 184 and 185; 187 and 188; 190 and 191; 193 and 194; 196 and 197; 199 and 200; 202 and 203; 205 and 206; 208 and 209; 211 and 212; 214 and 215; 217 and 218; 220 and 221; 223 and 224; 226 and 227; 229 and 230; 232 and 233; 235 and 236; 238 and 239; 241 and 242; 244 and 245; 247 and 248; 250 and 251; 253 and 254; 256 and 257; 259 and 260; 262 and 263; 265 and 266; 268 and 269; 271 and 272; 274 and 275; 277 and 278; 280 and 281; 283 and 284; 286 and 287; 289 and 290; 292 and 293; 295 and 296; 298 and 299; 301 and 302; 304 and 305; 307 and 308; 310 and 311; 313 and 314; 316 and 317; 139 and 320; 322 and 323; 325 and 326; 328 and 329; 331 and 332; 334 and 335; 337 and 338; 340 and 341; 343 and 344; 346 and 347; 349 and 350; 352 and 353; 355 and 356; 358 and 359; 361 and 362; 364 and 365; 367 and 368; 370 and 371; 373 and 374; 376 and 377; 379 and 380; 382 and 383; 385 and 386; 388 and 389; 391 and 392; 394 and 395; 397 and 398; 400 and 401; 403 and 404; 406 and 407; 409 and 410; 412 and 413; 416 and 417; 419 and 420; 422 and 423; 425 and 426; 428 and 429; 431 and 432; 434 and 435; 437 and 438; 440 and 441; 443 and 444; 458 and 459; 461 and 462; and/or 464 and 465.

By "reduces" or "reducing" the expression level of a polynucleotide or a polypeptide encoded thereby is intended to mean, the polynucleotide or polypeptide level of the target sequence is statistically lower than the polynucleotide level or polypeptide level of the same target sequence in an appropriate control pest which is not exposed to (i.e., has not ingested) the silencing element. In particular embodiments of the invention, reducing the polynucleotide level and/or the polypeptide level of the target sequence in a pest according to the invention results in less than 95%, less than 90%, less than 80%, less than 70%, less than 60%, less than 50%, less than 40%, less than 30%, less than 20%, less than 10%, or less than 5% of the polynucleotide level, or the level of the polypeptide encoded thereby, of the same target sequence in an appropriate control pest. Methods to assay for the level of the RNA transcript, the level of the encoded polypeptide, or the activity of the polynucleotide or polypeptide are discussed elsewhere herein.

i. Sense Suppression Elements

As used herein, a "sense suppression element" comprises a polynucleotide designed to express an RNA molecule corresponding to at least a part of a target messenger RNA in the "sense" orientation. Expression of the RNA molecule comprising the sense suppression element reduces or eliminates the level of the target polynucleotide or the polypeptide encoded thereby. The polynucleotide comprising the sense suppression element may correspond to all or part of the sequence of the target polynucleotide, all or part of the 5' and/or 3' untranslated region of the target polynucleotide, all or part of the coding sequence of the target polynucleotide, or all or part of both the coding sequence and the untranslated regions of the target polynucleotide.

Typically, a sense suppression element has substantial sequence identity to the target polynucleotide, typically greater than about 65% sequence identity, greater than about 85% sequence identity, about 90%, 91%, 92%, 93%, 94%, 95%, 96%, 97%, 98% or 99% sequence identity. See, U.S. Pat. Nos. 5,283,184 and 5,034,323; herein incorporated by reference. The sense suppression element can be any length so long as it allows for the suppression of the targeted sequence. The sense suppression element can be, for example, 15, 20, 22, 25, 30, 50, 100, 150, 200, 250, 300, 350, 400, 450, 500, 600, 700, 900 or longer.

ii. Antisense Suppression Elements

As used herein, an "antisense suppression element" comprises a polynucleotide which is designed to express an RNA molecule complementary to all or part of a target messenger RNA. Expression of the antisense RNA suppression element reduces or eliminates the level of the target polynucleotide. The polynucleotide for use in antisense suppression may correspond to all or part of the complement of the sequence encoding the target polynucleotide, all or part of the complement of the 5' and/or 3' untranslated region of the target polynucleotide, all or part of the complement of the coding sequence of the target polynucleotide, or all or part of the complement of both the coding sequence and the untranslated regions of the target polynucleotide. In addition, the antisense suppression element may be fully complementary (i.e., 100% identical to the complement of the target sequence) or partially complementary (i.e., less than 100% identical to the complement of the target sequence) to the target polynucleotide. In specific embodiments, the antisense suppression element comprises at least 85%, 90%, 91%, 92%, 93%, 94%, 95%, 96%, 97%, 98%, or 99% sequence complementarity to the target polynucleotide. Antisense suppression may be used to inhibit the expression of multiple proteins in the same plant. See, for example, U.S. Pat. No. 5,942,657. Furthermore, the antisense suppression element can be complementary to a portion of the target polynucleotide. Generally, sequences of at least 15, 20, 22, 25, 50, 100, 200, 300, 400, 450 nucleotides or greater may be used. Methods for using antisense suppression to inhibit the expression of endogenous genes in plants are described, for example, in Liu et al (2002) *Plant Physiol.* 129:1732-1743 and U.S. Pat. Nos. 5,759,829 and 5,942,657, each of which is herein incorporated by reference.

iii. Double Stranded RNA Suppression Element

A "double stranded RNA silencing element" or "dsRNA" comprises at least one transcript that is capable of forming a dsRNA either before or after ingestion by a pest. Thus, a "dsRNA silencing element" includes a dsRNA, a transcript or polyribonucleotide capable of forming a dsRNA or more than one transcript or polyribonucleotide capable of forming a dsRNA. "Double stranded RNA" or "dsRNA" refers to a polyribonucleotide structure formed either by a single self-complementary RNA molecule or a polyribonucleotide structure formed by the expression of least two distinct RNA strands. The dsRNA molecule(s) employed in the methods and compositions of the invention mediate the reduction of expression of a target sequence, for example, by mediating RNA interference "RNAi" or gene silencing in a sequence-specific manner. In the context of the present invention, the dsRNA is capable of reducing or eliminating the level or expression of a target polynucleotide or the polypeptide encoded thereby in a pest.

The dsRNA can reduce or eliminate the expression level of the target sequence by influencing the level of the target RNA transcript, by influencing translation and thereby affecting the level of the encoded polypeptide, or by influencing expression at the pre-transcriptional level (i.e., via the modulation of chromatin structure, methylation pattern, etc., to alter gene expression). See, for example, Verdel et al. (2004) *Science* 303:672-676; Pal-Bhadra et al. (2004) *Science* 303:669-672; Allshire (2002) *Science* 297:1818-1819; Volpe et al. (2002) *Science* 297:1833-1837; Jenuwein (2002) *Science* 297:2215-2218; and Hall et al. (2002) *Science* 297:2232-2237. Methods to assay for functional iRNA that are capable of reducing or eliminating the level of a sequence of interest are disclosed elsewhere herein. Accordingly, as used herein, the term "dsRNA" is meant to encompass other terms used to describe nucleic acid molecules that are capable of mediating RNA interference or gene silencing, including, for example, short-interfering RNA (siRNA), double-stranded RNA (dsRNA), micro-RNA (miRNA), hairpin RNA, short hairpin RNA (shRNA), post-transcriptional gene silencing RNA (ptgsRNA), and others.

In specific embodiments, at least one strand of the duplex or double-stranded region of the dsRNA shares sufficient sequence identity or sequence complementarity to the target polynucleotide to allow for the dsRNA to reduce the level of expression of the target sequence. As used herein, the strand that is complementary to the target polynucleotide is the "antisense strand" and the strand homologous to the target polynucleotide is the "sense strand."

In one embodiment, the dsRNA comprises a hairpin RNA. A hairpin RNA comprises an RNA molecule that is capable of folding back onto itself to form a double stranded structure. Multiple structures can be employed as hairpin elements. In specific embodiments, the dsRNA suppression element comprises a hairpin element which comprises in the following order, a first segment, a second segment, and a third segment, where the first and the third segment share sufficient complementarity to allow the transcribed RNA to form a double-stranded stem-loop structure.

The "second segment" of the hairpin comprises a "loop" or a "loop region." These terms are used synonymously herein and are to be construed broadly to comprise any nucleotide sequence that confers enough flexibility to allow self-pairing to occur between complementary regions of a polynucleotide (i.e., segments 1 and 3 which form the stem of the hairpin). For example, in some embodiments, the loop region may be substantially single stranded and act as a spacer between the self-complementary regions of the hairpin stem-loop. In some embodiments, the loop region can comprise a random or nonsense nucleotide sequence and thus not share sequence identity to a target polynucleotide. In other embodiments, the loop region comprises a sense or an antisense RNA sequence or fragment thereof that shares identity to a target polynucleotide. See, for example, International Patent Publication No. WO 02/00904, herein incorporated by reference. In specific embodiments, the loop region can be optimized to be as short as possible while still providing enough intramolecular flexibility to allow the formation of the base-paired stem region. Accordingly, the loop sequence is generally less than 1000, 900, 800, 700, 600, 500, 400, 300, 200, 100, 50, 25, 20, 15, 10 nucleotides or less.

The "first" and the "third" segment of the hairpin RNA molecule comprise the base-paired stem of the hairpin structure. The first and the third segments are inverted repeats of one another and share sufficient complementarity to allow the formation of the base-paired stem region. In specific embodiments, the first and the third segments are fully complementary to one another. Alternatively, the first and the third segment may be partially complementary to each other so long as they are capable of hybridizing to one another to form a base-paired stem region. The amount of complementarity between the first and the third segment can be calculated as a percentage of the entire segment. Thus, the first and the third segment of the hairpin RNA generally share at least 50%, 60%, 70%, 80%, 85%, 90%, 91%, 92%, 93%, 94%, 95%, 96%, 97%, 98%, 99%, up to and including 100% complementarity.

The first and the third segment are at least about 1000, 500, 400, 300, 200, 100, 50, 40, 30, 25, 22, 20, 15 or 10 nucleotides in length. In specific embodiments, the length of the first and/or the third segment is about 10-100 nucleotides, about 10 to about 75 nucleotides, about 10 to about 50 nucleotides, about 10 to about 40 nucleotides, about 10 to about 35 nucleotides, about 10 to about 30 nucleotides, about 10 to about 25 nucleotides, about 10 to about 20 nucleotides. In other embodiments, the length of the first and/or the third segment comprises at least 10-20 nucleotides, 20-35 nucleotides, 30-45 nucleotides, 40-50 nucleotides, 50-100 nucleotides, or 100-300 nucleotides. See, for example, International Publication No. WO 0200904. In specific embodiments, the first and the third segment comprise at least 20 nucleotides having at least 85% complementary to the first segment. In still other embodiments, the first and the third segments which form the stem-loop structure of the hairpin comprises 3' or 5' overhang regions having unpaired nucleotide residues.

In specific embodiments, the sequences used in the first, the second, and/or the third segments comprise domains that are designed to have sufficient sequence identity to a target polynucleotide of interest and thereby have the ability to decrease the level of expression of the target polynucleotide. The specificity of the inhibitory RNA transcripts is therefore generally conferred by these domains of the silencing element. Thus, in some embodiments of the invention, the first, second and/or third segment of the silencing element comprise a domain having at least 10, at least 15, at least 19, at least 20, at least 21, at least 22, at least 23, at least 24, at least 25, at least 30, at least 40, at least 50, at least 100, at least 200, at least 300, at least 500, at least 1000, or more than 1000 nucleotides that share sufficient sequence identity to the target polynucleotide to allow for a decrease in expression levels of the target polynucleotide when expressed in an appropriate cell. In other embodiments, the domain is between about 15 to 50 nucleotides, about 20-35 nucleotides, about 25-50 nucleotides, about 20 to 75 nucleotides, about 40-90 nucleotides about 15-100 nucleotides.

In specific embodiments, the domain of the first, the second, and/or the third segment has 100% sequence identity to the target polynucleotide. In other embodiments, the domain of the first, the second and/or the third segment having homology to the target polypeptide have at least 50%, 60%, 70%, 80%, 85%, 90%, 91%, 92%, 93%, 94%, 95%, 96%, 97%, 98%, 99%, or greater sequence identity to a region of the target polynucleotide. The sequence identity of the domains of the first, the second and/or the third segments to the target polynucleotide need only be sufficient to decrease expression of the target polynucleotide of interest. See, for example, Chuang and Meyerowitz (2000) *Proc. Natl. Acad. Sci. USA* 97:4985-4990; Stoutjesdijk et al. (2002) *Plant Physiol.* 129: 1723-1731; Waterhouse and Helliwell (2003) *Nat. Rev. Genet.* 4:29-38; Pandolfini et al. *BMC Biotechnology* 3:7, and U.S. Patent Publication No. 20030175965; each of which is herein incorporated by reference. A transient assay for the efficiency of hpRNA constructs to silence gene expression in vivo has been described by Panstruga et al. (2003) *Mol. Biol. Rep.* 30:135-140, herein incorporated by reference.

The amount of complementarity shared between the first, second, and/or third segment and the target polynucleotide or the amount of complementarity shared between the first segment and the third segment (i.e., the stem of the hairpin structure) may vary depending on the organism in which gene expression is to be controlled. Some organisms or cell types may require exact pairing or 100% identity, while other organisms or cell types may tolerate some mismatching. In some cells, for example, a single nucleotide mismatch in the targeting sequence abrogates the ability to suppress gene expression. In these cells, the suppression cassettes of the invention can be used to target the suppression of mutant genes, for example, oncogenes whose transcripts comprise point mutations and therefore they can be specifically targeted using the methods and compositions of the invention without altering the expression of the remaining wild-type allele.

Any region of the target polynucleotide can be used to design the domain of the silencing element that shares sufficient sequence identity to allow expression of the hairpin transcript to decrease the level of the target polynucleotide. For instance, the domain can be designed to share sequence identity to the 5' untranslated region of the target polynucleotide(s), the 3' untranslated region of the target polynucleotide(s), exonic regions of the target polynucleotide(s), intronic regions of the target polynucleotide(s), and any combination thereof. In specific embodiments a domain of the silencing element shares sufficient homology to at least about 15, 20, 22, 25 or 30 consecutive nucleotides from about nucleotides 1-50, 50-100, 100-150, 150-200, 200-250, 250-300, 300-350, 350-400, 400-450, 450-500, 550-600, 600-650, 650-700, 750-800, 850-900, 950-1000, 1000-1050, 1050-1100, 1100-1200, 1200-1300, 1300-1400, 1400-1500, 1500-1600, 1600-1700, 1700-1800, 1800-1900, 1900-2000 of the target sequence. In some instances to optimize the siRNA sequences employed in the hairpin, the synthetic oligodeoxyribonucleotide/RNAse H method can be used to determine sites on the target mRNA that are in a conformation that is susceptible to RNA silencing. See, for example, Vickers et al. (2003) *J. Biol. Chem.* 278:7108-7118 and Yang et al. (2002) *Proc. Natl. Acad. Sci. USA* 99:9442-9447, herein incorporated by reference. These studies indicate that there is a significant correlation between the RNase-H-sensitive sites and sites that promote efficient siRNA-directed mRNA degradation.

The hairpin silencing element may also be designed such that the sense sequence or the antisense sequence do not correspond to a target polynucleotide. In this embodiment, the sense and antisense sequence flank a loop sequence that comprises a nucleotide sequence corresponding to all or part of the target polynucleotide. Thus, it is the loop region that determines the specificity of the RNA interference. See, for example, WO 02/00904, herein incorporated by reference.

In specific embodiments, the silencing element comprising the hairpin comprises sequences selected from the group consisting of SEQ ID NO: 52 and 53; 55 and 56; 58 and 59; 61 and 62; 64 and 65; 67 and 68; 70 and 71; 73 and 74; 76 and 77; 79 and 80; 82 and 83; 85 and 86; 88 and 89; 91 and 92; 94 and 95; 97 and 98; 100 and 101; 103 and 104; 106 and 107; 109 and 110; 112 and 113; 115 and 116; 118 and 119; 121 and 122; 124 and 125; 127 and 128; 130 and 131; 133 and 134; 136 and 137; 139 and 140; 142 and 143; 145 and 146; 148 and 149; 151 and 152; 154 and 155; 157 and 158; 160 and 161; 163 and 164; 166 and 167; 169 and 170; 172 and 173; 175 and 176; 178 and 179; 181 and 182; 184 and 185; 187 and 188; 190 and 191; 193 and 194; 196 and 197; 199 and 200; 202 and 203; 205 and 206; 208 and 209; 211 and 212; 214 and 215; 217 and 218; 220 and 221; 223 and 224; 226 and 227; 229 and 230; 232 and 233; 235 and 236; 238 and 239; 241 and 242; 244 and 245; 247 and 248; 250 and 251; 253 and 254; 256 and 257; 259 and 260; 262 and 263; 265 and 266; 268 and 269; 271 and 272; 274 and 275; 277 and 278; 280 and 281; 283 and 284; 286 and 287; 289 and 290; 292 and 293; 295 and 296; 298 and 299; 301 and 302; 304 and 305; 307 and 308; 310 and 311; 313 and 314; 316 and 317; 139 and 320; 322 and 323; 325 and 326; 328 and 329; 331 and 332; 334 and 335; 337 and 338; 340 and 341; 343 and 344; 346 and 347; 349 and 350; 352 and 353; 355 and 356; 358 and 359; 361 and 362; 364 and 365; 367 and 368; 370 and 371; 373 and 374; 376 and 377; 379 and 380; 382 and 383; 385 and 386; 388 and 389; 391 and 392; 394 and 395; 397 and 398; 400 and 401; 403 and 404; 406 and 407; 409 and 410; 412 and 413; 416 and 417; 419 and 420; 422 and 423; 425 and 426; 428 and 429; 431 and 432; 434 and 435; 437 and 438; 440 and 441; 443 and 444; 458 and 459; 461 and 462; and/or 464 and 465.

In addition, transcriptional gene silencing (TGS) may be accomplished through use of a hairpin suppression element where the inverted repeat of the hairpin shares sequence identity with the promoter region of a target polynucleotide to be silenced. See, for example, Aufsatz et al. (2002) *PNAS* 99 (Suppl. 4):16499-16506 and Mette et al. (2000) *EMBO J.* 19(19):5194-5201.

In other embodiments, the dsRNA can comprise a small RNA (sRNA). sRNAs can comprise both micro RNA (miRNA) and short-interfering RNA (siRNA) (Meister and Tuschl (2004) *Nature* 431:343-349 and Bonetta et al. (2004) *Nature Methods* 1:79-86). miRNAs are regulatory agents comprising about 19 ribonucleotides which are highly efficient at inhibiting the expression of target polynucleotides. See, for example Javier et al. (2003) *Nature* 425: 257-263, herein incorporated by reference. For miRNA interference, the silencing element can be designed to express a dsRNA molecule that forms a hairpin structure containing a 19-nucleotide sequence that is complementary to the target polynucleotide of interest. The miRNA can be synthetically made, or transcribed as a longer RNA which is subsequently cleaved to produce the active miRNA. Specifically, the miRNA can comprise 19 nucleotides of the sequence having homology to a target polynucleotide in sense orientation and 19 nucleotides of a corresponding antisense sequence that is complementary to the sense sequence.

When expressing an miRNA, it is recognized that various forms of an miRNA can be transcribed including, for example, the primary transcript (termed the "pri-miRNA") which is processed through various nucleolytic steps to a shorter precursor miRNA (termed the "pre-miRNA"); the pre-miRNA; or the final (mature) miRNA is present in a duplex, the two strands being referred to as the miRNA (the strand that will eventually basepair with the target) and miRNA*. The pre-miRNA is a substrate for a form of dicer that removes the miRNA/miRNA* duplex from the precursor, after which, similarly to siRNAs, the duplex can be taken into the RISC complex. It has been demonstrated that miRNAs can be transgenically expressed and be effective through expression of a precursor form, rather than the entire primary form (Parizotto et al. (2004) *Genes & Development* 18:2237-2242 and Guo et al. (2005) *Plant Cell* 17:1376-1386).

The methods and compositions of the invention employ silencing elements that when transcribed "form" a dsRNA molecule. Accordingly, the heterologous polynucleotide being expressed need not form the dsRNA by itself, but can interact with other sequences in the plant cell or in the pest gut after ingestion to allow the formation of the dsRNA. For example, a chimeric polynucleotide that can selectively silence the target polynucleotide can be generated by expressing a chimeric construct comprising the target sequence for a miRNA or siRNA to a sequence corresponding to all or part of the gene or genes to be silenced. In this embodiment, the dsRNA is "formed" when the target for the miRNA or siRNA interacts with the miRNA present in the cell. The resulting dsRNA can then reduce the level of expression of the gene or genes to be silenced. See, for example, U.S. Provisional Application No. 60/691,613, filed Jun. 17, 2005, entitled "Methods and Compositions for Gene Silencing, herein incorporated by reference. The construct can be designed to have a target for an endogenous miRNA or alternatively, a target for a heterologous and/or synthetic miRNA can be employed in the construct. If a heterologous and/or synthetic miRNA is employed, it can be introduced into the cell on the same nucleotide construct as the chimeric polynucleotide or on a separate construct. As discussed elsewhere herein, any method can be used to introduce the construct comprising the heterologous miRNA.

IV. Variants and Fragments

By "fragment" is intended a portion of the polynucleotide or a portion of the amino acid sequence and hence protein encoded thereby. Fragments of a polynucleotide may encode protein fragments that retain the biological activity of the native protein. Alternatively, fragments of a polynucleotide that are useful as a silencing element do not need to encode fragment proteins that retain biological activity. Thus, fragments of a nucleotide sequence may range from at least about 10, about 15, about 20 nucleotides, about 22 nucleotides, about 50 nucleotides, about 75 nucleotides, about 100 nucleotides, 200 nucleotides, 300 nucleotides, 400 nucleotides, 500 nucleotides, 600 nucleotides, 700 nucleotides and up to the full-length polynucleotide employed in the invention. Methods to assay for the activity of a desired silencing element or a suppressor enhancer element are described elsewhere herein.

"Variants" is intended to mean substantially similar sequences. For polynucleotides, a variant comprises a deletion and/or addition of one or more nucleotides at one or more internal sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the polypeptides employed in the invention. Variant polynucleotides also include synthetically derived polynucleotide, such as those generated, for example, by using site-directed mutagenesis, but continue to retain the desired activity. Generally, variants of a particular polynucleotide of the invention (i.e., a silencing element) will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Percent sequence identity between any two polypeptides can be calculated using sequence alignment programs and parameters described elsewhere herein. Where any given pair of polynucleotides employed in the invention is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

"Variant" protein is intended to mean a protein derived from the native protein by deletion or addition of one or more amino acids at one or more internal sites in the native protein and/or substitution of one or more amino acids at one or more sites in the native protein. Variant proteins encompassed by the present invention are biologically active, that is they continue to possess the desired biological activity of the native protein, as discussed elsewhere herein. Such variants may result from, for example, genetic polymorphism or from human manipulation. Biologically active variants of a native protein will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the native protein as determined by sequence alignment programs and parameters described elsewhere herein. A biologically active variant of a protein of the invention may differ from that protein by as few as 1-15 amino acid residues, as few as 1-10, such as 6-10, as few as 5, as few as 4, 3, 2, or even 1 amino acid residue.

The following terms are used to describe the sequence relationships between two or more polynucleotides or polypeptides: (a) "reference sequence", (b) "comparison window", (c) "sequence identity", and, (d) "percentage of sequence identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

(c) As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

V. DNA constructs

The use of the term "polynucleotide" is not intended to limit the present invention to polynucleotides comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures, and the like.

The polynucleotide encoding the silencing element or in specific embodiments employed in the methods and compositions of the invention can be provided in expression cassettes for expression in a plant or organism of interest. It is recognized that multiple silencing elements including multiple identical silencing elements, multiple silencing elements targeting different regions of the target sequence, or multiple silencing elements from different target sequences can be used. In this embodiment, it is recognized that each silencing element can be contained in a single or separate cassette, DNA construct, or vector. As discussed, any means of providing the silencing element is contemplated. A plant or plant cell can be transformed with a single cassette comprising DNA encoding one or more silencing elements or separate cassettes comprising each silencing element can be used to transform a plant or plant cell or host cell. Likewise, a plant transformed with one component can be subsequently transformed with the second component. One or more silencing elements can also be brought together by sexual crossing. That is, a first plant comprising one component is crossed with a second plant comprising the second component. Progeny plants from the cross will comprise both components.

The expression cassette can include 5' and 3' regulatory sequences operably linked to the polynucleotide of the invention. "Operably linked" is intended to mean a functional linkage between two or more elements. For example, an operable linkage between a polynucleotide of the invention and a regulatory sequence (i.e., a promoter) is a functional link that allows for expression of the polynucleotide of the invention. Operably linked elements may be contiguous or non-contiguous. When used to refer to the joining of two protein coding regions, by operably linked is intended that the coding regions are in the same reading frame. The cassette may additionally contain at least one additional polynucleotide to be cotransformed into the organism. Alternatively, the additional polypeptide(s) can be provided on multiple expression cassettes. Expression cassettes can be provided with a plurality of restriction sites and/or recombination sites for insertion of the polynucleotide to be under the transcriptional regulation of the regulatory regions. The expression cassette may additionally contain selectable marker genes.

The expression cassette will include in the 5'-3' direction of transcription, a transcriptional and translational initiation region (i.e., a promoter), a polynucleotide comprising the silencing element employed in the methods and compositions of the invention, and a transcriptional and translational termination region (i.e., termination region) functional in plants. The regulatory regions (i.e., promoters, transcriptional regulatory regions, and translational termination regions) and/or the polynucleotides employed in the invention may be native/analogous to the host cell or to each other. Alternatively, the regulatory regions and/or the polynucleotide employed in the invention may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. As used herein, a chimeric gene comprises a coding sequence operably linked to a transcription initiation region that is heterologous to the coding sequence.

The termination region may be native with the transcriptional initiation region, may be native with the operably linked polynucleotide encoding the silencing element, may be native with the plant host, or may be derived from another source (i.e., foreign or heterologous) to the promoter, the polynucleotide comprising silencing element, the plant host, or any combination thereof. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The polynucleotide encoding the silencing element can be combined with constitutive, tissue-preferred, or other promoters for expression in plants.

Such constitutive promoters include, for example, the core promoter of the Rsyn7 promoter and other constitutive promoters disclosed in WO 99/43838 and U.S. Pat. No. 6,072,050; the core CaMV $^{35}$S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

An inducible promoter, for instance, a pathogen-inducible promoter could also be employed. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116. See also WO 99/43819, herein incorporated by reference.

Of interest are promoters that are expressed locally at or near the site of pathogen infection. See, for example, Marineau et al. (1987) *Plant Mol. Biol.* 9:335-342; Matton et al. (1989) *Molecular Plant-Microbe Interactions* 2:325-331; Somsisch et al. (1986) *Proc. Natl. Acad. Sci. USA* 83:2427-2430; Somsisch et al. (1988) *Mol. Gen. Genet.* 2:93-98; and Yang (1996) *Proc. Natl. Acad. Sci. USA* 93:14972-14977. See also, Chen et al. (1996) *Plant J.* 10:955-966; Zhang et al. (1994) *Proc. Natl. Acad. Sci. USA* 91:2507-2511; Warner et al. (1993) *Plant J* 3:191-201; Siebertz et al. (1989) *Plant Cell* 1:961-968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant. Path.* 41:189-200).

Additionally, as pathogens find entry into plants through wounds or insect damage, a wound-inducible promoter may be used in the constructions of the invention. Such wound-inducible promoters include potato proteinase inhibitor (pin II) gene (Ryan (1990) *Ann. Rev. Phytopath.* 28:425-449; Duan et al. (1996) *Nature Biotechnology* 14:494-498); wun1 and wun2, U.S. Pat. No. 5,428,148; win1 and win2 (Stanford et al. (1989) *Mol. Gen. Genet.* 215:200-208); systemin (McGurl et al. (1992) *Science* 225:1570-1573); WIP1 (Rohmeier et al. (1993) *Plant Mol. Biol.* 22:783-792; Eckelkamp et al. (1993) *FEBS Letters* 323:73-76); MPI gene (Corderok et al. (1994) *Plant J* 6(2):141-150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced expression within a particular plant tissue. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen. Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol. Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Leaf-preferred promoters are known in the art. See, for example, Yamamoto et al. (1997) *Plant J* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590.

Root-preferred promoters are known and can be selected from the many available from the literature or isolated de novo from various compatible species. See, for example, Hire et al. (1992) *Plant Mol. Biol.* 20(2):207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7): 633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed rolC and rolD root-inducing genes of *Agrobacterium rhizogenes* (see *Plant Science* (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2):343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and rolB promoter (Capana et al. (1994) *Plant Mol. Biol.* 25(4):681-691. See also U.S. Pat. Nos. 5,837,876; 5,750,386; 5,633,363; 5,459,252; 5,401,836; 5,110,732; and 5,023,179.

In one embodiment of this invention the plant-expressed promoter is a vascular-specific promoter such as a phloem-specific promoter. A "vascular-specific" promoter, as used herein, is a promoter which is at least expressed in vascular cells, or a promoter which is preferentially expressed in vascular cells. Expression of a vascular-specific promoter need not be exclusively in vascular cells, expression in other cell types or tissues is possible. A "phloem-specific promoter" as used herein, is a plant-expressible promoter which is at least expressed in phloem cells, or a promoter which is preferentially expressed in phloem cells.

Expression of a phloem-specific promoter need not be exclusively in phloem cells, expression in other cell types or tissues, e.g., xylem tissue, is possible. In one embodiment of this invention, a phloem-specific promoter is a plant-expressible promoter at least expressed in phloem cells, wherein the expression in non-phloem cells is more limited (or absent) compared to the expression in phloem cells. Examples of suitable vascular-specific or phloem-specific promoters in accordance with this invention include but are not limited to the promoters selected from the group consisting of: the SCSV3, SCSV4, SCSV5, and SCSV7 promoters (Schunmann et al. (2003) *Plant Functional Biology* 30:453-60; the rolC gene promoter of *Agrobacterium rhizogenes* (Kiyokawa et al. (1994) *Plant Physiology* 104:801-02; Pandolfini et al. (2003) BioMedCentral (BMC) Biotechnology 3:7, (.biomedcentral .com/1472-6750/3/7), which can be accessed on the world-wide web using the "www" prefix); Graham et al. (1997) *Plant Mol. Biol.* 33:729-35; Guivarc'h et al. (1996); Almon et al. (1997) *Plant Physiol.* 115:1599-607; the rolA gene promoter of *Agrobacterium rhizogenes* (Dehio et al. (1993) *Plant Mol. Biol.* 23:1199-210); the promoter of the *Agrobacterium tumefaciens* T-DNA gene 5 (Korber et al. (1991) *EMBO J.* 10:3983-91); the rice sucrose synthase RSs1 gene promoter (Shi et al. (1994) *J. Exp. Bot.* 45:623-31); the CoYMV or Commelina yellow mottle badnavirus promoter (Medberry et al. (1992) *Plant Cell* 4: 185-92; Zhou et al. (1998) *Chin. J. Biotechnol.* 14:9-16); the CFDV or coconut foliar decay virus promoter (Rohde et al. (1994) *Plant Mol. Biol.* 27:623-28; Hehn and Rhode (1998) *J. Gen. Virol.* 79:1495-99); the RTBV or rice tungro bacilliform virus promoter (Yin and Beachy (1995) Plant J. 7:969-80; Yin et al. (1997) *Plant J.* 12: 1179-80); the pea glutamin synthase GS3A gene (Edwards et al. (1990) *Proc. Natl. Acad. Sci. USA* 87:3459-63; Brears et al. (1991) *Plant J.* 1:235-44); the inv CD111 and inv CD141 promoters of the potato invertase genes (Hedley et al. (2000) *J. Exp. Botany* 51:817-21); the promoter isolated from Arabidopsis shown to have phloem-specific expression in tobacco by Kertbundit et al. (1991) *Proc. Natl. Acad. Sci. USA* 88:5212-16); the VAHOX1 promoter region (Tornero et al. (1996) *Plant J.* 9:639-48); the pea cell wall invertase gene promoter (Zhang et al. (1996) *Plant Physiol.* 112:1111-17); the promoter of the endogenous cotton protein related to chitinase of US published patent application 20030106097, an acid invertase gene promoter from carrot (Ramloch-Lorenz et al. (1993) *The Plant J.* 4:545-54); the promoter of the sulfate transporter geneSultr1; 3 (Yoshimoto et al. (2003) *Plant Physiol.* 131:1511-17); a promoter of a sucrose synthase gene (Nolte and Koch (1993) *Plant Physiol.* 101:899-905); and the promoter of a tobacco sucrose transporter gene (Kuhn et al. (1997) *Science* 275-1298-1300).

Possible promoters also include the Black Chemy promoter for Prunasin Hydrolase (PH DL1.4 PRO) (U.S. Pat. No. 6,797,859), Thioredoxin H promoter from cucumber and rice (Fukuda A et al. (2005). *Plant Cell Physiol.* 46(11):1779-86), Rice (RSs1) (Shi, T. Wang et al. (1994). *J. Exp. Bot.* 45(274): 623-631) and maize sucrose synthese-1 promoters (Yang., N-S. et al. (1990) *PNAS* 87:4144-4148), PP2 promoter from pumpkin Guo, H. et al. (2004) *Transgenic Research* 13:559-566), At SUC2 promoter (Truemit, E. et al. (1995) *Planta* 196(3):564-70., At SAM-1 (S-adenosylmethionine synthetase) (Mijnsbrugge K V. et al. (1996) *Planr. Cell. Physiol.* 37(8): 1108-1115), and the Rice tungro bacilliform virus (RTBV) promoter (Bhattacharyya-Pakrasi et al. (1993) *Plant J.* 4(1):71-79).

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85.610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987)

Cell 49:603-612; Figge et al. (1988) *Cell* 52:713-722; Deuschle et al. (1989) *Proc. Natl. Acad. Sci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference. The above list of selectable marker genes is not meant to be limiting. Any selectable marker gene can be used in the present invention.

VI. Compositions Comprising Silencing Elements

One or more of the polynucleotides comprising the silencing element can be provided as an external composition such as a spray or powder to the plant, plant part, seed, a pest, or an area of cultivation. In another example, a plant is transformed with a DNA construct or expression cassette for expression of at least one silencing element. In either compositions, the silencing element, when ingested by an insect, can reduce the level of a target pest sequence and thereby control the pest (i.e., any pest from the Lepidoptera order, such as, *Spodoptera frugiperda*). It is recognized that the composition can comprise a cell (such as plant cell or a bacterial cell), in which a polynucleotide encoding the silencing element is stably incorporated into the genome and operably linked to promoters active in the cell. Compositions comprising a mixture of cells, some cells expressing at least one silencing element are also encompassed. In other embodiments, compositions comprising the silencing elements are not contained in a cell. In such embodiments, the composition can be applied to an area inhabited by a pest. In one embodiment, the composition is applied externally to a plant (i.e., by spraying a field or area of cultivation) to protect the plant from the pest.

In one embodiment, the composition comprising the silencing element that controls a pest from the Lepidoptera order does not comprise a heterologous cationic oligopeptide to facilitate uptake of the RNAi into the insect cells. Accordingly, in such embodiments, insecticidal activity occurs in the compositions of the invention (i.e., the plant, plant part, plant cell, or microbe) in the absence of a cationic oligopeptide that is heterologous to the plant, plant part or microbe. The cationic oligopeptide is target non-specific and interacts non-specifically with RNA via electrostatic interactions and neutralization of charge to penetrate membranes and lacks a specific activity that promotes a specific interaction with a cell membrane.

The composition of the invention can further be formulated as bait. In this embodiment, the compositions comprise a food substance or an attractant which enhances the attractiveness of the composition to the pest.

The composition comprising the silencing element can be formulated in an agriculturally suitable and/or environmentally acceptable carrier. Such carriers can be any material that the animal, plant or environment to be treated can tolerate. Furthermore, the carrier must be such that the composition remains effective at controlling a pest. Examples of such carriers include water, saline, Ringer's solution, dextrose or other sugar solutions, Hank's solution, and other aqueous physiologically balanced salt solutions, phosphate buffer, bicarbonate buffer and Tris buffer. In addition, the composition may include compounds that increase the half-life of a composition.

It is recognized that the polynucleotides comprising sequences encoding the silencing element can be used to transform organisms to provide for host organism production of these components, and subsequent application of the host organism to the environment of the target pest(s). Such host organisms include baculoviruses, bacteria, and the like. In this manner, the combination of polynucleotides encoding the silencing element may be introduced via a suitable vector into a microbial host, and said host applied to the environment, or to plants or animals.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be stably incorporated into the genome of the cell (e.g., chromosome, plasmid, plastid, or mitochondrial DNA), converted into an autonomous replicon, or transiently expressed (e.g., transfected mRNA).

Microbial hosts that are known to occupy the "phytosphere" (phylloplane, phyllosphere, rhizosphere, and/or rhizoplana) of one or more crops of interest may be selected. These microorganisms are selected so as to be capable of successfully competing in the particular environment with the wild-type microorganisms, provide for stable maintenance and expression of the sequences encoding the silencing element, and desirably, provide for improved protection of the components from environmental degradation and inactivation.

Such microorganisms include bacteria, algae, and fungi. Of particular interest are microorganisms such as bacteria, e.g., *Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc*, and *Alcaligenes*, fungi, particularly yeast, e.g., *Saccharomyces, Cryptococcus, Kluyveromyces, Sporobolomyces, Rhodotorula*, and *Aureobasidium*. Of particular interest are such phytosphere bacterial species as *Pseudomonas syringae, Pseudomonasfluorescens, Serratia marcescens, Acetobacter xylinum, Agrobacteria, Rhodopseudomonas spheroides, Xanthomonas campestris, Rhizobium melioti, Alcaligenes entrophus, Clavibacter xyli* and *Azotobacter vinlandir*, and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces rosues, S. odorus, Kluyveromyces veronae*, and *Aureobasidium pollulans*. Of particular interest are the pigmented microorganisms.

A number of ways are available for introducing the polynucleotide comprising the silencing element into the microbial host under conditions that allow for stable maintenance and expression of such nucleotide encoding sequences. For example, expression cassettes can be constructed which include the nucleotide constructs of interest operably linked with the transcriptional and translational regulatory signals for expression of the nucleotide constructs, and a nucleotide sequence homologous with a sequence in the host organism, whereby integration will occur, and/or a replication system that is functional in the host, whereby integration or stable maintenance will occur.

Transcriptional and translational regulatory signals include, but are not limited to, promoters, transcriptional initiation start sites, operators, activators, enhancers, other regulatory elements, ribosomal binding sites, an initiation codon, termination signals, and the like. See, for example, U.S. Pat. Nos. 5,039,523 and 4,853,331; EPO 0480762A2; Sambrook et al. (2000); *Molecular Cloning: A Laboratory Manual* (3$^{rd}$ ed.; Cold Spring Harbor Laboratory Press, Plainview, N.Y.); Davis et al. (1980) Advanced Bacterial Genetics (Cold Spring Harbor Laboratory, Cold Spring Harbor, N.Y.); and the references cited therein.

Suitable host cells include the prokaryotes and the lower eukaryotes, such as fungi. Illustrative prokaryotes, both Gram-negative and Gram-positive, include Enterobacteriaceae, such as *Escherichia, Erwinia, Shigella, Salmonella*, and *Proteus*; Bacillaceae; Rhizobiceae, such as *Rhizobium*; Spirillaceae, such as *photobacterium, Zymomonas, Serratia, Aeromonas, Vibrio, Desulfovibrio, Spirillum*; Lactobacillaceae; Pseudomonadaceae, such as *Pseudomonas* and *Acetobacter*; Azotobacteraceae and Nitrobacteraceae. Among eukaryotes are fungi, such as Phycotnycetes and Ascomycetes, which includes yeast, such as *Saccharomyces* and *Schizosaccharomyces*; and Basidiomycetes yeast, such as *Rhodotorula, Aureobasidium, Sporobolomyces*, and the like.

Characteristics of particular interest in selecting a host cell for purposes of the invention include ease of introducing the coding sequence into the host, availability of expression systems, efficiency of expression, stability in the host, and the presence of auxiliary genetic capabilities. Characteristics of interest for use as a pesticide microcapsule include protective qualities, such as thick cell walls, pigmentation, and intracellular packaging or formation of inclusion bodies; leaf affinity; lack of mammalian toxicity; attractiveness to pests for ingestion; and the like. Other considerations include ease of formulation and handling, economics, storage stability, and the like.

Host organisms of particular interest include yeast, such as *Rhodotorula* spp., *Aureobasidium* spp., *Saccharomyces* spp., and *Sporobolomyces* spp., phylloplane organisms such as *Pseudomonas* spp., *Erwinia* spp., and *Flavobacterium* spp., and other such organisms, including *Pseudomonas aeruginosa, Pseudomonasfluorescens, Saccharomyces cerevisiae, Bacillus thuringiensis, Escherichia coli, Bacillus subtilis*, and the like.

The sequences encoding the silencing elements encompassed by the invention can be introduced into microorganisms that multiply on plants (epiphytes) to deliver these components to potential target pests. Epiphytes, for example, can be gram-positive or gram-negative bacteria.

The silencing element can be fermented in a bacterial host and the resulting bacteria processed and used as a microbial spray in the same manner that *Bacillus thuringiensis* strains have been used as insecticidal sprays. Any suitable microorganism can be used for this purpose. *Pseudomonas* has been used to express *Bacillus thuringiensis* endotoxins as encapsulated proteins and the resulting cells processed and sprayed as an insecticide Gaertner et al. (1993), in *Advanced Engineered Pesticides*, ed. L. Kim (Marcel Decker, Inc.).

Alternatively, the components of the invention are produced by introducing heterologous genes into a cellular host. Expression of the heterologous sequences results, directly or indirectly, in the intracellular production of the silencing element. These compositions may then be formulated in accordance with conventional techniques for application to the environment hosting a target pest, e.g., soil, water, and foliage of plants. See, for example, EPA 0192319, and the references cited therein.

In the present invention, a transformed microorganism can be formulated with an acceptable carrier into separate or combined compositions that are, for example, a suspension, a solution, an emulsion, a dusting powder, a dispersible granule, a wettable powder, and an emulsifiable concentrate, an aerosol, an impregnated granule, an adjuvant, a coatable paste, and also encapsulations in, for example, polymer substances.

Such compositions disclosed above may be obtained by the addition of a surface-active agent, an inert carrier, a preservative, a humectant, a feeding stimulant, an attractant, an encapsulating agent, a binder, an emulsifier, a dye, a UV protectant, a buffer, a flow agent or fertilizers, micronutrient donors, or other preparations that influence plant growth. One or more agrochemicals including, but not limited to, herbicides, insecticides, fungicides, bactericides, nematicides, molluscicides, acaracides, plant growth regulators, harvest aids, and fertilizers, can be combined with carriers, surfactants or adjuvants customarily employed in the art of formulation or other components to facilitate product handling and application for particular target pests. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers. The active ingredients of the present invention (i.e., at least one silencing element) are normally applied in the form of compositions and can be applied to the crop area, plant, or seed to be treated. For example, the compositions may be applied to grain in preparation for or during storage in a grain bin or silo, etc. The compositions may be applied simultaneously or in succession with other compounds. Methods of applying an active ingredient or a composition that contains at least one silencing element include, but are not limited to, foliar application, seed coating, and soil application. The number of applications and the rate of application depend on the intensity of infestation by the corresponding pest.

Suitable surface-active agents include, but are not limited to, anionic compounds such as a carboxylate of, for example, a metal; carboxylate of a long chain fatty acid; an N-acylsarcosinate; mono- or di-esters of phosphoric acid with fatty alcohol ethoxylates or salts of such esters; fatty alcohol sulfates such as sodium dodecyl sulfate, sodium octadecyl sulfate, or sodium cetyl sulfate; ethoxylated fatty alcohol sulfates; ethoxylated alkylphenol sulfates; lignin sulfonates; petroleum sulfonates; alkyl aryl sulfonates such as alkylbenzene sulfonates or lower alkylnaphtalene sulfonates, e.g., butyl-naphthalene sulfonate; salts of sulfonated naphthalene-formaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate or dioctyl succinate. Nonionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g., polyoxyethylene sorbitan fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine such as an acetate, naphthenate or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include, but are not limited to, inorganic minerals such as kaolin, phyllosilicates, carbonates, sulfates, phosphates, or botanical materials such as cork, powdered corncobs, peanut hulls, rice hulls, and walnut shells.

The compositions comprising the silencing element can be in a suitable form for direct application or as a concentrate of primary composition that requires dilution with a suitable quantity of water or other dilutant before application.

The compositions (including the transformed microorganisms) can be applied to the environment of an insect pest (such as a pest from the Lepidoptera order) by, for example, spraying, atomizing, dusting, scattering, coating or pouring, introducing into or on the soil, introducing into irrigation water, by seed treatment or general application or dusting at the time when the pest has begun to appear or before the appearance of pests as a protective measure. For example, the composition(s) and/or transformed microorganism(s) may be mixed with grain to protect the grain during storage. It is generally important to obtain good control of pests in the early stages of plant growth, as this is the time when the plant can be most severely damaged. The compositions can conveniently contain another insecticide if this is thought necessary. In an embodiment of the invention, the composition(s) is applied directly to the soil, at a time of planting, in granular form of a composition of a carrier and dead cells of a *Bacillus* strain or transformed microorganism of the invention. Another embodiment is a granular form of a composition comprising an agrochemical such as, for example, a herbicide, an insecticide, a fertilizer, in an inert carrier, and dead cells of a *Bacillus* strain or transformed microorganism of the invention.

VII. Plants, Plant Parts, and Methods of Introducing Sequences into Plants

In one embodiment, the methods of the invention involve introducing a polypeptide or polynucleotide into a plant. "Introducing" is intended to mean presenting to the plant the polynucleotide or polypeptide in such a manner that the sequence gains access to the interior of a cell of the plant. The methods of the invention do not depend on a particular method for introducing a sequence into a plant, only that the polynucleotide or polypeptides gains access to the interior of at least one cell of the plant. Methods for introducing polynucleotide or polypeptides into plants are known in the art including, but not limited to, stable transformation methods, transient transformation methods, and virus-mediated methods.

"Stable transformation" is intended to mean that the nucleotide construct introduced into a plant integrates into the genome of the plant and is capable of being inherited by the progeny thereof. "Transient transformation" is intended to mean that a polynucleotide is introduced into the plant and does not integrate into the genome of the plant or a polypeptide is introduced into a plant.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. Nos. 5,563,055 and 5,981,840), direct gene transfer (Paszkowski et al. (1984) *EMBO J.* 3:2717-2722), and ballistic particle acceleration (see, for example, U.S. Pat. Nos. 4,945,050; 5,879,918; 5,886,244; and, 5,932,782; Tomes et al. (1995) in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783; and, 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, New York), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

In specific embodiments, the silencing element sequences of the invention can be provided to a plant using a variety of transient transformation methods. Such transient transformation methods include, but are not limited to, the introduction of the protein or variants and fragments thereof directly into the plant or the introduction of the transcript into the plant. Such methods include, for example, microinjection or particle bombardment. See, for example, Crossway et al. (1986) *Mol. Gen. Genet.* 202:179-185; Nomura et al. (1986) *Plant Sci.* 44:53-58; Hepler et al. (1994) *Proc. Natl. Acad. Sci.* 91: 2176-2180 and Hush et al. (1994) *The Journal of Cell Science* 107:775-784, all of which are herein incorporated by reference. Alternatively, polynucleotides can be transiently transformed into the plant using techniques known in the art. Such techniques include viral vector system and the precipitation of the polynucleotide in a manner that precludes subsequent release of the DNA. Thus, the transcription from the particle-bound DNA can occur, but the frequency with which it is released to become integrated into the genome is greatly reduced. Such methods include the use of particles coated with polyethylimine (PEI; Sigma #P3143).

In other embodiments, the polynucleotide of the invention may be introduced into plants by contacting plants with a virus or viral nucleic acids. Generally, such methods involve incorporating a nucleotide construct of the invention within a viral DNA or RNA molecule. Further, it is recognized that promoters of the invention also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221; herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide of the invention can be contained in transfer cassette flanked by two non-recombinogenic recombination sites. The transfer cassette is introduced into a plant having stably incorporated into its genome a target site which is flanked by two non-recombinogenic recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a polynucleotide of the invention, for example, an expression cassette of the invention, stably incorporated into their genome.

As used herein, the term plant includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

The present invention may be used for transformation of any plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago saliva*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassaya (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). In specific embodiments, plants of the present invention are crop plants (for example, corn, alfalfa, sunflower, *Brassica*, soybean, cotton, safflower, peanut, sorghum, wheat, millet, tobacco, etc.). In other embodiments, corn and soybean plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

VIII. Methods of Use

The methods of the invention comprise methods for controlling a pest (i.e., pest from the Lepidoptera order, such as, *Spodoptera frugiperda*). The method comprises feeding to a pest a composition comprising a silencing element of the invention, wherein said silencing element, when ingested by a pest (i.e., pests from the Lepidoptera order, such as, *Spodoptera frugiperda*), reduces the level of a target polynucleotide of the pest and thereby controls the pest. The pest can be fed the silencing element in a variety of ways. For example, in one embodiment, the polynucleotide comprising the silencing element is introduced into a plant. As the Lepidoptera feeds on the plant or part thereof expressing these sequences, the silencing element is delivered to the pest. When the silencing element is delivered to the plant in this manner, it is recognized that the silencing element can be expressed constitutively or alternatively, it may be produced in a stage-specific manner by employing the various inducible or tissue-preferred or developmentally regulated promoters that are discussed elsewhere herein. In specific embodiments, the silencing element expressed in the roots, stalk or stem, leaf including pedicel, xylem and phloem, fruit or reproductive tissue, silk, flowers and all parts therein or any combination thereof.

In another method, a composition comprising at least one silencing element of the invention is applied to a plant. In such embodiments, the silencing element can be formulated in an agronomically suitable and/or environmentally acceptable carrier, which is preferably, suitable for dispersal in fields. In addition, the carrier can also include compounds that increase the half life of the composition. In specific embodiments, the composition comprising the silencing element is formulated in such a manner such that it persists in the environment for a length of time sufficient to allow it to be delivered to a pest. In such embodiments, the composition can be applied to an area inhabited by a pest. In one embodiment, the composition is applied externally to a plant (i.e., by spraying a field) to protect the plant from pests.

In certain embodiments, the constructs of the present invention can be stacked with any combination of polynucleotide sequences of interest in order to create plants with a desired trait. A trait, as used herein, refers to the phenotype derived from a particular sequence or groups of sequences. For example, the polynucleotides of the present invention may be stacked with any other polynucleotides encoding polypeptides having pesticidal and/or insecticidal activity, such as other *Bacillus thuringiensis* toxic proteins (described in U.S. Pat. Nos. 5,366,892; 5,747,450; 5,737,514; 5,723,756; 5,593,881; and Geiser et al. (1986) Gene 48:109), lectins (Van Damme et al. (1994) *Plant Mol. Biol.* 24:825, pentin (described in U.S. Pat. No. 5,981,722), and the like. The combinations generated can also include multiple copies of any one of the polynucleotides of interest. The polynucleotides of the present invention can also be stacked with any other gene or combination of genes to produce plants with a variety of desired trait combinations including, but not limited to, traits desirable for animal feed such as high oil genes (e.g., U.S. Pat. No. 6,232,529); balanced amino acids (e.g., hordothionins (U.S. Pat. Nos. 5,990,389; 5,885,801; 5,885,802; and 5,703,409); barley high lysine (Williamson et al. (1987) *Eur. J. Biochem.* 165:99-106; and WO 98/20122) and high methionine proteins (Pedersen et al. (1986) *J. Biol. Chem.* 261:6279; Kirihara et al. (1988) *Gene* 71:359; and Musumura et al. (1989) *Plant Mol. Biol.* 12:123)); increased digestibility (e.g., modified storage proteins) (U.S. Pat. No. 6,858,778); and thioredoxins (U.S. Pat. No. 7,009,087)); the disclosures of which are herein incorporated by reference.

The polynucleotides of the present invention can also be stacked with traits desirable for disease or herbicide resistance (e.g., fumonisin detoxification genes (U.S. Pat. No. 5,792,931); avirulence and disease resistance genes (Jones et al. (1994) Science 266:789; Martin et al. (1993) *Science* 262:1432; Mindrinos et al. (1994) Cell 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) J. Bacteriol. 170:5837-5847) facilitate expression of polyhydroxyalkanoates (PHAs)); the disclosures of which are herein incorporated by reference. One could also combine the polynucleotides of the present invention with polynucleotides providing agronomic traits such as male sterility (e.g., see U.S. Pat. No. 5,583,210), stalk strength, flowering time, or transformation technology traits such as cell cycle regulation or gene targeting (e.g., WO 99/61619, WO 00/17364, and WO 99/25821); the disclosures of which are herein incorporated by reference.

These stacked combinations can be created by any method including, but not limited to, cross-breeding plants by any conventional or TopCross methodology, or genetic transformation. If the sequences are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

Methods and compositions are further provided which allow for an increase in RNAi produced from the silencing element. In such embodiments, the methods and compositions employ a first polynucleotide comprising a silencing element for a target pest sequence operably linked to a promoter active in the plant cell; and, a second polynucleotide comprising a suppressor enhancer element comprising the target pest sequence or an active variant or fragment thereof operably linked to a promoter active in the plant cell. The combined expression of the silencing element with suppressor enhancer element leads to an increased amplification of the inhibitory RNA produced from the silencing element over that achievable with only the expression of the silencing element alone. In addition to the increased amplification of the specific RNAi species itself, the methods and compositions further allow for the production of a diverse population of RNAi species that can enhance the effectiveness of disrupting target gene expression. As such, when the suppressor enhancer element is expressed in a plant cell in combination with the silencing element, the methods and composition can allow for the systemic production of RNAi throughout the plant; the production of greater amounts of RNAi than would be observed with just the silencing element construct alone; and, the improved loading of RNAi into the phloem of the plant, thus providing better control of phloem feeding insects by an RNAi approach. Thus, the various methods and compositions provide improved methods for the delivery of inhibitory RNA to the target organism. See, for example, U.S. Provisional Application No. 61/021,676, entitled "Compositions and Methods for the Suppression of Target Polynucleotides", filed Jan. 17, 2008 and herein incorporated by reference in its entirety.

As used herein, a "suppressor enhancer element" comprises a polynucleotide comprising the target sequence to be suppressed or an active fragment or variant thereof. It is recognize that the suppressor enhancer element need not be identical to the target sequence, but rather, the suppressor enhancer element can comprise a variant of the target sequence, so long as the suppressor enhancer element has sufficient sequence identity to the target sequence to allow for an increased level of the RNAi produced by the silencing element over that achievable with only the expression of the silencing element. Similarly, the suppressor enhancer element can comprise a fragment of the target sequence, wherein the fragment is of sufficient length to allow for an increased level of the RNAi produced by the silencing element over that achievable with only the expression of the silencing element. Thus, in specific embodiments, the suppressor enhancer element comprises a fragment or a variant of a polynucleotide encoding a juvenile hormone polypeptide, a vacuolar polypeptide, a cadherin polypeptide, a cuticle polypeptide, a translation initiation factor, a SAR1 polypeptide, an elongation factor, a phosphooligosaccharide, a myosin polypeptide, a potassium channel amino acid transporter, a potassium inwardly rectifier polypeptide, an amino acid transporter, a tubulin polypeptide, a ubiquitin polypeptide, small nuclear ribonucleoprotein, or any other polynucleotide of interest disclosed herein. In still other embodiments, the suppressor enhancer element comprises a polynucleotide set forth in SEQ ID NO: 1-50 or an active variant or fragment thereof.

It is recognized that multiple suppressor enhancer elements from the same target sequence or from different target sequences, or from different regions of the same target sequence can be employed. For example, the suppressor enhancer elements employed can comprise fragments of the target sequence derived from different region of the target sequence (i.e., from the 3' UTR, coding sequence, intron, and/or 5' UTR). Further, the suppressor enhancer element can be contained in an expression cassette, as described elsewhere herein, and in specific embodiments, the suppressor enhancer element is on the same or on a different DNA vector or construct as the silencing element. The suppressor enhancer element can be operably linked to a promoter as disclosed herein. It is recognized that the suppressor enhancer element can be expressed constitutively or alternatively, it may be produced in a stage-specific manner employing the various inducible or tissue-preferred or developmentally regulated promoters that are discussed elsewhere herein.

In specific embodiments, employing both a silencing element and the suppressor enhancer element the systemic production of RNAi occurs throughout the entire plant. In further embodiments, the plant or plant parts of the invention have an improved loading of RNAi into the phloem of the plant than would be observed with the expression of the silencing element construct alone and, thus provide better control of phloem feeding insects by an RNAi approach. In specific embodiments, the plants, plant parts, and plant cells of the invention can further be characterized as allowing for the production of a diversity of RNAi species that can enhance the effectiveness of disrupting target gene expression.

In specific embodiments, the combined expression of the silencing element and the suppressor enhancer element increases the concentration of the inhibitory RNA in the plant cell, plant, plant part, plant tissue or phloem over the level that is achieved when the silencing element is expressed alone.

As used herein, an "increased level of inhibitory RNA" comprises any statistically significant increase in the level of RNAi produced in a plant having the combined expression when compared to an appropriate control plant. For example, an increase in the level of RNAi in the plant, plant part or the plant cell can comprise at least about a 1%, about a 1%-5%, about a 5%-10%, about a 10%-20%, about a 20%-30%, about a 30%-40%, about a 40%-50%, about a 50%-60%, about 60-70%, about 70%-80%, about a 80%-90%, about a 90%-100% or greater increase in the level of RNAi in the plant, plant part, plant cell, or phloem when compared to an appropriate control. In other embodiments, the increase in the level of RNAi in the plant, plant part, plant cell, or phloem can comprise at least about a 1 fold, about a 1 fold-5 fold, about a 5 fold-10 fold, about a 10 fold-20 fold, about a 20 fold-30 fold, about a 30 fold-40 fold, about a 40 fold-50 fold, about a 50 fold-60 fold, about 60 fold-70 fold, about 70 fold-80 fold, about a 80 fold-90 fold, about a 90 fold-100 fold or greater increase in the level of RNAi in the plant, plant part, plant cell or phloem when compared to an appropriate control. Methods to assay for an increase in the level of RNAi are discussed elsewhere herein.

The following examples are offered by way of illustration and not by way of limitation.

EXPERIMENTAL

Example 1

Specific Target Genes and Silencing Elements that Cause Insecticidal Activity Against *Spodoptera frugiperda*

Disruption of insect gene function via RNAi can produce specific activity against target insects. This specificity is enhanced by delivery of the dsRNAs via transgenic plants. Identification of gene function in insects via RNAi has been largely limited to injection of dsRNAs. In fact, past experiments have indicated that insects are not capable of systemic RNAi response based on exposure to dsRNAs.

As described below, we have demonstrated acute activity of numerous dsRNA pairs through injection experiments and additionally have demonstrated insect antagonism through ingestion of dsRNAs. This evidence identifies several gene/primer pair combinations with clear insecticidal properties. The use of dsRNAs in transgenic plants also addresses the potential complication of heterologous protein expression and the possible risks of allergic reaction, non-target activity, and environmental- or bioaccumulation. The data presented below represents the first test of disruption of these particular genes resulting in insecticidal activity in whole organisms and the first report of insecticidal activity of dsRNAs against *Spodoptera frugiperda*.

The invention describes specific target genes and the dsRNA sequences causing insecticidal activity against the Lepidopteran *Spodoptera frugiperda* through RNA interference of the target gene's expression. Disruption of the genes targeted by the dsRNA sequences may be broadly insecticidal in numerous species. The specific dsRNA sequences display insecticidal activity upon ingestion and can be utilized with a transgenic plant mode of delivery. Table 1 provides the polynucleotide of non-limiting examples of target sequence from *Spodoptera frugiperda*, a brief description of the function of the protein encoded by the target sequence, and a SEQ ID NO. Table 2 provides a summary of primers used to suppress the target polynucleotides.

TABLE 1

Target Polynucleotides from *Spodoptera frugiperda*.

SEQ ID NO: 1
>iselc.pk002.m13   Juvenile hormone query
CAAGCATCCAACATGGTATCCGACTTCAGGAAGAAGAAGCTCCTCCACGT
GTTCAAGTCCTTCTTCGACACGGACGGCAGCGGCAACATCGAGAAGGATG
ACTTCCTGATGGCCATCGAAAGGATAACCAAGACCAGAGGCTGGAAAGCT
GGAGACGACAAATACAAATTTGTCGAGGAGACCCTATTGAAGATCTGGGA
CGGCATCCAGAAGGTCGCTGACGAGAACAAGGACGGACAGGTCAGCCAGG
ACGAGTGGATCGCTATGTGGGACAAGTACTCCAAGAACCCGTCCGAGGCG TABLE 1-continued Target Polynucleotides from Spodoptera frugiperda.

TTCGAGTGGCAGACCCTGTACTGCAAGTTCGCGTTCACTCTTGAAGACGC
CAGCGACGATGGATCCATCGACAGCGAGGAGTTCTCCTCTGTGTACGCCT
CCTTCGGCCTGGACAANGACGANGCTGTGGCTGCCTTCAAGAAAGATGGC
TAACGGTAAGTCCGAAGTGTCCTGGGCTTGAGTTCCACGACCTGTGGAAN
GAGTACTTCTCATCCGGAAGACTNGAACGCTGCCGGCAAN

SEQ ID NO: 2
>ise1c.pk003.f7    Juvenile hormone query
CCAACATGGTATCCGACTTCAGGAAGAAGAAGCTCCTCCACGTGTTCAAG
TCCTTCTTCGACACGGACGGCAGCGGCAACATCGAGAAGGATGATTTCCT
GATGGCCATCGAAAGGATAACCAAGACCAGAGGCTGGAAAGCTGGAGACA
ACAAATACAAATTTGTCGAGGAAACCCTATTGAAGATCTGGGACGGCATC
CAGAAGGTCGCTGACGAGAACAAGGACGGACAGGTCAGCCAGGACGAGTG
GATCGCTATGTGGGACAAGTACTCCAAGAACCCATCCGAGGCGTTCGAGT
GGCAGACCCTGTACTGCAAGTTCGCGTTCACTCTTGAAGACGCCAGCGAC
GACGGATNCATCGACAGCGAAGAGTTCTCCTCTGTGTACGCCTCCTTCGG
GCTGGACAANGGACGAGGCGGTGGCTGCCTTCAAGAAGATGNTAACGGTA
AGTCCGAATGTCCTGGGGCTGAGTTTCAAGANCTGTTGGAAGGATACTTC
TCAAC SEQ ID NO: 3
>ise1c.pk005.a15    Juvenile hormone query
CAACATGGTATCCGACTTCAGGAAGAATAAGCTCCTCCACGTGTTCAAG
CCTTCTTCGACACGGACGGCAGCGGCAACATCGAGAAGGATGACTTCCTG
ATGGCCATCGAAAGGATAACCAAGACCAGAGGCTGGAAAGCTGGAGACGA
CAAATACAAATTTGTCGAGGAGACCCTATTGAAGATCTGGGACGGCATCC
AGAAGGTCGCTGACGAGAACAAGGACGGACAGGTCAGCCAGGACGAGTGG
ATCGCTATGTGGGACAAGTANTCCAAGAACCCGTCCGAGGCGTTCGAGTG
GCAGACCCTGTACTGCAAGTTCGCGTTCACTCTTGAAGACGCCAGNGACG
ATGGATCCATCGACAGCGAGGAGTTCTCCTCTGTGTACGCCTCCTTCGGC
CTGGACAAGG SEQ ID NO: 4
>ise1c.pk006.d24    Juvenile hormone query
GAGAGAGAGAGAGAGAGAACTAGTCTCGAGTTTTTTTTTTTTTT
TTTTTTTTTTTTTTNGGAAANTACTATTTTATTGTACAACTGCCCCTT
AACCTCATCTATGAGTCACCCATAAATGTTATTTTGGTAAAATGTTTGAC
ACACTTCACACTAATATTTATAAATGTGAAAGTTTGTTTGTTTGAATGTT
TGTATATTTGTCTGTCAATCACGCTGAAACCACTGTATAGAATTTGACCT
AATTTGGTATACANACAGGGTATGAGCTGACTTGATAGGATACTTT
TTATCCCACAGGAACGCGGGTAAAGTCCNTGGGCAGAAGCTAGTATGTAA
TAATTATNTCCCTCTACCTACCCTATATGGGGGTGGACCGTCATGTTCTT
TACNCNACAACCNGTTTGTCCACCTCNCCTTTAAAGTTTTGTNAG SEQ ID NO: 5
>ise2c.pk009.i4    Juvenile hormone query
GCACGAGGGCCGTGTCGACTTCGCACCAGTCCCCTATTTATTTACCTTGA
CAAAAATATGGCGCGCCTATTGTTTATTGCGCCTATCCTGGCGTTGGCTA
TAATGCCAGTATACTTCTTATTCCTAAAAGGACCACCCCCACTACCCGAA
CTAGATATGAACGAGTGGTGGGGCCCAGAGAAGCTAAAGCAAAACCTGAC
ACTAGTATAAAACCCTTTAAAATTGCTTTTGGAGACACTGTTGTAAAAG
ACTTAAAAGACCGTCTCAAACGTTCTCGGTCTTTCACTGCTCCGCTGGAG
GGTGTGGCATTCCAGTACGGCTTCAACACTGCTCAGCTGGATGGTTGGCT
GAAGTACTGGGCTAATGAGTATAAGTTCAAGGAGAGAGAGACCTTCCTCA
ACCAGTACCCTCAGTACAAAACCAATATCCAGGGTCTTGACATCCACTTC
ATCAGGGTTACACCGAAGGTACCGGCAGGAGTGGAGGTGGTACCCATGCT
ACTCCTCCACGCTGGCCAGGCTCTGTCAGGGAGTTCTACGAGGCTATTC
CTCTCATCACAGCAGTCAGCAAGGACCGTGACTTCGCTGTGGAAGTCATC
GTTCCAAGTCTACCTGGCTATGGATTCTCTGATGCCGCAGTTCGTCCCGG
CnnnnnnnnCCCCACAAATGnnn SEQ ID NO: 6
>ise2c.pk001.d19    vacuolar query
GCACGAGGCTTGGACGTGATGTTACCTGGGAATTCAACCCCTTGAATGTT
AAGGTCGGCTCCCACATCACCGGAGGAGCTTGTACGGTATCGTACACGA
GAACACATTGGTTAAGCACAAGATGTTGATCCCACCCAAGGCCAAGGGTA
CCGTCACCTACGTCGCGCCCTCCGGCAACTACAAAGTCACTGACGTAGTG
TTGGAGACGGAGTTCGACGGCGAGAAGGAGAAGTACACCATGTTGCAAGT
ATGGCCGGTGCGCCAGCCGCGCCCCGTCACTGAAGAAGCTGTCCGCCAACC
ACCCCCTGCTCACCGGACAGAGAGTGCTCGACTCTCTCTTCCCTTGTGTC
CAGGGTGGTACCACGGCCATCCCCGGCGCCTTCGGTTGTGGCAAGACTGT
CGTCTCACAGGCTCTGTCCAAGTACTCCAACTCTGACGTCATCATCTACG
TCGGATGCGGTGAACGTGGTAACGAGATGTCTGAGGTACTGCGTGACTTC
CCCGAGCTGACGGTGGAGATCGAGGGCATGACCGAGTCCATCATGAAGCG
TACCGCGCTCGTCGCCAACACCTCCAACATGCCTGTAGCCGCCCG
CTTCCATCTACACCGGTATCACCCTCTCCGAGTACTTCCGTGACATGGGT
TACAACGTGTCCATGATGGCTGACTCCACCTCGTTGGGCCAG SEQ ID NO: 7
>ise2c.pk001.e14    vacuolar query
GCACGAGGCAGATAGTCATCACTGTTTTTGGGACCTGTnnnTACTCCCTC
AATAAACCTACAAAATGGCCGAAAACCCAATCTACGGACCCTTCTTTGGA
GTTATGGGGCGGCGTCTGCTATCATCTTTAGCGCGCTGGGAGCTGCCTA
TGGAACTGCTAnGnCnnnnACCGGTATCGCCGCCATGTCGGTGATGCGGC
CCGAGCTCATCATGAAGTCCAACAACTACACCCTTTACAAGnGGTTCATC
CACCTTGGCGCTGGTCTnnnCGTAAGTTTCTCCGGTCTAGCGnnnGGCnn SEQ ID NO: 8
>ise2c.pk001.f20    vacuolar query
GCACGAGGCTCACAGGCTCTGTCCAAGTACTCCAACTCTGACGTCATCAT
CTACGTCGGATGCGGTGAACGTGGTAACGAGATGTCTGAGGTACTGCGTG
ACTTCCCCGAGCTGACGGTGGAGATCGAGGGCATGACCGAGTCCATCATG
AAGCGTACCGCGCTCGTCGCCAACACCTCCAACATGCCTGTAGCCGCCCG
AGAGGCTTCCATCTACACCGGTATCACCCTCTCCGAGTACTTCCGTGACA
TGGGTTACAACGTGTCCATGATGGCTGACTCCACCTCGTTGGGCCGAG
GCTCTTCGTGAGATCTCnnnnCGTCTGGCTGAGATGCCTGCCGACTCGGG
TTACCCCGCCTACCTGGGAGCCCGTCTGGCCTCGTTCTACGAGCGTGCCG
GACGTGTGAAGTGCTTGGGTAACCCCGACAGGGAGGGCTCCGTGTCCATC
GTGGGCGCCGTGTCGCCGCCCGGAGGTGACTTCTCCGACCCCGTGACGGC
CGCCACGCTGGGTATCGTCAGGTGTTCTGGGGGTTGGACAAGAAGCTCG
CGCAGCGCAAGCACTTCCCCGCCCATCAACTGGCTCATCTCTACAGCAAG
TACATGCGAGCGCTGGACGACTTCTATGAAGAACTACCCCGAGTTCGT
GCCCCTCnnnnnnCAAGGGTCAAGGAGATCCTGCAGnnn SEQ ID NO: 9
>ise2c.pk010.h3    cadherin query
GCACGAGGTATCTAAAACAGTGCGTCGTAATATATTCAAGATGTCTCGTC
TTAGGTTTTGTTTTTTATTAGCAGTACTATGCAGTTGTTTGCAGAATGGT
TACGGTTTTACAACAGAAAAGCCAGTTACCCAGCATGTAGATCCTAAACC
AGAAGTTCCTGAAACGTTGCCTGAAACAACACGAGTGCCTGCGCCGAGCT
CGTCGACGGCAGCGCCGACCACACCAGCTCCGACACCGGCACCAACGCCA
GCACCCACACCAGCTCCTACACCAGCTCCTACTCCAGCTCCTACCCCTGC
GCCTACTCTGCGCCTACTCCTGCGCCTACTCCTGCGCCTACCCCGCAC
CTACACCAGCGCCCCATCCTGCTCCCACCCCAGCTCCTCCCGCCCCC
GACCAAGGCACATGGTCCTTCACTGATGAAAAGGCCAATCAGACATGCAT
TGTGGCCCAATTCGCAGCCCAACTGAATGTCACATACACCAAGTTAGTGG
AGAATGCAACGTCTCTATCGTACGTGAGGCTCAACGTGCCCGCGAACGCG
TCGGTCCTCAACGGCAGCTGTTCGGACCCCGACCAATGGATCCAGATCAC
CTGAAGACCAACGACGACAGCAGAGACGAACAACACCATGACCCTCGTGT
ACAACAAGAATGCCACCACCAAGnnCTACGGCCTG SEQ ID NO: 10
>ise2c.pk011.a10    cuticle protein
GCACGAGGGCGGTTTGAAGTGATCTAGTTCGTCAGAAAAAACACAGACCA
CGTTCACAATGAAATCGATGGTGGTGTTATTCGCTGTGTGCGCCGTGGCG
TGCCGCTCCCTGGTGCCGCTGGCGCAGCCTCCTCATCACCCCGCCGTCGT
GCTGGAACCGCACGGCCGCGCTCGACACCGCGAGGTGATCAACGCCC
GCGCCTCCACCTGCAGGCTAAGGCCCTGGATGGACACTACGCTCCCCTC
GCGCACGCTGCCGTCGTGCCTGTTGCCCACTCCGTGGTAGCCGCCCCCGC
TGTGGTCGCCGTCGCCGCCCGCCGTGTCCCACCAGTCCGTGTGGATGTGC
GCACAGCCCCGCCATCGTGAGCCACGCCGTCGCTGTCCCGTAGTAGCC
CACGGTGTCTACTCCGCTCCCCTGCTGGCCCACTCCGCTCTCGGCTACGC
CGGTCACGGACACTACCTGAAGAAGCGCTCCCTGGGACACCTCGCCTACG
CCGCTCCCGTCGTCGCCCACGTAGCTCCCTCCGCGGGTGTCGCACCAGTCC
CGCGTGGNCnTCGTCTCCAGCCnnnCTGTCGTGTCTCAnnnnnnTnnnTnC
CGTnnTGTCCCn SEQ ID NO: 11
>ise2c.pk011.h12    cuticle protein
GCACGAGGGACGTTGAACGAAAGAAAATGCTACGCGTTACGATTTTAGC
CGCAGTGGTGGTGTTCGCCTCAGGCGCGCCCCCAGAACAACTTCATCTTCA
AGAATGACATCACTCCTGAGGAAGCCCAGCAGTACCTCAAACAACTGCCG
TTCACCTCACCCCAGCTCTCTGGACGCACCGCTGTACTGCCTCTGGTTCG
CTACGACGACCCCAGGTTTCGTTCAGCTGAAGCTGGCCCAACCCTTGGAC
ACTACTGGAAGAATGGACAGGAGATCAGAACACAGAGGACTACTTAGAA
GAGGTCTACAACGCGGCTCAATACCACGGCCAGGACGGTCTTGGCAACTA
CGCCTACGGTTATGACACCCTGAATCTTCAAGGTTGAGAACCGTGAAG
GTTCCGGAGTCGTCCAAGGATCCTATGTGTACCAGGTTCCCGGAATGAAG
GATCTCGTCnnGGTCCGTTACTGGGCTGACAGCCnnnnnTTCCACCAGnA
nGACAATCTTCCCAAGGTTGAACTGAnnnCCGCTnnnnnnnnnCCCGCTCT SEQ ID NO: 12
>ise2c.pk001.d22    translation initiation factor
GCACGAGGTATCACTCCTGACCGTATCTAAAACTCGGCACACAACACAAT
GGCTGACATCGAAGATACACATTTCGAGACCGGGGACTCCGGTGCCTCCG
CCACCTTCCCTATGCAATGCTCGGCCCTGCGCAAGAACGGTTTCGTCATG TABLE 1-continued Target Polynucleotides from Spodoptera frugiperda.

CTTAAGGGTCGCCCCTGCAAAATCGTCGAGATGTCCACTTCCAAAACCGG
AAAGCACGGCCACGCTAAAGTTCACTTGGTTGGAATCGATATTTTTAACG
GCAAGAAATACGAAGATATCTGCCCTTCCACCCACnnnCATGGACGTGCC
CCACGTGAAGCGTGAGGACTACCAGCTCACCGATATCTCTGACGACGGCT
ACCTTACCCTCATGGCTGACAACGGCGATCTCCGCGAGGACCTCAAGATC
CCAGACGGTGACCTCGGCACCCAGTTGCGTTCTGACTTCGATAGCGGCAA
AGAGCTGTTGTGCACTGTGCTGAAGTCTTGCGGTGAGGAGTGTGTAATCG
CAGTCAAGGCAAACACAGCTCTCGACAAATAAACCAACTCAGCATTTATA
GGGATATACATACATATAATTTTTTACAATCAACAGCTCTTACATAAAT
GTAAAACATAATACTATGTATAATTTAACATnnnnnATTATGGTGTGACG
CGGTGCTGGCTTGTCGCCGTCCACTCCACCCCCGAAG SEQ ID NO: 13
>ise2c.pk001.d9  translation initiation factor
GCACGAGGCGCGATTGTAACATGTCGTATTCACCAGAAGAAGATCAGAA
GATTGGCCGGAAGATTCCAAAAATGGCCCGTCTAAGGATCAAGGCAACTA
TGATGGGCCTCCAGGAATGGAACCCCAAGGGGCACTTGATACAAACTGGC
ACCAGGTCGTGGAAAGCTTTGACGACATGAATCTGAAGGAAGAATTGTTG
AGAGGAATTTATGCTTACGGTTTTGAAAAGCCGTCTGCTATCCAACAACG
CGCTATTATGCCTTGCATTCAAGGCCGTGATGTCATAGCTCAAGCCCAGT
CTGGTACTGGGAAGACTGCTACCTTCTCTATTTCAATTCTTCAGCAAATC
GATACCAGTATTCGTGAATGCCAAGCACTGATTTTGGCCCCTACTAGAGA
GCTGGCTCAGCAGATCCAAAAGGTGGTGATTGCTCTTGGGGATCACTTGA
ATGCTAAATGCCATGCTTGCATCGGCGGCACTAATnnnGCGCGAAGATGT
TCGTCAGCTnnnnn SEQ ID NO: 14
>ise2c.pk001.i23  translation initiation factor
GCACGAGGGTCGTATTCACCAGAAAGAAGATCAGAAGATTGGCCGGAAGA
TTCCAAAAATGGCCCGTCTAAGGATCAAGGCAACTATGATGGGCCTCCAG
GAATGGAACCCCAAGGGGCACTTGATACAAACTGGCACCAGGTCGTGGAA
AGCTTCGACGACATGAATCTGAAGGAAGAATTGTTGAGAGGAATTTATGC
TTACGGTTTTGAAAAGCCGTCTGCTATCCAACAACGCGCTATTATGCCTT
GCATTCAAGGCCGTGATGTCATAGCTCAAGCCCAGTCTGGTACTGGGAAG
ACTGCTACCTTCTCTATTTCAATTCTTCAGCAAATCGATACCAGTATTCG
TGAATGCCAAGCACTGATTTTGGCCCCTACTAGAGAGCTGGCTCAGCAGA
TCCAAAAGGTGGTGATTGCTCTTGGGGATCACTTGAATGCTAAATGCCAT
GCTTGCATCGGCGGCACTAATGTGCGCGAAGATGTTCGTCAGCTGGAGAG
TGGTGTGCATGTGGTGGTGGGTACACCTGGTCGCGTGTACGACATGAAA
CTCGTCGTGCTCTCCGTGCTAACACTATCAAGCTGTTTGTACTTGATGAA
GCTGATGAAATGCTGTCAAGAGGATTTAAAGATCnn SEQ ID NO: 15
>ise2c.pk001.l24  translation initiation factor
GCACGAGGGCCATCCTGTCACACATCTACCACCACGCCCTGCACGATAAC
TGGTTCCAAGCTCGAGACTTGCTCTTGATGTCACACTTGCAAGAGACTGT
TCAACATTCAGACCCGAGCACTCAGATTTTGTACAATCGTACTATGGCCA
ATCTAGGTTTGTGCGCTTTTCGAAGGGCAATGTTAAAGAAGCCCATGGC
TGCCTAGCTGAACTGATGACTGGCAAACCCAAGGAACTGTTAGCTCA
AGGTCTGCTACCTCAGCGTCAACACGAGCGTTCAAAGGAACAGGAAAGA
TAGAGAAGCAACGCCAAATGCCGTTCCACATGCACATCAACTTGGAACTG
CTTGAATGTGTGTATTTAGTGTCTGCCATGCTGATTGAAATTCCATACAT
GGCCGCCCACGAATTCGATGCTCGCCGGCGCATGATTAGTAAGACTTTCT
ATCAGAATTTGCGCGCAAGTGAGCGTCAGGCTTTGGTAGGCCCGCCCGAA
TCCATGCGTGAGCATGCTGTGGCTGCCGCCAGGGCGATGCGCCGCGAGA
CTGGCGTGCTTGCCTCAATTTTATTGTnnnTGnnnAATGAAT SEQ ID NO: 16
>ise2c.pk005.b9  translation initiation factor
GCACGAGGCTGATAGCCACCTGCCAAATTATCTTGAAATATAACCATTCA
CTAAAATATTTAACGTAATTTAGTGGTTAATTCTAAACTTAATCATGGAC
GACGACATGGTATTTGATCCATCTTTAAAGAAAAGAAGAAGAAGAAGAC
CGGTTTCGACTTAGATGCCGCTCTCGCAGGCGAACAAGGTGAGAGCACGA
GCGTGGAGGCGCCCGCTGGGTCGGGTGACGTCGACTTGCCGAGGATGAT
AACCTCGATTTGGATAATTTTGGAAAGAAAAAGAAGAAGAAGAGAAGGGG
AGTCTTCAACATGGAAGAACTTGAAAGTACGTTACCGGAAACACCTCCGG
CCGAAGAGCCGGAACAGCAGGAGGACGAAGTTATTGACGATTTAGATCTA
GATATTGACTTCTCTAAAACGAAAAAGAAGAAGAAGAAGAAAAACATnnn
AnGAGCTCGTCTTGAAGATGACACCAAGGGAGAAGATCAAGAGAATGTC
GAGGATGTTAGTGGTGATTATGGAGCGGCACAGACCGTGACTACACGTA
CGACGAGCTACTAGAGCGAGTGTTCGACATCATGCGAGAAAAGAnnnnnA
GCATGGTTT SEQ ID NO: 17
>ise2c.pk002.m10  SAR1
GCACGAGGCAGATTCATATTTCCATCGCTTATTCGTTGCTGAGAAAAATC
GTCGGTTTTAGCACGTAACATATTGCTAATAAGTGTGAAATATTGTGAT
AAACTTCCTTTTAGCATTAGTTAATCTAGTTCAATTTTAAATAATTCAAA ATGTTTATCTTGGATTGGTTCACTGGTGTTCTCGGATTCCTTGGTCTGTG
GAAGAAATCAGGCAAGCTACTGTTCCTGGGACTGGACAATGCTGGCAAGA
CCACACTCCTGCACATGCTGAAGGATGACAGATTGGCGCAGCATGTACCC
ACATTGCATCCCACGTCGGAGGAACTGTCAATAGGCAGTATGCGTTTCAC
GACGTTCGACTTGGGCGGGCATCAGCAGGCGCGGCGTGTGGCGCGACT
ACTTCCCGGCGGTGGACGCCATCGTGTTCCTGGTGGACGGTGCGACCGC
CCGCGACTGCCCGAGTCCAAGGCCGAGCTGGACTCGCTGCTCACTGACGA
GACGCTCAGCnnACTGCCCCGTGCTCATCCTCCGGCAACAAGATCGACAAG
CCCGGCGCAGCTAGTGAGGACGAGCTCCGTCAGTTCTTCAACCTGTACCA
ACAGACCACTGGAAnAnGnCAAAGTATCnAGnTCAnnnnT SEQ ID NO: 18
>ise2c.pk001.c14  Elongation factor
GCACGAGGGTCTATCTCGGATATTACACGTGGATTGTAATCCGTGACTAA
CCAAAAATGGGCAAGGAAAAGnnnCACATTAACATTGTCGTCATTGGACA
CGTCGACTCCGGCAAGTCCACCACCACCGGTCACTTGATCTACAAATGCG
GTGGTATCGACAAACGTACCATCGAGAAGTTCGAGAAGGnnnCCCAGGAA
ATGGGGTAAGGGTTCCTTCAAATACGCCTGGGTATTGGACAAACTGAAGG
CTGAGCGTGAACGTGGTATCACCATCGATATTGCTCTGTGGAAGTTCGAA
ACCGCTAAATACTATGTCACCATCATTGACGCTCCCGGACACAGAGATTT
CATCAAGAACATGATCACTGGAACTTCCCAGGCTGATTGCGCCGTACTCA
TTGTCGCCGCTGGTACCGGTGAGTTCGAGGCTGGTATCTCGAAGAACGGA
CAGACCCGTGAGCACGCTCTGCTCGCTTTCACACTCGGTGTCAAGCAGCT
GATTGTGGGCGTCAACAAAATGGACTCCACTGAGCCCCCATACAGCGAAT
CCCGTTTCGAGGAAATCnnnnnnn SEQ ID NO: 19
>ise2c.pk001.d16  Elongation factor
GCACGAGGCGGATATTACACGTGGATTGTAATCCGTGACTAACCAAAAAT
GGGCAAGGAAAAGnTTCACATTAACATTGTCGTCATTGGACACGTCGACT
CCGGCAAGTCCACCACCACCGGTCACTTGATCTACAAATGCGGTGGTATC
GAnnnACGTACCATnnnnn SEQ ID NO: 20
>ise2c.pk001.j9  myosin
GCACGAGGCTCAGTCCCGTCACCGTCGCCAGTAGGGGGCGCCACAAGAA
CAGAAAGAGAATTATTTCAAACTCCAATTATAACCTACTAGATAACTCCA
AAAGTTCTGTCAGTTCTAACTTTAATTTAACGGGGACGTCAGAGTTTATG
GATAGGACCGATAAGATAAATCGGACGCGACTGAGCTACAAGCAATGCA
GAACTTTATCATGGAGAAGATTTACGAAATGGAACCTAATGAGAAGAAGA
AGCAATCTGAGGTCGACAGGGTATTCAAACACGCATTATTAGAATTCAAA
GACAATTTAGTAGCGACGTACAGCATAGTGGAGACGCGGGGCTCTGCGCT
GAAGTACAAGGATCTGATCGGCAACTTCCTGCACGTCATGGAGACGGTTT
GTGCCAGGGAGGGGTCCACGCTCTCCATCACCATGGGGGTCAACGCCTTT
AGGGGTTTCATGGACGAGTTTTATGAGCGCAACATGACACTGATAAAGCTAG
GACGnnnnGnnnAAGGATAAAAGAnnnnnnTGGACGATCCAATACAATA
CAAAGGCCATACGTTCATACTGTCCATGATCAACATACCAAnnnnAGTGT
GAGATCTGCAAGACATTTCTTCATGTGGCCCATAGAGCGGTCACTCATATG
CCAGACGTGTAAACTTGCCTCGCATAAnnnTnnnACACTA SEQ ID NO: 21
>ise2c.pk001.b14  potassium channel amino acid
                  transporter
TGACTCCACAGTGGGACAAACTCATAGAGCTTGATGTGTGGTACGCTGCT
GTGACCCAAGTGTTCTTCTCTGTCTGTGTGCACCGGTGCCATCATTAT
GTTCTCGTCCTACATGGATTCAGACAAAATGTTTACAGAGACGCGATGA
TTGGTCACTACTTTGGACACCTTCACCAGTTGTTATCCGGTTTCACGATC
TTCGGTATCCTGGGTAACTTGGCGTACGAGTTGGACAAAGATGTGGATGA
CGTCACTGGTTCTGCAGGAACTGGACTTGCCTTCATTTCATACCCTGACG
CGATCTCCAAAACTTTCCAGCCACAGTTGTTCGCAGTGCTGTTCTTCTTG
ATGATGACGGTTACTAGGTATCGGCAGTCAGCGTTGCTTTACTTTTCCAA
CAACACCTGATGATGGACGCGTTCCCTCGCATCAAGACCATCTACATGAT
CCGCCTTCTGCTGCACTATTGGATTTGCCATCGGTGTCATTTACGTCACA
CCTGGTGGCCAATATATTCTCGAGCTGGTGGATTACTTCGGTGGAACCTT
CCTGATTCTCTTCTGTGCTATCGCTGAAATTATTGGTGTATTTGTGGATTT
ACGGCTTGGAGnnnATGCCTGGATATTGAGTACATGTTGGGAGTTAAAC
TTCTTCTACTGGnnnTnnnTGTTGGGGCGTTATTATGCCTGCCATGATGAT
nACCGnnnnnn SEQ ID NO: 22
>ise2c.pk003.f2  potassium inwardly
                 rectifier . . .
GCACGAGGGTAAACAGAATTTAACATACATTAATTTGTTCTAGAGTTAA
ATGTATTAATTCCGACTTAAAAACAGTGCTTGTGATAAGTGAACACAAAT
TATTGAGCAATGACTGACTTTATAAAACAATATTTCAAGGAACAATATGA
AATAAATGAAAAATGCTTTCGAAAATTGACGCGGATCTGCGAACCTGCG
GAGCACACTTAGTAGCAGTGAAGTTAATGGTGACTGCCCTCGAGTTGAAA
ATGACTTCGATGAAGACAATGTATCAGGATCTAATGGAACTCAGAGAAAT TABLE 1-continued Target Polynucleotides from *Spodoptera frugiperda*.

AATCGTTCTTTTAAATCCACACTTGAAGAAACCGAGATAATAATACAATA
CAGTAAGGTTAACGAATACTATCTTTTAATTTCCTTAAATTATGTTCATA
AAAATGATTAAGTTGTTTAGCTGAACACAGTGGTGTACTGACAGGATAGG
TTTCATTAAACTTTGCATAATCGATCAGAAAACCGTGCTTTTCTTTTTTG
TACTCGACCATTTCAATAAAGCGATGACCCCATAGGATTnnnnTGGGTGG
TGTAGCTCGACTTCGCTTGGACAGGCTGACCAGTTGATTCTATAGTGCCT
TCAAACACTACGAnnATTTCCATAT SEQ ID NO: 23
>ise2c.pk005.120  amino acid transporter
GCACGAGGATTTTCTTAAAACGGTACTGCAGCAAAAAGACGGCATTGAAG
GTGGACTCGGTCTGCCTATCTGGTACCTGGTGGTTTGTCTGTTCGGGTCA
TGGTTTATCATCTTCGTGATTGTGTCCCGAGGTGTAAAGAGTTCCGGTAA
AGCTGCATACTTCTTGGCTCTCTTCCCCTACGTTGTGATGCTCATTTTGC
TTATAACGACCTCTATTCTGCCCGGAGCCGGCACCGGCATTCTTTTCTTC
CTGACTCCACAGTGGGACAAACTCATAGAGCTTGATGTGTGGTACGCTGC
CGTGACCCAAGTGTTCTTCTCTCTGTCTGTGTGCACCGGTGCCATCATTA
TGTTCTCGTCCTACAATGGATTCAGACAAAATGTTTACAGAGACGCGATG
ATTGTCACTACTTTGGACACCTTCACCAGTTTGTTATCCGGTTTCACGAT
CTTnnnTATCCTnnnnTAACTTG SEQ ID NO: 24
>ise2c.pk001.d1  tubulin
GCACGAGGCCGGTCTTCAGGGCTTCCTTATCTTCCACTCCTTCGGTGGAG
GTACTGGATCTGGTTTCACTTCCTCCTGATGGAGCGACTCTCCGTGGAC
TACGGCAAGAAGTCCAAGCTGGAGTTCGCCATCTACCCGGCGCCTCAGGT
GTCCACCGCTGTCGTGGAGCCCTACAACTCCATCTCCACCACCCACACCA
CCCTTGAGCACTCCGACTGCGCCTTCATGGTCGACAACGAGGCCATCTAC
GACATCTGCCGCCGCAACCTCGACATCGAGCGCCCACGTACACCAACCT
GAACCGTCTCATCGGGCAGATCGTGTCCTCCATCACGGCCTCCCTGCGCT
TCGACGGCGCCCTCAACGTCGATCTTACCGAGTTCCAGACCAACTTGGTG
CCCTACCCCGTATCCACTTCCCTCTGGTCACATACGCCCCGGTCATCTC
TGCCGAGAAGGCGTACCACGAGCAGCTGTCGGTGGCTGAAATCACCAACG
CATGCTTCGAGCCCGCCAACCAGATGGTCAAGTGCGACCCTCGTCACGGC
AAGTACATGGCTnnnnTGCATGTTGTACCGTGGTGACGTCGTCCCCAAGG
ACGTGAACGCCGCCATCGCCACCATCAAGACCAAGCGTACCATCCAGnnn
CGTCnnTTGGTGTCCnnCnnnGTnnn SEQ ID NO: 25
>ise2c.pk001.k6  tubulin
GCACGAGGATTCGTTTGGCAAGCCTCTTAACCGGTCGCGCTGAACGACGA
CTGATATTTAATTAATTTATATTCTACGTTAAGTTCAACAAAACTCAATT
CAAAATGCGTGAGTGCATCTCAGTACACGTTGGACAAGCCGGAGTCCAGA
TCGGTAATGCCTGCTGGGAATTATATTGCCTTGAGCATGGAATCCAGCCT
GACGGCCAGATGCCCACAGACAAGACCGTGGGCGGTGGTGATGACTCCTT
CAACACCTTCTTCAGCGAGACCGGTGCCGGCAAGCACGTCCCCAGGGCTG
TGTTTGTTGACTTGGAACCCACAGTAGTTGATGAGGTCCGCACTGGCACA
TACGACAGTTGTTTCATCCAGAACAACTTATCACTGGTAAGGAAGATGCC
GGCCAACAACTACGCCCGTGGTCACTACACCATCGGCAAGGAAATCGTAG
ACCTAGTCCTCGACCGCATCCGTAAGCTCGCCGACCAGTGCACCGGTCTC
CAGGGCTTCCTTATCTTCCACnnnnnTCGGTGnnnnnACTGGGATCTGGT
TTCACTTCCCTCCTGATGGAGCGACTCTCCGTGCACTACGGCAAGAAGTn
nAAGCTGGAGTTCGCCATCTnnCnGCnnCTCnnnnnTCnnnnnnCTGTC SEQ ID NO: 26
>ise2c.pk001.l2  tubulin
TTCGGCACGAGGGGCAAGCCTCTTAACCGGTCGCGCTGAACGACGACTGA
TATTTAATTAATTTATATTCTACGTTAAGTTCAACAAAACTCAATTCAAA
ATGCGTGAGTGCATCTCAGTACACGTTGGACAAGCCGGAGTCCAGATCGG
TAATGCTGCTGGGAATTATATTGCCTTGAGCATGGAATCCAGCCTGATG
GCCAGATGCCCACAGACAAGACCGTGGGCGGTGGTGATGACTCCTTCAAC
ACCTTCTTCAGCGAGACCGGTGCCGGCAAGCACGTCCCCAGGGCTGTGTT
TGTTGACTTGGAACCCACAGTAGTTGATGAGGTCCGCACTGGCACATACA
GACAGTTGTTTCATCCAGAACAACTTATCACTGGTAAGGAAGATGCGGCC
AACAACTACGCCCGTGGTCACTACACCATCGGCAAGGAAATCGTAGACCT
AGTCCTCGACCGCATCCGTAAGCTCGCCGACCAGTGCACCGGTCTCCAGG
GCTTCCTTATCTTCCACTCCnnnCnGTGGAGnTnnnTGGATCTGGTTTCA
CTTCCCTCCTGATGGAGCGACTCTCCGTGGACTACGGCAAGAAGTnnAAG
CTGGAGTTCGCCATCTAnnnn SEQ ID NO: 27
>ise2c.pk002.b4  ubiquitin
GCACGAGGACAAAGAGTTACGACCGTCACCATACTGAAGGAGATACCA
TTCGTCGTGCCATTCTCAACACGCGTCCTTATATTCCAAGGACTTTTAGC
GAGAGAAGAAGCACGACCACTGGTACGAAATGACGAACTTCAACGAGGGG
CCTCGATCAACATCAGTGTTCGAAGGACGCATTTATATGAAGATGCATTT
GATAAACTTAGTCCGGATAATGAACCTGATTTGAAGTTGAAACTTCGCT
GCAACTGATCAACCAGGCCGGTGCGGAGGAAGCTGGTGTCGACGGCGGTG GACTATTCCGAGAGTTTCTTTCTGAGCTCTTAAAATCTGCATTTGATCCG
AACAGGGGTCTGTTCCGGCTGACAATAGACAACATGTTGTATCGCAACCC
CGCCGTACATCTACTGTACGATGACTTCCCCATGCACTACTACTTCGTCG
GCAGGATGCTGGGAAAGGCGATGTACGAGAACCTGTTGGTGGAGCTGCCG
CTGGCGGAGTTCTTCCTGGGCAAGCTGTGCGGCTGCGGGGAGGCCGACGT
GCACGCGCTGGCCTCGCTCGACCCCGCGCTGCACCGCGGGTTGTTACTAC
TC SEQ ID NO: 28
>ise2c.pk001.j16  small nuclear ribonucleoprotein
GCACGAGGGCCGGCCGCCGTGTTCGTGCCGTCCCGCGGGGCGCGCGCCT
ACTGGCCGCCGACCTGCTGGCGCTGGCCGCGGCGCACGCGCAGCCCGCCG
CCTTCCTGCGCGCGCGCCCCGACGTGCTGCAGCCCTTCCTCAAGAGGATC
AACGACAAGATGCTGAAGGAGACGGTGGCTGCGGGCGTGGCGTACCTGCA
CGAGGGCGTGGACCCGGCGGAnnGGCGCCTGGTGCAACAACTGCTGGAGT
CGGGGCGCGCTGGCGCTCTGCGTCGTGGCCGCCGAGCTGGCCTGGGGACT SEQ ID NO: 29
>ise2c.pk006.h23  small nuclear ribonucleoprotein
GCACGAGGCGAAGATAAAGGTCGCGTGTGGACCTTAGGTTTAAGTTTATT
ATTAAATAATTTAGCCTAAACATAAGTCATGGCCAATAACGACAACTTTG
CACAAGATGTTACTGATAATCAACTAAATGGAAATGCCGAAAATGGTGGT
GGCGATACGCAAGAACATAATAGTGCCGAAGCCCCTGGGCGTGATGATGA
CAGAAAACTTTTTGTCGGAGGCCTGAGCTGGGAAACCACAGACAAGGAGT
TACGTGACCACTTCAGTGCATATGGTGAGATTGAGAGCATCAATGTCAAG
ACTGATCCAAACACTGGCAGATCAAGAGGATTTGCCTTTATTGTGTTCAA
GGCACCAGATTCAATAGACAAAGTGATGGCTGCTGGAGAGCACACTATTA
ACAACAAAAAAGTTGATCCGAAAAAAGCAAAGGTAGACATGGAAAGATC
TTTGTTGGTGGTCTTAGCAGTGAAATATCAGATGATGAGATCAAAAACTT
CTTCAGTAATTTTGGAACAATAATTGAAGTCGAGATGCCCTTTGACAAAA
CCAAGAATCAGnnnAAGGGGATTCTGCTTTATAACATTCGAGTCTGAACAG
GTGGTCAATGAGCTGCTGAnnnCn SEQ ID NO: 30
>ise2c.pk006.m8
GCACGAGGCGCGTGTGGACCTTAGGTTTAAGTTTATTATTAAATAATTTA
GCCTAAACATAAGTCATGGCCAATAACGACAACTTTGCACAAGATGTTAC
TGATAATCAACTAAATGGAAATGCCGAAAATGGTGGTGGCGATACGCAAG
AACATAATAGTGCCGAAGCCCCTGGGCGTGATGATGACAGAAAACTTTTT
GTCGGAGGCCTGAGCTGGGAAACCACAGACAAGGAGTTACGTGACCACTT
CAGTGCATATGGTGAGATTGAGAGCATCAATGTCAAGACTGATCCAAACA
CTGGCAGATCAAGAGGATTTGCCTTTATTGTTCAAGGCACCAGATTCA
ATAGACAAAGTGATGGCTGCTGGAGAGCACACTATTAACAACAAAAAAGT
TGATCCGAAAAAAGCAAAGGCTAGACATGGAAAGATCTTTGTTGGTGGTC
TTAGCAGTGAAATATCAGATGATGAGATCAAAAACTTCTTCAGTAATTTT
GGAACAATAATTGAAGTCGAGATGCCCTTTGACAAAATAAGAATCAGAG
GAAGGGATTCTGCTTTATAACATTCGAGTCTGAACAGGTGGTCAATGAGC
TGCTGAnGACTCCTAAGCAGnnnATTGGTGGCAnnnnnnnCGAC SEQ ID NO: 31
>ise2c.pk001.a23
GCACGAGGATGAAGTTGGGTCTGACACTCTTGGCTCTGGCGGCGGTGGCC
ACCGCTAAAAACATCAACGTCGAGGATGCCATCGACCTAGAGGACATCAC
CGCCTACGGATACTTGGCTAAGATCGGTAAACCTCTTGCCGACGAAATCC
GCAAAGCTGAGGAGGCAGAGAGCGCATCCAGAATTGTTGGTGGTCAGGCC
TCCAGCTCGGACAGTTCCCCTACCAGGCTGGTCTTCTCGCTGACTTCTC
CGCTGGCCAAGGTGTGTGGTGGTTCTTGGTGCGTGCCAACCGTGTTC
TTACTGCTGCTCACTGCTGGTTCGATGGCCAGAACAGGCCTGGAGATTC
ACCGTTGTTCTTGGCTCCATCCGTTTGTTCTCCGGTGGTACCAGAGTTCA
AACCTCCAACGTTGTTATGCATGGAAGCTGGAACCCCAGTAACATCCGTA
ATGACGTCGCCATGATCAGGCTGAACTCCAACGTTGGTCTTTCAAACACC
ATTGCACTCATCGTCTGCCCAGCGGTACCAGCTCAACGAAAACTTCGC
CGGTGAAAACGCCGTCGCnnnCTGGATTCG SEQ ID NO: 32
>ise2c.pk001.a7
GCACGAGGATCAAAATGAAACTGTTCCTCGCAGTCGTGTGCTTGGCCGTT
GCCGCATCCGCGGTGGAGATTGGAGTTCCGTCTCAGGAAACCCAGTCTT
TGGCTACCATCAAACTTCGGTATTGCCGAAGCTGCCAGGATCAAGAAGG
CTGAGGAAGAACCAGCCCTAGCGCCCAGAGGATCTCGGAGGATCTGTC
ACTGACATTTCCAACGTCCCTTACCAGGCTGGTCTCGTGATCCAAGTTTT
GGTCATCTTCCAATCCGTGTGCGGTGGTTCCATCATCTCCCACAACCGCA
TCGTGACCGCTGCTCACTGCAACGTTGGACGGTTCTATCCACCGCTAACT
TTCACCGTCGTACTTGGCTCCAACTTCCTCTTCTCCGGCGGTAACCGCAT
CACCACCAGAGATGTTGTCATGCACCCCAACTGGACCCAACACCGCTG
CCAACGACATTGCTGTCCTCCGCATTAGCTCCGTTACTTTCACCAACGTG
ATCCAGCCCATCGCTCTGCCCAGCGGCAACGAGCTCAACAACGACTTCGT
CAACTGGAACGCTATCGCTTCCGGATACGGTCTTACCGCTGATGGTGCTA TABLE 1-continued Target Polynucleotides from Spodoptera frugiperda.

ACATCGGTACTACCCAACGTGTCAGCTCCGTGGTACTCCCCGTGATCnnn
nnnCGCCAGnnCGCTACCGTnnnnnn

SEQ ID NO: 33
>ise2c.pk004.c4
GCACGAGGAATCTTAGTTACATTGGAGTGACTTTTATTTATCAATAACAT
TTTTATTTGAAGACTCAGTACGTATTATCGCGTAGTTCAACAGAGTTGCT
AGTGTAGTTTTCTGAAAGTTGCCATCTTGCTTTTGCAACTTTTAAATATA
AAAGTCTTATTAGATCGTTTTTACTACCGATAAATTTACTAAAAATATAA
AAGTGCAATTTACAATTACTCTGTTAGTGTCAGTTTGTGTGAATTTGTCG
TAGTTATAAAAGGACACTGTATTGATTTTGTCAATCAGTTTGACGCATGC
GCTCATTGGGTGCCGTAAAAAAGGGTTGGCCAACATTCCGAACAGTGTCG
TTCCGGTCGCCGTTGTCGTGGTGTCGGTGAAGTTAGTGGTGGAATTTTTA
CGTGTATAACATCAAAAAATGGCGTCTGGTGTGACAGTTTCGGACGCGTG
CAAAACGACGTACGAGGAGATTAAGAAAGACAAGAAGCACCGCTACGTGG
TGTTCTACATCAGGGATGAGAAACAAATTGACGTAGAGACCGTCGGCGAA
CGTAACGCGGAATACGATCAGTTCCTTGAGGATCTGCAGnnnGGTGGCAC
CGGnnAGTGCn SEQ ID NO: 34
>ise2c.pk004.14
GCACGAGGCTGATATCTAATCTTAGTTACATTGGATTGACTTTTATTTAT
CAATAACATTTTTATTTGAAGACTCAGTACGTATTATCGCGTAGTTCAAC
GGAGTTGCTAGTGTAGTTTTCTGAAAGTTGCCATCTTGCTTTTGCAACTT
TTAAATATAAAAGTCTTATTAGATCGTTTTTACTACCGATAAATTTATCA
AAAATATAAAAGTGCAATTTACAATTACTCTGTTAGTGTCAGTTTGTGTG
AATTTGTCTTAGTTATAAAAGGACACTGTATTGATTTTGTCAATCAGTTT
GACGCATGCGCTCATTGGGTGCCGTAAAAAAGGGTTGGCCAACATTCCGA
ACAGTGTCGTTCCGGTCGCCGTTGTCGTGGTGTCGGTGAAGTTAGTGGTG
GAATTTTTACGTGTATAACATCAAAAAATGGCGTCTGGTGTGACAGTTTC
GGACGCGTGCAAAACGACGTACGAGGAGATTAAGAAAGACAAGAAGnnnC
CGCTACGTGGTGTTCTACATCAGGGATGAGAAACAAATTGACGTAGAGAC
CGTCGGCGAACGTAACGCGGAATACGATCAGTTCCTTGAGGATCTGCAGA
AGGGTGGCACCGGAGAGTGCAGATATGGCCTCTTCGACTTCGAGTACACG
CACCAGTGCCAAGGCACGTCGnnn SEQ ID NO: 35
>ise2c.pk004.n19
GCACGAGGCCTCGTGCCGCGCGAATAGACAGTTTTGTGTGCACAATGTTG
ATCCTTTGGCTAAATATCATCGCAATAATTTGTGTCATACCCTACGCAAA
TGGAGAAGGAAGGGTTGCAATAGCGCATTTACAATCGCTAAAGTCAGTGA
CTGGTCAAATTCAATTTACGGAGACGGCAAAAGGGCTTCATGTCGAAGGA
GTTATATTTGGTTTACCACCCGGTGCCTACGGGTTTCACGTTCACGAATT
AGGAGATGTTGCACCTGGTTGCGACCAGGCGGGCCGGCACTTCAACCCTG
AGGGATCCACCCACGGTGGCAGGAACTCCACCGTACGCCATGTCGGTGAC
CTCGGAAATGTAGTGTTCGTTAGCGAGCGAGCCGCTTATGCTACAGTAGA
CTTTGTAGATAGTCTATTGGCACTTCAAGGACGTAATAGTATATTGGGGC
GCTCTTTGGTCTTGCATGAACAACGGATGACCTAGGTTTGGAGGAAAC
GCGACGTCTTTGACTACAGGTAACTCGGGGCCCCGGGATAGCATGTGGTGC
TATTGGAATCAAATCACCTTATGACCCTTGGAATGCTGCTAGCTCTATGT
CTCCGTCGATGCTACTATTTATCACATCTTTAACTTTATTTACTTTAnnn
TnnnAAnTnnnnGTATnAGTATTTAATTTnnnnn SEQ ID NO: 36
>ise2c.pk005.f21
GCACGAGGCTTCCACATACGCGAATAGACAGTTTTGTGTGCACAATGTTG
GTCCTTTGGCTAAATATCATCGCAATAATTTGTGTCATACCCTACGCAAA
TGGAGAAGGAAGGGTTGCAATAGCGCATTTACAATCGCTAAAGTCAGTGA
CTGGTCAAATTCAATTTACGGAGACGGCAAAAGGGCTTCATGTCGAAGGA
GTTATATTTGGTTTACCACCCGGTGCCTACGGGTTTCATGTTCACGAATT
AGGAGATGTTGCACCTGGTTGCGACCAGGCGGGCCGGCACTTCAACCCTG
AGGGATCCAACCACGGTGGCnnnnnCTCCACCGTGCGCCATGTCGGTGAC
CTCnnAAATGTAGTGnTTGTTAGCGAGCGAGCCGCTTATGCTACAGTnnn
Cn SEQ ID NO: 37
>ise2c.pk010.h5
GCACGAGGGTCGAGAGATACGGTGCGCACATAGCAACAATATCAAAGTAC
AAAGGTCAGTAACTATGAGTGGTAAATTGTTAAAAACTCTAATCCTTGGG
GCACCTGCTTCAGGCAAGGGGACTATATCGTCTCGGATAGTGAAGAAATA
TGCTGTGGCACACGTGTCCAGTGGGACAAGCTGAGGGACCACATTGAGA
AACAAACTGACCTAGGTAAAGAAGTCAAAAAGTACTTGAATGAAGGGAAA
CTTGTACCTGATGATGTCATGATAAAGTTTATGATCACAGAATTAAAAAA
AGTTGAAGATAAACCATGCTACTGGATGGATTCCCGAGGACTGTGGGAC
AGGCTGATGCTTTGTGAAGGTACAACCGTTGATGTAGTAGnnnnnTTA
GTAGTGCCTTTTGAGGTAATCATAGACAGAGTGAnnnAnCGCTGGGTGCA
CTTGCCTTCGGGCCGAGTGTATAACATTGGCTTCAACACTCCTAAAGTGG
AAGGTAAGGATGATGAGACAGGTGAGGACTTGGTTCAGAGACCTGACGAC AAGCCAGAGGCTGTGCGCAAGCGGCTGGAGATCTATGAGAGTGTGACGAG
GCCAGTCATAGAGTTCTAnnnGCTAA SEQ ID NO: 38
>ise2c.pk001.c18
TGCTGCTGCTGGAAGCTGGGCCCAACCCTCCCGAGGAGAGCATTATACCA
GGCTTAAGACAAACCTTGAAAGAAACGCCCTACGACTGGAACTTCACCAC
CATTGACGACGGGGTCACGAGCGAGGCGCTGGCGGGCCACGTGCAGAGAC
AGCCGCGGGCAAGATGCTGGGCGGCAGCGGCTCGCTCAACGACATGGTG
TACGCGCGGGGCCACCCCGAGGACTACTACGAGTGGGCCGACATCGCCGG
CGACGTCTGGAACTGGACCAACGTGCTGGACTACTTCAAGCGGACGGAGC
ACATGACGGACGCCAATATCGTTCACAACnnnnAGCTCATGCAGTACCAG
GGCACGGnnnnnnCCATnnnnnnnnTnnnGnnnGCAnTnnnnnnnnn SEQ ID NO: 39
>ise2c.pk004.p1
GCACGAGGGGAAAACATGGGAAGGAGGTCGCATCAAGATGTTAGTGCTCG
ACTTGAACTGCCCGGTCGTTGGAGACGACTGCAAAGACAGCCGCAAGAAG
TTGCTTGTGGACTACTTCCATACAAACCTGCATACCCAGAACTTCTACGC
GTTCCGCTTCTTTATCTGCGAAGTGTTGAACTTCATCAACGTCGTGGGCC
AGATCTTCTTCATGGACTTTTTCCTGGACGGCGAGTTCTCCACGTACGGC
AGTGACGTGGTCAGTTTCACCGAGATGGAGCCGGAGGAGCGTGTGGACCC
GATGGCTAGAGTGTTCCCGAAAGTGACCAAGTGCACCTTCCACAAATACG
GTCCTTCAGGAACCGTGCGAAGTTCGACGGTCTGTGCGTGCTGCCATTG
AACATCGTCAATGAAAAGATCTACGTGTTCCTGTGGTTCTGGTTTATGAT
CCTGTCGATCCTGAGTGGAATTTCGCTGATTTACCGCATGGCCGTGGTGG
CTGGACCGCGCGTGCGCCTGTACCTGCTGCGTGCGCGCAGCCGCCTGGCC
CCGCnnnCGCnnnnnGnnnn SEQ ID NO: 40
>ise2c.pk005.p13
GCACGAGGATTTTAATAGCTATTATGACTTTACAGACTAGACGGATCAAG
GCCATGCCTCTCGCTTGCATACTCACCATCCGCACATACCGTATTGCGGT
ATGTCAATAAGTTGCAAATAATGTCTGTTCAGTTTTACAAGGATAAGATC
AGCAGTATTTGCGAACTGTACCTACTACTAAGCTGATAATGTAATAATTA
AACTTTATTATTGAAATAGATATGTATAATTGACATCTTTCTCAAATGGG
TGTCAATACTGCCAACTCTATTACCACAATTTCTTTTCGTATTTGCTTTT
ATACTGAGCCTGATGACGTACTGTACTTTTTATTAGAATTTAATTTTTCT
TATTTTTCTTACTACGTAGTCATTAAATCTGAGAAATTAAAAATTACTAA
TTTAGAACTCCCAAATTCTGAATGAGGTTCTAAAAAGTTGTTAGGAATAC
TAAATACCATTTTACCAACATAAATCTAATTTCGTTACTTAAAATATTAA
ATGTATAATGAAATGTCTATGATAAGTGTTTACTATCTTTATATCGACAA
AATTTATTTTCCATGTTTTAAAATTTATTTTTCAGATGTTTTGACGTGAT
AAGTTTGTATTTTATCAATATCTGATAGTCGAGAGTTAnnnAnTATTG SEQ ID NO: 41
>ise2c.pk001.f12
GCACGAGGAGGAGAGGTGGTGGCTGGCTTCCTTGCAAACGAAGCGTCGT
AAATTACATCTTATTTGTAAATTTTAATAAAAATTTGATCGTTAAACGAT
CGAATCAGTAGTGATTTAAGTGCTCAAGCAGTTTCACATCCAATCGACAA
TGAGTTCGAGTGTATGCTACAAGTGTAACCGGACAGGGCACTTCGCCCGC
GAGTGCACCCAGGGTGGTGTTGCCGCTCGTGACTCTGGTTTCAACCGTCA
GCGCGAAAAGTGCTTCAAGTCAACGCGCTGGGCACTTCGCTCGGGATT
GCAAGGAGGAGGCCGACCGTTGCTACAGATGTAACGGACACGGGACATA
GCGCGTGAGTGCGCAAAGTTCCGGACGAGCCGTCGTGTTTACACTTGCAA
CAAGACCGGGCACATCGCACGGAACTGCCCAGAGGGCGGGCGACAGCT
CCAACCAGACCTGCTACAACTGCAACAAGTCCGGCCACATCTCACGCAAC
TGCCCCGACGGCACCAAGACTTGTTACGTGTGCGGAAAGCCCGGACACAT
CTCCCGCGATTGCGATGAGGAGCGGAACTAACACACGCCTCTTCGCGACT
GCCTATATATATnnnnTAAACTATGTATATTATGATGCCACGCACGGACGAT
AAGCAAAGGACGCGATACGCGACACTAGATGTAAGACCACACGGACTGTA
TGnnnnTAATGCAACG SEQ ID NO: 42
>ise2c.pk001.n21
GCACGAGGATAATAAACGTTAATATTTAACAAGTTGAAAAGTTTGTCTTT
CAATTTGTGATTTTGTAAAGATCATTCTATGGAATGGACAGTTTGCTATC
TGTGAAACATCCATTAGCTTTGTGTTGAGAGCAGAGGTCGCGGCGGCGGG
GTGATGCGGCCATGGCTTCGCGGCGCGTGACGCGCAAGTGGGAGGTGTTC
GCGGGACGGAACCGATTCTGGTGCGACGGCCGCCTCATGCACGGCGCCGCA
CCCCGGCGTGTTCCTGCTCACGCTCGCGTCATCTGCGGCACGTGCGCCC
TGCACTTCGCCTTCGACTGCCCCTTCCTGGCCGTGCGCGTGTCGCCCGCC
GTGCCCGCGGCCGGCGCCGCGCTGTGCGCGCTGACGCTGGCGGCGCTGCT
GCGCACGGCGCTGTCCGACCCCGGCATCATCCCGCGCGCCGCCGCGGCCG
AGGCGGCGGCGCTGGAGGCGGnG

TABLE 1-continued

Target Polynucleotides from *Spodoptera frugiperda*.

SEQ ID NO: 43
>ise2c.pk004.e20
CGCGCACGTCGCTCnnCAAGCCCGCTGCAGCGCCGGCCAAGCCCGCCCCC
GCGGCGGCGCGCGCCACCAGTGCGACCAGCCGCGCGGCCCCCGCGGCCCG
GCCGGCCCCCAAGTCCGCAGTAGGCGCAGCGCGGCCCGCAGCACAAAAGA
CAGATGCGGCCGCCAAACCCGCGGCGACCCGGGTTGCGGCTCCGCGTCCC
GCGCTGTCGGCGCCCAGGCCCCAGCCTAAGCCGGCAGACAAGAAGCCAGT
ACCGAATGGTGACGTGAAAGACTCCAAGCCAGCCGCGCGGCCCGCGCCCC
GGCCGGCCGCGGCCGCGCGCCCCGCGCCGCGCCCCACTCCCCGCGCCCCC
GCCGCACnGGTCGCACCCACTACTnnnnnGAGTGCCCCCAAGCCGGCGCC
GCGTGCTCCCCTGGACAAGCAGAGCnnnGACCTCGCTAACAAACGCATCn
nnGnCAnGGCAGCACCGCCTAGGACTGCTCCCCCTAAGACGACAACGACG
ACAACAGGnnnnnnnnnnnnnGTnnCGAAGnnnnn SEQ ID NO: 44
>ise2c.pk005.n11
GCACGAGGCTATAACAAGCAGCATATAAAAATGAAATTCTTGCTGTCTTT
CGCTGCCGTCATCGCCGTGGCCGCCGCTGGCCTGGTGCCCGTTGGACCCG
CCGGCCCTGCGCCCGCTCCTGAGGCCCCTGAGGTCTTCGAGCCCGTCGCT
ATTGGACCCGCTGTCATTGACTCCTTGAGCCCATCGCCATCGGACCCGC
TATCATCGACTCCTTCGAGCCCATCGCCATCGGACCCGCTATTGTTCAT
CTCCCGAGCCCGTCGCCATCGGACCCGCCATCATTGAGAGCCCAGAGCCC
GTTGCTGTCGGACCTGCATGGATTGGTTGCCCCTGCCCGACGGTGGTGC
TGCCGTTGCCCCCGTTGAGCCCTCTCCCGTGGCTGTTATCCCCGGTCCCG
TGTCCACTGAGGTTGCTTCAGGCACTCCCCTGGTTCAGATCATCCTGAAC
ATCAACnnnnnnTCTGCTGACGTTAGCCCCGTTGCTGTnGGCCCCGCTGT
CGAGnnnACACCCGTGGACGTTGTGGAGTCTGCCCCTGAACCCGTCCACG
TTGTGnnnnnnnGCCCCnnnnnCnATCnnnnnGTCGn SEQ ID NO: 45
>ise2c.pk003.l14
GCACGAGGCTTAGAGTAAGCATAGGTGTATTTATGTATTGAGTCGGAAGA
AGCAATGGACGATCCAAATAGGATGATGGCGCATAGCGGCGGGCTTATGG
GGCCGCAGGGCTACGGCCTGCCTGGCGGCGAGGGAACTCCAACCGCAGGC
GAAGGTGAAGCCCGCAAGCAAGATATTGGTGAAATATTGCAACAGATCAT
GAATATTACAGATCAAAGTCTTGATGAAGCGCAAGCAGGAGAAAACATACTC
TCAACTGTCACAGAATGAAGCCTGCCCTATTTTCAGTGTTGTGTGAAATC
AAAGAGAAAACAGTGCTGTCCCTCCGCAACACGCAAGAGGAGGAGCCCCC
AGATCCCCAGCTGATGCGCTTGGACAACATGCTCATAGCCGAGGGGGTCG
CTGGCCCTGAAAAGGGTGGTGGTGCGGGCGCTGCAGCTTCGGCATCAGT
GCTGCTGGTGAATGGGACAATGCCATCGAGCACTCTGACTACCGTGCGAA
GTTGGCGCAGATCCGCCAGATCTACCACCAGGAGCTGGACAAGTATGAGA
ATGCTTGTAATGnnnnnnCCACCCACGTGATGAACTTACTCCGCGAGCAG
AGCCGCACCAGGCCTATCACAnn SEQ ID NO: 46
>ise2c.pk003.e24
GCACGAGGCCAGGTTTGAGAAAAACGCTTAAACTGCCACAAAATCCCGTT
CTCGAAGAAGCACTTTTCACTTATTAATAAGTAACTTGTGTAAAATGTGG
TTTAAATGTGTATTTTACTAAACCTCAATAAATATATTTATATCAAAATA
TTTTTTTTCTATACTGTATTATTTATTCCTATAGTACATATTATAATCCG
AACGCTCCGTGAGTCCGAACAGGGTAATTTTTTGGTGATTATC
GAGGCTCTACTGTATACCTACTTTTTGTTAAAATATTTTAGTCTTATATA
CGACTTCCTAACTAATCCATATCTCTTAGAGCTTTCGAATATCCATTTGC
CTTTTTCTTAAAAGATTAATAACTATTTATATATATCCCAAATATATAAA
AAACAACCACTCCAATTATTATTATTCAAATATGACAAACTAGATAGAAT
GTCCCAAGAAATTTGCAAAAAAGTAATGTTCAAATTATTAACCGAAGAAC
GAATTnnnGAGTGTATAATATTTATACAGACATTTAGAAATTTTTAATAGG
CTCCAATCGCATGAGAGGTCGCTTTAAAATTCGGCATTGGTGTGTGCGTT
GCAATTTAATCTTTAACACCCnnn SEQ ID NO: 47
>ise2c.pk005.l5
GCACGAGGGGACGTGTTTACAATTTACTTTCGTGCTCGTGTGATTTTAAT
TAAAACAGTGCTAAGTGCTCTAGGACGCTGAATAACTGATATTTGTTTTA AAAGTTGATATAAATTAATCACAATGAATAGAGATAAACGAGAACCAGAG
TATCCAACGGAGTTGGAGTCTCAATTCGTAATGCGTTTACCTGAGGAGCC
TGCAAAAGTTTTGAGAGAAGTGTTGAAATCCGGAGAGAACCTGAAAAACA
GACTGACGATACAAATAGAAAACGACATGCGCACGGGCGAGGTAAGGTTT
GATCACTGGTTGATGCACGCCAAGATCGTGGATCTACCAACCATCATAGA
ATCTCTAAAAACGATCGACAACAAGAGTTTCTACAAAACAGCAGATATAT
GCCAAATGATGATTTGTAAAGAAGAACCTGACCAACCATCCACAGAGGAA
GAGTCACCAGCTAAAAATAAGAAAAAAGATCCATACAAAGTTGACAAAAA
GTTCCTATGGCCACACGGCATCACACCGCCTACGAAGAACGTACGGAAGC
GTCGATTTAGAAAAACCCTTAAAAAGAAATATGTAGAAGCACCAGAAATT
GAAAAGGAAGTGAAGAGGCTGCTGAGnGCAnnCnATGAGGCTGTTAGTGT
TAACTGGGAGGTCATCAAnnnnnnnnGAT SEQ ID NO: 48
>ise2c.pk006.k12
GCACGAGGGTCGAATGGAACATGGCGGTGCTAGGCAGGATGTGCATAAGT
TTTTGATTTTTGCATTTTTAACGAGTTGCTTATATCAGTTAGCTTTCTAA
ATAATTTCTGACTTATTTCGTGTGTTATAATATTTGTTATAGTGTAAAAG
CTTATCCACCCAGGAATTTCCTATCTGGACTTACTTAGTTCTGCAATGA
AAATTATTATTCGTTGGTAGTGTAAAAATAATTGTGACAAATATATCACT
TTGCTTCAGTGTGCCGTGTTGGTCATGGCTACGCTCCTCCAAGAGAATGG
TATAAAGGAGTTAAGCAAAGTTGTGCCTAACCGTGGTATATCCTACATA
GTGTAACAAATCATATGGTGCCTGATCATGAATATTGCGAAGCTGGGTCA
ACTAGCACGTCACAGATGAAGTGTACCATACAAGTGAGGCGATGGCGCC
ACCCGCCGCCATTGAAGAAGAGGAGGATACACCAGAAATAGATATAATGA
TAAACAATGTTGTGTGCAGTTTTAGTGTTAAGTGCCACCTGAACCTTAGA
CAGATAGCATTnnnTGGTGTGAACGTTGAATTTCGCCGCGAGAACGGCAT
GGTAACTATGAAGTTACGGCGTCCATACACTACTGCGTCCATCTGGTCGT
CCGGCCGCGTGACGTGCACTGGTGCAACCAGCG SEQ ID NO: 49
>ise2c.pk010.i8
GCACGAGGGAATATTGCGAAGCTGGGTCAACTAGCACGTCACAGATGAAG
TGTACCGATACAAGTGAGGCGATGGCGCCACCCGCCGCCATTGAAGAAGA
GGAGGATACACCAGAAATAGATATAATGATAAACAATGTTGTGTGCAGTT
TTAGTGTTAAGTGCCACCTGAACCTTAGACAGATAGCATTAATGGTGTG
AACGTTGAATTTCGCCGCGAGAACGGCATGGTAACTATGAAGTTACGGCG
TCCATACACTACTGCGTCCATCTGGTCGTCCGGCCGCGTGACGTGCACTG
GTGCAACCAGCGAGGACCAGGCGAAGGTTGCCGCACGACGGTATGCGCGC
GCCCTTCAGAAGCTCGGCTTCCAAGTGCGTTTCCGCAATTTCCGTGTAGT
CAATGTATTAGGCACCTGTCGGATGCCGTTTGGTATAAGGATCATATCTT
TTTCGAAAAAATACAAGGAAGCAGACTATGAACCTGAGCTCCATCCTGGA
GTCACATATAAGTTATACAATCCTAAAGCCACACTCAAGATATTCTCCAC
TGGTGGTGTGACTATCACAGCTCGGAGTGTGAGTGACGTTCAGTCAGCCG
TGGAACGCATCTTCCCTTTGnTGTACGAGTTCCGCAAGCCTCnnnnACCG
GCAnnnnA SEQ ID NO: 50
>ise2c.pk010.b12
GCACGAGGGTACCAAAAGCTCTTTTCATTGCAGCTGAAGGGTCACTGCAA
CTTGGCCAATCAGAATTAGCATTGAAACTATTCAAAGAACTAAAACAAGA
AGGAATGGAAATCAGGCAACATTTCTATTGGCCTTTGTTAGTTCAGAAGG
CAAAGGAAAATGATGAGGAAGGCCTCTTGCAAATTTTAAAAGAAATGAGC
AGCAATGACTTTACTGTTACTGGAGAAGCGTTAAGAGACTATGTTATCCC
TTACTTGATAAAAAAGATTCTCCACAGAATGTCTTACTTAAACTTCAAA
TTGCAAATGTACCAACAATCCATGCTGCAAGAAATCTAATGGTTGATCTT
TTTGGATTCTGGAGACATAAAAGGCGCAGCGGAAATAGCTCTGCAATATAG
ACCTTGGGGCAACTACTCTCTTGTTGCCAGGTCCCTCATCAATGCAGTGA
ATAAGACAAAAGATGTAGAATCGTTTGCTAAAATTCTTCATGCTATAAGC
AGTAAACCTTTGTCACAGGGTGAAGAAGATGTTGCTGCCAACAATGAGGA
AGGTCAAAGTGATGAAAATAATGATATTCATGAAGTCGGCCGTATTGTGA
GGTCGTCTGCCAAGAGTTTGGCTAAACCAGACTTAATAGnAAnnnnTTTA
GA

TABLE 2

List of dsRNA primers.

| Primer # | Target Gene ID | Seq ID | Target | Sense strand | Antisense strand | SEQ ID NO Target/sense/ antisense |
|---|---|---|---|---|---|---|
| 0075 | juvenile hormone diol kinase | ise1c.pk002.m13 | AACATGGTATCCGACTTCAGGAA | CAUGGUAUCCGACUUCAG G | CCUGAAGUCGGAUACCAUG | 51/52/53 |

TABLE 2-continued

List of dsRNA primers.

| Primer # | Target Gene ID | Seq ID | Target | Sense strand | Antisense strand | SEQ ID NO Target/sense/antisense |
|---|---|---|---|---|---|---|
| 0076 | juvenile hormone diol kinase | ise1c.pk002.m13 | AAGGTCGCTGACGAGAACAAGGA | GGUCGCUGACGAGAACAAG | CUUGUUCUCGUCAGCGACC | 54/55/56 |
| 0077 | juvenile hormone diol kinase | ise1c.pk002.m13 | AAGTGTCCTGGGCTTGAGTTCCA | GUGUCCUGGGCUUGAGUUC | GAACUCAAGCCCAGGACAC | 57/58/59 |
| 0078 | juvenile hormone diol kinase | ise1c.pk003.f7 | AAGAAGAAGCTCCTCCACGTCGTGTT | GAAGAAGCUCCUCCACGUG | CACGUGGAGGAGCUUCUUC | 60/61/62 |
| 0079 | juvenile hormone diol kinase | ise1c.pk003.f7 | AAGGTCGCTGACGAGAACAAGGA | GGUCGCUGACGAGAACAAG | CUUGUUCUCGUCAGCGACC | 63/64/65 |
| 0080 | juvenile hormone diol kinase | ise1c.pk003.f7 | AATGTCCTGGGGCTGAGTTTCAA | UGUCCUGGGGCUGAGUUUC | GAAACUCAGCCCCAGGACA | 66/67/68 |
| 0081 | juvenile hormone diol kinase | ise1c.pk005.a15 | AAGAATAAGCTCCTCCACGTCGTGTT | GAAUAAGCUCCUCCACGUG | CACGUGGAGGAGCUUAUUC | 69/70/71 |
| 0082 | juvenile hormone diol kinase | ise1c.pk005.a15 | AATTTGTCGAGGAGACCCTATTG | UUUGUCGAGGAGACCCUAU | AUAGGGUCUCCUCGACAAA | 72/73/74 |
| 0083 | juvenile hormone diol kinase | ise1c.pk005.a15 | AAGTTCGCGTTCACTCTTGAAGA | GUUCGCGUUCACUCUUGAA | UUCAAGAGUGAACGCGAAC | 75/76/77 |
| 0084 | ribosomal protein L18a | ise1c.pk006.d24 | AACTGCCCCTTAACCTCATCTAT | CUGCCCCUUAACCUCAUCU | AGAUGAGGUUAAGGGGCAG | 78/79/80 |
| 0085 | ribosomal protein L18a | ise1c.pk006.d24 | AATCACGCTGAAACCACTGTATA | UCACGCUGAAACCACUGUA | UACAGUGGUUUCAGCGUGA | 81/82/83 |
| 0086 | epoxide hydrolase | ise2c.pk009.i4 | AAAATATGGCGCGCCTATTGTTT | AAUAUGGCGCGCCUAUUGU | ACAAUAGGCGCGCCAUAUU | 84/85/86 |
| 0087 | epoxide hydrolase | ise2c.pk009.i4 | AACGTTCTCGGTCTTTCACTGCT | CGUUCUCGGUCUUUCACUG | CAGUGAAAGACCGAGAACG | 87/88/89 |
| 0088 | epoxide hydrolase | ise2c.pk009.i4 | AAGTCATCGTTCCAAGTCTACCT | GUCAUCGUUCCAAGUCUAC | GUAGACUUGGAACGAUGAC | 90/91/92 |
| 0089 | V-ATPase A subunit | ise2c.pk001.d19 | AACCCCTTGAATGTTAAGGTCGG | CCCCUUGAAUGUUAAGGUC | GACCUUAACAUUCAAGGGG | 93/94/95 |
| 0090 | V-ATPase A subunit | ise2c.pk001.d19 | AAGTACACCATGTTGCAAGTATG | GUACACCAUGUUGCAAGUA | UACUUGCAACAUGGUGUAC | 96/97/98 |
| 0091 | V-ATPase A subunit | ise2c.pk001.d19 | AACGTGTCCATGATGGCTGACTC | CGUGUCCAUGAUGGCUGAC | GUCAGCCAUCAUGGACACG | 99/100/101 |
| 0092 | H+-ATPase V-type subunit | ise2c.pk001.e14 | AAACCTACAAAATGGCCGAAAAC | ACCUACAAAAUGGCCGAAA | UUUCGGCCAUUUUGUAGGU | 102/103/104 |
| 0093 | H+-ATPase V-type subunit | ise2c.pk001.e14 | AATCTACGGACCCTTCTTTGGAG | UCUACGGACCCUUCUUUGC | CCAAAGAAGGGUCCGUAGA | 105/106/107 |
| 0094 | V-ATPase A subunit | ise2c.pk001.f20 | AACTCTGACGTCATCATCTACGT | CUCUGACGUCAUCAUCUAC | GUAGAUGAUGACGUCAGAG | 108/109/110 |
| 0095 | V-ATPase A subunit | ise2c.pk001.f20 | AAGTGCTTGGGTAACCCCGACAG | GUGCUUGGGUAACCCCGAC | GUCGGGGUUACCCAAGCAC | 111/112/113 |
| 0096 | V-ATPase A subunit | ise2c.pk001.f20 | AACTGGCTCATCTCCTACAGCAA | CUGGCUCAUCUCCUACAGC | GCUGUAGGAGAUGAGCCAG | 114/115/116 |
| 0097 | novel sequence | ise2c.pk010.h3 | AAACAGTGCGTCGTAATATATTC | ACAGUGCGUCGUAAUAUAU | AUAUAUUACGACGCACUGU | 117/118/119 |

TABLE 2-continued

List of dsRNA primers.

| Primer # | Target Gene ID | Seq ID | Target | Sense strand | Antisense strand | SEQ ID NO Target/sense/antisense |
|---|---|---|---|---|---|---|
| 0098 | novel sequence | ise2c.pk010.h3 | AAGGCACATGGTCCTTCACTGAT | GGCACAUGGUCCUUCACUC | CAGUGAAGGACCAUGUGCC | 120/121/122 |
| 0099 | novel sequence | ise2c.pk010.h3 | AACACCATGACCCTCGTGTACACAA | CACCAUGACCCUCGUGUACA | GUACACGAGGGUCAUGGUG | 123/124/125 |
| 0100 | Larval cuticle protein LCP-17 | ise2c.pk007.k24 | AACGAGGCCGGATCTCTTAAGCA | CGAGGCCGGAUCUCUUAAG | CUUAAGAGAUCCGGCCUCG | 457/458/459 |
| 0101 | Larval cuticle protein LCP-17 | ise2c.pk007.k24 | AACTTCACACATAACTAGACAAA | CUUCACACAUAACUAGACA | UGUCUAGUUAUGUGUGAAG | 460/461/462 |
| 0102 | Larval cuticle protein LCP-17 | ise2c.pk007.k24 | AATGCGTGGCGATTTCAAACTTA | UUAGAAAUUAUAAGCCCAG | CUGGGCUUAUAAUUUCUAA | 463/464/465 |
| 0103 | transcriptional repressor | ise2c.pk011.a10 | AAAAAACACAGACCACGTTCACA | AAAACACAGACCACGUUCA | UGAACGUGGUCUGUGUUUU | 126/127/128 |
| 0104 | transcriptional repressor | ise2c.pk011.a10 | AATCGATGGTGGTGTTATTCGCT | UCGAUGGUGGUGUUAUUCG | CGAAUAACACCACCAUCGA | 129/130/131 |
| 0105 | novel sequence | ise2c.pk011.h12 | AAAGAAAATGCTACGCGTTACGA | AGAAAAUGCUACGCGUUAC | GUAACGCGUAGCAUUUUCU | 132/133/134 |
| 0106 | novel sequence | ise2c.pk011.h12 | AACCCTTGGACACTACTGGAAGA | CCCUUGGACACUACUGGAA | UUCCAGUAGUGUCCAAGGG | 135/136/137 |
| 0107 | novel sequence | ise2c.pk011.h12 | AAGGATCCTATGTGTACCAGGTT | GGAUCCUAUGUGUACCAGG | CCUGGUACACAUAGGAUCC | 138/139/140 |
| 0108 | translation initiation factor | ise2c.pk001.d22 | AAACTCGGCACACAACACAATGG | ACUCGGCACACAACACAAU | AUUGUGUUGUGUGCCGAGU | 141/142/143 |
| 0109 | translation initiation factor 5A | ise2c.pk001.d22 | AATACGAAGATATCTGCCCTTCC | UACGAAGAUAUCUGCCCUU | AAGGGCAGAUAUCUUCGUA | 144/145/146 |
| 0110 | translation initiation factor 5A | ise2c.pk001.d22 | AATCAACAGCTCTTACATAAAATG | UCAACAGCUCUUACAUAAA | UUUAUGUAAGAGCUGUUGA | 147/148/149 |
| 0111 | eukaryotic initiation factor eIF-4A | isc2c.pk001.d9 | AAAGAAGATCAGAAGATTGGCCG | AGAAGAUCAGAAGAUUGGC | GCCAAUCUUCUGAUCUUCU | 150/151/152 |
| 0112 | eukaryotic initiation factor eIF-4A | isc2c.pk001.d9 | AAAAGCCGTCTGCTATCCAACAA | AAGCCGUCUGCUAUCCAAC | GUUGGAUAGCAGACGGCUU | 153/154/155 |
| 0113 | eukaryotic initiation factor eIF-4A | isc2c.pk001.d9 | AATGCTAAATGCCATGCTTGCAT | UGCUAAAUGCCAUGCUUGC | GCAAGCAUGGCAUUUAGCA | 156/157/158 |
| 0114 | Eukaryotic initiation factor 4A | ise2c.pk001.i23 | AAGATCAGAAGATTGGCCGGAAG | GAUCAGAAGAUUGGCCGGA | UCCGGCCAAUCUUCUGAUC | 159/160/161 |
| 0115 | Eukaryotic initiation factor 4A | ise2c.pk001.i23 | AATTCTTCAGCAAATCGATACCA | UUCUUCAGCAAAUCGAUAC | GUAUCGAUUUGCUGAAGAA | 162/163/164 |

TABLE 2-continued

List of dsRNA primers.

| Primer # | Target Gene ID | Seq ID | Target | Sense strand | Antisense strand | SEQ ID NO Target/sense/antisense |
|---|---|---|---|---|---|---|
| 0116 | Eukaryotic initiation factor 4A | ise2c.pk001.i23 | AAATGCTGTCAAGAGGATTTAAA | AUGCUGUCAAGAGGAUUUA | UAAAUCCUCUUGACAGCAU | 165/166/167 |
| 0117 | RNA polymerase sigma subunit SigE | ise2c.pk001.l24 | AAGCTCGAGACTTGCTCTTGATG | GCUCGAGACUUGCUCUUGA | UCAAGAGCAAGUCUCGAGC | 168/169/170 |
| 0118 | RNA polymerase sigma subunit SigE | ise2c.pk001.l24 | AACTGTTAGCTCAAGGTCTGCTA | CUGUUAGCUCAAGGUCUGC | GCAGACCUUGAGCUAACAG | 171/172/173 |
| 0119 | RNA polymerase sigma subunit SigE | ise2c.pk001.l24 | AAGACTTTCTATCAGAATTTGCG | GACUUUCUAUCAGAAUUUG | CAAAUUCUGAUAGAAAGUC | 174/175/176 |
| 0120 | translation initiation factor 2, subunit 2 beta | ise2c.pk005.b9 | AAACTTAATCATGGACGACGACA | ACUUAAUCAUGGACGACGA | UCGUCGUCCAUGAUUAAGU | 177/178/179 |
| 0121 | translation initiation factor 2, subunit 2 beta | ise2c.pk005.b9 | AAAGAAGAAGAAGAAGGGAG | AGAAGAAGAAGAAGAAGG | CCCUUCUUCUUCUUCUUCU | 180/181/182 |
| 0122 | translation initiation factor 2, subunit 2 beta | ise2c.pk005.b9 | AAGATCAAGAGAATGTCGAGGAT | GAUCAAGAGAAUGUCGAGG | CCUCGACAUUCUCUUGAUC | 183/184/185 |
| 0123 | putative sar1 protein | ise2c.pk002.m10 | AAAATCGTCGGTTTTAGCGACGT | AAUCGUCGGUUUUAGCGAC | GUCGCUAAAACCGACGAUU | 186/187/188 |
| 0124 | putative sar1 protein | ise2c.pk002.m10 | AACTGTCAATAGGCAGTATGCGT | CUGUCAAUAGGCAGUAUGC | GCAUACUGCCUAUUGACAG | 189/190/191 |
| 0125 | putative sar1 protein | ise2c.pk002.m10 | AACCTGTACCAACAGACCACTGG | CCUGUACCAACAGACCACU | AGUGGUCUGUUGGUACAGG | 192/193/194 |
| 0126 | elongation factor 1-alpha | ise2c.pk001.c14 | AACCAAAATGGGCAAGGAAAAG | CCAAAAUGGGCAAGGAA | UUUCCUUGCCCAUUUUGG | 195/196/197 |
| 0127 | elongation factor 1-alpha | ise2c.pk001.c14 | AACGTGGTATCACCATCGATATT | CGUGGUAUCACCAUCGAUA | UAUCGAUGGUGAUACCACG | 198/199/200 |
| 0128 | elongation factor 1-alpha | ise2c.pk001.c14 | AACAAAATGGACTCCACTGAGCC | CAAAAUGGACUCCACUGAG | CUCAGUGGAGUCCAUUUUG | 201/202/203 |
| 0129 | elongation factor-1alpha F2 | ise2c.pk001.d16 | AATCCGTGACTAACCAAAATGG | UCCGUGACUAACCAAAAAU | AUUUUUGGUUAGUCACGGA | 204/205/206 |
| 0130 | elongation factor-1alpha F3 | ise2c.pk001.d16 | AACATTGTCGTCATTGGACACGT | CAUUGUCGUCAUUGGACAC | GUGUCCAAUGACGACAAUG | 207/208/209 |
| 0131 | Oligosaccharyl transferase 48 kDa subunit | ise2c.pk005.h3 | AATTTGTGAGACTGGTGGCCGAA | UUUGUGAGACUGGUGGCCG | CGGCCACCAGUCUCACAAA | 421/422/423 |

TABLE 2-continued

List of dsRNA primers.

| Primer # | Target Gene ID | Seq ID | Target | Sense strand | Antisense strand | SEQ ID NO Target/sense/ antisense |
|---|---|---|---|---|---|---|
| 0132 | Oligo-saccharyl transferase 48 kDa subunit | ise2c.pk005.h3 | AATCTGATTGTATTCGCC CCCTC | UCUGAUUGUAUUCGCCCC C | GGGGGCGAAUACAA UCAGA | 424/425/426 |
| 0133 | Oligo-saccharyl transferase 48 kDa subunit | ise2c.pk005.h3 | AACACTCTAGTTCTGCCT ATTCT | CACUCUAGUUCUGCCUAU U | AAUAGGCAGAACUA GAGUG | 427/428/429 |
| 0134 | Myosin regulatory light chain | ise2c.pk001.d21 | AACACACATCACAATGG CGGATA | CACACAUCACAAUGGCGG A | UCCGCCAUUGUGAU GUGUG | 430/431/432 |
| 0135 | Myosin regulatory light chain | ise2c.pk001.d21 | AAGGATGGCATCATCGG CAAGAA | GGAUGGCAUCAUCGGCAA G | CUUGCCGAUGAUGC CAUCC | 433/434/435 |
| 0136 | Myosin regulatory light chain | ise2c.pk001.d21 | AAAGGCTTCATCGACAC CGCGAA | AGGCUUCAUCGACACCGC G | CGCGGUGUCGAUGA AGCCU | 436/437/438 |
| 0137 | novel sequence | ise2c.pk001.j9 | AAACTCCAATTATAACCT ACTAG | ACUCCAAUUAUAACCUAC U | AGUAGGUUAUAAUU GGAGU | 210/211/212 |
| 0138 | novel sequence | ise2c.pk001.j9 | AAGTACAAGGATCTGAT CGGCAA | GUACAAGGAUCUGAUCGG C | GCCGAUCAGAUCCU UGUAC | 213/214/215 |
| 0139 | novel sequence | ise2c.pk001.j9 | AAGACTTTCTTCATGTGG CCCAT | GACUUUCUUCAUGUGGCC C | GGGCCACAUGAAGA AAGUC | 216/217/218 |
| 0140 | novel sequence | ise2c.pk002.f12 | AAACAAAGTATCGCCTA CACCGC | ACAAAGUAUCGCCUACAC C | GGUGUAGGCGAUAC UUUGU | 439/440/441 |
| 0141 | novel sequence | ise2c.pk002.f12 | AATAGCGTCGATCTTCAA CGACT | UAGCGUCGAUCUUCAACG A | UCGUUGAAGAUCGA CGCUA | 442/443/444 |
| 0142 | potassium coupled amino acid transporter | ise2c.pk001.b14 | AACTCATAGAGCTTGATG TGTGG | CUCAUAGAGCUUGAUGUG U | ACACAUCAAGCUCU AUGAG | 219/220/221 |
| 0143 | potassium coupled amino acid transporter | ise2c.pk001.b14 | AAGATGTGGATGACGTC ACTGGT | GAUGUGGAUGACGUCACU G | CAGUGACGUCAUCC ACAUC | 222/223/224 |
| 0144 | potassium coupled amino acid transporter | ise2c.pk001.b14 | AACCTTCCTGATTCTCTT CTGTG | CCUUCCUGAUUCUCUUCU G | CAGAAGAGAAUCAG GAAGG | 225/226/227 |
| 0145 | inwardly rectifying K+ channel protein | ise2c.pk003.f2 | AACAGTGCTTGTGATAA GTGAAC | CAGUGCUUGUGAUAAGUG A | UCACUUAUCACAAG CACUG | 228/229/230 |
| 0146 | inwardly rectifying K+ channel protein | ise2c.pk003.f2 | AAGTTAATGGTGACTGCC CTCGA | GUUAAUGGUGACUGCCCU C | GAGGGCAGUCACCA UUAAC | 231/232/233 |
| 0147 | inwardly rectifying K+ channel protein | ise2c.pk003.f2 | AATAAAGCGATGACCCC ATAGGA | UAAAGCGAUGACCCCAUA G | CUAUGGGGUCAUCG CUUUA | 234/235/236 |

TABLE 2-continued

List of dsRNA primers.

| Primer # | Target Gene ID | Seq ID | Target | Sense strand | Antisense strand | SEQ ID NO Target/sense/ antisense |
|---|---|---|---|---|---|---|
| 0148 | potassium coupled amino acid transporter | ise2c.pk005.120 | AAACGGTACTGCAGCAA AAAGAC | ACGGUACUGCAGCAAAAA G | CUUUUUGCUGCAGU ACCGU | 237/238/239 |
| 0149 | potassium coupled amino acid transporter | ise2c.pk005.120 | AAGCTGCATACTTCTTGG CTCTC | GCUGCAUACUUCUUGGCU C | GAGCCAAGAAGUAU GCAGC | 240/241/242 |
| 0150 | potassium coupled amino acid transporter | ise2c.pk005.120 | AAATGTTTACAGAGACG CGATGA | AUGUUUACAGAGACGCGA U | AUCGCGUCUCUGUA AACAU | 243/244/245 |
| 0151 | alpha tubulin | ise2c.pk001.d1 | AACGTCGATCTTACCGAG TTCCA | CGUCGAUCUUACCGAGUU C | GAACUCGGUAAGAU CGACG | 246/247/248 |
| 0152 | tubulin alpha chain | ise2c.pk001.k6 | AATTCAAAATGCGTGAG TGCATC | UUCAAAAUGCGUGAGUGC A | UGCACUCACGCAUU UUGAA | 249/250/251 |
| 0153 | tubulin alpha chain | ise2c.pk001.k6 | AAATCGTAGACCTAGTCC TCGAC | AUCGUAGACCUAGUCCUC G | CGAGGACUAGGUCU ACGAU | 252/253/254 |
| 0154 | tubulin alpha chain | ise2c.pk001.l2 | AAACTCAATTCAAAATG CGTGAG | ACUCAAUUCAAAAUGCGU G | CACGCAUUUUGAAU UGAGU | 255/256/257 |
| 0155 | tubulin alpha chain | ise2c.pk001.l2 | AACTTATCACTGGTAAGG AAGAT | CUUAUCACUGGUAAGGAA G | CUUCCUUACCAGUG AUAAG | 258/259/260 |
| 0156 | ubiquitin kinase | ise2c.pk002.b4 | AAGAGTTACGAACCGTC ACCATA | GAGUUACGAACCGUCACC A | UGGUGACGGUUCGU AACUC | 261/262/263 |
| 0157 | ubiquitin kinase | ise2c.pk002.b4 | AAACTTAGTCCGGATAAT GAACC | ACUUAGUCCGGAUAAUGA A | UUCAUUAUCCGGAC UAAGU | 264/265/266 |
| 0158 | ubiquitin kinase | ise2c.pk002.b4 | AAGGCGATGTACGAGAA CCTGTT | GGCGAUGUACGAGAACCU G | CAGGUUCUCGUACA UCGCC | 267/268/269 |
| 0159 | nuclear ribonucleo- protein 200 kDa helicase | ise2c.pk001.j16 | AACGACAAGATGCTGAA GGAGAC | CGACAAGAUGCUGAAGGA G | CUCCUUCAGCAUCU UGUCG | 270/271/272 |
| 0160 | Sqd protein homologue (RNA binding) | ise2c.pk006.h23 | AAGATAAAGGTCGCGTG TGGACC | GAUAAAGGUCGCGUGUGG A | UCCACACGCGACCU UUAUC | 273/274/275 |
| 0161 | Sqd protein homologue (RNA binding) | ise2c.pk006.h23 | AATGTCAAGACTGATCC AAACAC | UGUCAAGACUGAUCCAAA C | GUUUGGAUCAGUCU UGACA | 276/277/278 |
| 0162 | Sqd protein homologue (RNA binding) | ise2c.pk006.h23 | AACATTCGAGTCTGAAC AGGTGG | CAUUCGAGUCUGAACAGG U | ACCUGUUCAGACUC GAAUG | 279/280/281 |
| 0163 | pre-mRNA- binding protein | ise2c.pk006.m8 | AACATAAGTCATGGCCA ATAACG | CAUAAGUCAUGGCCAAUA A | UUAUUGGCCAUGAC UUAUG | 282/283/284 |
| 0164 | pre-mRNA- binding protein | ise2c.pk006.m8 | AAGAACATAATAGTGCC GAAGCC | GAACAUAAUAGUGCCGAA G | CUUCGGCACUAUUA UGUUC | 285/286/287 |
| 0165 | pre-mRNA- binding protein | ise2c.pk006.m8 | AAACACTGGCAGATCAA GAGGAT | ACACUGGCAGAUCAAGAG G | CCUCUUGAUCUGCC AGUGU | 288/289/290 |
| 0166 | pre-mRNA- binding protein | ise2c.pk006.m8 | AAGATCTTTGTTGGTGGT CTTAG | GAUCUUUGUUGGUGGUCU U | AAGACCACCAACAA AGAUC | 291/292/293 |

TABLE 2-continued

List of dsRNA primers.

| Primer # | Target Gene ID | Seq ID | Target | Sense strand | Antisense strand | SEQ ID NO Target/sense/ antisense |
|---|---|---|---|---|---|---|
| 0167 | pre-mRNA-binding protein | ise2c.pk006.m8 | AACAGGTGGTCAATGAGCTGCTG | CAGGUGGUCAAUGAGCUGC | GCAGCUCAUUGACCACCUG | 294/295/296 |
| 0168 | chymotrypsin-like; protease | ise2c.pk001.a23 | AAGTTGGCTCTGACACTCTTGGC | GUUGGCUCUGACACUCUUG | CAAGAGUGUCAGAGCCAAC | 297/298/299 |
| 0169 | chymotrypsin-like; protease | ise2c.pk001.a23 | AAATCCGCAAAGCTGAGGAGGCA | AUCCGCAAAGCUGAGGAG | CCUCCUCAGCUUUGCGGAU | 300/301/302 |
| 0170 | chymotrypsin-like; protease | ise2c.pk001.a23 | AACCGTGTTCTTACTGCTGCTCA | CCGUGUUCUUACUGCUGCU | AGCAGCAGUAAGAACACGG | 303/304/305 |
| 0171 | chymotrypsin-like; protease | ise2c.pk001.a23 | AACGTTGTTATGCATGGAAGCTG | CGUUGUUAUGCAUGGAAGC | GCUUCCAUGCAUAACAACG | 306/307/308 |
| 0172 | chymotrypsin-like; protease | ise2c.pk001.a23 | AAAACTTCGCCGGTGAAAACGCC | AACUUCGCCGGUGAAAACG | CGUUUUCACCGGCGAAGUU | 309/310/311 |
| 0173 | chymotrypsinogen; protease | ise2c.pk001.a7 | AAATGAAACTGTTCCTCGCAGTC | AUGAAACUGUUCCUCGCAG | CUGCGAGGAACAGUUUCAU | 312/313/314 |
| 0174 | chymotrypsinogen; protease | ise2c.pk001.a7 | AAGAAGGCTGAGGAAGAAACCAG | GAAGGCUGAGGAAGAAACC | GGUUUCUUCCUCAGCCUUC | 315/316/317 |
| 0175 | chymotrypsinogen; protease | ise2c.pk001.a7 | AACTCTTTCACCGTCGTACTTGG | CUCUUUCACCGUCGUACUU | AAGUACGACGGUGAAAGAG | 318/319/320 |
| 0176 | chymotrypsinogen; protease | ise2c.pk001.a7 | AACGACATTGCTGTCCTCCGCAT | CGACAUUGCUGUCCUCCGC | GCGGAGGACAGCAAUGUCG | 321/322/323 |
| 0177 | chymotrypsinogen; protease | ise2c.pk001.a7 | AACATCGGTACTACCCAACGTGT | CAUCGGUACUACCCAACGU | ACGUUGGGUAGUACCGAUG | 324/325/326 |
| 0178 | actin-depoly-merizing | ise2c.pk004.c4 | AAGACTCAGTACGTATTATCGCG | GACUCAGUACGUAUUAUCG | CGAUAAUACGUACUGAGUC | 327/328/329 |
| 0179 | actin-depoly-merizing | ise2c.pk004.c4 | AAGTTGCCATCTTGCTTTTGCAA | GUUGCCAUCUUGCUUUUGC | GCAAAAGCAAGAUGGCAAC | 330/331/332 |
| 0180 | actin-depoly-merizing | ise2c.pk004.c4 | AATCAGTTTGACGCATGCGCTCA | UCAGUUUGACGCAUGCGCU | AGCGCAUGCGUCAAACUGA | 333/334/335 |
| 0181 | actin-depoly-merizing | ise2c.pk004.c4 | AATGGCGTCTGGTGTGACAGTTT | UGGCGUCUGGUGUGACAGU | ACUGUCACACCAGACGCCA | 336/337/338 |
| 0182 | actin-depoly-merizing | ise2c.pk004.c4 | AACGCGGAATACGATCAGTTCCT | CGCGGAAUACGAUCAGUUC | GAACUGAUCGUAUUCCGCG | 339/340/341 |
| 0183 | actin depoly-merizing factor | ise2c.pk004.14 | AAGACTCAGTACGTATTATCGCG | GACUCAGUACGUAUUAUCG | CGAUAAUACGUACUGAGUC | 342/343/344 |
| 0184 | actin depoly-merizing factor | ise2c.pk004.14 | AAGTTGCCATCTTGCTTTTGCAA | GUUGCCAUCUUGCUUUUGC | GCAAAAGCAAGAUGGCAAC | 345/346/347 |

TABLE 2-continued

List of dsRNA primers.

| Primer # | Target Gene ID | Seq ID | Target | Sense strand | Antisense strand | SEQ ID NO Target/sense/antisense |
|---|---|---|---|---|---|---|
| 0185 | actin depoly-merizing factor | ise2c.pk004.14 | AATCAGTTTGACGCATGCGCTCA | UCAGUUUGACGCAUGCGCU | AGCGCAUGCGUCAAACUGA | 348/349/350 |
| 0186 | actin depoly-merizing factor | ise2c.pk004.14 | AAAAATGGCGTCTGGTGTGACAG | AAAUGGCGUCUGGUGUGAC | GUCACACCAGACGCCAUUU | 351/352/353 |
| 0187 | actin depoly-merizing factor | ise2c.pk004.14 | AATACGATCAGTTCCTTGAGGAT | UACGAUCAGUUCCUUGAGG | CCUCAAGGAACUGAUCGUA | 354/355/356 |
| 0188 | dismutase; superoxide | ise2c.pk004.n19 | AATAATTTGTGTCATACCCTACG | UAAUUUGUGUCAUACCCUA | UAGGGUAUGACACAAAUUA | 357/358/359 |
| 0189 | dismutase; superoxide | ise2c.pk004.n19 | AAGTCAGTGACTGGTCAAATTCA | GUCAGUGACUGGUCAAAU | AAUUUGACCAGUCACUGAC | 360/361/362 |
| 0190 | dismutase; superoxide | ise2c.pk004.n19 | AATTAGGAGATGTTGCACCTGGT | UUAGGAGAUGUUGCACCUG | CAGGUGCAACAUCUCCUAA | 363/364/365 |
| 0191 | dismutase; superoxide | ise2c.pk004.n19 | AACAAACGGATGACCTAGGTTTG | CAAACGGAUGACCUAGGU | AACCUAGGUCAUCCGUUUG | 366/367/368 |
| 0192 | dismutase; superoxide | ise2c.pk004.n19 | AATGCTGCTAGCTCTATGTCTCC | UGCUGCUAGCUCUAUGUCU | AGACAUAGAGCUAGCAGCA | 369/370/371 |
| 0193 | superoxide dismutase | ise2c.pk005.f21 | AATTTGTGTCATACCCTACGCAA | UUUGUGUCAUACCCUACGC | GCGUAGGGUAUGACACAAA | 372/373/374 |
| 0194 | superoxide dismutase | ise2c.pk005.f21 | AAAAGGGCTTCATGTCGAAGGAG | AAGGGCUUCAUGUCGAAGG | CCUUCGACAUGAAGCCCUU | 375/376/377 |
| 0195 | superoxide dismutase | ise2c.pk005.f21 | AATTAGGAGATGTTGCACCTGGT | UUAGGAGAUGUUGCACCUG | CAGGUGCAACAUCUCCUAA | 378/379/380 |
| 0196 | adenylate kinase isozyme 3 | ise2c.pk010.h5 | AAAGGTCAGTAACTATGAGTGGT | AGGUCAGUAACUAUGAGUG | CACUCAUAGUUACUGACCU | 381/382/383 |
| 0197 | adenylate kinase isozyme 3 | ise2c.pk010.h5 | AAGAAATATGCTGTGGCACACGT | GAAAUAUGCUGUGGCACAC | GUGUGCCACAGCAUAUUUC | 384/385/386 |
| 0198 | adenylate kinase isozyme 3 | ise2c.pk010.h5 | AACTTGTACCTGATGATGTCATG | CUUGUACCUGAUGAUGUCA | UGACAUCAUCAGGUACAAG | 387/388/389 |
| 0199 | adenylate kinase isozyme 3 | ise2c.pk010.h5 | AACATTGGCTTCAACACTCCTAA | CAUUGGCUUCAACACUCCU | AGGAGUGUUGAAGCCAAUG | 390/391/392 |
| 0200 | adenylate kinase isozyme 3 | ise2c.pk010.h5 | AAGCGGCTGGAGATCTATGAGAG | GCGGCUGGAGAUCUAUGAG | CUCAUAGAUCUCCAGCCGC | 393/394/395 |
| 0201 | cedysone oxidase | ise2c.pk001.c18 | AACCCTCCCGAGGAGAGCATTAT | CCCUCCCGAGGAGAGCAU | AAUGCUCUCCUCGGGAGGG | 396/397/398 |
| 0202 | cedysone oxidase | ise2c.pk001.c18 | AACGCCCTACGACTGGAACTTCA | CGCCCUACGACUGGAACU | AGUUCCAGUCGUAGGGCG | 399/400/401 |
| 0203 | ecdysone oxidase | ise2c.pk001.c18 | AACTGGACCAACGTGCTGGACTA | CUGGACCAACGUGCUGGAC | GUCCAGCACGUUGGUCCAG | 402/403/404 |
| 0204 | innexin-2 | ise2c.pk004.p1 | AAAACATGGGAAGGAGGTCGCAT | AACAUGGGAAGGAGGUCGC | GCGACCUCCUUCCCAUGUU | 405/406/407 |
| 0205 | innexin-2 | ise2c.pk004.p1 | AAGTTGCTTGTGGACTACTTCCA | GUUGCUUGUGGACUACUUC | GAAGUAGUCCACAAGCAAC | 408/409/410 |

TABLE 2-continued

List of dsRNA primers.

| Primer # | Target Gene ID | Seq ID | Target | Sense strand | Antisense strand | SEQ ID NO Target/sense/antisense |
|---|---|---|---|---|---|---|
| 0206 | innexin-2 | ise2c.pk004.p1 | AACGTCGTGGGCCAGATCTTCTT | CGUCGUGGGCCAGAUCUUC | GAAGAUCUGGCCCACGACG | 411/412/413 |
| 0207 | innexin-2 | ise2c.pk004.p1 | AATACGGTCCTTCAGGAACCGTG | UACGGUCCUUCAGGAACCG | CGGUUCCUGAAGGACCGUA | 415/416/417 |
| 0208 | innexin-2 | ise2c.pk004.p1 | AATTTCGCTGATTTACCGCATGG | UUUCGCUGAUUUACCGCAU | AUGCGGUAAAUCAGCGAAA | 418/419/420 |

(Note:
the sense RNA primer sequence and the antisense RNA primer sequences shown in table 2 were generated with 2 thymine residues at the 3' end.)

Droplet Feeding Assay for Evaluation of 21 mer dsRNA Insecticidal Properties Against the Fall Armyworm *Spodoptera frugiperda*

10 nanoMole quantities of 21 mer desalted primers were purchased from Proligo (Sigma Aldrich, St. Louis, Mo.). The lyophilized sample is solubilized in nuclease free water at a 100 uMolar concentration. The stock solution was then diluted in 20% sucrose containing blue McCormick food coloring. 0.5 ul droplets of this solution were dispensed in a circle in a parafilm-lined 65 mm petridish. Sucrose blanks were used as controls. Between 20 and 30 neonate fall armyworms were then added to the middle of the droplet circle and the petri dish sealed with parafilm. After two hours, the neonates with blue digestive tracts were removed and placed on standard multispecies lepidopteran insect diet. Insects were evaluated at 48, 72, and 96 hours post challenge for mortality and growth inhibition.

Serial dilution assays starting with a high dose of 20 uM and including 10, 5, 2.5, 1.25, 0.6, and 0 uMolar concentrations were also performed in this manner.

Injection Feeding Assay for Evaluation of 21 mer dsRNA Insecticidal Properties Against the Fall Armyworm *Spodoptera frugiperda*

Second instar fall armyworm were injected using a micromanipulator and microinjection needles pulled on a Sutter Instrument (Novato, Calif.) P-2000 horizontal needle puller. The needle was back loaded with dsRNA solution. Initial injection experiments employed a concentration of 2 ug/ul (see Table X). This rate produced high mortality across all primers tested. Subsequent assays were performed with lower concentrations. Blue McCormick food coloring was included in the dsRNA solution to better visualize the injection process. Prior to injection, the insects were affixed to a microscope slide using a glue stick (Office Depot, Delray Beach, Fla.). The injection needle was connected to a 20 ml hypodermic syringe via Teflon tubing. The injection needle was then mounted on a Leitz micromanipulator. The dsRNA solution was dispensed from the microinjection needle by pressing on the plunger of the 20 ml syringe. Injection volumes were variable but averaged approximately 250mL (based on

TABLE 3

| | | Rep 1 | | Rep 2 | | |
|---|---|---|---|---|---|---|
| Primer # | Target gene | Insects treated | 72 H ave. weight | Insects treated | 72 H ave. weight | Combined ave. |
| 75 | juvenile hormone diol kinase | 9 | 10 | 11 | 11 | 11 |
| 83 | juvenile hormone diol kinase | 15 | 14 | 14 | 12 | 13 |
| 91 | V-ATPase A subunit | 14 | 14 | 11 | 15 | 14 |
| 99 | conserved hypothetical protein | 16 | 15 | 19 | 16 | 16 |
| 107 | novel sequence (cuticular protein?) | 16 | 14 | 13 | 15 | 14 |
| 115 | Eukaryotic initiation factor 4A | 16 | 9 | 18 | 14 | 12 |
| 123 | putative sar1 protein | 16 | 15 | 16 | 17 | 16 |
| 131 | Oligosaccharyl transferase 48 kDa subunit | 17 | 13 | 14 | 15 | 14 |
| 139 | myosin protein | 13 | 15 | 16 | 18 | 17 |
| 147 | inwardly rectifying K+ channel protein | 15 | 11 | 15 | 16 | 14 |
| 155 | alpha tubulin chain | 15 | 10 | 16 | 19 | 15 |
| | sucrose control | 14 | 17 | 15 | 18 | 18 |

Sucrose Droplet Feeding Assay.

Neonate larvae were fed 25 uMolar dsRNAs. Treated insects were weighed en masse at 72 hours and compared to sucrose controls. 2 replicates of the experiment were averaged.

injection of approximately 20 insects injected from a 5 ul volume loaded into the needle). Following injection, insects were removed from the microscope slide with the aid of a moistened fine camelhair brush. The insects were then placed on multispecies diet and were evaluated for mortality at 24 and 48 hours. Water injections were used as controls. Silencer® Negative Control #1, 2, and 3 siRNA control primers from Ambion (Austin, Tex.) were also included as negative controls.

TABLE 4

| Primer # | Target gene | No. injected | Alive | Dead |
|---|---|---|---|---|
| 75 | juvenile hormone diol kinase | 6 | 0 | 6 |
| 83 | juvenile hormone diol kinase | 6 | 0 | 6 |
| 91 | V-ATPase A subunit | 8 | 3 | 5 |
| 99 | conserved hypothetical sequence | 8 | 0 | 8 |
| 107 | novel sequence (cuticular protein | 8 | 0 | 8 |
| 115 | Eukaryotic initiation factor 4A | 8 | 0 | 8 |
| 123 | putative sar1 protein | 8 | 1 | 8 |
| 131 | Oligosaccharyl transferase 48 kDa subunit | 8 | 2 | 8 |
| 147 | inwardly rectifying K+ channel protein | 8 | 1 | 7 |
|  | Water | 8 | 7 | 1 |

Microinjection of dsRNAs [2 ug/ul].

TABLE 5

Microinjection of dsRNAs [0.7 ug/ul] into FAW neonate larvae

| | | Rep 1 | | | Rep 2 | | |
|---|---|---|---|---|---|---|---|
| Primer # | Target gene | # Injected | 24 H dead | 48 H dead | # Injected | 24 H dead | 48 H dead |
| 75 | juvenile hormone diol kinase 1 | 7 | 2 | 3 | 11 | 7 | 7 |
| 83 | juvenile hormone diol kinase 2 | 11 | 10 | 10 | 12 | 6 | 5 |
| 91 | V-ATPase A subunit | 13 | 9 | 7 | 9 | 9 | 9 |
| 99 | conserved hypothetical protein 1 | | | | 9 | 2 | 2 |
| 107 | novel sequence (cuticular protein?) | | | | 11 | 5 | 6 |
| 115 | Eukaryotic initiation factor 4A | | | | 8 | 6 | 6 |
| 123 | putative sar1 protein | | | | 13 | 9 | 9 |
| 131 | Oligosaccharyl transferase 48 kDa subunit | | | | 8 | 6 | 4 |
| 139 | myosin protein | | | | 10 | 4 | 4 |
| 147 | inwardly rectifying K+ channel protein | | | | 14 | 8 | 9 |
| 155 | alpha tubulin chain | | | | 11 | 9 | 9 |
|  | Ambion control primer 1 | 6 | 0 | 0 | 11 | 0 | 0 |
|  | Ambion control primer 2 | 11 | 0 | 0 | 8 | 0 | 0 |
|  | Ambion control primer 3 | 12 | 1 | 1 | 9 | 1 | 1 |

Microinjection Assay using 0.7 ug/ul dose of dsRNA 21 mers. Note; On some occasions, the mortality was lower at 48 hours than at 24 hours. This is due to moribund insects recovering at the later time point.

Topical Diet Assay for Evaluation of 21 mer dsRNA Insecticidal Properties Against the Fall Armyworm *Spodoptera frugiperda*

The term "topical diet assay" refers to assays where artificial diets are pipetted into microtiter plates and the dsRNA solution is dispensed on the surface of the diet. In the dsRNA experiments, 100 ul of diet was dispensed per well. The surface of the well was then treated with 10 ul of a dsRNA solution of varying concentrations. The plates were then infested with 1 neonate fall armyworm per well and sealed with mylar. The mylar seal was punctured with a small insect pin to allow for air exchange. Plates were then stored in a growth chamber at 28 C and the assay was scored for stunting or mortality at 4 days. Table 6-12 represents several experiments using this method. Table 13 provides a summary of the data.

In topical assay #1, the primers that previously showed activity in injection assays were tested in a FAW topical diet assay. These results are shown in Table 6. A 50 uMolar solution (0.66 ug/ul) was used as the test concentration. 5 ul of this sample was loaded onto the top of 100 ul of diet producing a final concentration of 2.5 uMolar or 30 ppm. In addition to A1-A11 (A12 is a negative control), the other samples are those with no known human orthologs. The plate was infested with aprox. 5 neonates/well. The scoring period was 72 hours.

In topical assay #2, primers were tested in a FAW topical diet assay, and the results are shown in table 7. In this experiment, the 2.7 ug/ul stock was diluted to a starting concentration of 0.67 ug/ul. 2 fold serial dilution was carried out to produce stocks of 0.32 ug/ul and 0.16 ug/ul. 5 ul of these stocks were added to the 100 ul of diet producing final concentrations of 30, 15, and 8 ppm in diet. The scoring period was 72 hours.

In topical assay #3, primers were tested in a FAW topical diet assay, and the results are shown in table 8. In this experiment, the 2.7 ug/ul stock was diluted to a starting concentration of 0.67 ug/ul. 2 fold serial dilution was carried out to produce stocks of 0.32 ug/ul and 0.16 ug/ul. 5 ul of these stocks were added to the 100 ul of diet producing final concentrations of 30, 15, and 8 ppm in diet. This is a replicate of the previous experiment. The scoring period was 72 hours.

In topical assay #4, primers were tested in a FAW topical diet assay, and the results are shown in table 9. In this experiment, the 2.7 ug/ul stock was diluted to a starting concentration of 0.67 ug/ul. 2 fold serial dilution was carried out to produce stocks of 0.32 ug/ul and 0.16 ug/ul. 5 ul of these stocks were added to the 100 ul of diet producing final concentrations of 30, 15, and 8 ppm in diet. The scoring period was 72 hours.

A summary of the topical assay data shown in tables 6-9 appears in Table 10.

In topical assay #5, primers were tested in a FAW topical diet assay and the results are shown in Table 11. 50 ul of 0.16 ug/ul primers were mixed with 50 ul water and then serially diluted. 10 ul of the sample then added to the wells. Therefore the first concentration was 10 ul×0.08 ug/ul=0.8 ug total dsRNA/100 ul diet=8 ppm. This was ½ the rate of previous experiments (assays # 1-4) where 5 ul of 0.32 showed activity. The scoring period was 72 hours. A score of "S" indicates clear stunting compared to untreated controls. A score of "ss" indicates live insects but exhibiting severe stunting defined as little or no growth beyond the neonate body size.

In topical assay #6, primers were tested in a FAW topical diet assay and the results are shown in Table 12. The first rate is 10 ul of the 0.16 ug/ul primer stock. From there, 50 ul of 0.16 ug/ul primer mixed with 50 ul water and then serially diluted. 10 ul of the sample was then added to the wells. Therefore first concentration was 10 ul×0.16 ug/ul=1.6 ug total dsRNA/100 ul diet=16 ppm. The scoring period was 72 hours.

TABLE 6

| Sample seq id | gene id | Target sequence | forward | reverse | 30 ppm | SEQ ID NO Target region/sense/antisense |
|---|---|---|---|---|---|---|
| 0075 | ise1c.pk002.m13 | Juvenile hormone query | AACATGGTATCCGACTTCAGGAA | CAUGGUAUCCGACUUCAGG | CCUGAAGUCGGAUACCAUG | | 51/52/53 |
| 0083 | ise1c.pk005.a15 | Juvenile hormone query | AAGTTCGCGTTCACTCTTGAAGA | GUUCGCGUUCACUCUUGAA | UUCAAGAGUGAACGCGAAC | + | 75/76/77 |
| 0085 | ise1c.pk006.d24 | Juvenile hormone query | AATCACGCTGAAACCACTGTATA | UCACGCUGAAACCACUGUA | UACAGUGGUUUCAGCGUGA | + | 81/82/83 |
| 0086 | ise1c.pk009.i4 | Juvenile hormone query | AAAATATGGCGCGCCTATTGTTT | AAUAUGGCGCGCCUAUUGU | ACAAUAGGCGCGCCAUAUU | | 84/85/86 |
| 0088 | ise1c.pk009.i5 | Juvenile hormone query | AAGTCATCGTTCCAAGTCTACCT | GUCAUCGUUCCAAGUCUAC | GUAGACUUGGAACGAUGAC | + | 90/91/92 |
| 0089 | ise1c.pk001.d19 | vacuolar query | AACCCCTTGAATGTTAAGGTCGG | CCCCUUGAAUGUUAAGGUC | GACCUUAACAUUCAAGGGG | + | 93/94/95 |
| 0091 | ise2c.pk001.d20 | vacuolar query | AACGTGTCCATGATGGCTGACTC | CGUGUCCAUGAUGGCUGAC | GUCAGCCAUCAUGGACACG | + | 99/100/101 |
| 0094 | ise2e.pk001.f20 | vacuolar query | AACTCTGACGTCATCATCTACGT | CUCUGACGUCAUCAUCUAC | GUAGAUGAUGACGUCAGAG | + | 108/109/110 |
| 0095 | ise2c.pk001.f21 | vacuolar query | AAGTGCTTGGGTAACCCCGACAG | GUGCUUGGGUAACCCCGAC | GUCGGGGUUACCCAAGCAC | + | 111/112/113 |
| 0099 | ise2c.pk010.h3 | cadherin query | AACACCATGACCCTCGTGTACAA | CACCAUGACCCUCGUGUAC | GUACACGAGGGUCAUGGUG | | 123/124/125 |
| 0107 | ise2c.pk011.h12 | cuticle protein | AAGGATCCTATGTGTACCAGGTT | GGAUCCUAUGUGUACCAGG | CCUGGUACACAUAGGAUCC | + | 138/139/140 |
| 0115 | ise2c.pk001.i23 | Translation initiation factor | AATTCTTCAGCAAATCGATACCA | UUCUUCAGCAAAUCGAUAC | GUAUCGAUUUGCUGAAGAA | | 162/163/164 |
| 0123 | ise2c.pk002.m10 | SAR1 | AAAATCGTCGGTTTTAGCGACGT | AAUCGUCGGUUUUAGCGAC | GUCGCUAAAACCGACGAUU | | 186/187/188 |
| 0131 | ise2c.pk005.h3 | phospho-oligo-saccha-ride . . . | AATTTGTGAGACTGGTGGCCGAA | UUUGUGAGACUGGUGGCCG | CGGCCACCAGUCUCACAAA | | 421/422/423 |
| 0139 | ise2c.pk001.j9 | Myosin | AAGACTTTCTTCATGTGGCCCAT | GACUUUCUUCAUGUGGCCC | GGGCCACAUGAAGAAAGUC | | 216/217/218 |
| 0147 | ise2c.pk003.f2 | Potassium inwardly rectifying protein | AATAAAGCGATGACCCCATAGGA | UAAAGCGAUGACCCCAUAG | CUAUGGGGUCAUCGCUUUA | + | 234/235/236 |
| 0155 | ise2c.pk001.l2 | Tubulin | AACTTATCACTGGTAAGGAAGAT | CUUAUCACUGGUAAGGAAG | CUUCCUUACCAGUGAUAAG | | 258/259/260 |

(Note:
the sense RNA primer sequence and the antisen RNA primer sequences shown in table 6 were generated with 2 thymine residues at the 3' end.)

TABLE 7

| Sample seq id | gene id | Target sequence | forward | reverse | 30 ppm | SEQ ID NO Target region/sense/antisense |
|---|---|---|---|---|---|---|
| 0075 | ise1c.pk002.m13 | Juvenile hormone query | AACATGGTATCCGACTTCAGGAA | CAUGGUAUCCGACUUCAGG | CCUGAAGUCGGAUACCAUG | | 51/52/53 |

TABLE 7-continued

| Sample seq id | gene id | Target sequence | forward | reverse | 30 ppm | SEQ ID NO Target region/ sense/antisense |
|---|---|---|---|---|---|---|
| 0076 | | AAGGTCGCTGACGA GAACAAGGA | GGUCGCUGACGAGAAC AAG | CUUGUUCUCGUCA GCGACC | | 54/55/56 |
| 0077 | | AAGTGTCCTGGGCTT GAGTTCCA | GUGUCCUGGGCUUGAG UUC | GAACUCAAGCCCA GGACAC | | 57/58/59 |
| 0078 | ise1c.pk003.f7 | Juvenile hormone query | AAGAAGAAGCTCCT CCACGTGTT | GAAGAAGCUCCUCCAC GUG | CACGUGGAGGAGC UUCUUC | | 60/61/62 |
| 0079 | | AAGGTCGCTGACGA GAACAAGGA | GGUCGCUGACGAGAAC AAG | CUUGUUCUCGUCA GCGACC | | 63/64/65 |
| 0080 | | AATGTCCTGGGGCTG AGTTTCAA | UGUCCUGGGGCUGAGU UUC | GAAACUCAGCCCCA GGACA | | 66/67/68 |
| 0081 | ise1c.pk005.a15 | Juvenile hormone query | AAGAATAAGCTCCTC CACGTGTT | GAAUAAGCUCCUCCAC GUG | CACGUGGAGGAGC UUAUUC | | 69/70/71 |
| 0082 | | AATTTGTCGAGGAG ACCCTATTG | UUUGUCGAGGAGACCC UAU | AUAGGGUCUCCUC GACAAA | | 72/73/74 |
| 0083 | | AAGTTCGCGTTCACT CTTGAAGA | GUUCGCGUUCACUCUU GAA | UUCAAGAGUGAAC GCGAAC | + | 75/76/77 |
| 0084 | ise1c.pk006.d24 | Juvenile hormone query | AACTGCCCCTTAACC TCATCTAT | CUGCCCCUUAACCUCA UCU | AGAUGAGGUUAAG GGGCAG | | 78/79/80 |
| 0085 | | AATCACGCTGAAAC CACTGTATA | UCACGCUGAAACCACU GUA | UACAGUGGUUUCA GCGUGA | | 81/82/83 |
| 0086 | ise2c.pk009.i4 | Juvenile hormone query | AAAATATGGCGCGC CTATTGTTT | AAUAUGGCGCGCCUAU UGU | ACAAUAGGCGCGC CAUAUU | | 84/85/86 |
| 0087 | | AACGTTCTCGGTCTT TCACTGCT | CGUUCUCGGUCUUUCA CUG | CAGUGAAAGACCG AGAACG | | 87/88/89 |
| 0088 | | AAGTCATCGTTCCAA GTCTACCT | GUCAUCGUUCCAAGUC UAC | GUAGACUUGGAAC GAUGAC | | 90/91/92 |
| 0089 | ise2c.pk001.d19 | vacuolar query | AACCCCTTGAATGTT AAGGTCGG | CCCCUUGAAUGUUAAG GUC | GACCUUAACAUUC AAGGGG | | 93/94/95 |
| 0090 | | AAGTACACCATGTTG CAAGTATG | GUACACCAUGUUGCAA GUA | UACUUGCAACAUG GUGUAC | | 96/97/98 |
| 0091 | | AACGTGTCCATGATG GCTGACTC | CGUGUCCAUGAUGGCU GAC | GUCAGCCAUCAUG GACACG | | 99/100/101 |
| 0092 | ise2c.pk001.e14 | vacuolar query | AAACCTACAAAATG GCCGAAAAC | ACCUACAAAAUGGCCG AAA | UUUCGGCCAUUUU GUAGGU | | 102/103/104 |
| 0093 | | AATCTACGGACCCTT CTTTGGAG | UCUACGGACCCUUCUU UGG | CCAAAGAAGGGUC CGUAGA | | 105/106/107 |
| 0094 | ise2c.pk001.f20 | vacuolar query | AACTCTGACGTCATC ATCTACGT | CUCUGACGUCAUCAUC UAC | GUAGAUGAUGACG UCAGAG | | 108/109/110 |
| 0095 | | AAGTGCTTGGGTAAC CCCGACAG | GUGCUUGGGUAACCCC GAC | GUCGGGGUUACCC AAGCAC | | 111/112/113 |
| 0096 | | AACTGGCTCATCTCC TACAGCAA | CUGGCUCAUCUCCUAC AGC | GCUGUAGGAGAUG AGCCAG | | 114/115/116 |
| 0097 | ise2c.pk010.h3 | cadherin query | AAACAGTGCGTCGT AATATATTC | ACAGUGCGUCGUAAUA UAU | AUAUAUUACGACG CACUGU | | 117/118/119 |
| 0098 | | AAGGCACATGGTCCT TCACTGAT | GGCACAUGGUCCUUCA CUG | CAGUGAAGGACCA UGUGCC | + | 120/121/122 |
| 0099 | | AACACCATGACCCTC GTGTACAA | CACCAUGACCCUCGUG UAC | GUACACGAGGGUC AUGGUG | | 123/124/125 |

TABLE 7-continued

| Sample seq id | gene id | Target sequence | forward | reverse | 30 ppm | SEQ ID NO Target region/sense/antisense |
|---|---|---|---|---|---|---|
| 0100 | ise2c.pk007.k24 | cuticle protein | AACGAGGCCGGATCTCTTAAGCA | CGAGGCCGGAUCUCUUAAG | CUUAAGAGAUCCGGCCUCG | | 457/458/459 |
| 0101 | | | AACTTCACACATAACTAGACAAA | CUUCACACAUAACUAGACA | UGUCUAGUUAUGUGUGAAG | | 460/461/462 |
| 0102 | | | AATGCGTGGCGATTTCAAACTTA | UUAGAAAUUAUAAGCCCAG | CUGGGCUUAUAAUUUCUAA | | 463/464/465 |
| 0103 | ise2c.pk011.a10 | cuticle protein | AAAAACACAGACCACGTTCACA | AAAACACAGACCACGUUCA | UGAACGUGGUCUGUGUUUU | + | 126/127/128 |
| 0104 | | | AATCGATGGTGGTGTTATTCGCT | UCGAUGGUGGUGUUAUUCG | CGAAUAACACCACCAUCGA | + | 129/130/131 |
| 0105 | ise2c.pk011.h12 | cuticle protein | AAAGAAAATGCTACGCGTTACGA | AGAAAAUGCUACGCGUAC | GUAACGCGUAGCAUUUUCU | | 132/133/134 |
| 0106 | | | AACCCTTGGACACTACTGGAAGA | CCCUUGGACACUACUGGAA | UUCCAGUAGUGUCCAAGGG | + | 135/136/137 |
| 0107 | | | AAGGATCCTATGTGTACCAGGTT | GGAUCCUAUGUGUACCAGG | CCUGGUACACAUAGGAUCC | | 138/139/140 |
| 0108 | ise2c.pk001.d22 | translation initiation factor | AAACTCGGCACACAACACAATGG | ACUCGGCACACAACACAAU | AUUGUGUUGUGUGCCGAGU | | 141/142/143 |
| 0109 | | | AATACGAAGATATCTGCCCTTCC | UACGAAGAUAUCUGCCCUU | AAGGGCAGAUAUCUUCGUA | + | 144/145/146 |
| 0110 | | | AATCAACAGCTCTTACATAAATG | UCAACAGCUCUUACAUAAA | UUUAUGUAAGAGCUGUUGA | | 147/148/149 |
| 0111 | ise2c.pk001.d9 | translation initiation factor | AAAGAAGATCAGAAGATTGGCCG | AGAAGAUCAGAAGAUUGGC | GCCAAUCUUCUGAUCUUCU | | 150/151/152 |
| 0112 | | | AAAAGCCGTCTGCTATCCAACAA | AAGCCGUCUGCUAUCCAAC | GUUGGAUAGCAGACGGCUU | + | 153/154/155 |
| 0113 | | | AATGCTAAATGCCATGCTTGCAT | UGCUAAAUGCCAUGCUUGC | GCAAGCAUGGCAUUUAGCA | | 156/157/158 |
| 0114 | ise2c.pk001.i23 | translation initiation factor | AAGATCAGAAGATTGGCCGGAAG | GAUCAGAAGAUUGGCCGGA | UCCGGCCAAUCUUCUGAUC | + | 159/160/161 |
| 0115 | | | AATTCTTCAGCAAATCGATACCA | UUCUUCAGCAAAUCGAUAC | GUAUCGAUUUGCUGAAGAA | | 162/163/164 |
| 0116 | | | AAATGCTGTCAAGAGGATTTAAA | AUGCUGUCAAGAGGAUUUA | UAAAUCCUCUUGACAGCAU | | 165/166/167 |
| 0117 | ise2c.pk001.l24 | translation initiation factor | AAGCTCGAGACTTGCTCTTGATG | GCUCGAGACUUGCUCUUGA | UCAAGAGCAAGUCUCGAGC | | 168/169/170 |
| 0118 | | | AACTGTTAGCTCAAGGTCTGCTA | CUGUUAGCUCAAGGUCUGC | GCAGACCUUGAGCUAACAG | | 171/172/173 |
| 0119 | | | AAGACTTTCTATCAGAATTTGCG | GACUUUCUAUCAGAAUUUG | CAAAUUCUGAUAGAAAGUC | + | 174/175/176 |
| 0120 | ise2c.pk005.b9 | translation initiation factor | AAACTTAATCATGGACGACGACA | ACUUAAUCAUGGACGACGA | UCGUCGUCCAUGAUUAAGU | | 177/178/179 |
| 0121 | | | AAAGAAGAAGAAGAAGGGAG | AGAAGAAGAAGAAGGGAG | CCCUUCUUCUUCUUCUUCU | + | 180/181/182 |
| 0122 | | | AAGATCAAGAGAATGTCGAGGAT | GAUCAAGAGAAUGUCGAGG | CCUCGACAUUCUCUUGAUC | + | 183/184/185 |
| 0123 | ise2c.pk002.m10 | SAR1 | AAAATCGTCGGTTTTAGCGACGT | AAUCGUCGGUUUUAGCGAC | GUCGCUAAAACCGACGAUU | | 186/187/188 |

TABLE 7-continued

| Sample seq id | gene id | Target sequence | forward | reverse | 30 ppm | SEQ ID NO Target region/sense/antisense |
|---|---|---|---|---|---|---|
| 0124 | | AACTGTCAATAGGCAGTATGCGT | CUGUCAAUAGGCAGUAUGC | GCAUACUGCCUAUUGACAG | | 189/190/191 |
| 0125 | | AACCTGTACCAACAGACCACTGG | CCUGUACCAACAGACCACU | AGUGGUCUGUUGGUACAGG | + | 192/193/194 |
| 0126 | ise2c.pk001.c14 | Elongation factor | AACCAAAAATGGGCAAGGAAAAG | CCAAAAAUGGGCAAGGAAA | UUUCCUUGCCCAUUUUUGG | + | 195/196/197 |
| 0127 | | AACGTGGTATCACCATCGATATT | CGUGGUAUCACCAUCGAUA | UAUCGAUGGUGAUACCACG | + | 198/199/200 |
| 0128 | | AACAAAATGGACTCCACTGAGCC | CAAAAUGGACUCCACUGAG | CUCAGUGGAGUCCAUUUUG | | 201/202/203 |
| 0129 | ise2c.pk001.d16 | Elongation factor | AATCCGTGACTAACCAAAAATGG | UCCGUGACUAACCAAAAAU | AUUUUUGGUUAGUCACGGA | + | 204/205/206 |
| 0130 | | AACATTGTCGTCATTGGACACGT | CAUUGUCGUCAUUGGACAC | GUGUCCAAUGACGACAAUG | | 207/208/209 |
| 0131 | ise2c.pk005.h3 | phospho-oligo-saccharide | AATTTGTGAGACTGGTGGCCGAA | UUUGUGAGACUGGUGGCCG | CGGCCACCAGUCUCACAAA | | 421/422/423 |
| 0132 | | AATCTGATTGTATTCGCCCCCTC | UCUGAUUGUAUUCGCCCCC | GGGGGCGAAUACAAUCAGA | | 424/245/426 |
| 0133 | | AACACTCTAGTTCTGCCTATTCT | CACUCUAGUUCUGCCUAUU | AAUAGGCAGAACUAGAGUG | | 427/228/429 |
| 0134 | ise2c.pk001.d21 | myosin | AACACACATCACAATGGCGGATA | CACACAUCACAAUGGCGGA | UCCGCCAUUGUGAUGUGUG | | 430/431/432 |
| 0135 | | AAGGATGGCATCATCGGCAAGAA | GGAUGGCAUCAUCGGCAAG | CUUGCCGAUGAUGCCAUCC | | 433/434/435 |
| 0136 | | AAAGGCTTCATCGACACCGCGAA | AGGCUUCAUCGACACCGCG | CGCGGUGUCGAUGAAGCCU | | 436/437/438 |
| 0137 | ise2c.pk001.j9 | myosin | AAACTCCAATTATAACCTACTAG | ACUCCAAUUAUAACCUACU | AGUAGGUUAUAAUUGGAGU | | 210/211/212 |
| 0138 | | AAGTACAAGGATCTGATCGGCAA | GUACAAGGAUCUGAUCGGC | GCCGAUCAGAUCCUUGUAC | + | 213/214/215 |
| 0139 | | AAGACTTTCTTCATGTGGCCCAT | GACUUUCUUCAUGUGGCCC | GGGCCACAUGAAGAAAGUC | | 216/217/218 |
| 0140 | ise2c.pk002.f12 | myosin | AAACAAAGTATCGCCTACACCGC | ACAAAGUAUCGCCUACACC | GGUGUAGGCGAUACUUUGU | | 439/440/441 |
| 0141 | | AATAGCGTCGATCTTCAACGACT | UAGCGUCGAUCUUCAACGA | UCGUUGAAGAUCGACGCUA | | 442/443/444 |
| 0142 | ise2c.pk001.b14 | potassium channel amino acid transporter | AACTCATAGAGCTTGATGTGTGG | CUCAUAGAGCUUGAUGUGU | ACACAUCAAGCUCUAUGAG | | 219/220/221 |
| 0143 | | AAGATGTGGATGACGTCACTGGT | GAUGUGGAUGACGUCACUG | CAGUGACGUCAUCCACAUC | | 221/223/224 |
| 0144 | | AACCTTCCTGATTCTCTTCTGTG | CCUUCCUGAUUCUCUUCUG | CAGAAGAGAAUCAGGAAGG | | 225/226/227 |
| 0145 | ise2c.pk003.f2 | potassium inwardly recti- fier . . . | AACAGTGCTTGTGATAAGTGAAC | CAGUGCUUGUGAUAAGUGA | UCACUUAUCACAAGCACUG | + | 228/229/230 |
| 0146 | | AAGTTAATGGTGACTGCCCTCGA | GUUAAUGGUGACUGCCCUC | GAGGGCAGUCACCAUUAAC | + | 231/232/233 |
| 0147 | | AATAAAGCGATGACCCCATAGGA | UAAAGCGAUGACCCCAUAG | CUAUGGGGUCAUCGCUUUA | + | 234/235/236 |

TABLE 7-continued

| Sample seq id | gene id | Target sequence | forward | reverse | 30 ppm | SEQ ID NO Target region/ sense/antisense |
|---|---|---|---|---|---|---|
| 0148 | ise2c.pk005.l20 amino acid transporter | AAACGGTACTGCAG CAAAAAGAC | ACGGUACUGCAGCAAA AAG | CUUUUUGCUGCAG UACCGU | + | 237/238/239 |
| 0149 | | AAGCTGCATACTTCT TGGCTCTC | GCUGCAUACUUCUUGG CUC | GAGCCAAGAAGUA UGCAGC | + | 240/241/242 |
| 0150 | | AAATGTTTACAGAG ACGCGATGA | AUGUUUACAGAGACGC GAU | AUCGCGUCUCUGU AAACAU | | 243/244/245 |
| 0151 | ise2c.pk001.d1 tubulin | AACGTCGATCTTACC GAGTTCCA | CGUCGAUCUUACCGAG UUC | GAACUCGGUAAGA UCGACG | + | 246/247/248 |
| 0152 | ise2c.pk001.k6 tubulin | AATTCAAAATGCGTG AGTGCATC | UUCAAAAUGCGUGAGU GCA | UGCACUCACGCAU UUUGAA | | 249/250/251 |
| 0153 | | AAATCGTAGACCTA GTCCTCGAC | AUCGUAGACCUAGUCC UCG | CGAGGACUAGGUC UACGAU | + | 252/253/254 |
| 0154 | ise2c.pk001.l2 tubulin | AAACTCAATTCAAA ATGCGTGAG | ACUCAAUUCAAAAUGC GUG | CACGCAUUUUGAA UUGAGU | + | 255/256/257 |
| 0155 | | AACTTATCACTGGTA AGGAAGAT | CUUAUCACUGGUAAGG AAG | CUUCCUUACCAGU GAUAAG | | 258/259/260 |
| 0156 | ise2c.pk002.b4 ubiquitin | AAGAGTTACGAACC GTCACCATA | GAGUUACGAACCGUCA CCA | UGGUGACGGUUCG UAACUC | | 261/262/263 |
| 0157 | | AAACTTAGTCCGGAT AATGAACC | ACUUAGUCCGGAUAAU GAA | UUCAUUAUCCGGA CUAAGU | + | 264/265/266 |
| 0158 | | AAGGCGATGTACGA GAACCTGTT | GGCGAUGUACGAGAAC CUG | CAGGUUCUCGUAC AUCGCC | + | 267/268/269 |
| 0159 | ise2c.pk001.j16 small nuclear ribonucleo- protein | AACGACAAGATGCT GAAGGAGAC | CGACAAGAUGCUGAAG GAG | CUCCUUCAGCAUCU UGUCG | + | 270/271/272 |
| 0160 | ise2c.pk006.h23 small nuclear ribonucleo- protein | AAGATAAAGGTCGC GTGTGGACC | GAUAAAGGUCGCGUGU GGA | UCCACACGCGACCU UUAUC | | 273/274/275 |
| 0161 | | AATGTCAAGACTGAT CCAAACAC | UGUCAAGACUGAUCCA AAC | GUUUGGAUCAGUC UUGACA | | 276/277/278 |
| 0162 | | AACATTCGAGTCTGA ACAGGTGG | CAUUCGAGUCUGAACA GGU | ACCUGUUCAGACU CGAAUG | + | 279/280/281 |

(Note: the sense RNA primer sequence and the antisense RNA primer sequences shown in table 7 were generated with 2 thymine residues at the 3' end.)

TABLE 8

| Sample seq id | gene id | Target sequence | forward | reverse | 30 ppm | SEQ ID NO Target region/ sense/antisense |
|---|---|---|---|---|---|---|
| 0075 | ise1c.pk002.m13 Juvenile hormone query | AACATGGTATCCGAC TTCAGGAA | CUGGUAUCCGACUUC AGG | CCUGAAGUCGGAU ACCAUG | | 51/52/53 |
| 0076 | | AAGGTCGCTGACGA GAACAAGGA | GGUCGCUGACGAGAAC AAG | CUUGUUCUCGUCA GCGACC | | 54/55/56 |
| 0077 | | AAGTGTCCTGGGCTT GAGTTCCA | GUGUCCUGGGCUUGAG UUC | GAACUCAAGCCCA GGACAC | | 57/58/59 |
| 0078 | ise1c.pk003.f7 Juvenile hormone query | AAGAAGAAGCTCCT CCACGTGTT | GAAGAAGCUCCUCCAC GUG | CACGUGGAGGAGC UUCUUC | | 60/61/62 |
| 0079 | | AAGGTCGCTGACGA GAACAAGGA | GGUCGCUGACGAGAAC AAG | CUUGUUCUCGUCA GCGACC | | 63/64/65 |

TABLE 8-continued

| Sample seq id | gene id | Target sequence | forward | reverse | 30 ppm | SEQ ID NO Target region/ sense/antisense |
|---|---|---|---|---|---|---|
| 0080 | | AATGTCCTGGGGCTGAGTTTCAA | UGUCCUGGGGCUGAGUUUC | GAAACUCAGCCCCAGGACA | + | 66/67/68 |
| 0081 | ise1c.pk005.a15 | Juvenile hormone query | AAGAATAAGCTCCTCCACGTGTT | GAAUAAGCUCCUCCACGUG | CACGUGGAGGAGCUUAUUC | | 69/70/71 |
| 0082 | | AATTTGTCGAGGAGACCCTATTG | UUUGUCGAGGAGACCCUAU | AUAGGGUCUCCUCGACAAA | | 72/73/74 |
| 0083 | | AAGTTCGCGTTCACTCTTGAAGA | GUUCGCGUUCACUCUUGAA | UUCAAGAGUGAACGCGAAC | NT | 75/76/77 |
| 0084 | ise1c.pk006.d24 | Juvenile hormone query | AACTGCCCCTTAACCTCATCTAT | CUGCCCCUUAACCUCAUCU | AGAUGAGGUUAAGGGGCAG | + | 78/79/80 |
| 0085 | | AATCACGCTGAAACCACTGTATA | UCACGCUGAAACCACUGUA | UACAGUGGUUUCAGCGUGA | | 81/82/83 |
| 0086 | ise2c.pk009.i4 | Juvenile hormone query | AAAATATGGCGCGCCTATTGTTT | AAUAUGGCGCGCCUAUUGU | ACAAUAGGCGCGCCAUAUU | | 84/85/86 |
| 0087 | | AACGTTCTCGGTCTTTCACTGCT | CGUUCUCGGUCUUUCACUG | CAGUGAAAGACCGAGAACG | | 87/88/89 |
| 0088 | | AAGTCATCGTTCCAAGTCTACCT | GUCAUCGUUCCAAGUCUAC | GUAGACUUGGAACGAUGAC | | 90/91/92 |
| 0089 | ise2c.pk001.d19 | vacuolar query | AACCCCTTGAATGTTAAGGTCGG | CCCCUUGAAUGUUAAGGUC | GACCUUAACAUUCAAGGGG | + | 93/94/95 |
| 0090 | | AAGTACACCATGTTGCAAGTATG | GUACACCAUGUUGCAAGUA | UACUUGCAACAUGGUGUAC | | 96/97/98 |
| 0091 | | AACGTGTCCATGATGGCTGACTC | CGUGUCCAUGAUGGCUGAC | GUCAGCCAUCAUGGACACG | + | 99/100/101 |
| 0092 | ise2c.pk001.e14 | vacuolar query | AAACCTACAAAATGGCCGAAAAC | ACCUACAAAAUGGCCGAAAA | UUUUCGGCCAUUUUGUAGGU | | 102/103/104 |
| 0093 | | AATCTACGGACCCTTCTTTGGAG | UCUACGGACCCUUCUUUGG | CCAAAGAAGGGUCCGUAGA | | 105/106/107 |
| 0094 | ise2c.pk001.f20 | vacuolar query | AACTCTGACGTCATCATCTACGT | CUCUGACGUCAUCAUCUAC | GUAGAUGAUGACGUCAGAG | | 108/109/110 |
| 0095 | | AAGTGCTTGGGTAACCCCGACAG | GUGCUUGGGUAACCCCGAC | GUCGGGGUUACCCAAGCAC | | 111/112/113 |
| 0096 | | AACTGGCTCATCTCCTACAGCAA | CUGGCUCAUCUCCUACAGC | GCUGUAGGAGAUGAGCCAG | | 114/115/116 |
| 0097 | ise2c.pk010.h3 | cadherin query | AAACAGTGCGTCGTAATATATTC | ACAGUGCGUCGUAAUAUAU | AUAUAUUACGACGCACUGU | | 117/118/119 |
| 0098 | | AAGGCACATGGTCCTTCACTGAT | GGCACAUGGUCCUUCACUG | CAGUGAAGGACCAUGUGCC | | 120/121/122 |
| 0099 | | AACACCATGACCCTCGTGTACAA | CACCAUGACCCUCGUGUAC | GUACACGAGGGUCAUGGUG | | 123/124/125 |
| 0100 | ise2c.pk007.k24 | cuticle protein | AACGAGGCCGGATCTCTTAAGCA | CGAGGCCGGAUCUCUUAAG | CUUAAGAGAUCCGGCCUCG | | 457/458/459 |
| 0101 | | AACTTCACACATAACTAGACAAA | CUUCACACAUAACUAGACA | UGUCUAGUUAUGUGUGAAG | | 460/461/462 |
| 0102 | | AATGCGTGGCGATTTCAAACTTA | UUAGAAAUUAUAAGCCCAG | CUGGGCUUAUAAUUUCUAA | | 463/464/465 |
| 0103 | ise2c.pk011.a10 | cuticle protein | AAAAAACACAGACCACGTTCACA | AAAACACAGACCACGUUCA | UGAACGUGGUCUGUGUUUU | | 126/127/128 |

TABLE 8-continued

| Sample seq id | gene id | Target sequence | forward | reverse | 30 ppm | SEQ ID NO Target region/ sense/antisense |
|---|---|---|---|---|---|---|
| 0104 | | AATCGATGGTGGTGT TATTCGCT | UCGAUGGUGGUGUUAU UCG | CGAAUAACACCACC AUCGA | + | 129/130/131 |
| 0105 | ise2c.pk011.h12 | cuticle protein | AAAGAAAATGCTAC GCGTTACGA | AGAAAAUGCUACGCGU UAC | GUAACGCGUAGCA UUUUCU | | 132/133/134 |
| 0106 | | AACCCTTGGACACTA CTGGAAGA | CCCUUGGACACUACUG GAA | UUCCAGUAGUGUC CAAGGG | | 135/136/137 |
| 0107 | | AAGGATCCTATGTGT ACCAGGTT | GGAUCCUAUGUGUACC AGG | CCUGGUACACAUA GGAUCC | | 138/139/140 |
| 0108 | ise2c.pk001.d22 | translation initiation factor | AAACTCGGCACACA ACACAATGG | ACUCGGCACACAACAC AAU | AUUGUGUUGUGUG CCGAGU | + | 141/142/143 |
| 0109 | | AATACGAAGATATCT GCCCTTCC | UACGAAGAUAUCUGCC CUU | AAGGGCAGAUAUC UUCGUA | + | 144/145/146 |
| 0110 | | AATCAACAGCTCTTA CATAAATG | UCAACAGCUCUUACAU AAA | UUUAUGUAAGAGC UGUUGA | + | 147/148/149 |
| 0111 | ise2c.pk001.d9 | translation initiation factor | AAAGAAGATCAGAA GATTGGCCG | AGAAGAUCAGAAGAUU GGC | GCCAAUCUUCUGA UCUUCU | | 150/151/152 |
| 0112 | | AAAAGCCGTCTGCTA TCCAACAA | AAGCCGUCUGCUAUCC AAC | GUUGGAUAGCAGA CGGCUU | | 153/154/155 |
| 0113 | | AATGCTAAATGCCAT GCTTGCAT | UGCUAAAUGCCAUGCU UGC | GCAAGCAUGGCAU UUAGCA | | 156/157/158 |
| 0114 | ise2c.pk001.i23 | translation initiation factor | AAGATCAGAAGATT GGCCGGAAG | GAUCAGAAGAUUGGCC GGA | UCCGGCCAAUCUUC UGAUC | + | 159/160/161 |
| 0115 | | AATTCTTCAGCAAAT CGATACCA | UUCUUCAGCAAAUCGA UAC | GUAUCGAUUUGCU GAAGAA | NT | 162/163/164 |
| 0116 | | AAATGCTGTCAAGA GGATTTAAA | AUGCUGUCAAGAGGAU UUA | UAAAUCCUCUUGA CAGCAU | | 165/166/167 |
| 0117 | ise2c.pk001.l24 | translation initiation factor | AAGCTCGAGACTTGC TCTTGATG | GCUCGAGACUUGCUCU UGA | UCAAGAGCAAGUC UCGAGC | + | 168/169/170 |
| 0118 | | AACTGTTAGCTCAAG GTCTGCTA | CUGUUAGCUCAAGGUC UGC | GCAGACCUUGAGC UAACAG | + | 171/172/173 |
| 0119 | | AAGACTTTCTATCAG AATTTGCG | GACUUUCUAUCAGAAU UUG | CAAAUUCUGAUAG AAAGUC | | 174/175/176 |
| 0120 | ise2c.pk005.b9 | translation initiation factor | AAACTTAATCATGGA CGACGACA | ACUUAAUCAUGGACGA CGA | UCGUCGUCCAUGA UUAAGU | | 177/178/179 |
| 0121 | | AAAGAAGAAGAAGA AGAAGGGAG | AGAAGAAGAAGAAGAA GGG | CCCUUCUUCUUCUU CUUCU | + | 180/181/182 |
| 0122 | | AAGATCAAGAGAAT GTCGAGGAT | GAUCAAGAGAAUGUCG AGG | CCUCGACAUUCUCU UGAUC | + | 183/184/185 |
| 0123 | ise2c.pk002.m10 | SAR1 | AAAATCGTCGGTTTT AGCGACGT | AAUCGUCGGUUUUAGC GAC | GUCGCUAAAACCG ACGAUU | + | 186/187/188 |
| 0124 | | AACTGTCAATAGGC AGTATGCGT | CUGUCAAUAGGCAGUA UGC | GCAUACUGCCUAU UGACAG | + | 189/190/191 |
| 0125 | | AACCTGTACCAACA GACCACTGG | CCUGUACCAACAGACC ACU | AGUGGUCUGUUGG UACAGG | + | 192/193/194 |
| 0126 | ise2c.pk001.c14 | Elongation factor | AACCAAAAATGGGC AAGGAAAAG | CCAAAAAUGGGCAAGG AAA | UUUCCUUGCCCAU UUUUGG | + | 195/196/197 |
| 0127 | | AACGTGGTATCACCA TCGATATT | CGUGGUAUCACCAUCG AUA | UAUCGAUGGUGAU ACCACG | + | 198/199/200 |

TABLE 8-continued

| Sample seq id | gene id | Target sequence | forward | reverse | 30 ppm | SEQ ID NO Target region/ sense/antisense |
|---|---|---|---|---|---|---|
| 0128 | | AACAAAATGGACTCCACTGAGCC | CAAAAUGGACUCCACUGAG | CUCAGUGGAGUCCAUUUUG | + | 201/202/203 |
| 0129 | ise2c.pk001.d16 | Elongation factor | AATCCGTGACTAACCAAAAATGG | UCCGUGACUAACCAAAAAU | AUUUUUGGUUAGUCACGGA | + | 204/205/206 |
| 0130 | | AACATTGTCGTCATTGGACACGT | CAUUGUCGUCAUUGGACAC | GUGUCCAAUGACGACAAUG | + | 207/208/209 |
| 0131 | ise2c.pk005.h3 | phospho-oligo-saccha-ride... | AATTTGTGAGACTGGTGGCCGAA | UUUGUGAGACUGGUGGCCG | CGGCCACCAGUCUCACAAA | | 421/422/423 |
| 0132 | | AATCTGATTGTATTCGCCCCCTC | UCUGAUUGUAUUCGCCCCC | GGGGGCGAAUACAAUCAGA | | 424/425/426 |
| 0133 | | AACACTCTAGTTCTGCCTATTCT | CACUCUAGUUCUGCCUAUU | AAUAGGCAGAACUAGAGUG | | 427/428/429 |
| 0134 | ise2c.pk001.d21 | myosin | AACACACATCACAATGGCGGATA | CACACAUCACAAUGGCGGA | UCCGCCAUUGUGAUGUGUG | | 430/431/432 |
| 0135 | | AAGGATGGCATCATCGGCAAGAA | GGAUGGCAUCAUCGGCAAG | CUUGCCGAUGAUGCCAUCC | | 433/434/435 |
| 0136 | | AAAGGCTTCATCGACACCGCGAA | AGGCUUCAUCGACACCGCG | CGCGGUGUCGAUGAAGCCU | | 436/437/438 |
| 0137 | ise2c.pk001.j9 | myosin | AAACTCCAATTATAACCTACTAG | ACUCCAAUUAUAACCUACU | AGUAGGUUAUAAUUGGAGU | | 210/211/212 |
| 0138 | | AAGTACAAGGATCTGATCGGCAA | GUACAAGGAUCUGAUCGGC | GCCGAUCAGAUCCUUGUAC | | 213/214/215 |
| 0139 | | AAGACTTTCTTCATGTGGCCCAT | GACUUUCUUCAUGUGGCCC | GGGCCACAUGAAGAAAGUC | | 216/217/218 |
| 0140 | ise2c.pk002.f12 | myosin | AAACAAAGTATCGCCTACACCGC | ACAAAGUAUCGCCUACACC | GGUGUAGGCGAUACUUUGU | | 439/440/441 |
| 0141 | | AATAGCGTCGATCTTCAACGACT | UAGCGUCGAUCUUCAACGA | UCGUUGAAGAUCGACGCUA | | 442/443/444 |
| 0142 | ise2c.pk001.b14 | potassium channel amino acid transporter | AACTCATAGAGCTTGATGTGTGG | CUCAUAGAGCUUGAUGUGU | ACACAUCAAGCUCUAUGAG | | 219/220/221 |
| 0143 | | AAGATGTGGATGACGTCACTGGT | GAUGUGGAUGACGUCACUG | CAGUGACGUCAUCCACAUC | + | 221/223/224 |
| 0144 | | AACCTTCCTGATTCTCTTCTGTG | CCUUCCUGAUUCUCUUCUG | CAGAAGAGAAUCAGGAAGG | + | 225/226/227 |
| 0145 | ise2c.pk003.f2 | potassium inwardly recti-fier... | AACAGTGCTTGTGATAAGTGAAC | CAGUGCUUGUGAUAAGUGA | UCACUUAUCACAAGCACUG | + | 228/229/230 |
| 0146 | | AAGTTAATGGTGACTGCCCTCGA | GUUAAUGGUGACUGCCCUC | GAGGGCAGUCACCAUUAAC | + | 231/232/233 |
| 0147 | | AATAAAGCGATGACCCCATAGGA | UAAAGCGAUGACCCCAUAG | CUAUGGGGUCAUCGCUUUA | + | 234/235/236 |
| 0148 | ise2c.pk005.l20 | amino acid transporter | AAACGGTACTGCAGCAAAAAGAC | ACGGUACUGCAGCAAAAAG | CUUUUUGCUGCAGUACCGU | + | 237/238/239 |
| 0149 | | AAGCTGCATACTTCTTGGCTCTC | GCUGCAUACUUCUUGGCUC | GAGCCAAGAAGUAUGCAGC | + | 240/241/242 |
| 0150 | | AAATGTTTACAGAGACGCGATGA | AUGUUUACAGAGACGCGAU | AUCGCGUCUCUGUAAACAU | + | 243/244/245 |

TABLE 8-continued

| Sample seq id | gene id | Target sequence | forward | reverse | 30 ppm | SEQ ID NO Target region/ sense/antisense |
|---|---|---|---|---|---|---|
| 0151 | ise2c.pk001.d1 | tubulin | AACGTCGATCTTACCGAGTTCCA | CGUCGAUCUUACCGAGUUC | GAACUCGGUAAGAUCGACG | + | 246/247/248 |
| 0152 | ise2c.pk001.k6 | tubulin | AATTCAAAATGCGTGAGTGCATC | UUCAAAAUGCGUGAGUGCA | UGCACUCACGCAUUUUGAA | + | 249/250/251 |
| 0153 | | | AAATCGTAGACCTAGTCCTCGAC | AUCGUAGACCUAGUCCUCG | CGAGGACUAGGUCUACGAU | + | 252/253/254 |
| 0154 | ise2c.pk001.l2 | tubulin | AAACTCAATTCAAAATGCGTGAG | ACUCAAUUCAAAAUGCGUG | CACGCAUUUUGAAUUGAGU | + | 255/256/257 |
| 0155 | | | AACTTATCACTGGTAAGGAAGAT | CUUAUCACUGGUAAGGAAG | CUUCCUUACCAGUGAUAAG | | 258/259/260 |
| 0156 | ihse2c.pk002.b4 | ubiquitin | AAGAGTTACGAACCGTCACCATA | GAGUUACGAACCGUCACCA | UGGUGACGGUUCGUAACUC | + | 261/262/263 |
| 0157 | | | AAACTTAGTCCGGATAATGAACC | ACUUAGUCCGGAUAAUGAAt | UUCAUUAUCCGGACUAAGU | + | 264/265/266 |
| 0158 | | | AAGGCGATGTACGAGAACCTGTT | GGCGAUGUACGAGAACCUG | CAGGUUCUCGUACAUCGCC | + | 267/268/269 |
| 0159 | ise2c.pk001.j16 | small nuclear ribonucleo-protein | AACGACAAGATGCTGAAGGAGAC | CGACAAGAUGCUGAAGGAG | CUCCUUCAGCAUCUUGUCG | + | 270/271/272 |
| 0160 | ise2c.pk006.h23 | small nuclear ribonucleo-protein | AAGATAAAGGTCGCGTGTGGACC | GAUAAAGGUCGCGUGUGGA | UCCACACGCGACCUUUAUC | + | 273/274/275 |
| 0161 | | | AATGTCAAGACTGATCCAAACAC | UGUCAAGACUGAUCCAAAC | GUUUGGAUCAGUCUUGACA | + | 276/277/278 |
| 0162 | | | AACATTCGAGTCTGAACAGGTGG | CAUUCGAGUCUGAACAGGUt | ACCUGUUCAGACUCGAAUG | + | 279/280/281 |

(Note:
the sense RNA primer sequence and the antisense RNA primer sequences shown in table 8 were generated with 2 thymine residues at the 3' end.)

TABLE 9

| Sample seq id | gene id | Target sequence | forward | reverse | 30 ppm | 15 ppm | 8 ppm | SEQ ID NO Target region/ sense/antisense |
|---|---|---|---|---|---|---|---|---|
| 0075 | | | AAGGTCGCTGACGAGAACAAGGA | GGUCGCUGACGAGAACAAG | CUUGUUCUGGUCAGCGACC | | | | 51/52/53 |
| 0076 | | | AAGTGTCCTGGGCTTGAGTTCCA | GUGUCCUGGGCUUGAGUUC | GAACUCAAGCCCAGGACAC | + | | | 54/55/56 |
| 0077 | ise1c.pk003.f7 | Juvenile hormone query | AAGAAGAAGCTCCTCCACGTGTT | GAAGAAGCUCCUCCACGUG | CACGUGGAGGAGCUUCUUC | | | | 57/58/59 |
| 0078 | | | AAGGTCGCTGACGAGAACAAGGA | GGUCGCUGACGAGAACAAG | CUUGUUCUCGUCAGCGACC | | | | 60/61/62 |
| 0079 | | | AATGTCCTGGGCTGAGTTTCAA | UGUCCUGGGCUGAGUUUC | GAAACUCAGCCCAGGACA | | | | 63/64/65 |
| 0080 | ise1c.pk005.a15 | Juvenile hormone query | AAGAATAAGCTCCTCCACGTGTT | GAAUAAGCUCCUCCACGUG | CACGUGGAGGAGCUUAUUC | + | + | | 66/67/68 |
| 0081 | | | AATTTGTCGAGGAGACCCTATTG | UUUGUCGAGGAGACCCUAU | AUAGGGUCUCCUCGACAAA | | | | 69/70/71 |
| 0082 | | | AAGTTCGCGTTCACTCTTGAAGA | GUUCGCGUUCACUCUUGAA | UUCAAGAGUGAACGCGAAC | | | NT | 72/73/74 |

TABLE 9-continued

| Sample seq id | gene id | Target sequence | forward | reverse | 30 ppm | 15 ppm | 8 ppm | SEQ ID NO Target region/ sense/antisense |
|---|---|---|---|---|---|---|---|---|
| 0083 | ise1c.pk006.d24 | Juvenile hormone query | AACTGCCCCTTAACC TCATCTAT | CUGCCCCUUAA CCUCAUCUtt | AGAUGAGGUUAA GGGGCAG | | | | 75/76/77 |
| 0084 | | | AATCACGCTGAAAC CACTGTATA | UCACGCUGAAA CCACUGUAtt | UACAGUGGUUUC AGCGUGA | + | | | 78/79/80 |
| 0085 | ise2c.pk009.j4 | Juvenile hormone query | AAAATATGGCGCGC CTATTGTTT | AAUAUGGCGCG CCUAUUGU | ACAAUAGGCGCGC CAUAUU | | | | 81/82/83 |
| 0086 | | | AACGTTCTCGGTCTT TCACTGCT | CGUUCUCGGUC UUUCACUG | CAGUGAAAGACCG AGAACG | | | | 84/85/86 |
| 0087 | | | AAGTCATCGTTCCAA GTCTACCT | GUCAUCGUUCC AAGUCUAC | GUAGACUUGGAA CGAUGAC | + | | | 87/88/89 |
| 0088 | ise2c.pk001.d19 | vacuolar query | AACCCCTTGAATGTT AAGGTCGG | CCCCUUGAAUG UUAAGGUC | GACCUUAACAUUC AAGGGG | + | | | 90/91/92 |
| 0089 | | | AAGTACACCATGTT GCAAGTATG | GUACACCAUGU UGCAAGUA | UACUUGCAACAUG GUGUAC | | | | 93/94/95 |
| 0090 | | | AACGTGTCCATGAT GGCTGACTC | CGUGUCCAUGA UGGCUGAC | GUCAGCCAUCAUG GACACG | NT | | | 96/97/98 |
| 0091 | ise2c.pk001.e14 | vacuolar query | AAACCTACAAAATG GCCGAAAAC | ACCUACAAAAU GGCCGAAA | UUUCGGCCAUUUU GUAGGU | | | | 99/100/101 |
| 0092 | | | AATCTACGGACCCTT CTTTGGAG | UCUACGGACCC UUCUUUGG | CCAAAGAAGGGUC CGUAGA | + | | | 102/103/104 |
| 0093 | ise2c.pk001.f20 | vacuolar query | AACTCTGACGTCATC ATCTACGT | CUCUGACGUCA UCAUCUAC | GUAGAUGAUGAC GUCAGAG | | | | 105/106/107 |
| 0094 | | | AAGTGCTTGGGTAA CCCCGACAG | GUGCUUGGGUA ACCCCGAC | GUCGGGGUUACCC AAGCAC | | | | 108/109/110 |
| 0095 | | | AACTGGCTCATCTCC TACAGCAA | CUGGCUCAUCU CCUACAGC | GCUGUAGGAGAU GAGCCAG | | | | 111/112/113 |
| 0096 | ise2c.pk010.h3 | cadherin query | AAACAGTGCGTCGT AATATATTC | ACAGUGCGUCG UAAUAUAU | AUAUAUUACGAC GCACUGU | | | | 114/115/116 |
| 0097 | | | AAGGCACATGGTCC TTCACTGAT | GGCACAUGGUC CUUCACUG | CAGUGAAGGACCA UGUGCC | | | | 117/118/119 |
| 0098 | | | AACACCATGACCCT CGTGTACAA | CACCAUGACCC UCGUGUAC | GUACACGAGGGUC AUGGUG | NT | | | 120/121/122 |
| 0099 | ise2c.pk007.k24 | cuticle protein | AACGAGGCCGGATC TCTTAAGCA | CGAGGCCGGAU CUCUUAAG | CUUAAGAGAUCCG GCCUCG | | | | 123/124/125 |
| 0100 | | | AACTTCACACATAA CTAGACAAA | CUUCACACAUA ACUAGACA | UGUCUAGUUAUG UGUGAAG | | | | 457/458/459 |
| 0101 | | | AATGCGTGGCGATTT CAAACTTA | UUAGAAAUUAU AAGCCCAG | CUGGGCUUAUAA UUUCUAA | | | | 460/461/462 |
| 0102 | ise2c.pk011.a10 | cuticle protein | AAAAAACACAGACC ACGTTCACA | AAAACACAGAC CACGUUCA | UGAACGUGGUCU GUGUUUU | | | | 463/464/465 |
| 0103 | | | AATCGATGGTGGTG TTATTCGCT | UCGAUGGUGGU GUUAUUCG | CGAAUAACACCAC CAUCGA | + | | | 126/127/128 |
| 0104 | ise2c.pk011.h12 | cuticle protein | AAAGAAAATGCTAC GCGTTACGA | AGAAAAUGCUA CGCGUUAC | GUAACGCGUAGCA UUUUCU | | | | 129/130/131 |
| 0105 | | | AACCCTTGGACACT ACTGGAAGA | CCCUUGGACAC UACUGGAA | UUCCAGUAGUGUC CAAGGG | + | | | 132/133/134 |
| 0106 | | | AAGGATCCTATGTGT ACCAGGTT | AGGAUCCUAUGU GUACCAGG | CCUGGUACACAUA GGAUCC | NT | | | 135/136/137 |

TABLE 9-continued

| Sample seq id | gene id | Target sequence | forward | reverse | 30 ppm | 15 ppm | 8 ppm | SEQ ID NO Target region/ sense/antisense |
|---|---|---|---|---|---|---|---|---|
| 0107 | ise2c.pk001.d22 | translation initiation factor | AAACTCGGCACACA ACACAATGG | ACUCGGCACAC AACACAAU | AUUGUGUUGUGU GCCGAGU | | | | 138/139/140 |
| 0108 | | | AATACGAAGATATC TGCCCTTCC | UACGAAGAUAU CUGCCCUU | AAGGGCAGAUAU CUUCGUA | + | | | 141/142/143 |
| 0109 | | | AATCAACAGCTCTTA CATAAATG | UCAACAGCUCU UACAUAAA | UUUAUGUAAGAG CUGUUGA | + | | | 144/145/146 |
| 0110 | ise2c.pk001.d9 | translation initiation factor | AAAGAAGATCAGAA GATTGGCCG | AGAAGAUCAGA AGAUUGGC | GCCAAUCUUCUGA UCUUCU | | | | 147/148/149 |
| 0111 | | | AAAAGCCGTCTGCT ATCCAACAA | AAGCCGUCUGC UAUCCAAC | GUUGGAUAGCAG ACGGCUU | | | | 150/151/152 |
| 0112 | | | AATGGTAAATGCCA TGCTTGCAT | UGCUAAAUGCC AUGCUUGC | GCAAGCAUGGCAU UUAGCA | + | | | 153/154/155 |
| 0113 | ise2c.pk001.i23 | translation initiation factor | AAGATCAGAAGATT GGCCGGAAG | GAUCAGAAGAU UGGCCGGA | UCCGGCCAAUCUU CUGAUC | + | | | 156/157/158 |
| 0114 | | | AATTCTTCAGCAAAT CGATACCA | UUCUUCAGCAA AUCGAUAC | GUAUCGAUUUGC UGAAGAA | NT | | | 159/160/161 |
| 0115 | | | AAATGCTGTCAAGA GGATTTAAA | AUGCUGUCAAG AGGAUUUA | UAAAUCCUCUUGA CAGCAU | + | | | 162/163/164 |
| 0116 | ise2cpk001.l24 | translation initiation factor | AAGCTCGAGACTTG CTCTTGATG | GCUCGAGACUU GCUCUUGA | UCAAGAGCAAGUC UCGAGC | + | | | 165/166/167 |
| 0117 | | | AACTGTTAGCTCAA GGTCTGCTA | CUGUUAGCUCA AGGUCUGC | GCAGACCUUGAGC UAACAG | + | | | 168/169/170 |
| 0118 | | | AAGACTTTCTATCAG AATTTGCG | GACUUUCUAUC AGAAUUUG | CAAAUUCUGAUA GAAAGUC | | | | 171/172/173 |
| 0119 | ise2c.pk005.b9 | translation initiation factor | AAACTTAATCATGG ACGACGACA | ACUUAAUCAUG GACGACGA | UCGUCGUCCAUGA UUAAGU | | | | 174/175/176 |
| 0120 | | | AAAGAAGAAGAAGA AGAAGGGAG | AGAAGAAGAAG AAGAAGGG | CCCUUCUUCUUCU UCUUCU | + | | | 177/178/179 |
| 0121 | | | AAGATCAAGAGAAT GTCGAGGAT | GAUCAAGAGAA UGUCGAGG | CCUCGACAUUCUC UUGAUC | + | + | + | 180/181/182 |
| 0122 | ise2c.pk002.m10 | | AAAATCGTCGGTTTT AGCGACGT | AAUCGUCGGUU UUAGCGAC | GUCGCUAAAACCG ACGAUU | NT | | | 183/184/185 |
| 0123 | | SAR1 | AACTGTCAATAGGC AGTATGCGT | CUGUCAAUAGG CAGUAUGC | GCAUACUGCCUAU UGACAG | + | | | 186/187/188 |
| 0124 | | | AACCTGTACCAACA GACCACTGG | CCUGUACCAAC AGACCACU | AGUGGUCUGUUG GUACAGG | + | | | 189/190/191 |
| 0125 | ise2c.pk001.c14 | Elongation factor | AACCAAAAATGGGC AAGGAAAAG | CCAAAAAUGGG CAAGGAAA | UUUCCUUGCCCAU UUUUGG | + | | | 192/193/194 |
| 0126 | | | AACGTGGTATCACC ATCGATATT | CGUGGUAUCAC CAUCGAUA | UAUCGAUGGUGA UACCACG | + | | | 195/196/197 |
| 0127 | | | AACAAAATGGACTC CACTGAGCC | CAAAAUGGACU CCACUGAG | CUCAGUGGAGUCC AUUUUG | + | | | 198/199/200 |
| 0128 | ise2c.pk001.d16 | Elongation factor | AATCCGTGACTAAC CAAAATGG | UCCGUGACUAA CCAAAAU | AUUUUUGGUUAG UCACGGA | + | | | 201/202/203 |
| 0129 | | | AACATTGTCGTCATT GGACACGT | CAUUGUCGUCA UUGGACAC | GUGUCCAAUGACG ACAAUG | | | | 204/205/206 |

TABLE 9-continued

| Sample seq id | gene id | Target sequence | forward | reverse | 30 ppm | 15 ppm | 8 ppm | SEQ ID NO Target region/ sense/antisense |
|---|---|---|---|---|---|---|---|---|
| 0130 | ise2c.pk005.h3 | phospho- oligo- saccha- ride . . . | AATTTGTGAGACTG GTGGCCGAA | UUUGUGAGACU GGUGGCCG | CGGCCACCAGUCU CACAAA | | | NT | 207/208/209 |
| 0131 | | | AATCTGATTGTATTC GCCCCCTC | UCUGAUUGUAU UCGCCCCC | GGGGGCGAAUAC AAUCAGA | | | | 421/422/423 |
| 0132 | | | AACACTCTAGTTCTG CCTATTCT | CACUCUAGUUC UGCCUAUU | AAUAGGCAGAAC UAGAGUG | | | | 424/425/426 |
| 0133 | ise2c.pk001.d21 | myosin | AACACACATCACAA TGCGGATA | CACACAUCACA AUGGCGGA | UCCGCCAUUGUGA UGUGUG | | | | 427/428/429 |
| 0134 | | | AAGGATGGCATCAT CGGCAAGAA | GGAUGGCAUCA UCGGCAAG | CUUGCCGAUGAUG CCAUCC | | | | 430/431/432 |
| 0135 | | | AAAGGCTTCATCGA CACCGCGAA | AGGCUUCAUCG ACACCGCG | CGCGGUGUCGAUG AAGCCU | | | | 433/434/435 |
| 0136 | ise2c.pk001.j9 | myosin | AAACTCCAATTATA ACCTACTAG | ACUCCAAUUAU AACCUACU | AGUAGGUUAUAA UUGGAGU | | | | 436/437/438 |
| 0137 | | | AAGTACAAGGATCT GATCGGCAA | GUACAAGGAUC UGAUCGGC | GCCGAUCAGAUCC UUGUAC | | | | 210/211/212 |
| 0138 | | | AAGACTTTCTTCATG TGGCCCAT | GACUUUCUUCA UGUGGCCC | GGGCCACAUGAAG AAAGUC | | | NT | 213/214/215 |
| 0139 | ise2c.pk002.f12 | myosin | AAACAAAGTATCGC CTACACCGC | ACAAAGUAUCG CUACACCG | GGUGUAGGGGAU ACUUUGU | | | | 216/217/218 |
| 0140 | | | AATAGCGTCGATCTT CAACGACT | UAGCGUCGAUC UUCAACGA | UCGUUGAAGAUC GACGCUA | | | | 439/440/441 |
| 0141 | ise2c.pk001.b14 | potassium channel amino acid transporter | AACTCATAGAGCTT GATGTGTGG | CUCAUAGAGCU UGAUGUGU | ACACAUCAAGCUC UAUGAG | | | | 442/443/444 |
| 0142 | | | AAGATGTGGATGAC GTCACTGGT | GAUGUGGAUGA CGUCACUG | CAGUGACGUCAUC CACAUC | | | | 219/220/221 |
| 0143 | | | AACCTTCCTGATTCT CTTCTGTG | CCUUCCUGAUU CUCUUCUG | CAGAAGAGAAUC AGGAAGG | + | | | 222/223/224 |
| 0144 | ise2c.pk003.f2 | potassium inwardly recti- fier . . . | AACAGTGCTTGTGAT AAGTGAAC | CAGUGCUUGUG AUAAGUGA | UCACUUAUCACAA GCACUG | + | + | | 225/226/227 |
| 0145 | | | AAGTTAATGGTGAC TGCCCTCGA | GUUAAUGGUGA CUGCCCUC | GAGGGCAGUCACC AUUAAC | + | | | 228/229/230 |
| 0146 | | | AATAAAGCGATGAC CCCATAGGA | UAAAGCGAUGA CCCCAUAG | CUAUGGGGUCAUC GCUUUA | | | NT | 231/232/233 |
| 0147 | ise2c.pk005.l20 | amino acid transporter | AAACGGTACTGCAG CAAAAAGAC | ACGGUACUGCA GCAAAAAG | CUUUUUGCUGCAG UACCGU | + | | | 234/235/236 |
| 0148 | | | AAGCTGCATACTTCT TGGCTCTC | GCUGCAUACUU CUUGGCUC | GAGCCAAGAAGU AUGCAGC | | | | 237/238/239 |
| 0149 | | | AAATGTTTACAGAG ACGCGATGA | AUGUUUACAGA GACGCGAU | AUCGCGUCUCUGU AAACAU | + | | | 240/241/242 |
| 0150 | ise2c.pk001.d1 | tubulin | AACGTCGATCTTACC GAGTTCCA | CGUCGAUCUUA CCGAGUUC | GAACUCGGUAAG AUCGACG | + | + | | 243/244/245 |
| 0151 | ise2c.pk001.k6 | tubulin | AATTCAAAATGCGT GAGTGCATC | UUCAAAAUGCG UGAGUGCA | UGCACUCACGCAU UUUGAA | + | | | 246/247/248 |
| 0152 | | | AAATCGTAGACCTA GTCCTCGAC | AUCGUAGACCU AGUCGUCG | CGAGGACUAGGUC UACGAU | + | + | | 249/250/251 |

TABLE 9-continued

| Sample seq id | gene id | Target sequence | forward | reverse | 30 ppm | 15 ppm | 8 ppm | SEQ ID NO Target region/ sense/antisense |
|---|---|---|---|---|---|---|---|---|
| 0153 | ise2c.pk001.l2 | tubulin | AAACTCAATTCAAA ATGCGTGAG | ACUCAAUUCAA AAUGCGUG | CACGCAUUUGAA UUGAGU | + | + | | 252/253/254 |
| 0154 | | | AACTTATCACTGGTA AGGAAGAT | CUUAUCACUGG UAAGGAAG | CUUCCUUACCAGU GAUAAG | NT | | | 255/256/257 |
| 0155 | ise2c.pk002.b4 | ubiquitin | AAGAGTTACGAACC GTCACCATA | GAGUUACGAAC CGUCACCA | UGGUGACGGUUC GUAACUC | + | | | 258/259/260 |
| 0156 | | | AAACTTAGTCCGGA TAATGAACC | ACUUAGUCCGG AUAAUGAA | UUCAUUAUCCGGA CUAAGU | + | + | | 261/262/263 |
| 0157 | | | AAGGCGATGTACGA GAACCTGTT | GGCGAUGUACG AGAACCUG | CAGGUUCUCGUAC AUCGCC | + | | | 264/265/266 |
| 0158 | ise2c.pk001.j16 | small nuclear ribonucleo-protein | AACGACAAGATGCT GAAGGAGAC | CGACAAGAUGC UGAAGGAG | CUCCUUCAGCAUC UUGUCG | + | | | 267/268/269 |
| 0159 | ise2c.pk006.h23 | small nuclear ribonucleo-protein | AAGATAAAGGTCGC GTGTGGACC | GAUAAAGGUCG CGUGUGGA | UCCACACGCGACC UUUAUC | + | | | 270/271/272 |
| 0160 | | | AATGTCAAGACTGA TCCAAACAC | UGUCAAGACUG AUCCAAAC | GUUUGGAUCAGU CUUGACA | + | | | 273/274/275 |
| 0161 | | | AACATTCGAGTCTG AACAGGTGG | CAUUCGAGUCU GAACAGGU | ACCUGUUCAGACU CGAAUG | + | + | | 276/277/278 |

(Note:
the sense RNA primer sequence and the antisense RNA primer sequences shown in table 9 were generated with 2 thymine residues at the 3' end.)

TABLE 10

| well | seq i.d. | midgut | gene id | Injection Mortality (%) | Droplet Feeding Result | Topical assay 1 30 ppm | Topical Assay 2 30 ppm | Topical Assay 3 30 ppm | Topical Assay 4 30 ppm | Topical Assay 4 15 ppm | Topical Assay 4 8 ppm | Top. 5 15 ppm | Top. 5 8 ppm |
|---|---|---|---|---|---|---|---|---|---|---|---|---|---|
| 77 | ise1c.pk002.m13 | no | Juvenile hormone query | NT | NT | NT | − | − | + | | | + | |
| 81 | ise1c.pk005.a15 | no | Juvenile hormone query | NT | NT | NT | − | − | + | + | | + | |
| 114 | ise2c.pk001.i23 | no | translation initiation factor | NT | NT | NT | + | + | + | | | + | |
| 122 | ise2c.pk005.b9 | Yes | translation initiation factor | NT | NT | NT | + | + | + | + | + | + | + |
| 143 | ise2c.pk001.b14 | no | potassium channel ami-acid transporter | NT | NT | NT | − | + | | | | + | |
| 145 | ise2c.pk003.f2 | Yes | potassium inwardly rectifier . . . | NT | NT | NT | + | + | + | + | | + | |
| 146 | ise2c.pk003.f2 | Yes | potassium inwardly rectifier . . . | NT | NT | NT | + | + | | | | + | |
| 149 | ise2c.pk005.l20 | Yes | hypothetical sodium dependent transport | NT | NT | NT | + | + | | | | + | |
| 151 | ise2c.pk001.d1 | No | alpha tubulin | NT | NT | NT | + | + | + | + | | + | |
| 154 | ise2c.pk001.l2 | No | alpha tubulin | NT | NT | NT | + | + | + | + | | + | |
| 157 | ise2c.pk002.b4 | yes | Probable ubiquitin--protein ligase | NT | NT | NT | + | + | + | + | | + | |

TABLE 10-continued

| well | seq i.d. | midgut | gene id | Injection Mortality (%) | Droplet Feeding Result | Topical assay 1 30 ppm | Topical Assay 2 30 ppm | Topical Assay 3 30 ppm | Topical Assay 4 30 ppm | Topical Assay 4 15 ppm | Topical Assay 4 8 ppm | Top. 5 15 ppm | Top. 5 8 ppm |
|---|---|---|---|---|---|---|---|---|---|---|---|---|---|
| 158 | ise2c.pk002.b4 | Yes | Probable ubiquitin-- protein ligase | NT | NT | NT | + | + | − | | | + | |
| 162 | ise2c.pk006.h23 | Yes | RNA- binding protein squid | NT | NT | NT | + | + | + | + | | + | |

TABLE 11

| DsRNA # | gene id | seqID | Comment | 8 ppm | 4 ppm | 2 ppm |
|---|---|---|---|---|---|---|
| 0163 | pre-mRNA-binding protein | ise2c.pk006.m8 | Plate 2 A1 | | | |
| 0164 | pre-mRNA-binding protein | ise2c.pk006.m8 | Plate 2 B1 | | | |
| 0165 | pre-mRNA-binding protein | ise2c.pk006.m8 | Plate 2 C1 | | | |
| 0166 | pre-mRNA-binding protein | ise2c.pk006.m8 | Plate 2 D1 | S | | |
| 0167 | pre-mRNA-binding protein | ise2c.pk006.m8 | Plate 2 E1 | S | | |
| 0168 | chymotrypsin-like; protease | ise2c.pk001.a23 | Plate 2 F1 | S | | |
| 0169 | chymotrypsin-like; protease | ise2c.pk001.a23 | Plate 2 G1 | | | |
| 0170 | chymotrypsin-like; protease | ise2c.pk001.a23 | Plate 2 H1 | | | |
| 0171 | chymotiypsin-like; protease | ise2c.pk001.a23 | Plate 2 A2 | S | | |
| 0172 | chymotrypsin-like; protease | ise2c.pk001.a23 | Plate 2 B2 | S | | |
| 0173 | chymotrypsinogen; protease | ise2c.pk001.a7 | Plate 2 C2 | S | | |
| 0174 | chymotrypsinogen; protease | ise2c.pk001.a7 | Plate 2 D2 | | | |
| 0175 | chymotrypsinogen; protease | ise2c.pk001.a7 | Plate 2 E2 | | | |
| 0176 | chymotrypsinogen; protease | ise2c.pk001.a7 | Plate 2 F2 | | | |
| 0177 | chymotrypsinogen; protease | ise2c.pk001.a7 | Plate 2 G2 | | | |
| 0178 | actin-depolymerizing | ise2c.pk004.c4 | Plate 2 H2 | | | |
| 0179 | actin-depolymerizing | ise2c.pk004.c4 | Plate 2 A3 | | | |
| 0180 | actin-depolymerizing | ise2c.pk004.c4 | Plate 2 B3 | | | |
| 0181 | actin-depolymerizing | ise2c.pk004.c4 | Plate 2 C3 | | | |
| 0182 | actin-depolymerizing | ise2c.pk004.c4 | Plate 2 D3 | | | |
| 0183 | actin depolymerizing factor | ise2c.pk004.l4 | Plate 2 E3 | | | |
| 0184 | actin depolymerizing factor | ise2c.pk004.l4 | Plate 2 F3 | | | |
| 0185 | actin depolymerizing factor | ise2c.pk004.l4 | Plate 2 G3 | | | |
| 0186 | actin depolymerizing factor | ise2c.pk004.l4 | Plate 2 H3 | | | |
| 0187 | actin depolymerizing factor | ise2c.pk004.l4 | Plate 2 A4 | | | |
| 0188 | dismutase; superoxide | ise2c.pk004.n19 | Plate 2 B4 | | | |
| 0189 | dismutase; superoxide | ise2c.pk004.n19 | Plate 2 C4 | | | |
| 0190 | dismutase; superoxide | ise2c.pk004.n19 | Plate 2 D4 | | | |
| 0191 | dismutase; superoxide | ise2c.pk004.n19 | Plate 2 E4 | | | |
| 0192 | dismutase; superoxide | ise2c.pk004.n19 | Plate 2 F4 | | | |
| 0193 | superoxide dismutase | ise2c.pk005.f21 | Plate 2 G4 | | | |
| 0194 | superoxide dismutase | ise2c.pk005.f21 | Plate 2 H4 | | | |
| 0195 | superoxide dismutase | ise2c.pk005.f21 | Plate 2 A5 | | | |
| 0196 | adenylate kinase isozyme 3 | ise2c.pk010.h5 | Plate 2 B5 | | | |
| 0197 | adenylate kinase isozyme 3 | ise2c.pk010.h5 | Plate 2 C5 | | | |
| 0198 | adenylate kinase isozyme 3 | ise2c.pk010.h5 | Plate 2 D5 | | | |
| 0199 | adenylate kinase isozyme 3 | ise2c.pk010.h5 | Plate 2 E5 | | | |
| 0200 | adenylate kinase isozyme 3 | ise2c.pk010.h5 | Plate 2 F5 | | | |
| 0201 | ecdysone oxidase | ise2c.pk001.c18 | Plate 2 G5 | | | |
| 0202 | ecdysone oxidase | ise2c.pk001.c18 | Plate 2 H5 | | | |
| 0203 | ecdysone oxidase | ise2c.pk001.c18 | Plate 2 A6 | | | |
| 0204 | innexin-2 | ise2c.pk004.p1 | Plate 2 B6 | | | |
| 0205 | innexin-2 | ise2c.pk004.p1 | Plate 2 C6 | | | |
| 0206 | innexin-2 | ise2c.pk004.p1 | Plate 2 D6 | | | |
| 0207 | innexin-2 | ise2c.pk004.p1 | Plate 2 E6 | | | |
| 0208 | innexin-2 | ise2c.pk004.p1 | Plate 2 F6 | | | |

TABLE 12

| DsRNA# | gene id | seqID | Comment | 16 ppm | 8 ppm | 4 ppm |
|---|---|---|---|---|---|---|
| 0163 | pre-mRNA-binding protein | ise2c.pk006.m8 | Plate 2 A1 | S | | |
| 0164 | pre-mRNA-binding protein | ise2c.pk006.m8 | Plate 2 B1 | S | | |
| 0165 | pre-mRNA-binding protein | ise2c.pk006.m8 | Plate 2 C1 | S | | |
| 0166 | pre-mRNA-binding protein | ise2c.pk006.m8 | Plate 2 D1 | S | | |
| 0167 | pre-mRNA-binding protein | ise2c.pk006.m8 | Plate 2 E1 | S | | |
| 0168 | chymotrypsin-like; protease | ise2c.pk001.a23 | Plate 2 F1 | ss | S | |
| 0169 | chymotrypsin-like; protease | ise2c.pk001.a23 | Plate 2 G1 | ss | | |
| 0170 | chymotrypsin-like; protease | ise2c.pk001.a23 | Plate 2 H1 | | | |

TABLE 12-continued

| DsRNA# | gene id | seqID | Comment | 16 ppm | 8 ppm | 4 ppm |
|---|---|---|---|---|---|---|
| 0171 | chymotrypsin-like; protease | ise2c.pk001.a23 | Plate 2 A2 | | | |
| 0172 | chymotrypsin-like; protease | ise2c.pk001.a23 | Plate 2 B2 | | | |
| 0173 | chymotrypsinogen; protease | ise2c.pk001.a7 | Plate 2 C2 | ss | | |
| 0174 | chymotrypsinogen; protease | ise2c.pk001.a7 | Plate 2 D2 | S | | |
| 0175 | chymotrypsinogen; protease | ise2c.pk001.a7 | Plate 2 E2 | S | | |
| 0176 | chymotrypsinogen; protease | ise2c.pk001.a7 | Plate 2 F2 | S | | |
| 0177 | chymotrypsinogen; protease | ise2c.pk001.a7 | Plate 2 G2 | S | | |
| 0178 | actin-depolymerizing | ise2c.pk004.c4 | Plate 2 H2 | | | |
| 0179 | actin-depolymerizing | ise2c.pk004.c4 | Plate 2 A3 | ss | | |
| 0180 | actin-depolymerizing | ise2c.pk004.c4 | Plate 2 B3 | s | | |
| 0181 | actin-depolymerizing | ise2c.pk004.c4 | Plate 2 C3 | | | |
| 0182 | actin-depolymerizing | ise2c.pk004.c4 | Plate 2 D3 | | | |
| 0183 | actin depolymerizing factor | ise2c.pk004.l4 | Plate 2 E3 | | | |
| 0184 | actin depolymerizing factor | ise2c.pk004.l4 | Plate 2 F3 | | | |
| 0185 | actin depolymerizing factor | ise2c.pk004.l4 | Plate 2 G3 | | | |
| 0186 | actin depolymerizing factor | ise2c.pk004.l4 | Plate 2 H3 | | | |
| 0187 | actin depolymerizing factor | ise2c.pk004.l4 | Plate 2 A4 | | | |
| 0188 | dismutase; superoxide | ise2c.pk004.n19 | Plate 2 B4 | | | |
| 0189 | dismutase; superoxide | ise2c.pk004.n19 | Plate 2 C4 | s | | |
| 0190 | dismutase; superoxide | ise2c.pk004.n19 | Plate 2 D4 | | | |
| 0191 | dismutase; superoxide | ise2c.pk004.n19 | Plate 2 E4 | | | |
| 0192 | dismutase; superoxide | ise2c.pk004.n19 | Plate 2 F4 | s | | |
| 0193 | superoxide dismutase | ise2c.pk005.f21 | Plate 2 G4 | | | |
| 0194 | superoxide dismutase | ise2c.pk005.f21 | Plate 2 H4 | | | |
| 0195 | superoxide dismutase | ise2c.pk005.f21 | Plate 2 A5 | | | |
| 0196 | adenylate kinase isozyme 3 | ise2c.pk010.h5 | Plate 2 B5 | | | |
| 0197 | adenylate kinase isozyme 3 | ise2c.pk010.h5 | Plate 2 C5 | | | |
| 0198 | adenylate kinase isozyme 3 | ise2c.pk010.h5 | Plate 2 D5 | | | |
| 0199 | adenylate kinase isozyme 3 | ise2c.pk010.h5 | Plate 2 E5 | | | |
| 0200 | adenylate kinase isozyme 3 | ise2c.pk010.h5 | Plate 2 F5 | | | |
| 0201 | ecdysone oxidase | ise2c.pk001.c18 | Plate 2 G5 | | | |
| 0202 | ecdysone oxidase | ise2c.pk001.c18 | Plate 2 H5 | | | |
| 0203 | ecdysone oxidase | ise2c.pk001.c18 | Plate 2 A6 | | | |
| 0204 | innexin-2 | ise2c.pk004.p1 | Plate 2 B6 | | | |
| 0205 | innexin-2 | ise2c.pk004.p1 | Plate 2 C6 | | | |
| 0206 | innexin-2 | ise2c.pk004.p1 | Plate 2 D6 | | | |
| 0207 | innexin-2 | ise2c.pk004.p1 | Plate 2 E6 | | | |
| 0208 | innexin-2 | ise2c.pk004.p1 | Plate 2 F6 | | | |

TABLE 13

Summary of FAW droplet feeding data for the first set of synthetic dsRNA primers

| | | | Assay #1 (table 6) | Assay #2 (table 7) | Assay #3 (table 8) | Assay #4 (table 8) | | |
|---|---|---|---|---|---|---|---|---|
| | | | 30 ppm | 30 ppm | 30 ppm | 30 ppm | 15 ppm | 8 ppm |
| 0075 | ise1c.pk002.m13 | Juvenile hormone query | − | − | − | NT | − | − |
| 0076 | | | NT | − | − | − | − | − |
| 0077 | | | NT | − | − | + | − | − |
| 0078 | ise1c.pk003.f7 | Juvenile hormone query | NT | − | − | − | − | − |
| 0079 | | | NT | − | − | − | − | − |
| 0080 | | | NT | − | + | − | − | − |
| 0081 | ise1c.pk005.a15 | Juvenile hormone query | NT | − | − | + | + | − |
| 0082 | | | NT | − | − | − | − | − |
| 0083 | | | + | + | NT | NT | − | − |
| 0084 | ise1c.pk006.d24 | Juvenile hormone query | NT | − | + | − | − | − |
| 0085 | | | + | − | − | + | − | − |
| 0086 | ise2c.pk009.i4 | Juvenile hormone query | − | − | − | − | − | − |
| 0087 | | | NT | − | − | − | − | − |
| 0088 | | | + | − | − | + | − | − |
| 0089 | ise2c.pk001.d19 | vacuolar query | + | − | + | + | − | − |
| 0090 | | | NT | − | − | − | − | − |
| 0091 | | | + | − | + | NT | − | − |
| 0092 | ise2c.pk001.e14 | vacuolar query | NT | − | − | − | − | − |
| 0093 | | | NT | − | − | + | − | − |
| 0094 | ise2c.pk001.f20 | vacuolar query | + | − | − | − | − | − |
| 0095 | | | + | − | − | − | − | − |
| 0096 | | | NT | − | − | − | − | − |
| 0097 | ise2c.pk010.h3 | cadherin query | NT | − | − | − | − | − |
| 0098 | | | NT | + | − | − | − | − |
| 0099 | | | NT | − | − | NT | − | − |

TABLE 13-continued

Summary of FAW droplet feeding data for the first set of synthetic dsRNA primers

| | | | Assay #1 (table 6) | Assay #2 (table 7) | Assay #3 (table 8) | Assay #4 (table 8) | | |
|---|---|---|---|---|---|---|---|---|
| | | | 30 ppm | 30 ppm | 30 ppm | 30 ppm | 15 ppm | 8 ppm |
| 0100 | ise2c.pk007.k24 | cuticle protein | NT | − | − | − | − | − |
| 0101 | | | NT | − | − | − | − | − |
| 0102 | | | NT | − | − | − | − | − |
| 0103 | ise2c.pk011.a10 | cuticle protein | NT | + | − | − | − | − |
| 0104 | | | NT | + | + | + | − | − |
| 0105 | ise2c.pk011.h12 | cuticle protein | NT | − | − | − | − | − |
| 0106 | | | NT | + | − | + | − | − |
| 0107 | | | + | − | − | NT | − | − |
| 0108 | ise2c.pk001.d22 | translation initiation factor | NT | − | + | − | − | − |
| 0109 | | | NT | + | + | + | − | − |
| 0110 | | | NT | − | + | + | − | − |
| 0111 | ise2c.pk001.d9 | translation initiation factor | NT | − | − | − | − | − |
| 0112 | | | NT | + | − | − | − | − |
| 0113 | | | NT | − | + | + | − | − |
| 0114 | ise2c.pk001.i23 | translation initiation factor | NT | + | + | + | − | − |
| 0115 | | | − | − | NT | NT | − | − |
| 0116 | | | NT | − | − | + | − | − |
| 0117 | ise2c.pk001.l24 | translation initiation factor | NT | − | + | + | − | − |
| 0118 | | | NT | − | + | + | − | − |
| 0119 | | | NT | + | − | − | − | − |
| 0120 | ise2c.pk005.b9 | translation initiation factor | NT | − | − | − | − | − |
| 0121 | | | NT | + | + | + | − | − |
| 0122 | | | NT | + | + | + | + | + |
| 0123 | ise2c.pk002.m10 | SAR1 | − | − | + | NT | − | − |
| 0124 | | | NT | − | + | + | − | − |
| 0125 | | | NT | + | + | + | − | − |
| 0126 | ise2c.pk001.c14 | Elongation factor | NT | + | + | + | − | − |
| 0127 | | | NT | + | + | + | − | − |
| 0128 | | | NT | − | + | + | − | − |
| 0129 | ise2c.pk001.d16 | Elongation factor | NT | + | + | + | − | − |
| 0130 | | | NT | − | + | − | − | − |
| 0131 | ise2c.pk005.h3 | phosphooligosaccharide . . . | − | − | − | NT | − | − |
| 0132 | | | NT | − | − | − | − | − |
| 0133 | | | NT | − | − | − | − | − |
| 0134 | ise2c.pk001.d21 | myosin | NT | − | − | − | − | − |
| 0135 | | | NT | − | − | − | − | − |
| 0136 | | | NT | − | − | − | − | − |
| 0137 | ise2c.pk001.j9 | myosin | NT | − | − | − | − | − |
| 0138 | | | NT | + | − | − | − | − |
| 0139 | | | − | − | − | NT | − | − |
| 0140 | ise2c.pk002.f12 | myosin | NT | − | − | − | − | − |
| 0141 | | | NT | − | − | − | − | − |
| 0142 | ise2c.pk001.b14 | potassium channel amino acid transporter | NT | − | − | − | − | − |
| 0143 | | | NT | − | + | − | − | − |
| 0144 | | | NT | − | + | + | − | − |
| 0145 | ise2c.pk003.f2 | potassium inwardly rectifier . . . | NT | + | + | + | + | − |
| 0146 | | | NT | + | + | + | − | − |
| 0147 | | | + | + | + | NT | − | − |
| 0148 | ise2c.pk005.120 | amino acid transporter | NT | + | + | + | − | − |
| 0149 | | | NT | + | + | − | − | − |
| 0150 | | | NT | − | + | + | − | − |
| 0151 | ise2c.pk001.d1 | tubulin | NT | + | + | + | + | − |
| 0152 | ise2c.pk001.k6 | tubulin | NT | − | − | + | − | − |
| 0153 | | | NT | + | + | + | + | − |
| 0154 | ise2c.pk001.l2 | tubulin | NT | + | + | + | + | − |
| 0155 | | | − | − | − | NT | − | − |
| 0156 | ise2c.pk002.b4 | ubiquitin | NT | − | + | + | − | − |
| 0157 | | | NT | + | + | + | + | − |
| 0158 | | | NT | + | + | + | − | − |
| 0159 | ise2c.pk001.j16 | small nuclear ribonucleoprotein | NT | + | + | + | − | − |
| 0160 | ise2c.pk006.h23 | small nuclear ribonucleoprotein | NT | − | + | + | − | − |
| 0161 | | | NT | − | + | + | − | − |
| 0162 | | | NT | + | + | + | + | − |

Example 2

Transformation of Maize

Immature maize embryos from greenhouse donor plants are bombarded with a plasmid containing the silencing element of the invention operably linked to either a tissue specific, tissue selective, or constitutive promoter and the selectable marker gene PAT (Wohlleben et al. (1988) *Gene* 70:25-37), which confers resistance to the herbicide Bialaphos. In one embodiment, the constructs will have 2 identical 2-300 bp segments of the target gene in opposite orientations with an "intron" segment between them acting as a hairpin loop. Such a construct can be linked to the dMMB promoter. Alternatively, the selectable marker gene is provided on a separate plasmid. Transformation is performed as follows. Media recipes follow below.

Preparation of Target Tissue

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5 cm target zone in preparation for bombardment.

A plasmid vector comprising the silencing element of interest operably linked to either the tissue specific, tissue selective, or constitutive promoter is made. This plasmid DNA plus plasmid DNA containing a PAT selectable marker is precipitated onto 1.1 µm (average diameter) tungsten pellets using a $CaCl_2$ precipitation procedure as follows: 100 µl prepared tungsten particles in water; 10 µl (1 µg) DNA in Tris EDTA buffer (1 µg total DNA); 100 µl 2.5 M $CaCl_2$; and, 10 µl 0.1 M spermidine.

Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 µl 100% ethanol is added to the final tungsten particle pellet. For particle gun bombardment, the tungsten/DNA particles are briefly sonicated and 10 µl spotted onto the center of each macrocarrier and allowed to dry about 2 minutes before bombardment.

The sample plates are bombarded at level #4 in a particle gun. All samples receive a single shot at 650 PSI, with a total of ten aliquots taken from each tube of prepared particles/DNA.

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity.

Plants are monitored and scored for the appropriate marker, such as the control of Lepidoptera and have insecticidal activity. For example, a FAW feeding assay could be preformed. In such assays, leaf discs from the transgenic plant are excised using a 1 cm cork borer or leaf punch. Six leaf discs are prepared for each plant. The leaves are placed in a 24 well microtiter plate on top of 500 ul of 0.8% agar. Each leaf disc is infested with 2 neonate Fall armyworm and the plate is then sealed with mylar. A small ventilation hole is made for each well and the plates are then stored in a 28 C growth chamber. The assay is scored for mortality, stunting, and leaf consumption at 96 hours.

Bombardment medium (560Y) comprises 4.0 g/l N6 basal salts (SIGMA C-1416), 1.0 ml/l Eriksson's Vitamin Mix (1000×SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000×SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite (added after bringing to volume with D-I $H_2O$); and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCl, 0.10 g/l pyridoxine HCl, and 0.40 g/l glycine brought to volume with polished D-I $H_2O$) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite (added after bringing to volume with D-I $H_2O$); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCl, 0.10 g/l pyridoxine HCl, and 0.40 g/l glycine brought to volume with polished D-I $H_2O$), 0.1 g/l myo-inositol, and 40.0 g/l sucrose (brought to volume with polished D-I $H_2O$ after adjusting pH to 5.6); and 6 g/l bacto-agar (added after bringing to volume with polished D-I $H_2O$), sterilized and cooled to 60° C.

Example 3

*Agrobacterium*-mediated Transformation of Maize

For *Agrobacterium*-mediated transformation of maize with a silencing element of the invention, the method of Zhao is employed (U.S. Pat. No. 5,981,840, and PCT patent publication WO98/32326; the contents of which are hereby incorporated by reference). Such as a construct can comprise 2 identical 2-300 bp segments of the target gene in opposite orientations with an "intron" segment between them acting as a hairpin loop. Such a construct can be linked to the dMMB promoter. Briefly, immature embryos are isolated from maize and the embryos contacted with a suspension of *Agrobacterium*, where the bacteria are capable of transferring the polynucleotide comprising the silencing element to at least one cell of at least one of the immature embryos (step 1; the infection step). In this step the immature embryos are immersed in an *Agrobacterium* suspension for the initiation of inoculation. The embryos are co-cultured for a time with the *Agrobacterium* (step 2: the co-cultivation step). The immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). The immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step).

The immature embryos are cultured on solid medium with a selective agent resulting in the selective growth of transformed cells. The callus is then regenerated into plants (step 5: the regeneration step), and calli grown on selective medium are cultured on solid medium to regenerate the plants.

Example 4

Soybean Embryo Transformation Culture Conditions

Soybean embryogenic suspension cultures (cv. Jack) are maintained in 35 ml liquid medium SB196 (see recipes below) on rotary shaker, 150 rpm, 26° C. with cool white fluorescent lights on 16:8 hr day/night photoperiod at light intensity of 60-85 µE/m2/s. Cultures are subcultured every 7 days to two weeks by inoculating approximately 35 mg of tissue into 35 ml of fresh liquid SB196 (the preferred subculture interval is every 7 days).

Soybean embryogenic suspension cultures are transformed with the plasmids and DNA fragments described in the examples above by the method of particle gun bombardment (Klein et al. (1987) *Nature*, 327:70).

Soybean Embryogenic Suspension Culture Initiation

Soybean cultures are initiated twice each month with 5-7 days between each initiation.

Pods with immature seeds from available soybean plants 45-55 days after planting are picked, removed from their shells and placed into a sterilized magenta box. The soybean seeds are sterilized by shaking them for 15 minutes in a 5% Clorox solution with 1 drop of ivory soap (95 ml of autoclaved distilled water plus 5 ml Clorox and I drop of soap). Mix well. Seeds are rinsed using 2 1-liter bottles of sterile distilled water and those less than 4 mm are placed on individual microscope slides. The small end of the seed are cut and the cotyledons pressed out of the seed coat. Cotyledons are transferred to plates containing SB1 medium (25-30 cotyledons per plate). Plates are wrapped with fiber tape and stored for 8 weeks. After this time secondary embryos are cut and placed into SB196 liquid media for 7 days.

Preparation of DNA for Bombardment

Either an intact plasmid or a DNA plasmid fragment containing the genes of interest and the selectable marker gene are used for bombardment. Plasmid DNA for bombardment are routinely prepared and purified using the method described in the Promega™ Protocols and Applications Guide, Second Edition (page 106). Fragments of the plasmids carrying the silencing element of interest are obtained by gel isolation of double digested plasmids. In each case, 100 ug of plasmid DNA is digested in 0.5 ml of the specific enzyme mix that is appropriate for the plasmid of interest. The resulting DNA fragments are separated by gel electrophoresis on 1% SeaPlaque GTG agarose (BioWhitaker Molecular Applications) and the DNA fragments containing silencing element of interest are cut from the agarose gel. DNA is purified from the agarose using the GELase digesting enzyme following the manufacturer's protocol.

A 50 µl aliquot of sterile distilled water containing 3 mg of gold particles (3 mg gold) is added to 5 µl of a 1 µg/µl DNA solution (either intact plasmid or DNA fragment prepared as described above), 50 µl 2.5M $CaCl_2$ and 20 µl of 0.1 M spermidine. The mixture is shaken 3 min on level 3 of a vortex shaker and spun for 10 sec in a bench microfuge. After a wash with 400 µl 100% ethanol the pellet is suspended by sonication in 40 µl of 100% ethanol. Five µl of DNA suspension is dispensed to each flying disk of the Biolistic PDS1000/HE instrument disk. Each 5 µl aliquot contains approximately 0.375 mg gold per bombardment (i.e. per disk).

Tissue Preparation and Bombardment with DNA

Approximately 150-200 mg of 7 day old embryonic suspension cultures are placed in an empty, sterile 60×15 mm petri dish and the dish covered with plastic mesh. Tissue is bombarded 1 or 2 shots per plate with membrane rupture pressure set at 1100 PSI and the chamber evacuated to a vacuum of 27-28 inches of mercury. Tissue is placed approximately 3.5 inches from the retaining/stopping screen.

Selection of Transformed Embryos

Transformed embryos were selected either using hygromycin (when the hygromycin phosphotransferase, HPT, gene was used as the selectable marker) or chlorsulfuron (when the acetolactate synthase, ALS, gene was used as the selectable marker).

Hygromycin (HPT) Selection

Following bombardment, the tissue is placed into fresh SB196 media and cultured as described above. Six days post-bombardment, the SB196 is exchanged with fresh SB196 containing a selection agent of 30 mg/L hygromycin. The selection media is refreshed weekly. Four to six weeks post selection, green, transformed tissue may be observed growing from untransformed, necrotic embryogenic clusters. Isolated, green tissue is removed and inoculated into multiwell plates to generate new, clonally propagated, transformed embryogenic suspension cultures.

Chlorsulfuron (ALS) Selection

Following bombardment, the tissue is divided between 2 flasks with fresh SB196 media and cultured as described above. Six to seven days post-bombardment, the SB196 is exchanged with fresh SB196 containing selection agent of 100 ng/ml Chlorsulfuron. The selection media is refreshed weekly. Four to six weeks post selection, green, transformed tissue may be observed growing from untransformed, necrotic embryogenic clusters. Isolated, green tissue is removed and inoculated into multiwell plates containing SB196 to generate new, clonally propagated, transformed embryogenic suspension cultures.

Regeneration of Soybean Somatic Embryos into Plants

In order to obtain whole plants from embryogenic suspension cultures, the tissue must be regenerated.

Embryo Maturation

Embryos are cultured for 4-6 weeks at 26° C. in SB196 under cool white fluorescent (Phillips cool white Econowatt F40/CW/RS/EW) and Agro (Phillips F40 Agro) bulbs (40 watt) on a 16:8 hr photoperiod with light intensity of 90-120 uE/m2s. After this time embryo clusters are removed to a solid agar media, SB166, for 1-2 weeks. Clusters are then subcultured to medium SB103 for 3 weeks. During this period, individual embryos can be removed from the clusters and screened for the appropriate marker or the ability of the plant, when injected with the silencing elements, to control the Lepidoptera.

Embryo Desiccation and Germination

Matured individual embryos are desiccated by placing them into an empty, small petri dish (35×10 mm) for approximately 4-7 days. The plates are sealed with fiber tape (creating a small humidity chamber). Desiccated embryos are planted into SB71-4 medium where they were left to germinate under the same culture conditions described above. Germinated plantlets are removed from germination medium and rinsed thoroughly with water and then planted in Redi-Earth in 24-cell pack tray, covered with clear plastic dome. After 2 weeks the dome is removed and plants hardened off for a further week. If plantlets looked hardy they are transplanted to 10" pot of Redi-Earth with up to 3 plantlets per pot.

| Media Recipes | | |
|---|---|---|
| SB 196 - FN Lite liquid proliferation medium (per liter) - | | |
| MS FeEDTA - 100x Stock 1 | 10 ml | |
| MS Sulfate - 100x Stock 2 | 10 ml | |
| FN Lite Halides - 100x Stock 3 | 10 ml | |
| FN Lite P, B, Mo - 100x Stock 4 | 10 ml | |
| B5 vitamins (1 ml/L) | 1.0 ml | |
| 2,4-D (10 mg/L final concentration) | 1.0 ml | |
| KNO3 | 2.83 gm | |
| (NH4)2 SO 4 | 0.463 gm | |
| Asparagine | 1.0 gm | |
| Sucrose (1%) | 10 gm | |
| pH 5.8 | | |
| FN Lite Stock Solutions | | |
| Stock # | 1000 ml | 500 ml |
| 1  MS Fe EDTA 100x Stock | | |
| Na$_2$ EDTA* | 3.724 g | 1.862 g |
| FeSO$_4$—7H$_2$O | 2.784 g | 1.392 g |
| 2  MS Sulfate 100x stock | | |
| MgSO$_4$—7H$_2$O | 37.0 g | 18.5 g |
| MnSO$_4$—H$_2$O | 1.69 g | 0.845 g |
| ZnSO$_4$—7H$_2$O | 0.86 g | 0.43 g |
| CuSO$_4$—5H$_2$O | 0.0025 g | 0.00125 g |
| 3  FN Lite Halides 100x Stock | | |
| CaCl$_2$—2H$_2$O | 30.0 g | 15.0 g |
| KI | 0.083 g | 0.0715 g |
| CoCl$_2$—6H$_2$O | 0.0025 g | 0.00125 g |
| 4  FN Lite P, B, Mo 100x Stock | | |
| KH$_2$PO$_4$ | 18.5 g | 9.25 g |
| H$_3$BO$_3$ | 0.62 g | 0.31 g |
| Na$_2$MoO$_4$—2H$_2$O | 0.025 g | 0.0125 g |

*Add first, dissolve in dark bottle while stirring

SB1 solid medium (per liter) comprises: 1 pkg. MS salts (Gibco/BRL-Cat# 11117-066); 1 ml B5 vitamins 1000× stock; 31.5 g sucrose; 2 ml 2,4-D (20 mg/L final concentration); pH 5.7; and, 8 g TC agar.

SB 166 solid medium (per liter) comprises: 1 pkg. MS salts (Gibco/BRL-Cat# 11117-066); 1 ml B5 vitamins 1000× stock; 60 g maltose; 750 mg MgCl2 hexahydrate; 5 g activated charcoal; pH 5.7; and, 2 g gelrite.

SB 103 solid medium (per liter) comprises: 1 pkg. MS salts (Gibco/BRL-Cat# 11117-066); 1 ml B5 vitamins 1000× stock; 60 g maltose; 750 mg MgCl2 hexahydrate; pH 5.7; and, 2 g gelrite.

SB 71-4 solid medium (per liter) comprises: 1 bottle Gamborg's B5 salts w/sucrose (Gibco/BRL-Cat#21153-036); pH 5.7; and, 5 g TC agar.

2,4-D stock is obtained premade from Phytotech cat#D 295-concentration is 1 mg/ml.

B5 Vitamins Stock (per 100 ml) which is stored in aliquots at −20 C comprises: 10 g myo-inositol; 100 mg nicotinic acid; 100 mg pyridoxine HCl; and, 1 g thiamine. If the solution does not dissolve quickly enough, apply a low level of heat via the hot stir plate. Chlorsulfuron Stock comprises 1 mg/ml in 0.01 N Ammonium Hydroxide The article "a" and "an" are used herein to refer to one or more than one (i.e., to at least one) of the grammatical object of the article. By way of example, "an element" means one or more element.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A plant cell having stably incorporated into its genome a heterologous polynucleotide comprising a silencing element, wherein said silencing element comprises a fragment of at least 20 consecutive nucleotides fully complementary to a target sequence of SEQ ID NO: 16, wherein said silencing element, when ingested by a pest from the Lepidoptera order, reduces the level of the target sequence in said pest and thereby controls the pest from the Lepidoptera order.

2. The plant cell of claim 1, wherein said pest comprises *Spodoptera frugiperda*.

3. The plant cell of claim 1, wherein said silencing element comprises
   a) a polynucleotide comprising the sense or antisense sequence of the sequence set forth in SEQ ID NO: 183; and
   b) a polynucleotide comprising the sequence set forth in SEQ ID NO: 184 and 185.

4. The plant cell of claim 3, wherein said silencing element encodes a hairpin RNA.

5. A plant cell having stably incorporated into its genome a heterologous polynucleotide comprising a silencing element, wherein said silencing element comprises, in the following order, a first segment, a second segment, and a third segment, wherein
   a) said first segment comprises at least 20 nucleotides fully complementary to a target sequence set forth in SEQ ID NO: 16;
   b) said second segment comprises a loop of sufficient length to allow the silencing element to be transcribed as a hairpin RNA; and,
   c) said third segment comprises at least 20 nucleotides fully complementary to the first segment, wherein said silencing element, when ingested by a pest from the Lepidoptera order, reduces the level of the target sequence in said pest and thereby controls the pest from the Lepidoptera order.

6. The plant cell of any one of claims 1-5, wherein said silencing element is operably linked to a heterologous promoter.

7. The plant cell of 3, wherein said plant cell has stably incorporated into its genome a second polynucleotide comprising a suppressor enhancer element comprising the target pest sequence or an active variant or fragment thereof, wherein combined expression of the silencing element and the suppressor enhancer element increases the concentration of an inhibitory RNAi specific for the pest target sequence in said plant cell.

8. The plant cell of claim 3, wherein said plant cell is from a monocot.

9. The plant cell of claim 8, wherein said monocot is maize, barley, millet, wheat or rice.

10. The plant cell of 3, wherein said plant cell is from a dicot.

11. The plant cell of claim 10, wherein said dicot is soybean, canola, alfalfa, sunflower, safflower, tobacco, Arabidopsis, or cotton.

12. A plant or plant part comprising a plant cell claim 3.

13. The plant cell of claim 7, wherein the combined expression of said silencing element and the suppressor enhancer element increases the concentration of an inhibitory RNA specific for the pest target sequence in the phloem of a plant or plant part.

14. A transgenic seed wherein the transgenic seed comprises the silencing element from the plant cell of claim 1.

15. A method for controlling a Lepidoptera pest comprising feeding to a Lepidoptera pest a composition comprising a silencing element, wherein said silencing element, when ingested by said Lepidoptera pest, reduces the level of a target Lepidoptera pest sequence and thereby controls the Lepidoptera pest and said silencing element comprises a fragment of at least 20 consecutive nucleotides fully complementary to a target sequence of SEQ ID NO: 16.

16. The method of claim 15, wherein said composition comprises a plant or plant part having stably incorporated into its genome a polynucleotide comprising said silencing element.

17. The method of claim 15, wherein said Lepidoptera pest comprises *Spodoptera frugiperda*.

18. The method of claim 15, wherein said silencing element encodes a hairpin RNA.

19. The method of claim 15, wherein said silencing element is operably linked to a heterologous promoter.

20. The method of claim 16, wherein said plant or plant part has stably incorporated into its genome a second polynucleotide comprising a suppressor enhancer element comprising the target pest sequence or an active variant or fragment thereof, wherein combined expression of the silencing element and the suppressor enhancer element increases the concentration of an inhibitory RNAi specific for the pest target sequence in said plant cell.

21. The method of claim 15, wherein said plant is a monocot.

22. The method of claim 21, wherein said monocot is maize, barley, millet, wheat or rice.

23. The method of claim 15, wherein said plant is a dicot.

24. The method of claim 23, wherein said plant is soybean, canola, alfalfa, sunflower, safflower, tobacco, Arabidopsis, or cotton.

* * * * *

SEQUENCE LISTING

```
<160> NUMBER OF SEQ ID NOS: 452

<210> SEQ ID NO 1
<211> LENGTH: 540
<212> TYPE: DNA
<213> ORGANISM: Spodoptera frugiperda
<220> FEATURE:
<221> NAME/KEY: misc_feature
<222> LOCATION: 417, 423, 500, 524, 540
<223> OTHER INFORMATION: n = A,T,C or G

<400> SEQUENCE: 1
caagcatcca acatggtatc cgacttcagg aagaagaagc tcctccacgt gttcaagtcc      60
ttcttcgaca cggacggcag cggcaacatc gagaaggatg acttcctgat ggccatcgaa     120
aggataacca agaccagagg ctggaaagct ggagacgaca aatacaaatt tgtcgaggag     180
accctattga agatctggga cggcatccag aaggtcgctg acgagaacaa ggacggacag     240
gtcagccagg acgagtggat cgctatgtgg gacaagtact ccaagaaccc gtccgaggcg     300
ttcgagtggc agaccctgta ctgcaagttc gcgttcactc ttgaagacgc cagcgacgat     360
ggatccatcg acagcgagga gttctcctct gtgtacgcct ccttcggcct ggacaangac     420
gangctgtgg ctgccttcaa gaaagatggc taacggtaag tccgaagtgt cctgggcttg     480
agttccacga cctgtggaan gagtacttct catccggaag actngaacgc tgccggcaan     540
```

```
<210> SEQ ID NO 2
<211> LENGTH: 505
<212> TYPE: DNA
<213> ORGANISM: Spodoptera frugiperda
<220> FEATURE:
<221> NAME/KEY: misc_feature
<222> LOCATION: 358, 410, 442, 482
<223> OTHER INFORMATION: n = A,T,C or G

<400> SEQUENCE: 2
ccaacatggt atccgacttc aggaagaaga agctcctcca cgtgttcaag tccttcttcg    60
acacggacgg cagcggcaac atcgagaagg atgatttcct gatggccatc gaaaggataa   120
ccaagaccag aggctggaaa gctggagaca acaaatacaa atttgtcgag gaaaccctat   180
tgaagatctg gacggcatc cagaaggtcg ctgacgagaa caaggacgga caggtcagcc    240
aggacgagtg gatcgctatg tgggacaagt actccaagaa cccatccgag gcgttcgagt   300
ggcagaccct gtactgcaag ttcgcgttca ctcttgaaga cgccagcgac gacggatnca   360
tcgacagcga agagttctcc tctgtgtacg cctccttcgg ctggacaan ggacgaggcg    420 gtggctgcct tcaagaagat gntaacggta agtccgaatg tcctggggct gagtttcaag   480
anctgttgga aggatacttc tcaac                                         505

<210> SEQ ID NO 3
<211> LENGTH: 410
<212> TYPE: DNA
<213> ORGANISM: Spodoptera frugiperda
<220> FEATURE:
<221> NAME/KEY: misc_feature
<222> LOCATION: 271, 346
<223> OTHER INFORMATION: n = A,T,C or G

<400> SEQUENCE: 3
caacatggta tccgacttca ggaagaataa gctcctccac gtgttcaagt ccttcttcga    60
cacggacggc agcggcaaca tcgagaagga tgacttcctg atggccatcg aaaggataac   120
caagaccaga ggctggaaag ctggagacga caaatacaaa tttgtcgagg agaccctatt   180
gaagatctgg acggcatcc agaaggtcgc tgacagagaac aaggacggac aggtcagcca   240
ggacgagtgg atcgctatgt gggacaagta ntccaagaac ccgtccgagg cgttcgagtg   300
gcagaccctg tactgcaagt tcgcgttcac tcttgaagac gccagngacg atggatccat   360
cgacagcgag gagttctcct ctgtgtacgc ctccttcggc tggacaagg               410

<210> SEQ ID NO 4
<211> LENGTH: 445
<212> TYPE: DNA
<213> ORGANISM: Spodoptera frugiperda
<220> FEATURE:
<221> NAME/KEY: misc_feature
<222> LOCATION: 66, 72, 264, 329, 358, 404, 406, 413, 427, 443
<223> OTHER INFORMATION: n = A,T,C or G

<400> SEQUENCE: 4
gagagagaga gagagagaga actagtctcg agtttttttt tttttttttt tttttttttt    60 ttttnggaa antactattt tattgtacca actgcccctt aacctcatct atgagtcacc    120
cataaatgtt attttggtaa aatgtttgac acacttcaca ctaatattta taaatgtgaa   180
agtttgtttg tttgaatgtt tgtatatttg tctgtcaatc acgctgaaac cactgtatag   240
aatttgacct aatttggtat acanacaggg tatgagctga cttgggtgat aggatacttt   300
ttatcccaca ggaacgcggg taaagtccnt gggcagaagc tagtatgtaa taattatntc   360
```

```
cctctaccta ccctatatgg gggtggaccg tcatgttctt tacncnacaa ccngtttgtc      420
cacctcncct ttaaagtttt gtnag                                           445
```

<210> SEQ ID NO 5
<211> LENGTH: 672
<212> TYPE: DNA
<213> ORGANISM: Spodoptera frugiperda
<220> FEATURE:
<221> NAME/KEY: misc_feature
<222> LOCATION: 652, 653, 654, 655, 656, 657, 658, 670, 671, 672
<223> OTHER INFORMATION: n = A,T,C or G

<400> SEQUENCE: 5

```
gcacgagggc cgtgtcgact tcgcaccagt cccctattta tttaccttga caaaaatatg      60
gcgcgcctat tgtttattgc gcctatcctg gcgttggcta taatgccagt atacttctta    120
ttcctaaagg gaccaccccc actacccgaa ctagatatga acgagtggtg gggcccagag    180
aagctaaaag caaacctga cactagtata aaccccttta aaattgcttt tggagacact     240
gttgtaaaag acttaaaaga ccgtctcaaa cgttctcggt ctttcactgc tccgctggag    300
ggtgtggcat tccagtacgg cttcaacact gctcagctgg atggttggct gaagtactgg    360
gctaatgagt ataagttcaa ggagagagag accttcctca accagtaccc tcagtacaaa    420
accaatatcc agggtcttga catccacttc atcagggtta caccgaaggt accggcagga    480
gtggaggtgg tacccatgct actcctccac ggctggccag gctctgtcag ggagttctac    540
gaggctattc ctctcatcac agcagtcagc aaggaccgtg acttcgctgt ggaagtcatc    600
gttccaagtc tacctggcta tggattctct gatgccgcag ttcgtcccgg cnnnnnnncc    660
ccacaaatgn nn                                                         672
```

<210> SEQ ID NO 6
<211> LENGTH: 693
<212> TYPE: DNA
<213> ORGANISM: Spodoptera frugiperda

<400> SEQUENCE: 6

```
gcacgaggct tggacgtgat gttacctggg aattcaaccc cttgaatgtt aaggtcggct      60
cccacatcac cggaggagac ttgtacggta tcgtacacga aacacattg gttaagcaca     120 agatgttgat cccacccaag gccaagggta ccgtcaccta cgtcgcgccc tccggcaact    180
acaaagtcac tgacgtagtg ttggagacgg agttcgacgg cgagaaggag aagtacacca    240
tgttgcaagt atggccggtg cgccagccgc gccccgtcac tgagaagctg tccgccaacc    300
accccctgct caccggacag agagtgctcg actctctctt cccttgtgtc cagggtggta    360
ccacggccat ccccggcgcc ttcggttgtg gcaagactgt cgtctcacag gctctgtcca    420
agtactccaa ctctgacgtc atcatctacg tcggatgcgg tgaacgtggt aacgagatgt    480
ctgaggtact gcgtgacttc cccgagctga cggtggagat cgagggcatg accgagtcca    540
tcatgaagcg taccgcgctc gtcgccaaca cctccaacat gcctgtagcc gcccgagagg    600
cttccatcta caccggtatc accctctccg agtacttccg tgacatgggt tacaacgtgt    660
ccatgatggc tgactccacc tctcgttggg ccg                                   693
```

<210> SEQ ID NO 7
<211> LENGTH: 300
<212> TYPE: DNA
<213> ORGANISM: Spodoptera frugiperda
<220> FEATURE:
<221> NAME/KEY: misc_feature

```
<222> LOCATION: 39, 40, 41, 162, 164, 166, 167, 168, 169, 242, 268, 269,
      270, 293, 294, 295, 299, 300
<223> OTHER INFORMATION: n = A,T,C or G

<400> SEQUENCE: 7
gcacgaggca gatagtcatc actgttttg ggacctgtnn ntactccctc aataaaccta      60
caaaatggcc gaaaacccaa tctacggacc cttctttgga gttatggggg cggcgtctgc    120
tatcatcttt agcgcgctgg gagctgccta tggaactgct angncnnnna ccggtatcgc    180
cgccatgtcg gtgatgcggc ccgagctcat catgaagtcc aacaactaca cccttttacaa   240 gnggttcatc caccttggcg ctggtctnnn cgtaagtttc tccggtctag cgnnnggcnn    300

<210> SEQ ID NO 8
<211> LENGTH: 688
<212> TYPE: DNA
<213> ORGANISM: Spodoptera frugiperda
<220> FEATURE:
<221> NAME/KEY: misc_feature
<222> LOCATION: 318, 319, 320, 321, 658, 659, 660, 661, 662, 686, 687,
      688
<223> OTHER INFORMATION: n = A,T,C or G

<400> SEQUENCE: 8
gcacgaggct cacaggctct gtccaagtac tccaactctg acgtcatcat ctacgtcgga    60
tgcggtgaac gtggtaacga gatgtctgag gtactgcgtg acttcccga gctgacggtg    120 gagatcgagg gcatgaccga gtccatcatg aagcgtaccg cgctcgtcgc caacacctcc   180
aacatgcctg tagccgcccg agaggcttcc atctacaccg gtatcaccct ctccgagtac   240
ttccgtgaca tgggttacaa cgtgtccatg atggctgact ccacctctcg ttgggccgag   300
gctcttcgtg agatctcnnn ncgtctggct gagatgcctg ccgactcggg ttaccccgcc   360
tacctgggag cccgtctggc ctcgttctac gagcgtgccg acgtgtgaa gtgcttgggt    420 aaccccgaca gggagggctc cgtgtccatc gtgggcgccg tgtcgccgcc cggaggtgac   480
ttctccgacc ccgtgacggc cgccacgctg gtatcgtgc aggtgttctg ggggttggac    540
aagaagctcg cgcagcgcaa gcacttcccc gccatcaact ggctcatctc ctacagcaag   600
tacatgcgag cgctggacga cttctatgag aagaactacc ccgagttcgt gcccctcnnn   660
nncaagggtc aaggagatcc tgcagnnn                                      688

<210> SEQ ID NO 9
<211> LENGTH: 685
<212> TYPE: DNA
<213> ORGANISM: Spodoptera frugiperda
<220> FEATURE:
<221> NAME/KEY: misc_feature
<222> LOCATION: 674, 675
<223> OTHER INFORMATION: n = A,T,C or G

<400> SEQUENCE: 9
gcacgaggta tctaaaacag tgcgtcgtaa tatattcaag atgtctcgtc ttaggttttg    60 tttttttatta gcagtactat gcagttgttt gcagaatggt tacggttta caacagaaaa    120 gccagttacc cagcatgtag atcctaaacc agaagttcct gaaacgttgc ctgaaacaac   180
acgagtgcct gcgccgagct cgtcgacggc agcgccgacc acaccagctc gacaccggc    240 accaacgcca gcacccacac cagctcctac accagctcct actccagctc ctacccctgc   300
gcctactcct gcgcctactc ctgcgcctac tcctgcgcct accccgcac ctacaccagc    360 gcccactcct gctcccaccc cagctcccct ccccgcccc gaccaaggca catggtcctt   420
```

```
cactgatgaa aaggccaatc agacatgcat tgtgggccaa ttcgcagccc aactgaatgt    480
cacatacacc aagttagtgg agaatgcaac gtctctatcg tacgtgaggc tcaacgtgcc    540
cgcgaacgcg tcggtcctca acggcagctg ttcggacccc gaccaatgga tccagatcac    600
ctggaagacc aacgacgaca gcgagacgaa caacaccatg accctcgtgt acaacaagaa    660
tgccaccacc aagnnctacg gcctg                                          685
```

<210> SEQ ID NO 10
<211> LENGTH: 612
<212> TYPE: DNA
<213> ORGANISM: Spodoptera frugiperda
<220> FEATURE:
<221> NAME/KEY: misc_feature
<222> LOCATION: 558, 560, 573, 574, 575, 589, 590, 591, 592, 593, 595,
      596, 597, 599, 604, 605, 612
<223> OTHER INFORMATION: n = A,T,C or G

<400> SEQUENCE: 10

```
gcacgagggc ggtttgaagt gatctagttc gtcagaaaaa acacagacca cgttcacaat     60
gaaatcgatg gtggtgttat tcgctgtgtg cgccgtggcg tgcggctccc tggtgccgct    120
ggcgcagcct cctcatcacc ccgccgtcgt gctggacccg cacggccgcc cgctcgacac    180
cgccgaggtg atcaacgccc gcgccctcca cctgcaggct aaggccctgg atggacacta    240
cgctcccctc gcgcacgctg ccgtcgtgcc tgttgcccac tccgtggtag ccgccccgc     300 tgtggtcgcc gctcccgccg ccgtgtccca ccagtcccgt gtggatgtgc gcaccagccc    360
cgccatcgtg agccacgccg tcgctgctcc cgtagtagcc cacggtgtct actccgctcc    420
cctgctggcc cactccgctc tcggctacgc cggtcacgga cactacctga gaagcgctc     480 cctgggacac ctcgcctacg ccgctcccgt cgtcgcccac gtagctccct ccgcggtgtc    540
gcaccagtcc cgcgtggncn tcgtctccag ccnnnctgtc gtgtctcann nnntnnntnc    600
cgtnntgtcc cn                                                        612
```

<210> SEQ ID NO 11
<211> LENGTH: 550
<212> TYPE: DNA
<213> ORGANISM: Spodoptera frugiperda
<220> FEATURE:
<221> NAME/KEY: misc_feature
<222> LOCATION: 460, 461, 485, 486, 487, 488, 489, 499, 501, 527, 528,
      529, 535, 536, 537, 538, 539, 540, 541, 542
<223> OTHER INFORMATION: n = A,T,C or G

<400> SEQUENCE: 11

```
gcacgagggg acgttgaacg aaagaaaatg ctacgcgtta cgattttagc cgcagtggtg     60
gtgttcgcct caggcgcgcc ccagaacaac ttcatcttca agaatgacat cactcctgag    120
gaagcccagc agtacctcaa acaactgccg ttcacctcac cccagctctc tggacgcacc    180
gctgtactgc ctctggttcg ctacgacgac cccaggtttc gttcagctga agctggccca    240
acccttggac actactggaa gaatggacag gagatccaga acacagagga ctacttagaa    300
gaggtctaca cgcggctca ataccacggc caggacggtc ttggcaacta cgcctacggt     360
tatgagaccc ctgaatcttc caaggttgag aaccgtgaag gttccggagt cgtccaagga    420
tcctatgtgt accaggttcc cggaatgaag gatctcgtcn nggtccgtta ctgggctgac    480
agccnnnnnt tccaccagna ngacaatctt cccaaggttg aactgannnc cgctnnnnnn    540 nncccgctct                                                           550
```

<210> SEQ ID NO 12
<211> LENGTH: 687
<212> TYPE: DNA
<213> ORGANISM: Spodoptera frugiperda
<220> FEATURE:
<221> NAME/KEY: misc_feature
<222> LOCATION: 286, 287, 288, 632, 633, 634, 635, 636
<223> OTHER INFORMATION: n = A,T,C or G

<400> SEQUENCE: 12

```
gcacgaggta tcactcctga ccgtatctaa aactcggcac acaacacaat ggctgacatc    60
gaagatacac atttcgagac cggggactcc ggtgcctccg ccaccttccc tatgcaatgc   120
tcggccctgc gcaagaacgg tttcgtcatg cttaagggtc gccccctgcaa aatcgtcgag   180 atgtccactt ccaaaaccgg aaagcacggc cacgctaaag ttcacttggt tggaatcgat   240 attttttaacg gcaagaaata cgaagatatc tgcccttcca cccacnnnca tggacgtgcc   300
ccacgtgaag cgtgaggact accagctcac cgatatctct gacgacggct accttaccct   360
catggctgac aacggcgatc tccgcgagga cctcaagatc ccagacggtg acctcggcac   420
ccagttgcgt tctgacttcg atagcggcaa agagctgttg tgcactgtgc tgaagtcttg   480
cggtgaggag tgtgtaatcg cagtcaaggc aaacacagct ctcgacaaat aaaccaactc   540
agcatttata gggatataca tacatataat ttttttacaa tcaacagctc ttacataaat   600
gtaaaacata atactatgta taatttaaca tnnnnnatta tggtgtgacg cggtgctggc   660
ttgtcgccgt ccactccacc cccgaag                                        687
```

<210> SEQ ID NO 13
<211> LENGTH: 514
<212> TYPE: DNA
<213> ORGANISM: Spodoptera frugiperda
<220> FEATURE:
<221> NAME/KEY: misc_feature
<222> LOCATION: 486, 487, 488, 510, 511, 512, 513, 514
<223> OTHER INFORMATION: n = A,T,C or G

<400> SEQUENCE: 13

```
gcacgaggcg cgattgtaac atgtcgtatt caccagaaag aagatcagaa gattggccgg    60
aagattccaa aaatggcccg tctaaggatc aaggcaacta tgatgggcct ccaggaatgg   120
aaccccaagg ggcacttgat acaaactggc accaggtcgt ggaaagcttt gacgacatga   180
atctgaagga agaattgttg agaggaattt atgcttacgg ttttgaaaag ccgtctgcta   240
tccaacaacg cgctattatg ccttgcattc aaggccgtga tgtcatagct caagcccagt   300
ctggtactgg gaagactgct accttctcta tttcaattct tcagcaaatc gataccagta   360
ttcgtgaatg ccaagcactg attttggccc ctactagaga gctggctcag cagatccaaa   420
aggtggtgat tgctcttggg gatcacttga atgctaaatg ccatgcttgc atcggcggca   480
ctaatnnngc gcgaagatgt tcgtcagctn nnnn                                514
```

<210> SEQ ID NO 14
<211> LENGTH: 636
<212> TYPE: DNA
<213> ORGANISM: Spodoptera frugiperda
<220> FEATURE:
<221> NAME/KEY: misc_feature
<222> LOCATION: 635, 636
<223> OTHER INFORMATION: n = A,T,C or G

<400> SEQUENCE: 14

```
gcacgagggt cgtattcacc agaaagaaga tcagaagatt ggccggaaga ttccaaaaat    60
```

```
ggcccgtcta aggatcaagg caactatgat gggcctccag gaatggaacc ccaaggggca    120
cttgatacaa actggcacca ggtcgtggaa agcttcgacg acatgaatct gaaggaagaa    180
ttgttgagag gaatttatgc ttacggtttt gaaaagccgt ctgctatcca acaacgcgct    240
attatgcctt gcattcaagg ccgtgatgtc atagctcaag cccagtctgg tactgggaag    300
actgctacct tctctatttc aattcttcag caaatcgata ccagtattcg tgaatgccaa    360
gcactgattt tggcccctac tagagagctg gctcagcaga tccaaaaggt ggtgattgct    420
cttggggatc acttgaatgc taaatgccat gcttgcatcg gcggcactaa tgtgcgcgaa    480
gatgttcgtc agctggagag tggtgtgcat gtggtggtgg gtacacctgg tcgcgtgtac    540
gacatgataa ctcgtcgtgc tctccgtgct aacactatca agctgtttgt acttgatgaa    600
gctgatgaaa tgctgtcaag aggatttaaa gatcnn                              636

<210> SEQ ID NO 15
<211> LENGTH: 592
<212> TYPE: DNA
<213> ORGANISM: Spodoptera frugiperda
<220> FEATURE:
<221> NAME/KEY: misc_feature
<222> LOCATION: 578, 579, 580, 583, 584, 585
<223> OTHER INFORMATION: n = A,T,C or G

<400> SEQUENCE: 15
gcacgagggt gatgtcacac ttgcaagaga ctgttcaaca ttcagacccg agcactcaga     60
ttttgtacaa tcgtactatg ccaccatcc tgtcacacat ctaccaccac gccctgcacg    120
ataactggtt ccaagctcga gacttgctct atctaggttt gtgcgctttt cgaaggggca    180
atgttaaaga agcccatggc tgcctagctg aactgatgat gactggcaaa cccaaggaac    240
tgttagctca aggtctgcta cctcagcgtc aacacgagcg ttcaaaggaa caggaaagaa    300
tagagaagca acgccaaatg ccgttccaca tgcacatcaa cttggaactg cttgaatgtg    360
tgtatttagt gtctgccatg ctgattgaaa ttccatacat ggccgcccac gaattcgatg    420
ctcgccggcg catgattagt aagactttct atcagaattt gcgcgcaagt gagcgtcagg    480 cttttggtagg cccgcccgaa tccatgcgtg agcatgctgt ggctgccgcc agggcgatgc    540
gccgcggaga ctggcgtgct tgcctcaatt ttattgtnnn tgnnnaatga at            592

<210> SEQ ID NO 16
<211> LENGTH: 609
<212> TYPE: DNA
<213> ORGANISM: Spodoptera frugiperda
<220> FEATURE:
<221> NAME/KEY: misc_feature
<222> LOCATION: 448, 449, 450, 452, 595, 596, 597, 598, 599
<223> OTHER INFORMATION: n = A,T,C or G

<400> SEQUENCE: 16
gcacgaggct gatagccacc tgccaaatta tcttgaaata taaccattca ctaaaatatt     60
taacgtaatt tagtggttaa ttctaaactt aatcatggac gacgacatgg tatttgatcc    120
atctttaaag aaaaagaaga agaagaagac cggtttcgac ttagatgccg ctctcgcagg    180
cgaacaaggt gagagcacga gcgtggaggc gcccgctggg tcgggtgacg tcgacttgcc    240
tgaggatgat aacctcgatt tggataattt tggaaagaaa aagaagaaga agaagaaggg    300
agtcttcaac atggaagaac ttgaaagtac gttaccggaa acacctccgg ccgaagagcc    360
ggaacagcag gaggacgaag ttattgacga tttagatcta gatattgact tctctaaaac    420
gaaaaagaag aagaagaaga aaacatnnn angagctcgt ccttgaagat gacaccaagg    480
```

```
gagaagatca agagaatgtc gaggatgtta gtggtgattt atggagcggc acagaccgtg    540
actacacgta cgacgagcta ctagagcgag tgttcgacat catgcgagaa aagannnnna    600
gcatggttt                                                            609
```

<210> SEQ ID NO 17
<211> LENGTH: 639
<212> TYPE: DNA
<213> ORGANISM: Spodoptera frugiperda
<220> FEATURE:
<221> NAME/KEY: misc_feature
<222> LOCATION: 511, 512, 614, 616, 618, 628, 631, 635, 636, 637, 638
<223> OTHER INFORMATION: n = A,T,C or G

<400> SEQUENCE: 17

```
gcacgaggca gattcatatt tccatcgctt attcgttgct gagaaaaatc gtcggtttta    60
gcgacgtaac atattgctaa taagtgtgaa atattgtgat aaacttcctt ttagcattag   120
ttaatctagt tcaattttaa ataattcaaa atgtttatct tggattggtt cactggtgtt   180
ctcggattcc ttggtctgtg aagaaatca  ggcaagctac tgttcctggg actggacaat   240
gctggcaaga ccacactcct gcacatgctg aaggatgaca gattggcgca gcatgtaccc   300
acattgcatc ccacgtcgga ggaactgtca ataggcagta tgcgtttcac gacgttcgac   360
ttgggcgggc atcagcaggc gcggcgcgtg tggcgcgact acttcccggc ggtgacgcc    420 atcgtgttcc tggtggacgc gtgcgaccgc ccgcgcctgc ccgagtccaa ggccgagctg   480
gactcgctgc tcactgacga gacgctcagc nnactgcccc gtgctcatcc tcggcaacaa   540
gatcgacaag cccggcgcag ctagtgagga cgagctccgt cagttcttca acctgtacca   600
acagaccact gganangnca aagtatcnag ntcannnnt                          639
```

<210> SEQ ID NO 18
<211> LENGTH: 574
<212> TYPE: DNA
<213> ORGANISM: Spodoptera frugiperda
<220> FEATURE:
<221> NAME/KEY: misc_feature
<222> LOCATION: 72, 73, 74, 190, 191, 192, 568, 569, 570, 571, 572, 573,
      574
<223> OTHER INFORMATION: n = A,T,C or G

<400> SEQUENCE: 18

```
gcacgagggt ctatctcgga tattacacgt ggattgtaat ccgtgactaa ccaaaaatgg    60
gcaaggaaaa gnnncacatt aacattgtcg tcattggaca cgtcgactcc ggcaagtcca   120
ccaccaccgg tcacttgatc tacaaatgcg gtggtatcga caaacgtacc atcgagaagt   180
tcgagaaggn nncccaggaa atggggtaag ggttccttca aatacgcctg ggtattggac   240
aaactgaagg ctgagcgtga acgtggtatc accatcgata ttgctctgtg aagttcgaa    300 accgctaaat actatgtcac catcattgac gctcccggac acagagattt catcaagaac   360
atgatcactg gaacttccca ggctgattgc gccgtactca ttgtcgccgc tggtaccggt   420
gagttcgagg ctggtatctc gaagaacgga cagacccgtg agcacgctct gctcgctttc   480
acactcggtg tcaagcagct gattgtgggc gtcaacaaaa tggactccac tgagccccca   540
tacagcgaat cccgtttcga ggaaatcnnn nnnn                               574
```

<210> SEQ ID NO 19
<211> LENGTH: 169
<212> TYPE: DNA
<213> ORGANISM: Spodoptera frugiperda
<220> FEATURE:
<221> NAME/KEY: misc_feature
<222> LOCATION: 64, 153, 154, 155, 165, 166, 167, 168, 169
<223> OTHER INFORMATION: n = A,T,C or G

<400> SEQUENCE: 19
gcacgaggcg gatattacac gtggattgta atccgtgact aaccaaaaat gggcaaggaa     60
aagnttcaca ttaacattgt cgtcattgga cacgtcgact ccggcaagtc caccaccacc    120
ggtcacttga tctacaaatg cggtggtatc gannnacgta ccatnnnnn                169

<210> SEQ ID NO 20
<211> LENGTH: 690
<212> TYPE: DNA
<213> ORGANISM: Spodoptera frugiperda
<220> FEATURE:
<221> NAME/KEY: misc_feature
<222> LOCATION: 505, 506, 507, 508, 510, 511, 512, 526, 527, 528, 529,
      530, 531, 592, 593, 594, 595, 678, 679, 680, 682, 683, 684
<223> OTHER INFORMATION: n = A,T,C or G

<400> SEQUENCE: 20
gcacgaggct ctagtcccgt caccgtcgcc agtagggggc gccacaagaa cagaaagaga     60
attatttcaa actccaatta taacctacta gataactcca aaagttctgt cagttctaac    120
tttaatttaa cggggacgtc agagtttatg gataggaccg ataagataat atcggacgcg    180
actgagctac aagcaatgca gaactttatc atggagaaga tttacgaaat ggaacctaat    240
gagaagaaga agcaatctga ggtcgacagg gtattcaaac acgcattatt agaattcaaa    300
gacaatttag tagcgacgta cagcatagtg gagacgcggg gctctgcgct gaagtacaag    360
gatctgatcg gcaacttcct gcacgtcatg gagacggttt gtgccaggga ggggtccacg    420
ctctccatca ccatgggggt caacgccttt aggggtttca tggacgagtt tatgagccaa    480
catgacactg ataaagctag gacgnnnngn nnaaggataa aaagannnnn ntggacgatc    540
caatacaata caaaggccat acgttcatac tgtccatgat caacatacca annnnagtgt    600
gagatctgca agactttctt catgtggccc atagagcggt cactcatatg ccagacgtgt    660
aaacttgcct cgcataannn tnnnacacta                                     690

<210> SEQ ID NO 21
<211> LENGTH: 711
<212> TYPE: DNA
<213> ORGANISM: Spodoptera frugiperda
<220> FEATURE:
<221> NAME/KEY: misc_feature
<222> LOCATION: 612, 613, 614, 663, 664, 665, 667, 668, 701, 706, 707,
      708, 709, 710, 711
<223> OTHER INFORMATION: n = A,T,C or G

<400> SEQUENCE: 21
tgactccaca gtgggacaaa ctcatagagc ttgatgtgtg gtacgctgct gtgacccaag     60
tgttcttctc tctgtctgtg tgcaccggtg ccatcattat gttctcgtcc tacaatggat    120
tcagacaaaa tgtttacaga gacgcgatga ttgtcactac tttggacacc ttcaccagtt    180
tgttatccgg tttcacgatc ttcggtatcc tgggtaactt ggcgtacgag ttggacaaag    240
atgtggatga cgtcactggt tctgcaggaa ctggacttgc cttcatttca taccctgacg    300
cgatctccaa aactttccag ccacagttgt tcgcagtgct gttcttcttg atgatgacgg    360
tactaggtat cggatcagca gttgctttac tttccaccat caacaccgtg atgatggacg    420
cgttccctcg catcaagacc atctacatgt ccgccttctg ctgcactatt ggatttgcca    480

```
tcggtctcat ttacgtcaca cctggtggcc aatatattct cgagctggtg gattacttcg    540
gtggaacctt cctgattctc ttctgtgcta tcgctgaaat tattggtgta ttctggattt    600
acggcttgga gnnntatgcc tggatattga gtacatgttg ggagttaaac ttcttctact    660
ggnnntnntg ttgggcgtt attatgcctg ccatgatgat naccgnnnnn n              711
```

<210> SEQ ID NO 22
<211> LENGTH: 625
<212> TYPE: DNA
<213> ORGANISM: Spodoptera frugiperda
<220> FEATURE:
<221> NAME/KEY: misc_feature
<222> LOCATION: 540, 541, 542, 543, 614, 615
<223> OTHER INFORMATION: n = A,T,C or G

<400> SEQUENCE: 22

```
gcacgagggt aaacagattt taacactaca ttaatttgtt ctagagttaa atgtattaat     60
tccgacttaa aaacagtgct tgtgataagt gaacacaaat tattgagcaa tgactgactt    120
tataaaacaa tatttcaagg aacaatatga ataaaatgaa aaaatgcttt cgaaaattga    180
cgcggatctg cgaacctgcg gagcacactt agtagcagtg aagttaatgg tgactgccct    240
cgagttgaaa atgacttcga tgaagacaat gtatcaggat ctaatggaac tcagagaaat    300
aatcgttctt ttaaatccac acttgaagaa accgagataa taatacaata cagtaaggtt    360
aacgaatact atcttttaat ttccttaaat tatgttcata aaaatgatta agttgtttag    420
ctgaacacag tggtgtactg acaggatagg tttcattaaa ctttgcataa tcgatcagaa    480
aaccgtgctt tcttttttg tactcgacca tttcaataaa gcgatgaccc cataggattn    540
nnntgggtgg tgtagctcga cttcgcttgg acaggctgac cagttgattc tatagtgcct    600
tcaaacacta cgannatttc catat                                         625
```

<210> SEQ ID NO 23
<211> LENGTH: 472
<212> TYPE: DNA
<213> ORGANISM: Spodoptera frugiperda
<220> FEATURE:
<221> NAME/KEY: misc_feature
<222> LOCATION: 454, 455, 456, 463, 464, 465
<223> OTHER INFORMATION: n = A,T,C or G

<400> SEQUENCE: 23

```
gcacgaggat tttcttaaaa cggtactgca gcaaaaagac ggcattgaag gtggactcgg     60
tctgcctatc tggtacctgg tggtttgtct gttcgggtca tggtttatca tcttcgtgat    120
tgtgtcccga ggtgtaaaga gttccggtaa agctgcatac ttcttggctc tcttccccta    180
cgttgtgatg ctcatttttgc ttataacgac ctctattctg cccggagccg gcaccggcat    240
tcttttcttc ctgactccac agtgggacaa actcatagag cttgatgtgt ggtacgctgc    300
cgtgacccaa gtgttcttct ctctgtctgt gtgcaccggt gccatcatta tgttctcgtc    360
ctacaatgga ttcagacaaa atgtttacag agacgcgatg attgtcacta ctttggacac    420
cttcaccagt ttgttatccg gtttcacgat cttnnntatc ctnnntaact tg            472
```

<210> SEQ ID NO 24
<211> LENGTH: 675
<212> TYPE: DNA
<213> ORGANISM: Spodoptera frugiperda
<220> FEATURE:
<221> NAME/KEY: misc_feature
<222> LOCATION: 563, 564, 565, 566, 648, 649, 650, 655, 656, 666, 667,
    669, 670, 671, 674, 675

<223> OTHER INFORMATION: n = A,T,C or G

<400> SEQUENCE: 24

```
gcacgaggcc ggtcttcagg gcttccttat cttccactcc ttcggtggag gtactggatc    60
tggtttcact tccctcctga tggagcgact ctccgtggac tacggcaaga agtccaagct   120
ggagttcgcc atctacccgg cgcctcaggt gtccaccgct gtcgtggagc cctacaactc   180
catcctcacc acccacacca cccttgagca ctccgactgc gccttcatgg tcgacaacga   240
ggccatctac gacatctgcc gccgcaacct cgacatcgag cgcccacgt acaccaacct    300
gaaccgtctc atcgggcaga tcgtgtcctc catcacggcc tccctgcgct tcgacggcgc   360
cctcaacgtc gatcttaccg agttccagac caacttggtg ccctacccc gtatccactt    420
ccctctggtc acatacgccc cggtcatctc tgccgagaag gcgtaccacg agcagctgtc   480
ggtggctgaa atcaccaacg catgcttcga gcccgccaac cagatggtca agtgcgaccc   540
tcgtcacggc aagtacatgg ctnnnntgca tgttgtaccg tggtgacgtc gtccccaagg   600
acgtgaacgc cgccatcgcc accatcaaga ccaagcgtac catccagnnn cgtcnnttgg   660
tgtccnncnn ngtnn                                                    675
```

<210> SEQ ID NO 25
<211> LENGTH: 650
<212> TYPE: DNA
<213> ORGANISM: Spodoptera frugiperda
<220> FEATURE:
<221> NAME/KEY: misc_feature
<222> LOCATION: 522, 523, 524, 525, 526, 533, 534, 535, 536, 537, 600,
      601, 621, 622, 623, 625, 628, 629, 633, 634, 635, 636, 637, 640,
      641, 642, 643, 644, 645
<223> OTHER INFORMATION: n = A,T,C or G

<400> SEQUENCE: 25

```
gcacgaggat tcgtttggca agcctcttaa ccggtcgcgc tgaacgacga ctgatatttta    60
attaatttat attctacgtt aagttcaaca aaactcaatt caaaatgcgt gagtgcatct   120
cagtacacgt tggacaagcc ggagtccaga tcggtaatgc ctgctgggaa ttatattgcc   180
ttgagcatgg aatccagcct gacgccaga tgcccacaga caagaccgtg ggcggtggtg    240
atgactcctt caacaccttc ttcagcgaga ccggtgccgg caagcacgtc cccagggctg   300
tgtttgttga cttggaaccc acagtagttg atgaggtccg cactggcaca tacagacagt   360
tgtttcatcc agaacaactt atcactggta aggaagatgc ggccaacaac tacgcccgtg   420
gtcactacac catcggcaag gaaatcgtag acctagtcct cgaccgcatc cgtaagctcg   480
ccgaccagtg caccggtctc cagggcttcc ttatcttcca cnnnnntcgg tgnnnnnact   540
gggatctggt ttcacttccc tcctgatgga gcgactctcc gtggactacg gcaagaagtn   600
naagctggag ttcgccatct nnncngcnnc tcnnnnntcn nnnnctgtc                650
```

<210> SEQ ID NO 26
<211> LENGTH: 621
<212> TYPE: DNA
<213> ORGANISM: Spodoptera frugiperda
<220> FEATURE:
<221> NAME/KEY: misc_feature
<222> LOCATION: 521, 522, 523, 525, 532, 534, 535, 536, 596, 597, 618,
      619, 620, 621
<223> OTHER INFORMATION: n = A,T,C or G

<400> SEQUENCE: 26

```
ttcggcacga ggggcaagcc tcttaaccgg tcgcgctgaa cgacgactga tatttaatta    60
```

```
atttatattc tacgttaagt tcaacaaaac tcaattcaaa atgcgtgagt gcatctcagt    120
acacgttgga caagccggag tccagatcgg taatgcctgc tgggaattat attgccttga    180
gcatggaatc cagcctgatg gccagatgcc cacagacaag accgtgggcg gtggtgatga    240
ctccttcaac accttcttca gcgagaccgg tgccggcaag cacgtcccca gggctgtgtt    300
tgttgacttg aacccacag tagttgatga ggtccgcact ggcacataca gacagttgtt    360
tcatccagaa caacttatca ctggtaagga agatgcggcc aacaactacg cccgtggtca    420
ctacaccatc ggcaaggaaa tcgtagacct agtcctcgac cgcatccgta agctcgccga    480
ccagtgcacc ggtctccagg gcttccttat cttccactcc nnncngtgga gntnnntgga    540
tctggtttca cttccctcct gatggagcga ctctccgtgg actacggcaa gaagtnnaag    600
ctggagttcg ccatctannn n                                              621
```

```
<210> SEQ ID NO 27
<211> LENGTH: 602
<212> TYPE: DNA
<213> ORGANISM: Spodoptera frugiperda

<400> SEQUENCE: 27
```

```
gcacgaggat caaagagtta cgaaccgtca ccatactgaa ggagatacca ttcgtcgtgc     60
cattctcaac acgcgtcctt atattccaag gactttttagc gagagagaag cacgaccact    120
ggtacgaaat gacgaacttc aacgaggggc cctcgatcaa catcagtgtt cgaaggacgc    180
atttatatga agatgcattt gataaactta gtccggataa tgaacctgat ttgaagttga    240
aacttcgcgt gcaactgatc aaccaggccg gtgcggagga agctggtgtc gacggcggtg    300
gactattccg agagtttctt tctgagctct taaaatctgc atttgatccg aacaggggtc    360
tgttccggct gacaatagac aacatgttgt atccgaaccc cgccgtacat ctactgtacg    420
atgacttccc catgcactac tacttcgtcg gcaggatgct gggaaaggcg atgtacgaga    480
acctgttggt ggagctgccg ctggcggagt tcttcctggg caagctgtgc ggctgcgggg    540
aggccgacgt gcacgcgctg gcctcgctcg accccgcgct gcaccgcggg ttgttactac    600
tc                                                                    602
```

```
<210> SEQ ID NO 28
<211> LENGTH: 299
<212> TYPE: DNA
<213> ORGANISM: Spodoptera frugiperda
<220> FEATURE:
<221> NAME/KEY: misc_feature
<222> LOCATION: 222, 223
<223> OTHER INFORMATION: n = A,T,C or G

<400> SEQUENCE: 28
```

```
gcacgagggc cggccgccgt gttcgtgccg tcccgccggg ccgcgcgcct actggccgcc     60
gacctgctgg cgctggccgc ggcgcacgcg cagcccgccg ccttcctgcg cgcgcgcccc    120
gacgtgctgc agcccttcct caagaggatc aacgacaaga tgctgaagga cacggtggct    180
gcgggcgtgg cgtacctgca cgagggcgtg gacccggcgg anngggcgcct ggtgcaacaa    240 ctgctggagt cgggcgcgct ggcgctctgc gtcgtggccg ccgagctggc ctggggact     299
```

```
<210> SEQ ID NO 29
<211> LENGTH: 624
<212> TYPE: DNA
<213> ORGANISM: Spodoptera frugiperda
<220> FEATURE:
<221> NAME/KEY: misc_feature
```

<222> LOCATION: 562, 563, 564, 620, 621, 622, 624
<223> OTHER INFORMATION: n = A,T,C or G

<400> SEQUENCE: 29

```
gcacgaggcg aagataaagg tcgcgtgtgg accttaggtt taagtttatt attaaataat    60
ttagcctaaa cataagtcat ggccaataac gacaactttg cacaagatgt tactgataat   120
caactaaatg gaaatgccga aaatggtggt ggcgatacgc aagaacataa tagtgccgaa   180
gccctgggc gtgatgatga cagaaaactt tttgtcggag gcctgagctg ggaaaccaca   240
gacaaggagt tacgtgacca cttcagtgca tatggtgaga ttgagagcat caatgtcaag   300
actgatccaa acactggcag atcaagagga tttgccttta ttgtgttcaa ggcaccagat   360
tcaatagaca aagtgatggc tgctggagag cacactatta acaacaaaaa agttgatccg   420
aaaaaagcaa aggctagaca tggaaagatc tttgttggtg gtcttagcag tgaaatatca   480
gatgatgaga tcaaaaactt cttcagtaat tttggaacaa taattgaagt cgagatgccc   540
tttgacaaaa ccaagaatca gnnnaaggga ttctgcttta taacattcga gtctgaacag   600
gtggtcaatg agctgctgan nncn                                          624
```

<210> SEQ ID NO 30
<211> LENGTH: 644
<212> TYPE: DNA
<213> ORGANISM: Spodoptera frugiperda
<220> FEATURE:
<221> NAME/KEY: misc_feature
<222> LOCATION: 607, 621, 622, 623, 634, 635, 636, 637, 638, 639, 640
<223> OTHER INFORMATION: n = A,T,C or G

<400> SEQUENCE: 30

```
gcacgaggcg cgtgtggacc ttaggtttaa gtttattatt aataatttta gcctaaacat    60
aagtcatggc caataacgac aactttgcac aagatgttac tgataatcaa ctaaatggaa   120
atgccgaaaa tggtggtggc gatacgcaag aacataatag tgccgaagcc cctgggcgtg   180
atgatgacag aaaacttttt gtcggaggcc tgagctggga accacagac aaggagttac   240
gtgaccactt cagtgcatat ggtgagattg agagcatcaa tgtcaagact gatccaaaca   300
ctggcagatc aagaggattt gccttttattg tgttcaaggc accagattca atagacaaag   360
tgatggctgc tggagagcac actattaaca caaaaaagt tgatccgaaa aaagcaaagg   420
ctagacatgg aaagatcttt gttggtggtc ttagcagtga aatatcagat gatgagatca   480
aaaacttctt cagtaatttt ggaacaataa ttgaagtcga gatgcccttt gacaaaacta   540
agaatcagag gaagggattc tgctttataa cattcgagtc tgaacaggtg gtcaatgagc   600
tgctgangac tcctaagcag nnnattggtg cannnnnnnn cgac                    644
```

<210> SEQ ID NO 31
<211> LENGTH: 580
<212> TYPE: DNA
<213> ORGANISM: Spodoptera frugiperda
<220> FEATURE:
<221> NAME/KEY: misc_feature
<222> LOCATION: 569, 570, 571
<223> OTHER INFORMATION: n = A,T,C or G

<400> SEQUENCE: 31

```
gcacgaggat gaagttggct ctgacactct tggctctggc ggcggtggcc accgctaaaa    60
acatcaacgt cgaggatgcc atcgacctag aggacatcac cgcctacgga tacttggcta   120
agatcggtaa acctcttgcc gacgaaatcc gcaaagctga ggaggcagag agcgcatcca   180
```

```
gaattgttgg tggtcaggcc tccagcctcg gacagttccc ctaccaggct ggtcttctcg    240
ctgacttctc cgctggccaa ggtgtgtgtg gtggttcctt ggtgcgtgcc aaccgtgttc    300
ttactgctgc tcactgctgg ttcgatggcc agaaccaggc ctggagattc accgttgttc    360
ttggctccat ccgtttgttc tccggtggta ccagagttca aacctccaac gttgttatgc    420
atggaagctg gaaccccagt aacatccgta atgacgtcgc catgatcagg ctgaactcca    480
acgttggtct ttcaaacacc attgcactca tcgctctgcc cagcggtagc cagctcaacg    540
aaaacttcgc cggtgaaaac gccgtcgcnn nctggattcg                          580
```

```
<210> SEQ ID NO 32
<211> LENGTH: 676
<212> TYPE: DNA
<213> ORGANISM: Spodoptera frugiperda
<220> FEATURE:
<221> NAME/KEY: misc_feature
<222> LOCATION: 648, 649, 650, 651, 652, 653, 660, 661, 671, 672, 673,
      674, 675, 676
<223> OTHER INFORMATION: n = A,T,C or G

<400> SEQUENCE: 32
```

```
gcacgaggat caaaatgaaa ctgttcctcg cagtcgtgtg cttggccgtt gccgcatccg    60
cggtggagat tggagttccg tctcaggaaa acccagtctt tggctaccat caaaacttcg    120
gtattgccga agctgccagg atcaagaagg ctgaggaaga accagccct agcgcccaga    180 ggatcgtcgg aggatctgtc actgacattt ccaacgtccc ttaccaggct ggtctcgtga    240
tccaagtttt ggtcatcttc caatccgtgt gcggtggttc catcatctcc cacaaccgca    300
tcgtgaccgc tgctcactgc aactgggacg gttctatcac cgctaactct ttcaccgtcg    360
tacttggctc caacttcctc ttctccggcg gtaaccgcat caccaccaga gatgttgtca    420
tgcaccccaa ctggaccccca accaccgctg ccaacgacat tgctgtcctc cgcattagct    480
ccgttacttt caccaacgtg atccagccca tcgctctgcc cagcggcaac gagctcaaca    540
acgacttcgt caactggaac gctatcgctt ccggatacgg tcttaccgct gatggtgcta    600
acatcggtac tacccaacgt gtcagctccg tggtactccc cgtgatcnnn nnncgccagn    660
ncgctaccgt nnnnnn                                                    676
```

```
<210> SEQ ID NO 33
<211> LENGTH: 611
<212> TYPE: DNA
<213> ORGANISM: Spodoptera frugiperda
<220> FEATURE:
<221> NAME/KEY: misc_feature
<222> LOCATION: 590, 591, 592, 604, 605, 611
<223> OTHER INFORMATION: n = A,T,C or G

<400> SEQUENCE: 33
```

```
gcacgaggaa tcttagttac attggagtga cttttatta  tcaataacat ttttatttga    60
agactcagta cgtattatcg cgtagttcaa cagagttgct agtgtagttt ctgaaaagtt    120
gccatcttgc ttttgcaact tttaaatata aagtcttat  tagatcgttt ttactaccga    180
taaatttact aaaaatataa aagtgcaatt tacaattact ctgttagtgt cagtttgtgt    240
gaatttgtcg tagtttataaa aggacactgt attgattttg tcaatcagtt tgacgcatgc    300
gctcattggg tgccgtaaaa aagggttggc caacattccg aacagtgtcg ttccggtcgc    360
cgttgtcgtg gtgtcggtga agttagtggt ggaattttta cgtgtataac atcaaaaaat    420
ggcgtctggt gtgacagttt cggacgcgtg caaaacgacg tacgaggaga ttaagaaaga    480
```

```
caagaagcac cgctacgtgg tgttctacat cagggatgag aaacaaattg acgtagagac      540
cgtcggcgaa cgtaacgcgg aatacgatca gttccttgag gatctgcagn nnggtggcac      600
cggnnagtgc n                                                           611

<210> SEQ ID NO 34
<211> LENGTH: 674
<212> TYPE: DNA
<213> ORGANISM: Spodoptera frugiperda
<220> FEATURE:
<221> NAME/KEY: misc_feature
<222> LOCATION: 497, 498, 499, 672, 673, 674
<223> OTHER INFORMATION: n = A,T,C or G

<400> SEQUENCE: 34
gcacgaggct gatatctaat cttagttaca ttggattgac ttttatttat caataacatt       60
tttatttgaa gactcagtac gtattatcgc gtagttcaac ggagttgcta gtgtagtttt      120
ctgaaagttg ccatcttgct tttgcaactt ttaaatataa aagtcttatt agatcgtttt      180
tactaccgat aaatttatca aaatataaa agtgcaattt acaattactc tgttagtgtc      240
agtttgtgtg aatttgtctt agttataaaa ggacactgta ttgattttgt caatcagttt      300
gacgcatgcg ctcattgggt gccgtaaaaa agggttggcc aacattccga acagtgtcgt      360
tccggtcgcc gttgtcgtgg tgtcggtgaa gttagtggtg aattttttac gtgtataaca      420
tcaaaaaatg gcgtctggtg tgacagtttc ggacgcgtgc aaaacgacgt acgaggagat      480
taagaaagac aagaagnnnc cgctacgtgg tgttctacat cagggatgag aaacaaattg      540
acgtagagac cgtcggcgaa cgtaacgcgg aatacgatca gttccttgag gatctgcaga      600
agggtggcac cggagagtgc agatatggcc tcttcgactt cgagtacacg caccagtgcc      660
aaggcacgtc gnnn                                                       674

<210> SEQ ID NO 35
<211> LENGTH: 684
<212> TYPE: DNA
<213> ORGANISM: Spodoptera frugiperda
<220> FEATURE:
<221> NAME/KEY: misc_feature
<222> LOCATION: 648, 649, 650, 652, 653, 654, 657, 659, 660, 661, 662,
      667, 680, 681, 682, 683, 684
<223> OTHER INFORMATION: n = A,T,C or G

<400> SEQUENCE: 35
gcacgaggcc tcgtgccgcg cgaatagaca gttttgtgtg cacaatgttg atcctttggc       60
taaatatcat cgcaataatt tgtgtcatac cctacgcaaa tggagaagga agggttgcaa      120
tagcgcattt acaatcgcta aagtcagtga ctggtcaaat tcaatttacg gagacggcaa      180
aagggcttca tgtcgaagga gttatatttg gttaccacc cggtgcctac gggtttcacg       240
ttcacgaatt aggagatgtt gcacctggtt gcgaccaggc gggccggcac ttcaaccctg      300
agggatccac ccacggtggc aggaactcca ccgtacgcca tgtcggtgac ctcggaaatg      360
tagtgttcgt tagcgagcga gccgcttatg ctacagtaga ctttgtagat agtctattgg      420
cacttcaagg acgtaatagt atattggggc gctcttggt cttgcatgaa caaacggatg        480
acctaggttt gggaggaaac gcgacgtctt tgactacagg taactcgggg ccccggatag      540
catgtggtgc tattggaatc aaatcacctt atgacccttg gaatgctgct agctctatgt      600
ctccgtcgat gctactattt atcacatctt taactttatt tactttannn tnnnaantnn      660
nngtatnagt atttaattn nnnn                                              684
```

<210> SEQ ID NO 36
<211> LENGTH: 402
<212> TYPE: DNA
<213> ORGANISM: Spodoptera frugiperda
<220> FEATURE:
<221> NAME/KEY: misc_feature
<222> LOCATION: 321, 322, 323, 324, 325, 354, 355, 366, 398, 399, 400, 402
<223> OTHER INFORMATION: n = A,T,C or G

<400> SEQUENCE: 36

```
gcacgaggct tccacatacg cgaatagaca gttttgtgtg cacaatgttg gtcctttggc      60
taaatatcat cgcaataatt tgtgtcatac cctacgcaaa tggagaagga agggttgcaa     120
tagcgcattt acaatcgcta aagtcagtga ctggtcaaat tcaatttacg gagacggcaa     180
aagggcttca tgtcgaagga gttatatttg gtttaccacc cggtgcctac gggtttcatg     240
ttcacgaatt aggagatgtt gcacctggtt gcgaccaggc gggccggcac ttcaaccctg     300
agggatccaa ccacggtggc nnnnnctcca ccgtgcgcca tgtcggtgac ctcnnaaatg     360
tagtgnttgt tagcgagcga gccgcttatg ctacagtnnn cn                       402
```

<210> SEQ ID NO 37
<211> LENGTH: 627
<212> TYPE: DNA
<213> ORGANISM: Spodoptera frugiperda
<220> FEATURE:
<221> NAME/KEY: misc_feature
<222> LOCATION: 393, 394, 395, 396, 397, 435, 436, 437, 439, 619, 620, 621, 622
<223> OTHER INFORMATION: n = A,T,C or G

<400> SEQUENCE: 37

```
gcacgagggt cgagagatac ggtgcgcaca tagcaacaat atcaaagtac aaaggtcagt      60
aactatgagt ggtaaattgt taaaaactct aatccttggg gcacctgctt caggcaaggg     120
gactatatcg tctcggatag tgaagaaata tgctgtggca cacgtgtcca gtggggacaa     180
gctgagggac cacattgaga acaaactga cctaggtaaa gaagtcaaaa agtacttgaa     240
tgaagggaaa cttgtacctg atgatgtcat gataaagttt atgatcacag aattaaaaaa     300
agttgaagat aaaccatggc tactggatgg attcccgagg actgtgggac aggctgatgc     360
tttgtggaag gtacaacctg ttgatgtagt agnnnnntta gtagtgcctt ttgaggtaat     420
catagacaga gtgannnanc gctgggtgca cttgccttcg ggccgagtgt ataacattgg     480
cttcaacact cctaaagtgg aaggtaagga tgatgagaca ggtgaggact tggttcagag     540
acctgacgac aagccagagg ctgtgcgcaa gcggctggag atctatgaga gtgtgacgag     600
gccagtcata gagttctann nngctaa                                          627
```

<210> SEQ ID NO 38
<211> LENGTH: 395
<212> TYPE: DNA
<213> ORGANISM: Spodoptera frugiperda
<220> FEATURE:
<221> NAME/KEY: misc_feature
<222> LOCATION: 330, 331, 332, 333, 358, 359, 360, 361, 362, 363, 368, 369, 370, 371, 372, 373, 374, 376, 377, 378, 380, 381, 382, 386, 388, 389, 390, 391, 392, 393, 394, 395
<223> OTHER INFORMATION: n = A,T,C or G

<400> SEQUENCE: 38

```
tgctgctgct ggaagctggg cccaaccctc ccgaggagag cattatacca ggcttaagac      60
aaaccttgaa agaaacgccc tacgactgga acttcaccac cattgacgac ggggtcacga     120
```

```
gccaggcgct ggcgggccac gtgcagagac agccgcgggg caagatgctg ggcggcagcg      180
gctcgctcaa cgacatggtg tacgcgcggg gccaccccga ggactactac gagtgggccg      240
acatcgccgg cgacgtctgg aactggacca acgtgctgga ctacttcaag cggacggagc      300
acatgacgga cgccaatatc gttcacaacn nnnagctcat gcagtaccac ggcacggnnn      360
nnnccatnnn nnnntnnngn nnccantnnn nnnnn                                 395
```

<210> SEQ ID NO 39
<211> LENGTH: 570
<212> TYPE: DNA
<213> ORGANISM: Spodoptera frugiperda
<220> FEATURE:
<221> NAME/KEY: misc_feature
<222> LOCATION: 555, 556, 557, 561, 562, 563, 564, 565, 567, 568, 569, 570
<223> OTHER INFORMATION: n = A,T,C or G

<400> SEQUENCE: 39

```
gcacgagggg aaaacatggg aaggaggtcg catcaagatg ttagtgctcg acttgaactg       60
cccggtcgtt ggagacgact gcaaagacag ccgcaagaag ttgcttgtgg actacttcca      120
tacaaacctg catacccaga acttctacgc gttccgcttc tttatctgcg aagtgttgaa      180
cttcatcaac gtcgtgggcc agatcttctt catggacttt ttcctggacg gcgagttctc      240
cacgtacggc agtgacgtgg tcagtttcac cgagatggag cccgaggagc gtgtggaccc      300
gatggctaga gtgttcccga aagtgaccaa gtgcaccttc cacaaatacg gtccttcagg      360
aaccgtgcag aagttcgacg gtctgtgcgt gctgccattg aacatcgtca atgaaaagat      420
ctacgtgttc ctgtggttct ggtttatgat cctgtcgatc ctgagtggaa tttcgctgat      480
ttaccgcatg gccgtggtgg ctggaccgcg cgtgcgcctg tacctgctgc gtgcgcgcag      540
ccgcctggcc ccgcnnncgc nnnnngnnnn                                       570
```

<210> SEQ ID NO 40
<211> LENGTH: 648
<212> TYPE: DNA
<213> ORGANISM: Spodoptera frugiperda
<220> FEATURE:
<221> NAME/KEY: misc_feature
<222> LOCATION: 639, 640, 641, 643
<223> OTHER INFORMATION: n = A,T,C or G

<400> SEQUENCE: 40

```
gcacgaggat tttaatagct attatgactt tacagactag acggatcaag gccatgcctc       60
tcgcttgcat actcaccatc cgcacatacc gtattgcggt atgtcaataa gttgcaaata      120
atgtctgttc agttttacaa ggataagatc agcagtattt gcgaactgta cctactacta      180
agctgataat gtaataatta aactttatta ttgaaataga tatgtataat tgacatcttt      240
ctcaaatggg tgtcaatact gccaactcta ttaccacaat ttcttttcgt atttgctttt      300
atactgagcc tgatgacgta ctgtactttt tattagaatt taattttct tattttctt       360 actacgtagt cattaaatct gagaaattaa aaattactaa tttagaactc ccaaattctg      420
aatgaggttc taaaaagttg ttaggaatac taaataccat tttaccaaca taaatctaat      480
ttcgttactt aaaatattaa atgtataatg aaatgtctat gataagtgtt tactatcttt      540
atatcgacaa aatttatttt ccatgtttta aaatttattt ttcagatgtt ttgacgtgat      600
aagtttgtat tttatcaata tctgatagtc gagagttann nantattg                   648
```

-continued

```
<210> SEQ ID NO 41
<211> LENGTH: 716
<212> TYPE: DNA
<213> ORGANISM: Spodoptera frugiperda
<220> FEATURE:
<221> NAME/KEY: misc_feature
<222> LOCATION: 612, 613, 614, 703, 704, 705, 706
<223> OTHER INFORMATION: n = A,T,C or G

<400> SEQUENCE: 41
gcacgaggga ggagaggtgg tggctggctt ccttgcaaac gaagcgtcgt aaattacatc    60
ttatttgtaa attttaataa aaatttgatc gttaaacgat cgaatcagta gtgatttaag   120
tgctcaagca gtttcacatc caatcgacaa tgagttcgag tgtatgctac aagtgtaacc   180
ggacagggca cttcgcccgc gagtgcaccc agggtggtgt tgccgctcgt gactctggtt   240
tcaaccgtca gcgcgaaaag tgcttcaagt gcaaccgcgc tgggcacttc gctcgggatt   300
gcaaggagga ggccgaccgt tgctacagat gtaacggcac gggacacata gcgcgtgagt   360
gcgcgcaaag tccggacgag ccgtcgtgtt acacttgcaa caagaccggg cacatcgcac   420
ggaactgccc agagggcggg cgcgacagct ccaaccagac ctgctacaac tgcaacaagt   480
ccggccacat ctcacgcaac tgccccgacg gcaccaagac ttgttacgtg tgcggaaagc   540
ccggacacat ctcccgcgat tgcgatgagg agcggaacta acacacgcct cttcgcgact   600
gcctatatat annntaaact atgtatatta tgatgccacg cacggacgat aagcaaagga   660
cgcgatacgc gacactagat cgtaagacca cacgactgta tgnnnntaat gcaacg       716

<210> SEQ ID NO 42
<211> LENGTH: 473
<212> TYPE: DNA
<213> ORGANISM: Spodoptera frugiperda
<220> FEATURE:
<221> NAME/KEY: misc_feature
<222> LOCATION: 472
<223> OTHER INFORMATION: n = A,T,C or G

<400> SEQUENCE: 42
gcacgaggat aataaacgtt aatatttaac aagttgaaaa gtttgtcttt caatttgtga    60
ttttgtaaag atcattctat ggaatggaca gtttgctatc tgtgaaacat ccattagctt   120
tgtgttgaga gcagaggtcg cggcggcggg gtgatgcggc catggcttcg cggcgcgtga   180
cgcgcaagtg ggaggtgttc gcgggacgga accgattctg gtgcgacggc cgcctcatga   240
cggcgccgca ccccggcgtg ttcctgctca cgctcgcgct catctgcggc acgtgcgccc   300
tgcacttcgc cttcgactgc cccttcctgg ccgtgcgcgt gtcgcccgcc gtgcccgcgg   360
ccggcgccgc gctgtgcgcg ctgacgctgg cggcgctgct gcgcacggcg ctgtccgacc   420
ccggcatcat cccgcgcgcc gccgcggccg aggcggcggc gctggaggcg gng          473

<210> SEQ ID NO 43
<211> LENGTH: 535
<212> TYPE: DNA
<213> ORGANISM: Spodoptera frugiperda
<220> FEATURE:
<221> NAME/KEY: misc_feature
<222> LOCATION: 15, 16, 358, 375, 376, 377, 378, 379, 426, 427, 428,
      450, 451, 452, 454, 457, 509, 510, 511, 512, 513, 514, 515, 516,
      517, 518, 519, 520, 521, 524, 525, 531, 532, 533, 534, 535
<223> OTHER INFORMATION: n = A,T,C or G

<400> SEQUENCE: 43
cgcgcacgtc gctcnncaag cccgctgcag cgccggccaa gcccgccccc gcggcggcgc    60
```

```
gcgccaccag tgcgaccagc cgcgcggccc ccgcggcccg gccggccccc aagtccgcag    120
taggcgcagc gcggcccgca gcacaaaaga cagatgcggc cgccaaaccc gcggcgaccc    180
gggttgcggc tccgcgtccc cgcgctgtcgg cgcccaggcc ccagcctaag ccggcagaca    240
agaagccagt accgaatggt gacgtgaaag actccaagcc agccgcgcgg cccgcgcccc    300
ggccggccgc ggccgcgcgc cccgcgccgc gccccactcc ccgcgccccc gccgcacngg    360
tcgcacccac tactnnnnng agtgccccca agccggcgcc cgtgctccc ctggacaagc    420 agagcnnnga cctcgctaac aaacgcatcn nngncanggc agcaccgcct aggactgctc    480
cccctaagac gacaacgacg acaacaggnn nnnnnnnnn ngtnncgaag nnnn           535
```

<210> SEQ ID NO 44
<211> LENGTH: 586
<212> TYPE: DNA
<213> ORGANISM: Spodoptera frugiperda
<220> FEATURE:
<221> NAME/KEY: misc_feature
<222> LOCATION: 457, 458, 459, 460, 461, 462, 489, 505, 506, 507, 556,
    557, 558, 559, 560, 561, 567, 568, 569, 570, 571, 573, 577, 578,
    579, 580, 581, 586
<223> OTHER INFORMATION: n = A,T,C or G

<400> SEQUENCE: 44

```
gcacgaggct ataacaagca gcatataaaa atgaaattct tgctgtcttt cgctgccgtc     60
atcgccgtgg ccgccgctgg cctggtgccc gttggacccg ccggccctgc gcccgctcct    120
gaggcccctg aggtcttcga gcccgtcgct attggacccg ctgtcattga ctccttcgag    180
cccatcgcca tcgacccgc tatcatcgac tccttcgagc ccatcgccat cggacccgct    240
attgttccat ctcccgagcc cgtcgccatc ggacccgcca tcattgagag cccagagccc    300
gttgctgtcg gacctgcatg gattgacttc ccctgcccg acgtggtgc tgccgttgcc    360 cccgttgagc cctctcccgt ggctgttatc cccggtcccg tgtccactga ggttgcttca    420
ggcactcccc tcgttcagat catcctgaac atcaacnnnn nntctgctga cgttagcccc    480
gttgctgtng gcccgctgt cgagnnnaca cccgtgcacg ttgtggactc tgcccctgaa    540
cccgtccacg ttgtgnnnnn ngccccnnnn ncnatcnnnn ngtcgn                   586
```

<210> SEQ ID NO 45
<211> LENGTH: 623
<212> TYPE: DNA
<213> ORGANISM: Spodoptera frugiperda
<220> FEATURE:
<221> NAME/KEY: misc_feature
<222> LOCATION: 563, 564, 565, 566, 567, 568, 622, 623
<223> OTHER INFORMATION: n = A,T,C or G

<400> SEQUENCE: 45

```
gcacgaggct tagagtaagc ataggtgtat ttatgtattg agtcggaaga agcaatggac     60
gatccaaata ggatgatggc gcatagcggc gggcttatgg ggccgcaggg ctacggcctg    120
cctggcggcg agggaactcc aaccgcaggc gaaggtgaag cccgcaagca agatattggt    180
gaaatattgc aacagatcat gaatattaca gatcaaagtc ttgatgaagc gcaagcgaga    240
aaacatactc tcaactgtca cagaatgaag cctgccctat tttcagtgtt gtgtgaaatc    300
aaagagaaaa cagtgctgtc cctccgcaac acgcaagagg aggagccccc agatccccag    360
ctgatgcgct tggacaacat gctcatagcc gaggggtcg ctggccctga aaagggtggt    420
ggtgcgggcg ctgcagcttc ggcatcagct gctgctggtg aatgggacaa tgccatcgag    480
cactctgact accgtgcgaa gttggcgcag atccgccaga tctaccacca ggagctggac    540
```

```
aagtatgaga atgcttgtaa tgnnnnnncc acccacgtga tgaacttact ccgcgagcag     600
agccgcacca ggcctatcac ann                                            623
```

<210> SEQ ID NO 46
<211> LENGTH: 624
<212> TYPE: DNA
<213> ORGANISM: Spodoptera frugiperda
<220> FEATURE:
<221> NAME/KEY: misc_feature
<222> LOCATION: 506, 507, 508, 622, 623, 624
<223> OTHER INFORMATION: n = A,T,C or G

<400> SEQUENCE: 46

```
gcacgaggcc aggtttgaga aaaacgctta aactgccaca aaatcccgtt ctcgaagaag     60
cacttttcac ttattaataa gtaacttgtg taaaatgtgg tttaaatgtg tattttacta    120
aacctcaata aatatattta tatcaaaata taattttttg gtagttcgga ttatcgaggc    180
tctactgtat acctactttt tgttaaaata ttttagtctt atatatttt tttctatact     240 gtattattta ttcctatagt acatattata atccgaacgc tccgtgagtc cgaacagggg    300
cgacttccta actaatccat atctcttaga gctttcgaat atccatttgc cttttcttta   360
aaaagattaa taactattta tatatatccc aaatatataa aaacaaccac tccaattatt    420
attattcaaa tatgacaaac tagatagaat gtcccaagaa atttgcaaaa aagtaatgtt    480
caaattatta accgaagaac gaattnnnga gtgtataata ttatacagac atttagaaat    540
ttttaatagg ctccaatcgc atgagaggtc gctttaaaat tcggcattgg tgtgtgcgtt    600
gcaatttaat ctttaacacc cnnn                                           624
```

<210> SEQ ID NO 47
<211> LENGTH: 678
<212> TYPE: DNA
<213> ORGANISM: Spodoptera frugiperda
<220> FEATURE:
<221> NAME/KEY: misc_feature
<222> LOCATION: 627, 631, 632, 634, 669, 670, 671, 672, 673, 674, 675
<223> OTHER INFORMATION: n = A,T,C or G

<400> SEQUENCE: 47

```
gcacgagggg acgtgtttac aatttacttt cgtgctcgtg tgattttaat taaaacagtg     60
ctaagtgctc taggacgctg aataactgat atttgtttta aaagttgata taaattaatc    120
acaatgaata gagataaacg agaaccagag tatccaacgg agttggagtc tcaattcgta    180
atgcgtttac ctgaggagcc tgcaaaagtt ttgagagaag tgttgaaatc cggagagaac    240
ctgaaaaaca gactgacgat acaaatagaa aacgacatgc gcacgggcga ggtaaggttt    300
gatcactggt tgatgcacgc caagatcgtg gatctaccaa ccatcataga atctctaaaa    360
acgatcgaca acaagagttt ctacaaaaca gcagatatat gccaaatgat gatttgtaaa    420
gaagaacctg accaaccatc cacagaggaa gagtcaccag ctaaaaataa gaaaaaagat    480
ccatacaaag ttgacaaaaa gttcctatgg ccacacggca tcacaccgcc tacgaagaac    540
gtacggaagc gtcgatttag aaaaacccctt aaaaagaaat atgtagaagc accagaaatt    600
gaaaaggaag tgaagaggct gctgagngca nncnatgagg ctgttagtgt taactgggag    660
gtcatcaann nnnnngat                                                  678
```

<210> SEQ ID NO 48
<211> LENGTH: 683
<212> TYPE: DNA

<213> ORGANISM: Spodoptera frugiperda
<220> FEATURE:
<221> NAME/KEY: misc_feature
<222> LOCATION: 562, 563, 564
<223> OTHER INFORMATION: n = A,T,C or G

<400> SEQUENCE: 48

```
gcacgagggt cgaatggaac atggcggtgc taggcaggat gtgcataagt tttgatttt      60
tgcattttta acgagttgct tatatcagtt agctttctaa ataatttctg acttatttcg    120
tgtgttataa tatttgttat agtgtaaaag cttatccacc ccaggaattt cctatctgga    180
cttacttagt tctgcaatga aaattattat tcgttggtag tgtaaaaata attgtgacaa    240
atatatcact ttgcttcagt gtgccgtgtt ggtcatggct acgctcctcc aagagaatgg    300
tataaaggag ttaagcaaag ttgtgcctaa ccgtggtata tcctcacata gtgtaacaaa    360
tcatatggtg cctgatcatg aatattgcga agctgggtca actagcacgt cacagatgaa    420
gtgtaccgat acaagtgagg cgatggcgcc cccgccgcc attgaagaag gaggatac       480
accagaaaata gatataatga taaacaatgt tgtgtgcagt tttagtgtta agtgccacct   540
gaaccttaga cagatagcat tnnntggtgt gaacgttgaa tttcgccgcg agaacggcat    600
ggtaactatg aagttacggc gtccatacac tactgcgtcc atctggtcgt ccggccgcgt    660
gacgtgcact ggtgcaacca gcg                                           683
```

<210> SEQ ID NO 49
<211> LENGTH: 658
<212> TYPE: DNA
<213> ORGANISM: Spodoptera frugiperda
<220> FEATURE:
<221> NAME/KEY: misc_feature
<222> LOCATION: 621, 643, 644, 645, 646, 654, 655, 656, 657
<223> OTHER INFORMATION: n = A,T,C or G

<400> SEQUENCE: 49

```
gcacgaggga atattgcgaa gctgggtcaa ctagcacgtc acagatgaag tgtaccgata     60
caagtgaggc gatggcgcca cccgccgcca ttgaagaaga ggaggataca ccagaaatag   120
atataatgat aaacaatgtt gtgtgcagtt ttagtgttaa gtgccacctg aaccttagac   180
agatagcatt aaatggtgtg aacgttgaat ttcgccgcga gaacggcatg gtaactatga   240
agttacggcg tccatacact actgcgtcca tctggtcgtc cggccgcgtg acgtgcactg   300
gtgcaaccag cgaggaccag gcgaaggttg ccgcacgacg gtatgcgcgc gcccttcaga   360
agctcggctt ccaagtgcgt ttccgcaatt tccgtgtagt caatgtatta ggcacctgtc   420
ggatgccgtt tggtataagg atcatatctt tttcgaaaaa atacaaggaa gcagactatg   480
aacctgagct ccatcctgga gtcacatata agttatacaa tcctaaagcc acactcaaga   540
tattctccac tggtggtgtg actatcacag ctcggagtgt gagtgacgtt cagtcagccg   600
tggaacgcat cttcccttg ntgtacgagt tccgcaagcc tcnnnnaccg gcannnna     658
```

<210> SEQ ID NO 50
<211> LENGTH: 652
<212> TYPE: DNA
<213> ORGANISM: Spodoptera frugiperda
<220> FEATURE:
<221> NAME/KEY: misc_feature
<222> LOCATION: 640, 643, 644, 645, 646
<223> OTHER INFORMATION: n = A,T,C or G

<400> SEQUENCE: 50

```
gcacgagggt accaaaagct cttttcattg cagctgaagg gtcactgcaa cttggccaat     60
```

-continued

```
cagaattagc attgaaacta ttcaaagaac taaaacaaga aggaatggaa atcaggcaac    120
atttctattg gcctttgtta gttcagaagg caaaggaaaa tgatgaggaa ggcctcttgc    180
aaattttaaa agaaatgagc agcaatgact ttactgttac tggagaagcg ttaagagact    240
atgttatccc ttacttgata aaaaagatt ctccacagaa tgtcttactt aaacttcaaa     300
ttgcaaatgt accaacaatc catgctgcaa gaaatctaat ggttgatctt ttggattctg    360
gagacataaa aggcgcagcg gaaatagctc tgcaatatag accttggggc aactactctc    420
ttgttgccag gtccctcatc aatgcagtga ataagacaaa agatgtagaa tcgtttgcta    480
aaattcttca tgctataagc agtaaacctt tgtcacaggg tgaagaagat gttgctgcca    540
acaatgagga aggtcaaagt gatgaaaata atgatattca tgaagtcggc cgtattgtga    600
ggtcgtctgc caagagtttg gctaaaccag acttaatagn aannnnttta ga           652
```

<210> SEQ ID NO 51
<211> LENGTH: 23
<212> TYPE: DNA
<213> ORGANISM: Spodoptera frugiperda

<400> SEQUENCE: 51
aacatggtat ccgacttcag gaa                                            23

<210> SEQ ID NO 52
<211> LENGTH: 19
<212> TYPE: RNA
<213> ORGANISM: Spodoptera frugiperda

<400> SEQUENCE: 52
caugguaucc gacuucagg                                                 19

<210> SEQ ID NO 53
<211> LENGTH: 19
<212> TYPE: RNA
<213> ORGANISM: Spodoptera frugiperda

<400> SEQUENCE: 53
ccugaagucg gauaccaug                                                 19

<210> SEQ ID NO 54
<211> LENGTH: 23
<212> TYPE: DNA
<213> ORGANISM: Spodoptera frugiperda

<400> SEQUENCE: 54
aaggtcgctg acgagaacaa gga                                            23

<210> SEQ ID NO 55
<211> LENGTH: 19
<212> TYPE: RNA
<213> ORGANISM: Spodoptera frugiperda

<400> SEQUENCE: 55
ggucgcugac gagaacaag                                                 19

<210> SEQ ID NO 56
<211> LENGTH: 19
<212> TYPE: RNA
<213> ORGANISM: Spodoptera frugiperda

<400> SEQUENCE: 56
cuuguucucg ucagcgacc    19

<210> SEQ ID NO 57
<211> LENGTH: 23
<212> TYPE: DNA
<213> ORGANISM: Spodoptera frugiperda

<400> SEQUENCE: 57
aagtgtcctg ggcttgagtt cca    23

<210> SEQ ID NO 58
<211> LENGTH: 19
<212> TYPE: RNA
<213> ORGANISM: Spodoptera frugiperda

<400> SEQUENCE: 58
guguccuggg cuugaguuc    19

<210> SEQ ID NO 59
<211> LENGTH: 19
<212> TYPE: RNA
<213> ORGANISM: Spodoptera frugiperda

<400> SEQUENCE: 59
gaacucaagc ccaggacac    19

<210> SEQ ID NO 60
<211> LENGTH: 23
<212> TYPE: DNA
<213> ORGANISM: Spodoptera frugiperda

<400> SEQUENCE: 60
aagaagaagc tcctccacgt gtt    23

<210> SEQ ID NO 61
<211> LENGTH: 19
<212> TYPE: RNA
<213> ORGANISM: Spodoptera frugiperda

<400> SEQUENCE: 61
gaagaagcuc cuccacgug    19

<210> SEQ ID NO 62
<211> LENGTH: 19
<212> TYPE: RNA
<213> ORGANISM: Spodoptera frugiperda

<400> SEQUENCE: 62
cacguggagg agcuucuuc    19

<210> SEQ ID NO 63
<211> LENGTH: 23
<212> TYPE: DNA
<213> ORGANISM: Spodoptera frugiperda

<400> SEQUENCE: 63
aaggtcgctg acgagaacaa gga    23

<210> SEQ ID NO 64
<211> LENGTH: 19
<212> TYPE: RNA
<213> ORGANISM: Spodoptera frugiperda

<400> SEQUENCE: 64
ggucgcugac gagaacaag                                                 19

<210> SEQ ID NO 65
<211> LENGTH: 19
<212> TYPE: RNA
<213> ORGANISM: Spodoptera frugiperda

<400> SEQUENCE: 65
cuuguucucg ucagcgacc                                                 19

<210> SEQ ID NO 66
<211> LENGTH: 23
<212> TYPE: DNA
<213> ORGANISM: Spodoptera frugiperda

<400> SEQUENCE: 66
aatgtcctgg ggctgagttt caa                                            23

<210> SEQ ID NO 67
<211> LENGTH: 19
<212> TYPE: RNA
<213> ORGANISM: Spodoptera frugiperda

<400> SEQUENCE: 67
uguccugggg cugaguuuc                                                 19

<210> SEQ ID NO 68
<211> LENGTH: 19
<212> TYPE: RNA
<213> ORGANISM: Spodoptera frugiperda

<400> SEQUENCE: 68
gaaacucagc cccaggaca                                                 19

<210> SEQ ID NO 69
<211> LENGTH: 23
<212> TYPE: DNA
<213> ORGANISM: Spodoptera frugiperda

<400> SEQUENCE: 69
aagaataagc tcctccacgt gtt                                            23

<210> SEQ ID NO 70
<211> LENGTH: 19
<212> TYPE: RNA
<213> ORGANISM: Spodoptera frugiperda

<400> SEQUENCE: 70
gaauaagcuc cuccacgug                                                 19

<210> SEQ ID NO 71
<211> LENGTH: 19
<212> TYPE: RNA
<213> ORGANISM: Spodoptera frugiperda

<400> SEQUENCE: 71
cacguggagg agcuuauuc                                                 19

<210> SEQ ID NO 72
<211> LENGTH: 23
<212> TYPE: DNA
<213> ORGANISM: Spodoptera frugiperda

<400> SEQUENCE: 72
aatttgtcga ggagacccta ttg                                          23

<210> SEQ ID NO 73
<211> LENGTH: 19
<212> TYPE: RNA
<213> ORGANISM: Spodoptera frugiperda

<400> SEQUENCE: 73
uuugucgagg agcccuau                                                19

<210> SEQ ID NO 74
<211> LENGTH: 19
<212> TYPE: RNA
<213> ORGANISM: Spodoptera frugiperda

<400> SEQUENCE: 74
auagggucuc cucgacaaa                                               19

<210> SEQ ID NO 75
<211> LENGTH: 23
<212> TYPE: DNA
<213> ORGANISM: Spodoptera frugiperda

<400> SEQUENCE: 75
aagttcgcgt tcactcttga aga                                          23

<210> SEQ ID NO 76
<211> LENGTH: 19
<212> TYPE: RNA
<213> ORGANISM: Spodoptera frugiperda

<400> SEQUENCE: 76
guucgcguuc acucuugaa                                               19

<210> SEQ ID NO 77
<211> LENGTH: 19
<212> TYPE: RNA
<213> ORGANISM: Spodoptera frugiperda

<400> SEQUENCE: 77
uucaagagug aacgcgaac                                               19

<210> SEQ ID NO 78
<211> LENGTH: 23
<212> TYPE: DNA
<213> ORGANISM: Spodoptera frugiperda

<400> SEQUENCE: 78
aactgcccct taacctcatc tat                                          23

<210> SEQ ID NO 79
<211> LENGTH: 19
<212> TYPE: RNA
<213> ORGANISM: Spodoptera frugiperda

<400> SEQUENCE: 79
cugccccuua accucaucu                                               19

<210> SEQ ID NO 80
<211> LENGTH: 19
<212> TYPE: RNA
<213> ORGANISM: Spodoptera frugiperda

```
<400> SEQUENCE: 80
agaugagguu aaggggcag                                              19

<210> SEQ ID NO 81
<211> LENGTH: 23
<212> TYPE: DNA
<213> ORGANISM: Spodoptera frugiperda

<400> SEQUENCE: 81
aatcacgctg aaaccactgt ata                                         23

<210> SEQ ID NO 82
<211> LENGTH: 19
<212> TYPE: RNA
<213> ORGANISM: Spodoptera frugiperda

<400> SEQUENCE: 82
ucacgcugaa accacugua                                              19

<210> SEQ ID NO 83
<211> LENGTH: 19
<212> TYPE: RNA
<213> ORGANISM: Spodoptera frugiperda

<400> SEQUENCE: 83
uacagugguu ucagcguga                                              19

<210> SEQ ID NO 84
<211> LENGTH: 23
<212> TYPE: DNA
<213> ORGANISM: Spodoptera frugiperda

<400> SEQUENCE: 84
aaaatatggc gcgcctattg ttt                                         23

<210> SEQ ID NO 85
<211> LENGTH: 19
<212> TYPE: RNA
<213> ORGANISM: Spodoptera frugiperda

<400> SEQUENCE: 85
aauauggcgc gccuauugu                                              19

<210> SEQ ID NO 86
<211> LENGTH: 19
<212> TYPE: RNA
<213> ORGANISM: Spodoptera frugiperda

<400> SEQUENCE: 86
acaauaggcg cgccauauu                                              19

<210> SEQ ID NO 87
<211> LENGTH: 23
<212> TYPE: DNA
<213> ORGANISM: Spodoptera frugiperda

<400> SEQUENCE: 87
aacgttctcg gtctttcact gct                                         23

<210> SEQ ID NO 88
<211> LENGTH: 19
<212> TYPE: RNA
```

```
<213> ORGANISM: Spodoptera frugiperda

<400> SEQUENCE: 88
cguucucggu cuuucacug                                              19

<210> SEQ ID NO 89
<211> LENGTH: 19
<212> TYPE: RNA
<213> ORGANISM: Spodoptera frugiperda

<400> SEQUENCE: 89
cagugaaaga ccgagaacg                                              19

<210> SEQ ID NO 90
<211> LENGTH: 23
<212> TYPE: DNA
<213> ORGANISM: Spodoptera frugiperda

<400> SEQUENCE: 90
aagtcatcgt tccaagtcta cct                                         23

<210> SEQ ID NO 91
<211> LENGTH: 19
<212> TYPE: RNA
<213> ORGANISM: Spodoptera frugiperda

<400> SEQUENCE: 91
gucaucguuc caagucuac                                              19

<210> SEQ ID NO 92
<211> LENGTH: 19
<212> TYPE: RNA
<213> ORGANISM: Spodoptera frugiperda

<400> SEQUENCE: 92
guagacuugg aacgaugac                                              19

<210> SEQ ID NO 93
<211> LENGTH: 23
<212> TYPE: DNA
<213> ORGANISM: Spodoptera frugiperda

<400> SEQUENCE: 93
aaccccttga atgttaaggt cgg                                         23

<210> SEQ ID NO 94
<211> LENGTH: 19
<212> TYPE: RNA
<213> ORGANISM: Spodoptera frugiperda

<400> SEQUENCE: 94
ccccuugaau guuaagguc                                              19

<210> SEQ ID NO 95
<211> LENGTH: 19
<212> TYPE: RNA
<213> ORGANISM: Spodoptera frugiperda

<400> SEQUENCE: 95
gaccuuaaca uucaagggg                                              19

<210> SEQ ID NO 96
<211> LENGTH: 23
```

```
<212> TYPE: DNA
<213> ORGANISM: Spodoptera frugiperda

<400> SEQUENCE: 96
aagtacacca tgttgcaagt atg                                    23

<210> SEQ ID NO 97
<211> LENGTH: 19
<212> TYPE: RNA
<213> ORGANISM: Spodoptera frugiperda

<400> SEQUENCE: 97
guacaccaug uugcaagua                                         19

<210> SEQ ID NO 98
<211> LENGTH: 19
<212> TYPE: RNA
<213> ORGANISM: Spodoptera frugiperda

<400> SEQUENCE: 98
uacuugcaac augguguac                                         19

<210> SEQ ID NO 99
<211> LENGTH: 23
<212> TYPE: DNA
<213> ORGANISM: Spodoptera frugiperda

<400> SEQUENCE: 99
aacgtgtcca tgatggctga ctc                                    23

<210> SEQ ID NO 100
<211> LENGTH: 19
<212> TYPE: RNA
<213> ORGANISM: Spodoptera frugiperda

<400> SEQUENCE: 100
cguguccaug auggcugac                                         19

<210> SEQ ID NO 101
<211> LENGTH: 19
<212> TYPE: RNA
<213> ORGANISM: Spodoptera frugiperda

<400> SEQUENCE: 101
gucagccauc auggacacg                                         19

<210> SEQ ID NO 102
<211> LENGTH: 23
<212> TYPE: DNA
<213> ORGANISM: Spodoptera frugiperda

<400> SEQUENCE: 102
aaacctacaa aatggccgaa aac                                    23

<210> SEQ ID NO 103
<211> LENGTH: 19
<212> TYPE: RNA
<213> ORGANISM: Spodoptera frugiperda

<400> SEQUENCE: 103
accuacaaaa uggccgaaa                                         19

<210> SEQ ID NO 104
```

-continued

```
<211> LENGTH: 19
<212> TYPE: RNA
<213> ORGANISM: Spodoptera frugiperda

<400> SEQUENCE: 104
uuucggccau uuuguaggu                                                    19

<210> SEQ ID NO 105
<211> LENGTH: 23
<212> TYPE: DNA
<213> ORGANISM: Spodoptera frugiperda

<400> SEQUENCE: 105
aatctacgga cccttctttg gag                                               23

<210> SEQ ID NO 106
<211> LENGTH: 19
<212> TYPE: RNA
<213> ORGANISM: Spodoptera frugiperda

<400> SEQUENCE: 106
ucuacggacc cuucuuugg                                                    19

<210> SEQ ID NO 107
<211> LENGTH: 19
<212> TYPE: RNA
<213> ORGANISM: Spodoptera frugiperda

<400> SEQUENCE: 107
ccaaagaagg guccguaga                                                    19

<210> SEQ ID NO 108
<211> LENGTH: 23
<212> TYPE: DNA
<213> ORGANISM: Spodoptera frugiperda

<400> SEQUENCE: 108
aactctgacg tcatcatcta cgt                                               23

<210> SEQ ID NO 109
<211> LENGTH: 19
<212> TYPE: RNA
<213> ORGANISM: Spodoptera frugiperda

<400> SEQUENCE: 109
cucugacguc aucaucuac                                                    19

<210> SEQ ID NO 110
<211> LENGTH: 19
<212> TYPE: RNA
<213> ORGANISM: Spodoptera frugiperda

<400> SEQUENCE: 110
guagaugaug acgucagag                                                    19

<210> SEQ ID NO 111
<211> LENGTH: 23
<212> TYPE: DNA
<213> ORGANISM: Spodoptera frugiperda

<400> SEQUENCE: 111
aagtgcttgg gtaaccccga cag                                               23
```

```
<210> SEQ ID NO 112
<211> LENGTH: 19
<212> TYPE: RNA
<213> ORGANISM: Spodoptera frugiperda

<400> SEQUENCE: 112
gugcuugggu aaccccgac                                                  19

<210> SEQ ID NO 113
<211> LENGTH: 19
<212> TYPE: RNA
<213> ORGANISM: Spodoptera frugiperda

<400> SEQUENCE: 113
gucgggguua cccaagcac                                                  19

<210> SEQ ID NO 114
<211> LENGTH: 23
<212> TYPE: DNA
<213> ORGANISM: Spodoptera frugiperda

<400> SEQUENCE: 114
aactggctca tctcctacag caa                                             23

<210> SEQ ID NO 115
<211> LENGTH: 19
<212> TYPE: RNA
<213> ORGANISM: Spodoptera frugiperda

<400> SEQUENCE: 115
cuggcucauc uccuacagc                                                  19

<210> SEQ ID NO 116
<211> LENGTH: 19
<212> TYPE: RNA
<213> ORGANISM: Spodoptera frugiperda

<400> SEQUENCE: 116
gcuguaggag augagccag                                                  19

<210> SEQ ID NO 117
<211> LENGTH: 23
<212> TYPE: DNA
<213> ORGANISM: Spodoptera frugiperda

<400> SEQUENCE: 117
aaacagtgcg tcgtaatata ttc                                             23

<210> SEQ ID NO 118
<211> LENGTH: 19
<212> TYPE: RNA
<213> ORGANISM: Spodoptera frugiperda

<400> SEQUENCE: 118
acagugcguc guaauauau                                                  19

<210> SEQ ID NO 119
<211> LENGTH: 19
<212> TYPE: RNA
<213> ORGANISM: Spodoptera frugiperda

<400> SEQUENCE: 119
auauauuacg acgcacugu                                                  19
```

```
<210> SEQ ID NO 120
<211> LENGTH: 23
<212> TYPE: DNA
<213> ORGANISM: Spodoptera frugiperda

<400> SEQUENCE: 120
aaggcacatg gtccttcact gat                                              23

<210> SEQ ID NO 121
<211> LENGTH: 19
<212> TYPE: RNA
<213> ORGANISM: Spodoptera frugiperda

<400> SEQUENCE: 121
ggcacauggu ccuucacug                                                   19

<210> SEQ ID NO 122
<211> LENGTH: 19
<212> TYPE: RNA
<213> ORGANISM: Spodoptera frugiperda

<400> SEQUENCE: 122
cagugaagga ccaugugcc                                                   19

<210> SEQ ID NO 123
<211> LENGTH: 23
<212> TYPE: DNA
<213> ORGANISM: Spodoptera frugiperda

<400> SEQUENCE: 123
aacaccatga ccctcgtgta caa                                              23

<210> SEQ ID NO 124
<211> LENGTH: 19
<212> TYPE: RNA
<213> ORGANISM: Spodoptera frugiperda

<400> SEQUENCE: 124
caccaugacc cucguguac                                                   19

<210> SEQ ID NO 125
<211> LENGTH: 19
<212> TYPE: RNA
<213> ORGANISM: Spodoptera frugiperda

<400> SEQUENCE: 125
guacacgagg gucauggug                                                   19

<210> SEQ ID NO 126
<211> LENGTH: 23
<212> TYPE: DNA
<213> ORGANISM: Spodoptera frugiperda

<400> SEQUENCE: 126
aaaaaacaca gaccacgttc aca                                              23

<210> SEQ ID NO 127
<211> LENGTH: 19
<212> TYPE: RNA
<213> ORGANISM: Spodoptera frugiperda

<400> SEQUENCE: 127
aaaacacaga ccacguuca                                                   19
```

<210> SEQ ID NO 128
<211> LENGTH: 19
<212> TYPE: RNA
<213> ORGANISM: Spodoptera frugiperda

<400> SEQUENCE: 128
ugaacguggu cuguguuuu                                                   19

<210> SEQ ID NO 129
<211> LENGTH: 23
<212> TYPE: DNA
<213> ORGANISM: Spodoptera frugiperda

<400> SEQUENCE: 129
aatcgatggt ggtgttattc gct                                              23

<210> SEQ ID NO 130
<211> LENGTH: 19
<212> TYPE: RNA
<213> ORGANISM: Spodoptera frugiperda

<400> SEQUENCE: 130
ucgauggugg uguuauucg                                                   19

<210> SEQ ID NO 131
<211> LENGTH: 19
<212> TYPE: RNA
<213> ORGANISM: Spodoptera frugiperda

<400> SEQUENCE: 131
cgaauaacac caccaucga                                                   19

<210> SEQ ID NO 132
<211> LENGTH: 23
<212> TYPE: DNA
<213> ORGANISM: Spodoptera frugiperda

<400> SEQUENCE: 132
aaagaaaatg ctacgcgtta cga                                              23

<210> SEQ ID NO 133
<211> LENGTH: 19
<212> TYPE: RNA
<213> ORGANISM: Spodoptera frugiperda

<400> SEQUENCE: 133
agaaaaugcu acgcguuac                                                   19

<210> SEQ ID NO 134
<211> LENGTH: 42
<212> TYPE: DNA
<213> ORGANISM: Spodoptera frugiperda

<400> SEQUENCE: 134
guaacgcgua gcauuuucua acccttggac actactggaa ga                         42

<210> SEQ ID NO 135
<211> LENGTH: 19
<212> TYPE: RNA
<213> ORGANISM: Spodoptera frugiperda

<400> SEQUENCE: 135
cccuuggaca cuacuggaa                                            19

<210> SEQ ID NO 136
<211> LENGTH: 19
<212> TYPE: RNA
<213> ORGANISM: Spodoptera frugiperda

<400> SEQUENCE: 136
uuccaguagu guccaaggg                                            19

<210> SEQ ID NO 137
<211> LENGTH: 23
<212> TYPE: DNA
<213> ORGANISM: Spodoptera frugiperda

<400> SEQUENCE: 137
aaggatccta tgtgtaccag gtt                                       23

<210> SEQ ID NO 138
<211> LENGTH: 19
<212> TYPE: RNA
<213> ORGANISM: Spodoptera frugiperda

<400> SEQUENCE: 138
ggauccuaug uguaccagg                                            19

<210> SEQ ID NO 139
<211> LENGTH: 19
<212> TYPE: RNA
<213> ORGANISM: Spodoptera frugiperda

<400> SEQUENCE: 139
ccugguacac auaggaucc                                            19

<210> SEQ ID NO 140
<211> LENGTH: 23
<212> TYPE: DNA
<213> ORGANISM: Spodoptera frugiperda

<400> SEQUENCE: 140
aaactcggca cacaacacaa tgg                                       23

<210> SEQ ID NO 141
<211> LENGTH: 19
<212> TYPE: RNA
<213> ORGANISM: Spodoptera frugiperda

<400> SEQUENCE: 141
acucggcaca caacacaau                                            19

<210> SEQ ID NO 142
<211> LENGTH: 19
<212> TYPE: RNA
<213> ORGANISM: Spodoptera frugiperda

<400> SEQUENCE: 142
auuguguugu gugccgagu                                            19

<210> SEQ ID NO 143
<211> LENGTH: 23
<212> TYPE: DNA
<213> ORGANISM: Spodoptera frugiperda

<400> SEQUENCE: 143

```
aatacgaaga tatctgccct tcc                                              23

<210> SEQ ID NO 144
<211> LENGTH: 19
<212> TYPE: RNA
<213> ORGANISM: Spodoptera frugiperda

<400> SEQUENCE: 144
uacgaagaua ucugcccuu                                                   19

<210> SEQ ID NO 145
<211> LENGTH: 19
<212> TYPE: RNA
<213> ORGANISM: Spodoptera frugiperda

<400> SEQUENCE: 145
aagggcagau aucuucgua                                                   19

<210> SEQ ID NO 146
<211> LENGTH: 23
<212> TYPE: DNA
<213> ORGANISM: Spodoptera frugiperda

<400> SEQUENCE: 146
aatcaacagc tcttacataa atg                                              23

<210> SEQ ID NO 147
<211> LENGTH: 19
<212> TYPE: RNA
<213> ORGANISM: Spodoptera frugiperda

<400> SEQUENCE: 147
ucaacagcuc uuacauaaa                                                   19

<210> SEQ ID NO 148
<211> LENGTH: 19
<212> TYPE: RNA
<213> ORGANISM: Spodoptera frugiperda

<400> SEQUENCE: 148
uuuauguaag agcuguuga                                                   19

<210> SEQ ID NO 149
<211> LENGTH: 23
<212> TYPE: DNA
<213> ORGANISM: Spodoptera frugiperda

<400> SEQUENCE: 149
aaagaagatc agaagattgg ccg                                              23

<210> SEQ ID NO 150
<211> LENGTH: 19
<212> TYPE: RNA
<213> ORGANISM: Spodoptera frugiperda

<400> SEQUENCE: 150
agaagaucag aagauuggc                                                   19

<210> SEQ ID NO 151
<211> LENGTH: 19
<212> TYPE: RNA
<213> ORGANISM: Spodoptera frugiperda
```

```
<400> SEQUENCE: 151
gccaaucuuc ugaucuucu                                               19

<210> SEQ ID NO 152
<211> LENGTH: 23
<212> TYPE: DNA
<213> ORGANISM: Spodoptera frugiperda

<400> SEQUENCE: 152
aaaagccgtc tgctatccaa caa                                          23

<210> SEQ ID NO 153
<211> LENGTH: 19
<212> TYPE: RNA
<213> ORGANISM: Spodoptera frugiperda

<400> SEQUENCE: 153
aagccgucug cuauccaac                                               19

<210> SEQ ID NO 154
<211> LENGTH: 19
<212> TYPE: RNA
<213> ORGANISM: Spodoptera frugiperda

<400> SEQUENCE: 154
guuggauagc agacggcuu                                               19

<210> SEQ ID NO 155
<211> LENGTH: 23
<212> TYPE: DNA
<213> ORGANISM: Spodoptera frugiperda

<400> SEQUENCE: 155
aatgctaaat gccatgcttg cat                                          23

<210> SEQ ID NO 156
<211> LENGTH: 19
<212> TYPE: RNA
<213> ORGANISM: Spodoptera frugiperda

<400> SEQUENCE: 156
ugcuaaaugc caugcuugc                                               19

<210> SEQ ID NO 157
<211> LENGTH: 19
<212> TYPE: RNA
<213> ORGANISM: Spodoptera frugiperda

<400> SEQUENCE: 157
gcaagcaugg cauuuagca                                               19

<210> SEQ ID NO 158
<211> LENGTH: 23
<212> TYPE: DNA
<213> ORGANISM: Spodoptera frugiperda

<400> SEQUENCE: 158
aagatcagaa gattggccgg aag                                          23

<210> SEQ ID NO 159
<211> LENGTH: 19
<212> TYPE: RNA
<213> ORGANISM: Spodoptera frugiperda
```

```
<400> SEQUENCE: 159
gaucagaaga uuggccgga                                          19

<210> SEQ ID NO 160
<211> LENGTH: 19
<212> TYPE: RNA
<213> ORGANISM: Spodoptera frugiperda

<400> SEQUENCE: 160
uccggccaau cuucugauc                                          19

<210> SEQ ID NO 161
<211> LENGTH: 23
<212> TYPE: DNA
<213> ORGANISM: Spodoptera frugiperda

<400> SEQUENCE: 161
aattcttcag caaatcgata cca                                     23

<210> SEQ ID NO 162
<211> LENGTH: 19
<212> TYPE: RNA
<213> ORGANISM: Spodoptera frugiperda

<400> SEQUENCE: 162
uucuucagca aaucgauac                                          19

<210> SEQ ID NO 163
<211> LENGTH: 19
<212> TYPE: RNA
<213> ORGANISM: Spodoptera frugiperda

<400> SEQUENCE: 163
guaucgauuu gcugaagaa                                          19

<210> SEQ ID NO 164
<211> LENGTH: 23
<212> TYPE: DNA
<213> ORGANISM: Spodoptera frugiperda

<400> SEQUENCE: 164
aaatgctgtc aagaggattt aaa                                     23

<210> SEQ ID NO 165
<211> LENGTH: 19
<212> TYPE: RNA
<213> ORGANISM: Spodoptera frugiperda

<400> SEQUENCE: 165
augcugucaa gaggauuua                                          19

<210> SEQ ID NO 166
<211> LENGTH: 19
<212> TYPE: RNA
<213> ORGANISM: Spodoptera frugiperda

<400> SEQUENCE: 166
uaaauccucu ugacagcau                                          19

<210> SEQ ID NO 167
<211> LENGTH: 23
<212> TYPE: DNA
```

```
<213> ORGANISM: Spodoptera frugiperda

<400> SEQUENCE: 167
aagctcgaga cttgctcttg atg                                              23

<210> SEQ ID NO 168
<211> LENGTH: 19
<212> TYPE: RNA
<213> ORGANISM: Spodoptera frugiperda

<400> SEQUENCE: 168
gcucgagacu ugcucuuga                                                   19

<210> SEQ ID NO 169
<211> LENGTH: 19
<212> TYPE: RNA
<213> ORGANISM: Spodoptera frugiperda

<400> SEQUENCE: 169
ucaagagcaa gucucgagc                                                   19

<210> SEQ ID NO 170
<211> LENGTH: 23
<212> TYPE: DNA
<213> ORGANISM: Spodoptera frugiperda

<400> SEQUENCE: 170
aactgttagc tcaaggtctg cta                                              23

<210> SEQ ID NO 171
<211> LENGTH: 19
<212> TYPE: RNA
<213> ORGANISM: Spodoptera frugiperda

<400> SEQUENCE: 171 cguuagcuc aaggucugc                                                    19

<210> SEQ ID NO 172
<211> LENGTH: 19
<212> TYPE: RNA
<213> ORGANISM: Spodoptera frugiperda

<400> SEQUENCE: 172
gcagaccuug agcuaacag                                                   19

<210> SEQ ID NO 173
<211> LENGTH: 23
<212> TYPE: DNA
<213> ORGANISM: Spodoptera frugiperda

<400> SEQUENCE: 173
aagactttct atcagaattt gcg                                              23

<210> SEQ ID NO 174
<211> LENGTH: 19
<212> TYPE: RNA
<213> ORGANISM: Spodoptera frugiperda

<400> SEQUENCE: 174
gacuuucuau cagaauuug                                                   19

<210> SEQ ID NO 175
<211> LENGTH: 19
```

```
<212> TYPE: RNA
<213> ORGANISM: Spodoptera frugiperda

<400> SEQUENCE: 175
caaauucuga uagaaaguc                                              19

<210> SEQ ID NO 176
<211> LENGTH: 23
<212> TYPE: DNA
<213> ORGANISM: Spodoptera frugiperda

<400> SEQUENCE: 176
aaacttaatc atggacgacg aca                                         23

<210> SEQ ID NO 177
<211> LENGTH: 19
<212> TYPE: RNA
<213> ORGANISM: Spodoptera frugiperda

<400> SEQUENCE: 177
acuuaaucau ggacgacga                                              19

<210> SEQ ID NO 178
<211> LENGTH: 19
<212> TYPE: RNA
<213> ORGANISM: Spodoptera frugiperda

<400> SEQUENCE: 178
ucgucgucca ugauuaagu                                              19

<210> SEQ ID NO 179
<211> LENGTH: 23
<212> TYPE: DNA
<213> ORGANISM: Spodoptera frugiperda

<400> SEQUENCE: 179
aaagaagaag aagaagaagg gag                                         23

<210> SEQ ID NO 180
<211> LENGTH: 19
<212> TYPE: RNA
<213> ORGANISM: Spodoptera frugiperda

<400> SEQUENCE: 180
agaagaagaa gaagaaggg                                              19

<210> SEQ ID NO 181
<211> LENGTH: 19
<212> TYPE: RNA
<213> ORGANISM: Spodoptera frugiperda

<400> SEQUENCE: 181
cccuucuucu ucuucuucu                                              19

<210> SEQ ID NO 182
<211> LENGTH: 23
<212> TYPE: DNA
<213> ORGANISM: Spodoptera frugiperda

<400> SEQUENCE: 182
aagatcaaga gaatgtcgag gat                                         23

<210> SEQ ID NO 183
```

```
<211> LENGTH: 19
<212> TYPE: RNA
<213> ORGANISM: Spodoptera frugiperda

<400> SEQUENCE: 183
gaucaagaga augucgagg                                                  19

<210> SEQ ID NO 184
<211> LENGTH: 19
<212> TYPE: RNA
<213> ORGANISM: Spodoptera frugiperda

<400> SEQUENCE: 184
ccucgacauu cucuugauc                                                  19

<210> SEQ ID NO 185
<211> LENGTH: 23
<212> TYPE: DNA
<213> ORGANISM: Spodoptera frugiperda

<400> SEQUENCE: 185
aaaatcgtcg gttttagcga cgt                                             23

<210> SEQ ID NO 186
<211> LENGTH: 19
<212> TYPE: RNA
<213> ORGANISM: Spodoptera frugiperda

<400> SEQUENCE: 186
aaucgucggu uuuagcgac                                                  19

<210> SEQ ID NO 187
<211> LENGTH: 19
<212> TYPE: RNA
<213> ORGANISM: Spodoptera frugiperda

<400> SEQUENCE: 187
gucgcuaaaa ccgacgauu                                                  19

<210> SEQ ID NO 188
<211> LENGTH: 23
<212> TYPE: DNA
<213> ORGANISM: Spodoptera frugiperda

<400> SEQUENCE: 188
aactgtcaat aggcagtatg cgt                                             23

<210> SEQ ID NO 189
<211> LENGTH: 19
<212> TYPE: RNA
<213> ORGANISM: Spodoptera frugiperda

<400> SEQUENCE: 189
cugucaauag gcaguaugc                                                  19

<210> SEQ ID NO 190
<211> LENGTH: 19
<212> TYPE: RNA
<213> ORGANISM: Spodoptera frugiperda

<400> SEQUENCE: 190
gcauacugcc uauugacag                                                  19
```

```
<210> SEQ ID NO 191
<211> LENGTH: 23
<212> TYPE: DNA
<213> ORGANISM: Spodoptera frugiperda

<400> SEQUENCE: 191
aacctgtacc aacagaccac tgg                                              23

<210> SEQ ID NO 192
<211> LENGTH: 19
<212> TYPE: RNA
<213> ORGANISM: Spodoptera frugiperda

<400> SEQUENCE: 192
ccuguaccaa cagaccacu                                                   19

<210> SEQ ID NO 193
<211> LENGTH: 19
<212> TYPE: RNA
<213> ORGANISM: Spodoptera frugiperda

<400> SEQUENCE: 193
aguggucugu ugguacagg                                                   19

<210> SEQ ID NO 194
<211> LENGTH: 23
<212> TYPE: DNA
<213> ORGANISM: Spodoptera frugiperda

<400> SEQUENCE: 194
aaccaaaaat gggcaaggaa aag                                              23

<210> SEQ ID NO 195
<211> LENGTH: 19
<212> TYPE: RNA
<213> ORGANISM: Spodoptera frugiperda

<400> SEQUENCE: 195
ccaaaaaugg gcaaggaaa                                                   19

<210> SEQ ID NO 196
<211> LENGTH: 19
<212> TYPE: RNA
<213> ORGANISM: Spodoptera frugiperda

<400> SEQUENCE: 196
uuuccuugcc cauuuuugg                                                   19

<210> SEQ ID NO 197
<211> LENGTH: 23
<212> TYPE: DNA
<213> ORGANISM: Spodoptera frugiperda

<400> SEQUENCE: 197
aacgtggtat caccatcgat att                                              23

<210> SEQ ID NO 198
<211> LENGTH: 19
<212> TYPE: RNA
<213> ORGANISM: Spodoptera frugiperda

<400> SEQUENCE: 198
cgugguauca ccaucgaua                                                   19
```

```
<210> SEQ ID NO 199
<211> LENGTH: 19
<212> TYPE: RNA
<213> ORGANISM: Spodoptera frugiperda

<400> SEQUENCE: 199
uaucgauggu gauaccacg                                               19

<210> SEQ ID NO 200
<211> LENGTH: 23
<212> TYPE: DNA
<213> ORGANISM: Spodoptera frugiperda

<400> SEQUENCE: 200
aacaaaatgg actccactga gcc                                          23

<210> SEQ ID NO 201
<211> LENGTH: 19
<212> TYPE: RNA
<213> ORGANISM: Spodoptera frugiperda

<400> SEQUENCE: 201
caaaauggac uccacugag                                               19

<210> SEQ ID NO 202
<211> LENGTH: 19
<212> TYPE: RNA
<213> ORGANISM: Spodoptera frugiperda

<400> SEQUENCE: 202
cucaguggag uccauuuug                                               19

<210> SEQ ID NO 203
<211> LENGTH: 23
<212> TYPE: DNA
<213> ORGANISM: Spodoptera frugiperda

<400> SEQUENCE: 203
aatccgtgac taaccaaaaa tgg                                          23

<210> SEQ ID NO 204
<211> LENGTH: 19
<212> TYPE: RNA
<213> ORGANISM: Spodoptera frugiperda

<400> SEQUENCE: 204
uccgugacua accaaaaau                                               19

<210> SEQ ID NO 205
<211> LENGTH: 19
<212> TYPE: RNA
<213> ORGANISM: Spodoptera frugiperda

<400> SEQUENCE: 205
auuuuugguu agucacgga                                               19

<210> SEQ ID NO 206
<211> LENGTH: 23
<212> TYPE: DNA
<213> ORGANISM: Spodoptera frugiperda

<400> SEQUENCE: 206
aacattgtcg tcattggaca cgt                                          23
```

<210> SEQ ID NO 207
<211> LENGTH: 19
<212> TYPE: RNA
<213> ORGANISM: Spodoptera frugiperda

<400> SEQUENCE: 207
cauugucguc auuggacac                                                    19

<210> SEQ ID NO 208
<211> LENGTH: 19
<212> TYPE: RNA
<213> ORGANISM: Spodoptera frugiperda

<400> SEQUENCE: 208
guguccaaug acgacaaug                                                    19

<210> SEQ ID NO 209
<211> LENGTH: 23
<212> TYPE: DNA
<213> ORGANISM: Spodoptera frugiperda

<400> SEQUENCE: 209
aaactccaat tataacctac tag                                               23

<210> SEQ ID NO 210
<211> LENGTH: 19
<212> TYPE: RNA
<213> ORGANISM: Spodoptera frugiperda

<400> SEQUENCE: 210
acuccaauua uaaccuacu                                                    19

<210> SEQ ID NO 211
<211> LENGTH: 19
<212> TYPE: RNA
<213> ORGANISM: Spodoptera frugiperda

<400> SEQUENCE: 211
aguagguuau aauuggagu                                                    19

<210> SEQ ID NO 212
<211> LENGTH: 23
<212> TYPE: DNA
<213> ORGANISM: Spodoptera frugiperda

<400> SEQUENCE: 212
aagtacaagg atctgatcgg caa                                               23

<210> SEQ ID NO 213
<211> LENGTH: 19
<212> TYPE: RNA
<213> ORGANISM: Spodoptera frugiperda

<400> SEQUENCE: 213
guacaaggau cugaucggc                                                    19

<210> SEQ ID NO 214
<211> LENGTH: 19
<212> TYPE: RNA
<213> ORGANISM: Spodoptera frugiperda

<400> SEQUENCE: 214

-continued

| | |
|---|---|
| gccgaucaga uccuuguac | 19 |

<210> SEQ ID NO 215
<211> LENGTH: 23
<212> TYPE: DNA
<213> ORGANISM: Spodoptera frugiperda

<400> SEQUENCE: 215

| | |
|---|---|
| aagactttct tcatgtggcc cat | 23 |

<210> SEQ ID NO 216
<211> LENGTH: 19
<212> TYPE: RNA
<213> ORGANISM: Spodoptera frugiperda

<400> SEQUENCE: 216

| | |
|---|---|
| gacuuucuuc auguggccc | 19 |

<210> SEQ ID NO 217
<211> LENGTH: 19
<212> TYPE: RNA
<213> ORGANISM: Spodoptera frugiperda

<400> SEQUENCE: 217

| | |
|---|---|
| gggccacaug aagaaaguc | 19 |

<210> SEQ ID NO 218
<211> LENGTH: 23
<212> TYPE: DNA
<213> ORGANISM: Spodoptera frugiperda

<400> SEQUENCE: 218

| | |
|---|---|
| aactcataga gcttgatgtg tgg | 23 |

<210> SEQ ID NO 219
<211> LENGTH: 19
<212> TYPE: RNA
<213> ORGANISM: Spodoptera frugiperda

<400> SEQUENCE: 219

| | |
|---|---|
| cucauagagc uugaugugu | 19 |

<210> SEQ ID NO 220
<211> LENGTH: 19
<212> TYPE: RNA
<213> ORGANISM: Spodoptera frugiperda

<400> SEQUENCE: 220

| | |
|---|---|
| acacaucaag cucuaugag | 19 |

<210> SEQ ID NO 221
<211> LENGTH: 23
<212> TYPE: DNA
<213> ORGANISM: Spodoptera frugiperda

<400> SEQUENCE: 221

| | |
|---|---|
| aagatgtgga tgacgtcact ggt | 23 |

<210> SEQ ID NO 222
<211> LENGTH: 19
<212> TYPE: RNA
<213> ORGANISM: Spodoptera frugiperda

<400> SEQUENCE: 222
gauguggaug acgucacug                                          19

<210> SEQ ID NO 223
<211> LENGTH: 19
<212> TYPE: RNA
<213> ORGANISM: Spodoptera frugiperda

<400> SEQUENCE: 223
cagugacguc auccacauc                                          19

<210> SEQ ID NO 224
<211> LENGTH: 23
<212> TYPE: DNA
<213> ORGANISM: Spodoptera frugiperda

<400> SEQUENCE: 224
aaccttcctg attctcttct gtg                                     23

<210> SEQ ID NO 225
<211> LENGTH: 19
<212> TYPE: RNA
<213> ORGANISM: Spodoptera frugiperda

<400> SEQUENCE: 225
ccuuccugau ucucuucug                                          19

<210> SEQ ID NO 226
<211> LENGTH: 19
<212> TYPE: RNA
<213> ORGANISM: Spodoptera frugiperda

<400> SEQUENCE: 226
cagaagagaa ucaggaagg                                          19

<210> SEQ ID NO 227
<211> LENGTH: 23
<212> TYPE: DNA
<213> ORGANISM: Spodoptera frugiperda

<400> SEQUENCE: 227
aacagtgctt gtgataagtg aac                                     23

<210> SEQ ID NO 228
<211> LENGTH: 19
<212> TYPE: RNA
<213> ORGANISM: Spodoptera frugiperda

<400> SEQUENCE: 228
cagugcuugu gauaaguga                                          19

<210> SEQ ID NO 229
<211> LENGTH: 19
<212> TYPE: RNA
<213> ORGANISM: Spodoptera frugiperda

<400> SEQUENCE: 229
ucacuuauca caagcacug                                          19

<210> SEQ ID NO 230
<211> LENGTH: 23
<212> TYPE: DNA
<213> ORGANISM: Spodoptera frugiperda

```
<400> SEQUENCE: 230
aagttaatgg tgactgccct cga                                          23

<210> SEQ ID NO 231
<211> LENGTH: 19
<212> TYPE: RNA
<213> ORGANISM: Spodoptera frugiperda

<400> SEQUENCE: 231
guuaauggug acugcccuc                                               19

<210> SEQ ID NO 232
<211> LENGTH: 19
<212> TYPE: RNA
<213> ORGANISM: Spodoptera frugiperda

<400> SEQUENCE: 232
gagggcaguc accauuaac                                               19

<210> SEQ ID NO 233
<211> LENGTH: 23
<212> TYPE: DNA
<213> ORGANISM: Spodoptera frugiperda

<400> SEQUENCE: 233
aataaagcga tgaccccata gga                                          23

<210> SEQ ID NO 234
<211> LENGTH: 19
<212> TYPE: RNA
<213> ORGANISM: Spodoptera frugiperda

<400> SEQUENCE: 234
uaaagcgaug accccauag                                               19

<210> SEQ ID NO 235
<211> LENGTH: 19
<212> TYPE: RNA
<213> ORGANISM: Spodoptera frugiperda

<400> SEQUENCE: 235 cuauggguc aucgcuuua                                                19

<210> SEQ ID NO 236
<211> LENGTH: 23
<212> TYPE: DNA
<213> ORGANISM: Spodoptera frugiperda

<400> SEQUENCE: 236
aaacggtact gcagcaaaaa gac                                          23

<210> SEQ ID NO 237
<211> LENGTH: 19
<212> TYPE: RNA
<213> ORGANISM: Spodoptera frugiperda

<400> SEQUENCE: 237
acgguacugc agcaaaaag                                               19

<210> SEQ ID NO 238
<211> LENGTH: 19
<212> TYPE: RNA
<213> ORGANISM: Spodoptera frugiperda
```

```
<400> SEQUENCE: 238
cuuuuugcug caguaccgu                                                  19

<210> SEQ ID NO 239
<211> LENGTH: 23
<212> TYPE: DNA
<213> ORGANISM: Spodoptera frugiperda

<400> SEQUENCE: 239
aagctgcata cttcttggct ctc                                             23

<210> SEQ ID NO 240
<211> LENGTH: 19
<212> TYPE: RNA
<213> ORGANISM: Spodoptera frugiperda

<400> SEQUENCE: 240
gcugcauacu ucuuggcuc                                                  19

<210> SEQ ID NO 241
<211> LENGTH: 19
<212> TYPE: RNA
<213> ORGANISM: Spodoptera frugiperda

<400> SEQUENCE: 241
gagccaagaa guaugcagc                                                  19

<210> SEQ ID NO 242
<211> LENGTH: 23
<212> TYPE: DNA
<213> ORGANISM: Spodoptera frugiperda

<400> SEQUENCE: 242
aaatgtttac agagacgcga tga                                             23

<210> SEQ ID NO 243
<211> LENGTH: 19
<212> TYPE: RNA
<213> ORGANISM: Spodoptera frugiperda

<400> SEQUENCE: 243
auguuuacag agacgcgau                                                  19

<210> SEQ ID NO 244
<211> LENGTH: 19
<212> TYPE: RNA
<213> ORGANISM: Spodoptera frugiperda

<400> SEQUENCE: 244
aucgcgucuc uguaaacau                                                  19

<210> SEQ ID NO 245
<211> LENGTH: 23
<212> TYPE: DNA
<213> ORGANISM: Spodoptera frugiperda

<400> SEQUENCE: 245
aacgtcgatc ttaccgagtt cca                                             23

<210> SEQ ID NO 246
<211> LENGTH: 19
<212> TYPE: RNA
```

```
<213> ORGANISM: Spodoptera frugiperda

<400> SEQUENCE: 246
cgucgaucuu accgaguuc                                              19

<210> SEQ ID NO 247
<211> LENGTH: 19
<212> TYPE: RNA
<213> ORGANISM: Spodoptera frugiperda

<400> SEQUENCE: 247
gaacucggua agaucgacg                                              19

<210> SEQ ID NO 248
<211> LENGTH: 23
<212> TYPE: DNA
<213> ORGANISM: Spodoptera frugiperda

<400> SEQUENCE: 248
aattcaaaat gcgtgagtgc atc                                         23

<210> SEQ ID NO 249
<211> LENGTH: 19
<212> TYPE: RNA
<213> ORGANISM: Spodoptera frugiperda

<400> SEQUENCE: 249
uucaaaaugc gugagugca                                              19

<210> SEQ ID NO 250
<211> LENGTH: 19
<212> TYPE: RNA
<213> ORGANISM: Spodoptera frugiperda

<400> SEQUENCE: 250
ugcacucacg cauuuugaa                                              19

<210> SEQ ID NO 251
<211> LENGTH: 23
<212> TYPE: DNA
<213> ORGANISM: Spodoptera frugiperda

<400> SEQUENCE: 251
aaatcgtaga cctagtcctc gac                                         23

<210> SEQ ID NO 252
<211> LENGTH: 19
<212> TYPE: RNA
<213> ORGANISM: Spodoptera frugiperda

<400> SEQUENCE: 252
aucguagacc uaguccucg                                              19

<210> SEQ ID NO 253
<211> LENGTH: 19
<212> TYPE: RNA
<213> ORGANISM: Spodoptera frugiperda

<400> SEQUENCE: 253
cgaggacuag gucuacgau                                              19

<210> SEQ ID NO 254
<211> LENGTH: 23
```

```
<212> TYPE: DNA
<213> ORGANISM: Spodoptera frugiperda

<400> SEQUENCE: 254
aaactcaatt caaaatgcgt gag                                            23

<210> SEQ ID NO 255
<211> LENGTH: 19
<212> TYPE: RNA
<213> ORGANISM: Spodoptera frugiperda

<400> SEQUENCE: 255
acucaauuca aaaugcgug                                                 19

<210> SEQ ID NO 256
<211> LENGTH: 19
<212> TYPE: RNA
<213> ORGANISM: Spodoptera frugiperda

<400> SEQUENCE: 256
cacgcauuuu gaauugagu                                                 19

<210> SEQ ID NO 257
<211> LENGTH: 23
<212> TYPE: DNA
<213> ORGANISM: Spodoptera frugiperda

<400> SEQUENCE: 257
aacttatcac tggtaaggaa gat                                            23

<210> SEQ ID NO 258
<211> LENGTH: 19
<212> TYPE: RNA
<213> ORGANISM: Spodoptera frugiperda

<400> SEQUENCE: 258
cuuaucacug guaaggaag                                                 19

<210> SEQ ID NO 259
<211> LENGTH: 19
<212> TYPE: RNA
<213> ORGANISM: Spodoptera frugiperda

<400> SEQUENCE: 259
cuuccuuacc agugauaag                                                 19

<210> SEQ ID NO 260
<211> LENGTH: 23
<212> TYPE: DNA
<213> ORGANISM: Spodoptera frugiperda

<400> SEQUENCE: 260
aagagttacg aaccgtcacc ata                                            23

<210> SEQ ID NO 261
<211> LENGTH: 19
<212> TYPE: RNA
<213> ORGANISM: Spodoptera frugiperda

<400> SEQUENCE: 261
gaguuacgaa ccgucacca                                                 19

<210> SEQ ID NO 262
```

```
<211> LENGTH: 19
<212> TYPE: RNA
<213> ORGANISM: Spodoptera frugiperda

<400> SEQUENCE: 262
uggugacggu ucguaacuc                                                  19

<210> SEQ ID NO 263
<211> LENGTH: 23
<212> TYPE: DNA
<213> ORGANISM: Spodoptera frugiperda

<400> SEQUENCE: 263
aaacttagtc cggataatga acc                                             23

<210> SEQ ID NO 264
<211> LENGTH: 19
<212> TYPE: RNA
<213> ORGANISM: Spodoptera frugiperda

<400> SEQUENCE: 264
acuuaguccg gauaaugaa                                                  19

<210> SEQ ID NO 265
<211> LENGTH: 19
<212> TYPE: RNA
<213> ORGANISM: Spodoptera frugiperda

<400> SEQUENCE: 265
uucauuaucc ggacuaagu                                                  19

<210> SEQ ID NO 266
<211> LENGTH: 23
<212> TYPE: DNA
<213> ORGANISM: Spodoptera frugiperda

<400> SEQUENCE: 266
aaggcgatgt acgagaacct gtt                                             23

<210> SEQ ID NO 267
<211> LENGTH: 19
<212> TYPE: RNA
<213> ORGANISM: Spodoptera frugiperda

<400> SEQUENCE: 267
ggcgauguac gagaaccug                                                  19

<210> SEQ ID NO 268
<211> LENGTH: 19
<212> TYPE: RNA
<213> ORGANISM: Spodoptera frugiperda

<400> SEQUENCE: 268
cagguucucg uacaucgcc                                                  19

<210> SEQ ID NO 269
<211> LENGTH: 23
<212> TYPE: DNA
<213> ORGANISM: Spodoptera frugiperda

<400> SEQUENCE: 269
aacgacaaga tgctgaagga gac                                             23
```

-continued

```
<210> SEQ ID NO 270
<211> LENGTH: 19
<212> TYPE: RNA
<213> ORGANISM: Spodoptera frugiperda

<400> SEQUENCE: 270
cgacaagaug cugaaggag                                                  19

<210> SEQ ID NO 271
<211> LENGTH: 19
<212> TYPE: RNA
<213> ORGANISM: Spodoptera frugiperda

<400> SEQUENCE: 271
cuccuucagc aucuugucg                                                  19

<210> SEQ ID NO 272
<211> LENGTH: 23
<212> TYPE: DNA
<213> ORGANISM: Spodoptera frugiperda

<400> SEQUENCE: 272
aagataaagg tcgcgtgtgg acc                                             23

<210> SEQ ID NO 273
<211> LENGTH: 19
<212> TYPE: RNA
<213> ORGANISM: Spodoptera frugiperda

<400> SEQUENCE: 273
gauaaagguc gcgugugga                                                  19

<210> SEQ ID NO 274
<211> LENGTH: 19
<212> TYPE: RNA
<213> ORGANISM: Spodoptera frugiperda

<400> SEQUENCE: 274
uccacacgcg accuuuauc                                                  19

<210> SEQ ID NO 275
<211> LENGTH: 23
<212> TYPE: DNA
<213> ORGANISM: Spodoptera frugiperda

<400> SEQUENCE: 275
aatgtcaaga ctgatccaaa cac                                             23

<210> SEQ ID NO 276
<211> LENGTH: 19
<212> TYPE: RNA
<213> ORGANISM: Spodoptera frugiperda

<400> SEQUENCE: 276
ugucaagacu gauccaaac                                                  19

<210> SEQ ID NO 277
<211> LENGTH: 19
<212> TYPE: RNA
<213> ORGANISM: Spodoptera frugiperda

<400> SEQUENCE: 277
guuuggauca gucuugaca                                                  19
```

```
<210> SEQ ID NO 278
<211> LENGTH: 23
<212> TYPE: DNA
<213> ORGANISM: Spodoptera frugiperda

<400> SEQUENCE: 278
aacattcgag tctgaacagg tgg                                         23

<210> SEQ ID NO 279
<211> LENGTH: 19
<212> TYPE: RNA
<213> ORGANISM: Spodoptera frugiperda

<400> SEQUENCE: 279
cauucgaguc ugaacaggu                                              19

<210> SEQ ID NO 280
<211> LENGTH: 19
<212> TYPE: RNA
<213> ORGANISM: Spodoptera frugiperda

<400> SEQUENCE: 280
accuguucag acucgaaug                                              19

<210> SEQ ID NO 281
<211> LENGTH: 23
<212> TYPE: DNA
<213> ORGANISM: Spodoptera frugiperda

<400> SEQUENCE: 281
aacataagtc atggccaata acg                                         23

<210> SEQ ID NO 282
<211> LENGTH: 19
<212> TYPE: RNA
<213> ORGANISM: Spodoptera frugiperda

<400> SEQUENCE: 282
cauaagucau ggccaauaa                                              19

<210> SEQ ID NO 283
<211> LENGTH: 19
<212> TYPE: RNA
<213> ORGANISM: Spodoptera frugiperda

<400> SEQUENCE: 283
uuauuggcca ugacuuaug                                              19

<210> SEQ ID NO 284
<211> LENGTH: 23
<212> TYPE: DNA
<213> ORGANISM: Spodoptera frugiperda

<400> SEQUENCE: 284
aagaacataa tagtgccgaa gcc                                         23

<210> SEQ ID NO 285
<211> LENGTH: 19
<212> TYPE: RNA
<213> ORGANISM: Spodoptera frugiperda

<400> SEQUENCE: 285
gaacauaaua gugccgaag                                              19
```

-continued

<210> SEQ ID NO 286
<211> LENGTH: 19
<212> TYPE: RNA
<213> ORGANISM: Spodoptera frugiperda

<400> SEQUENCE: 286
cuucggcacu auuauguuc                                               19

<210> SEQ ID NO 287
<211> LENGTH: 23
<212> TYPE: DNA
<213> ORGANISM: Spodoptera frugiperda

<400> SEQUENCE: 287
aaacactggc agatcaagag gat                                          23

<210> SEQ ID NO 288
<211> LENGTH: 19
<212> TYPE: RNA
<213> ORGANISM: Spodoptera frugiperda

<400> SEQUENCE: 288
acacuggcag aucaagagg                                               19

<210> SEQ ID NO 289
<211> LENGTH: 19
<212> TYPE: RNA
<213> ORGANISM: Spodoptera frugiperda

<400> SEQUENCE: 289
ccucuugauc ugccagugu                                               19

<210> SEQ ID NO 290
<211> LENGTH: 23
<212> TYPE: DNA
<213> ORGANISM: Spodoptera frugiperda

<400> SEQUENCE: 290
aagatctttg ttggtggtct tag                                          23

<210> SEQ ID NO 291
<211> LENGTH: 19
<212> TYPE: RNA
<213> ORGANISM: Spodoptera frugiperda

<400> SEQUENCE: 291
gaucuuuguu gguggucuu                                               19

<210> SEQ ID NO 292
<211> LENGTH: 19
<212> TYPE: RNA
<213> ORGANISM: Spodoptera frugiperda

<400> SEQUENCE: 292
aagaccacca acaaagauc                                               19

<210> SEQ ID NO 293
<211> LENGTH: 23
<212> TYPE: DNA
<213> ORGANISM: Spodoptera frugiperda

<400> SEQUENCE: 293

-continued

```
aacaggtggt caatgagctg ctg                                              23

<210> SEQ ID NO 294
<211> LENGTH: 19
<212> TYPE: RNA
<213> ORGANISM: Spodoptera frugiperda

<400> SEQUENCE: 294
caggugguca augagcugc                                                   19

<210> SEQ ID NO 295
<211> LENGTH: 19
<212> TYPE: RNA
<213> ORGANISM: Spodoptera frugiperda

<400> SEQUENCE: 295
gcagcucauu gaccaccug                                                   19

<210> SEQ ID NO 296
<211> LENGTH: 23
<212> TYPE: DNA
<213> ORGANISM: Spodoptera frugiperda

<400> SEQUENCE: 296
aagttggctc tgacactctt ggc                                              23

<210> SEQ ID NO 297
<211> LENGTH: 19
<212> TYPE: RNA
<213> ORGANISM: Spodoptera frugiperda

<400> SEQUENCE: 297
guuggcucug acacucuug                                                   19

<210> SEQ ID NO 298
<211> LENGTH: 19
<212> TYPE: RNA
<213> ORGANISM: Spodoptera frugiperda

<400> SEQUENCE: 298
caagaguguc agagccaac                                                   19

<210> SEQ ID NO 299
<211> LENGTH: 23
<212> TYPE: DNA
<213> ORGANISM: Spodoptera frugiperda

<400> SEQUENCE: 299
aaatccgcaa agctgaggag gca                                              23

<210> SEQ ID NO 300
<211> LENGTH: 19
<212> TYPE: RNA
<213> ORGANISM: Spodoptera frugiperda

<400> SEQUENCE: 300
auccgcaaag cugaggagg                                                   19

<210> SEQ ID NO 301
<211> LENGTH: 19
<212> TYPE: RNA
<213> ORGANISM: Spodoptera frugiperda

<400> SEQUENCE: 301
```

| | |
|---|---|
| ccuccucagc uuugcggau | 19 |

<210> SEQ ID NO 302
<211> LENGTH: 23
<212> TYPE: DNA
<213> ORGANISM: Spodoptera frugiperda

<400> SEQUENCE: 302

| | |
|---|---|
| aaccgtgttc ttactgctgc tca | 23 |

<210> SEQ ID NO 303
<211> LENGTH: 19
<212> TYPE: RNA
<213> ORGANISM: Spodoptera frugiperda

<400> SEQUENCE: 303

| | |
|---|---|
| ccguguucuu acugcugcu | 19 |

<210> SEQ ID NO 304
<211> LENGTH: 19
<212> TYPE: RNA
<213> ORGANISM: Spodoptera frugiperda

<400> SEQUENCE: 304

| | |
|---|---|
| agcagcagua agaacacgg | 19 |

<210> SEQ ID NO 305
<211> LENGTH: 23
<212> TYPE: DNA
<213> ORGANISM: Spodoptera frugiperda

<400> SEQUENCE: 305

| | |
|---|---|
| aacgttgtta tgcatggaag ctg | 23 |

<210> SEQ ID NO 306
<211> LENGTH: 19
<212> TYPE: RNA
<213> ORGANISM: Spodoptera frugiperda

<400> SEQUENCE: 306

| | |
|---|---|
| cguuguuaug cauggaagc | 19 |

<210> SEQ ID NO 307
<211> LENGTH: 19
<212> TYPE: RNA
<213> ORGANISM: Spodoptera frugiperda

<400> SEQUENCE: 307

| | |
|---|---|
| gcuuccaugc auaacaacg | 19 |

<210> SEQ ID NO 308
<211> LENGTH: 23
<212> TYPE: DNA
<213> ORGANISM: Spodoptera frugiperda

<400> SEQUENCE: 308

| | |
|---|---|
| aaaacttcgc cggtgaaaac gcc | 23 |

<210> SEQ ID NO 309
<211> LENGTH: 19
<212> TYPE: RNA
<213> ORGANISM: Spodoptera frugiperda

```
<400> SEQUENCE: 309
aacuucgccg gugaaaacg                                                      19

<210> SEQ ID NO 310
<211> LENGTH: 19
<212> TYPE: RNA
<213> ORGANISM: Spodoptera frugiperda

<400> SEQUENCE: 310 cguuucacc ggcgaaguu                                                       19

<210> SEQ ID NO 311
<211> LENGTH: 23
<212> TYPE: DNA
<213> ORGANISM: Spodoptera frugiperda

<400> SEQUENCE: 311
aaatgaaact gttcctcgca gtc                                                 23

<210> SEQ ID NO 312
<211> LENGTH: 19
<212> TYPE: RNA
<213> ORGANISM: Spodoptera frugiperda

<400> SEQUENCE: 312
augaaacugu uccucgcag                                                      19

<210> SEQ ID NO 313
<211> LENGTH: 19
<212> TYPE: RNA
<213> ORGANISM: Spodoptera frugiperda

<400> SEQUENCE: 313
cugcgaggaa caguuucau                                                      19

<210> SEQ ID NO 314
<211> LENGTH: 23
<212> TYPE: DNA
<213> ORGANISM: Spodoptera frugiperda

<400> SEQUENCE: 314
aagaaggctg aggaagaaac cag                                                 23

<210> SEQ ID NO 315
<211> LENGTH: 19
<212> TYPE: RNA
<213> ORGANISM: Spodoptera frugiperda

<400> SEQUENCE: 315
gaaggcugag gaagaaacc                                                      19

<210> SEQ ID NO 316
<211> LENGTH: 19
<212> TYPE: RNA
<213> ORGANISM: Spodoptera frugiperda

<400> SEQUENCE: 316
gguuucuucc ucagccuuc                                                      19

<210> SEQ ID NO 317
<211> LENGTH: 23
<212> TYPE: DNA
<213> ORGANISM: Spodoptera frugiperda
```

<400> SEQUENCE: 317
aactctttca ccgtcgtact tgg                                    23

<210> SEQ ID NO 318
<211> LENGTH: 19
<212> TYPE: RNA
<213> ORGANISM: Spodoptera frugiperda

<400> SEQUENCE: 318
cucuuucacc gucguacuu                                         19

<210> SEQ ID NO 319
<211> LENGTH: 19
<212> TYPE: RNA
<213> ORGANISM: Spodoptera frugiperda

<400> SEQUENCE: 319
aaguacgacg gugaaagag                                         19

<210> SEQ ID NO 320
<211> LENGTH: 23
<212> TYPE: DNA
<213> ORGANISM: Spodoptera frugiperda

<400> SEQUENCE: 320
aacgacattg ctgtcctccg cat                                    23

<210> SEQ ID NO 321
<211> LENGTH: 19
<212> TYPE: RNA
<213> ORGANISM: Spodoptera frugiperda

<400> SEQUENCE: 321
cgacauugcu guccuccgc                                         19

<210> SEQ ID NO 322
<211> LENGTH: 19
<212> TYPE: RNA
<213> ORGANISM: Spodoptera frugiperda

<400> SEQUENCE: 322
gcggaggaca gcaaugucg                                         19

<210> SEQ ID NO 323
<211> LENGTH: 23
<212> TYPE: DNA
<213> ORGANISM: Spodoptera frugiperda

<400> SEQUENCE: 323
aacatcggta ctacccaacg tgt                                    23

<210> SEQ ID NO 324
<211> LENGTH: 19
<212> TYPE: RNA
<213> ORGANISM: Spodoptera frugiperda

<400> SEQUENCE: 324
caucgguacu acccaacgu                                         19

<210> SEQ ID NO 325
<211> LENGTH: 19
<212> TYPE: RNA

```
<213> ORGANISM: Spodoptera frugiperda

<400> SEQUENCE: 325
acguugggua guaccgaug                                               19

<210> SEQ ID NO 326
<211> LENGTH: 23
<212> TYPE: DNA
<213> ORGANISM: Spodoptera frugiperda

<400> SEQUENCE: 326
aagactcagt acgtattatc gcg                                          23

<210> SEQ ID NO 327
<211> LENGTH: 19
<212> TYPE: RNA
<213> ORGANISM: Spodoptera frugiperda

<400> SEQUENCE: 327
gacucaguac guauuaucg                                               19

<210> SEQ ID NO 328
<211> LENGTH: 19
<212> TYPE: RNA
<213> ORGANISM: Spodoptera frugiperda

<400> SEQUENCE: 328
cgauaauacg uacugaguc                                               19

<210> SEQ ID NO 329
<211> LENGTH: 23
<212> TYPE: DNA
<213> ORGANISM: Spodoptera frugiperda

<400> SEQUENCE: 329
aagttgccat cttgcttttg caa                                          23

<210> SEQ ID NO 330
<211> LENGTH: 19
<212> TYPE: RNA
<213> ORGANISM: Spodoptera frugiperda

<400> SEQUENCE: 330
guugccaucu ugcuuuugc                                               19

<210> SEQ ID NO 331
<211> LENGTH: 19
<212> TYPE: RNA
<213> ORGANISM: Spodoptera frugiperda

<400> SEQUENCE: 331
gcaaaagcaa gauggcaac                                               19

<210> SEQ ID NO 332
<211> LENGTH: 23
<212> TYPE: DNA
<213> ORGANISM: Spodoptera frugiperda

<400> SEQUENCE: 332
aatcagtttg acgcatgcgc tca                                          23

<210> SEQ ID NO 333
<211> LENGTH: 19
```

```
<212> TYPE: RNA
<213> ORGANISM: Spodoptera frugiperda

<400> SEQUENCE: 333
ucaguuugac gcaugcgcu                                              19

<210> SEQ ID NO 334
<211> LENGTH: 19
<212> TYPE: RNA
<213> ORGANISM: Spodoptera frugiperda

<400> SEQUENCE: 334
agcgcaugcg ucaaacuga                                              19

<210> SEQ ID NO 335
<211> LENGTH: 23
<212> TYPE: DNA
<213> ORGANISM: Spodoptera frugiperda

<400> SEQUENCE: 335
aatggcgtct ggtgtgacag ttt                                         23

<210> SEQ ID NO 336
<211> LENGTH: 19
<212> TYPE: RNA
<213> ORGANISM: Spodoptera frugiperda

<400> SEQUENCE: 336
uggcgucugg ugugacagu                                              19

<210> SEQ ID NO 337
<211> LENGTH: 19
<212> TYPE: RNA
<213> ORGANISM: Spodoptera frugiperda

<400> SEQUENCE: 337
acugucacac cagacgcca                                              19

<210> SEQ ID NO 338
<211> LENGTH: 23
<212> TYPE: DNA
<213> ORGANISM: Spodoptera frugiperda

<400> SEQUENCE: 338
aacgcggaat acgatcagtt cct                                         23

<210> SEQ ID NO 339
<211> LENGTH: 19
<212> TYPE: RNA
<213> ORGANISM: Spodoptera frugiperda

<400> SEQUENCE: 339
cgcggaauac gaucaguuc                                              19

<210> SEQ ID NO 340
<211> LENGTH: 19
<212> TYPE: RNA
<213> ORGANISM: Spodoptera frugiperda

<400> SEQUENCE: 340
gaacugaucg uauuccgcg                                              19

<210> SEQ ID NO 341
```

```
<211> LENGTH: 23
<212> TYPE: DNA
<213> ORGANISM: Spodoptera frugiperda

<400> SEQUENCE: 341
aagactcagt acgtattatc gcg                                              23

<210> SEQ ID NO 342
<211> LENGTH: 19
<212> TYPE: RNA
<213> ORGANISM: Spodoptera frugiperda

<400> SEQUENCE: 342
gacucaguac guauuaucg                                                   19

<210> SEQ ID NO 343
<211> LENGTH: 19
<212> TYPE: RNA
<213> ORGANISM: Spodoptera frugiperda

<400> SEQUENCE: 343
cgauaauacg uacugaguc                                                   19

<210> SEQ ID NO 344
<211> LENGTH: 23
<212> TYPE: DNA
<213> ORGANISM: Spodoptera frugiperda

<400> SEQUENCE: 344
aagttgccat cttgcttttg caa                                              23

<210> SEQ ID NO 345
<211> LENGTH: 19
<212> TYPE: RNA
<213> ORGANISM: Spodoptera frugiperda

<400> SEQUENCE: 345
guugccaucu ugcuuuugc                                                   19

<210> SEQ ID NO 346
<211> LENGTH: 19
<212> TYPE: RNA
<213> ORGANISM: Spodoptera frugiperda

<400> SEQUENCE: 346
gcaaaagcaa gauggcaac                                                   19

<210> SEQ ID NO 347
<211> LENGTH: 23
<212> TYPE: DNA
<213> ORGANISM: Spodoptera frugiperda

<400> SEQUENCE: 347
aatcagtttg acgcatgcgc tca                                              23

<210> SEQ ID NO 348
<211> LENGTH: 19
<212> TYPE: RNA
<213> ORGANISM: Spodoptera frugiperda

<400> SEQUENCE: 348
ucaguuugac gcaugcgcu                                                   19
```

```
<210> SEQ ID NO 349
<211> LENGTH: 19
<212> TYPE: RNA
<213> ORGANISM: Spodoptera frugiperda

<400> SEQUENCE: 349
agcgcaugcg ucaaacuga                                            19

<210> SEQ ID NO 350
<211> LENGTH: 23
<212> TYPE: DNA
<213> ORGANISM: Spodoptera frugiperda

<400> SEQUENCE: 350
aaaaatggcg tctggtgtga cag                                       23

<210> SEQ ID NO 351
<211> LENGTH: 19
<212> TYPE: RNA
<213> ORGANISM: Spodoptera frugiperda

<400> SEQUENCE: 351
aaauggcguc uggugugac                                            19

<210> SEQ ID NO 352
<211> LENGTH: 19
<212> TYPE: RNA
<213> ORGANISM: Spodoptera frugiperda

<400> SEQUENCE: 352
gucacaccag acgccauuu                                            19

<210> SEQ ID NO 353
<211> LENGTH: 23
<212> TYPE: DNA
<213> ORGANISM: Spodoptera frugiperda

<400> SEQUENCE: 353
aatacgatca gttccttgag gat                                       23

<210> SEQ ID NO 354
<211> LENGTH: 19
<212> TYPE: RNA
<213> ORGANISM: Spodoptera frugiperda

<400> SEQUENCE: 354
uacgaucagu uccuugagg                                            19

<210> SEQ ID NO 355
<211> LENGTH: 19
<212> TYPE: RNA
<213> ORGANISM: Spodoptera frugiperda

<400> SEQUENCE: 355
ccucaaggaa cugaucgua                                            19

<210> SEQ ID NO 356
<211> LENGTH: 23
<212> TYPE: DNA
<213> ORGANISM: Spodoptera frugiperda

<400> SEQUENCE: 356
aataatttgt gtcatacect acg                                       23
```

```
<210> SEQ ID NO 357
<211> LENGTH: 19
<212> TYPE: RNA
<213> ORGANISM: Spodoptera frugiperda

<400> SEQUENCE: 357 uaauugugu cauacccua                                                 19

<210> SEQ ID NO 358
<211> LENGTH: 19
<212> TYPE: RNA
<213> ORGANISM: Spodoptera frugiperda

<400> SEQUENCE: 358
uaggguauga cacaaauua                                                19

<210> SEQ ID NO 359
<211> LENGTH: 23
<212> TYPE: DNA
<213> ORGANISM: Spodoptera frugiperda

<400> SEQUENCE: 359
aagtcagtga ctggtcaaat tca                                           23

<210> SEQ ID NO 360
<211> LENGTH: 19
<212> TYPE: RNA
<213> ORGANISM: Spodoptera frugiperda

<400> SEQUENCE: 360
gucagugacu ggucaaauu                                                19

<210> SEQ ID NO 361
<211> LENGTH: 19
<212> TYPE: RNA
<213> ORGANISM: Spodoptera frugiperda

<400> SEQUENCE: 361
aauuugacca gucacugac                                                19

<210> SEQ ID NO 362
<211> LENGTH: 23
<212> TYPE: DNA
<213> ORGANISM: Spodoptera frugiperda

<400> SEQUENCE: 362
aattaggaga tgttgcacct ggt                                           23

<210> SEQ ID NO 363
<211> LENGTH: 19
<212> TYPE: RNA
<213> ORGANISM: Spodoptera frugiperda

<400> SEQUENCE: 363
uuaggagaug uugcaccug                                                19

<210> SEQ ID NO 364
<211> LENGTH: 19
<212> TYPE: RNA
<213> ORGANISM: Spodoptera frugiperda

<400> SEQUENCE: 364
caggugcaac aucuccuaa                                                19
```

<210> SEQ ID NO 365
<211> LENGTH: 23
<212> TYPE: DNA
<213> ORGANISM: Spodoptera frugiperda

<400> SEQUENCE: 365
aacaaacgga tgacctaggt ttg                                        23

<210> SEQ ID NO 366
<211> LENGTH: 19
<212> TYPE: RNA
<213> ORGANISM: Spodoptera frugiperda

<400> SEQUENCE: 366
caaacggaug accuagguu                                             19

<210> SEQ ID NO 367
<211> LENGTH: 19
<212> TYPE: RNA
<213> ORGANISM: Spodoptera frugiperda

<400> SEQUENCE: 367
aaccuagguc auccguuug                                             19

<210> SEQ ID NO 368
<211> LENGTH: 23
<212> TYPE: DNA
<213> ORGANISM: Spodoptera frugiperda

<400> SEQUENCE: 368
aatgctgcta gctctatgtc tcc                                        23

<210> SEQ ID NO 369
<211> LENGTH: 19
<212> TYPE: RNA
<213> ORGANISM: Spodoptera frugiperda

<400> SEQUENCE: 369
ugcugcuagc ucuaugucu                                             19

<210> SEQ ID NO 370
<211> LENGTH: 19
<212> TYPE: RNA
<213> ORGANISM: Spodoptera frugiperda

<400> SEQUENCE: 370
agacauagag cuagcagca                                             19

<210> SEQ ID NO 371
<211> LENGTH: 23
<212> TYPE: DNA
<213> ORGANISM: Spodoptera frugiperda

<400> SEQUENCE: 371
aatttgtgtc ataccctacg caa                                        23

<210> SEQ ID NO 372
<211> LENGTH: 19
<212> TYPE: RNA
<213> ORGANISM: Spodoptera frugiperda

<400> SEQUENCE: 372

-continued uugugucau acccuacgc                    19

<210> SEQ ID NO 373
<211> LENGTH: 19
<212> TYPE: RNA
<213> ORGANISM: Spodoptera frugiperda

<400> SEQUENCE: 373
gcguagggua ugacacaaa                    19

<210> SEQ ID NO 374
<211> LENGTH: 23
<212> TYPE: DNA
<213> ORGANISM: Spodoptera frugiperda

<400> SEQUENCE: 374
aaaagggctt catgtcgaag gag               23

<210> SEQ ID NO 375
<211> LENGTH: 19
<212> TYPE: RNA
<213> ORGANISM: Spodoptera frugiperda

<400> SEQUENCE: 375
aagggcuuca ugucgaagg                    19

<210> SEQ ID NO 376
<211> LENGTH: 19
<212> TYPE: RNA
<213> ORGANISM: Spodoptera frugiperda

<400> SEQUENCE: 376
ccuucgacau gaagcccuu                    19

<210> SEQ ID NO 377
<211> LENGTH: 23
<212> TYPE: DNA
<213> ORGANISM: Spodoptera frugiperda

<400> SEQUENCE: 377
aattaggaga tgttgcacct ggt               23

<210> SEQ ID NO 378
<211> LENGTH: 19
<212> TYPE: RNA
<213> ORGANISM: Spodoptera frugiperda

<400> SEQUENCE: 378
uuaggagaug uugcaccug                    19

<210> SEQ ID NO 379
<211> LENGTH: 19
<212> TYPE: RNA
<213> ORGANISM: Spodoptera frugiperda

<400> SEQUENCE: 379
caggugcaac aucccuaa                     19

<210> SEQ ID NO 380
<211> LENGTH: 23
<212> TYPE: DNA
<213> ORGANISM: Spodoptera frugiperda

<400> SEQUENCE: 380

```
aaaggtcagt aactatgagt ggt                                          23

<210> SEQ ID NO 381
<211> LENGTH: 19
<212> TYPE: RNA
<213> ORGANISM: Spodoptera frugiperda

<400> SEQUENCE: 381
aggucaguaa cuaugagug                                               19

<210> SEQ ID NO 382
<211> LENGTH: 19
<212> TYPE: RNA
<213> ORGANISM: Spodoptera frugiperda

<400> SEQUENCE: 382
cacucauagu uacugaccu                                               19

<210> SEQ ID NO 383
<211> LENGTH: 23
<212> TYPE: DNA
<213> ORGANISM: Spodoptera frugiperda

<400> SEQUENCE: 383
aagaaatatg ctgtggcaca cgt                                          23

<210> SEQ ID NO 384
<211> LENGTH: 19
<212> TYPE: RNA
<213> ORGANISM: Spodoptera frugiperda

<400> SEQUENCE: 384
gaaauaugcu guggcacac                                               19

<210> SEQ ID NO 385
<211> LENGTH: 19
<212> TYPE: RNA
<213> ORGANISM: Spodoptera frugiperda

<400> SEQUENCE: 385
gugugccaca gcauauuuc                                               19

<210> SEQ ID NO 386
<211> LENGTH: 23
<212> TYPE: DNA
<213> ORGANISM: Spodoptera frugiperda

<400> SEQUENCE: 386
aacttgtacc tgatgatgtc atg                                          23

<210> SEQ ID NO 387
<211> LENGTH: 19
<212> TYPE: RNA
<213> ORGANISM: Spodoptera frugiperda

<400> SEQUENCE: 387
cuuguaccug augauguca                                               19

<210> SEQ ID NO 388
<211> LENGTH: 19
<212> TYPE: RNA
<213> ORGANISM: Spodoptera frugiperda
```

```
<400> SEQUENCE: 388
ugacaucauc agguacaag                                               19

<210> SEQ ID NO 389
<211> LENGTH: 23
<212> TYPE: DNA
<213> ORGANISM: Spodoptera frugiperda

<400> SEQUENCE: 389
aacattggct tcaacactcc taa                                          23

<210> SEQ ID NO 390
<211> LENGTH: 19
<212> TYPE: RNA
<213> ORGANISM: Spodoptera frugiperda

<400> SEQUENCE: 390
cauuggcuuc aacacuccu                                               19

<210> SEQ ID NO 391
<211> LENGTH: 19
<212> TYPE: RNA
<213> ORGANISM: Spodoptera frugiperda

<400> SEQUENCE: 391
aggaguguug aagccaaug                                               19

<210> SEQ ID NO 392
<211> LENGTH: 23
<212> TYPE: DNA
<213> ORGANISM: Spodoptera frugiperda

<400> SEQUENCE: 392
aagcggctgg agatctatga gag                                          23

<210> SEQ ID NO 393
<211> LENGTH: 19
<212> TYPE: RNA
<213> ORGANISM: Spodoptera frugiperda

<400> SEQUENCE: 393
gcggcuggag aucuaugag                                               19

<210> SEQ ID NO 394
<211> LENGTH: 19
<212> TYPE: RNA
<213> ORGANISM: Spodoptera frugiperda

<400> SEQUENCE: 394
cucauagauc uccagccgc                                               19

<210> SEQ ID NO 395
<211> LENGTH: 23
<212> TYPE: DNA
<213> ORGANISM: Spodoptera frugiperda

<400> SEQUENCE: 395
aaccctcccg aggagagcat tat                                          23

<210> SEQ ID NO 396
<211> LENGTH: 19
<212> TYPE: RNA
<213> ORGANISM: Spodoptera frugiperda
```

```
<400> SEQUENCE: 396
cccucccgag gagagcauu                                                    19

<210> SEQ ID NO 397
<211> LENGTH: 19
<212> TYPE: RNA
<213> ORGANISM: Spodoptera frugiperda

<400> SEQUENCE: 397
aaugcucucc ucgggaggg                                                    19

<210> SEQ ID NO 398
<211> LENGTH: 23
<212> TYPE: DNA
<213> ORGANISM: Spodoptera frugiperda

<400> SEQUENCE: 398
aacgccctac gactggaact tca                                               23

<210> SEQ ID NO 399
<211> LENGTH: 19
<212> TYPE: RNA
<213> ORGANISM: Spodoptera frugiperda

<400> SEQUENCE: 399
cgcccuacga cuggaacuu                                                    19

<210> SEQ ID NO 400
<211> LENGTH: 19
<212> TYPE: RNA
<213> ORGANISM: Spodoptera frugiperda

<400> SEQUENCE: 400 aaguccagu cguagggcg                                                     19

<210> SEQ ID NO 401
<211> LENGTH: 23
<212> TYPE: DNA
<213> ORGANISM: Spodoptera frugiperda

<400> SEQUENCE: 401
aactggacca acgtgctgga cta                                               23

<210> SEQ ID NO 402
<211> LENGTH: 19
<212> TYPE: RNA
<213> ORGANISM: Spodoptera frugiperda

<400> SEQUENCE: 402
cuggaccaac gugcuggac                                                    19

<210> SEQ ID NO 403
<211> LENGTH: 19
<212> TYPE: RNA
<213> ORGANISM: Spodoptera frugiperda

<400> SEQUENCE: 403
guccagcacg uugguccag                                                    19

<210> SEQ ID NO 404
<211> LENGTH: 23
<212> TYPE: DNA
```

```
<213> ORGANISM: Spodoptera frugiperda

<400> SEQUENCE: 404
aaaacatggg aaggaggtcg cat                                              23

<210> SEQ ID NO 405
<211> LENGTH: 19
<212> TYPE: RNA
<213> ORGANISM: Spodoptera frugiperda

<400> SEQUENCE: 405
aacaugggaa ggaggucgc                                                   19

<210> SEQ ID NO 406
<211> LENGTH: 19
<212> TYPE: RNA
<213> ORGANISM: Spodoptera frugiperda

<400> SEQUENCE: 406
gcgaccuccu ucccauguu                                                   19

<210> SEQ ID NO 407
<211> LENGTH: 23
<212> TYPE: DNA
<213> ORGANISM: Spodoptera frugiperda

<400> SEQUENCE: 407
aagttgcttg tggactactt cca                                              23

<210> SEQ ID NO 408
<211> LENGTH: 19
<212> TYPE: RNA
<213> ORGANISM: Spodoptera frugiperda

<400> SEQUENCE: 408
guugcuugug gacuacuuc                                                   19

<210> SEQ ID NO 409
<211> LENGTH: 19
<212> TYPE: RNA
<213> ORGANISM: Spodoptera frugiperda

<400> SEQUENCE: 409
gaaguagucc acaagcaac                                                   19

<210> SEQ ID NO 410
<211> LENGTH: 23
<212> TYPE: DNA
<213> ORGANISM: Spodoptera frugiperda

<400> SEQUENCE: 410
aacgtcgtgg gccagatctt ctt                                              23

<210> SEQ ID NO 411
<211> LENGTH: 19
<212> TYPE: RNA
<213> ORGANISM: Spodoptera frugiperda

<400> SEQUENCE: 411
cgucgugggc cagaucuuc                                                   19

<210> SEQ ID NO 412
<211> LENGTH: 19
```

```
<212> TYPE: RNA
<213> ORGANISM: Spodoptera frugiperda

<400> SEQUENCE: 412
gaagaucugg cccacgacg                                                  19

<210> SEQ ID NO 413
<211> LENGTH: 23
<212> TYPE: DNA
<213> ORGANISM: Spodoptera frugiperda

<400> SEQUENCE: 413
aatgcgtggc gatttcaaac tta                                             23

<210> SEQ ID NO 414
<211> LENGTH: 23
<212> TYPE: DNA
<213> ORGANISM: Spodoptera frugiperda

<400> SEQUENCE: 414
aatacggtcc ttcaggaacc gtg                                             23

<210> SEQ ID NO 415
<211> LENGTH: 19
<212> TYPE: RNA
<213> ORGANISM: Spodoptera frugiperda

<400> SEQUENCE: 415
uacgguccuu caggaaccg                                                  19

<210> SEQ ID NO 416
<211> LENGTH: 19
<212> TYPE: RNA
<213> ORGANISM: Spodoptera frugiperda

<400> SEQUENCE: 416
cgguuccuga aggaccgua                                                  19

<210> SEQ ID NO 417
<211> LENGTH: 23
<212> TYPE: DNA
<213> ORGANISM: Spodoptera frugiperda

<400> SEQUENCE: 417
aatttcgctg atttaccgca tgg                                             23

<210> SEQ ID NO 418
<211> LENGTH: 19
<212> TYPE: RNA
<213> ORGANISM: Spodoptera frugiperda

<400> SEQUENCE: 418
uuucgcugau uuaccgcau                                                  19

<210> SEQ ID NO 419
<211> LENGTH: 19
<212> TYPE: RNA
<213> ORGANISM: Spodoptera frugiperda

<400> SEQUENCE: 419
augcgguaaa ucagcgaaa                                                  19

<210> SEQ ID NO 420
```

```
<211> LENGTH: 23
<212> TYPE: DNA
<213> ORGANISM: Spodoptera frugiperda

<400> SEQUENCE: 420
aatttgtgag actggtggcc gaa                                              23

<210> SEQ ID NO 421
<211> LENGTH: 19
<212> TYPE: RNA
<213> ORGANISM: Spodoptera frugiperda

<400> SEQUENCE: 421
uuugugagac ugguggccg                                                   19

<210> SEQ ID NO 422
<211> LENGTH: 19
<212> TYPE: RNA
<213> ORGANISM: Spodoptera frugiperda

<400> SEQUENCE: 422
cggccaccag ucucacaaa                                                   19

<210> SEQ ID NO 423
<211> LENGTH: 23
<212> TYPE: DNA
<213> ORGANISM: Spodoptera frugiperda

<400> SEQUENCE: 423
aatctgattg tattcgcccc ctc                                              23

<210> SEQ ID NO 424
<211> LENGTH: 19
<212> TYPE: RNA
<213> ORGANISM: Spodoptera frugiperda

<400> SEQUENCE: 424
ucugauugua uucgccccc                                                   19

<210> SEQ ID NO 425
<211> LENGTH: 19
<212> TYPE: RNA
<213> ORGANISM: Spodoptera frugiperda

<400> SEQUENCE: 425
gggggcgaau acaaucaga                                                   19

<210> SEQ ID NO 426
<211> LENGTH: 23
<212> TYPE: DNA
<213> ORGANISM: Spodoptera frugiperda

<400> SEQUENCE: 426
aacactctag ttctgcctat tct                                              23

<210> SEQ ID NO 427
<211> LENGTH: 19
<212> TYPE: RNA
<213> ORGANISM: Spodoptera frugiperda

<400> SEQUENCE: 427
cacucuaguu cugccuauu                                                   19
```

```
<210> SEQ ID NO 428
<211> LENGTH: 19
<212> TYPE: RNA
<213> ORGANISM: Spodoptera frugiperda

<400> SEQUENCE: 428
aauaggcaga acuagagug                                            19

<210> SEQ ID NO 429
<211> LENGTH: 23
<212> TYPE: DNA
<213> ORGANISM: Spodoptera frugiperda

<400> SEQUENCE: 429
aacacacatc acaatggcgg ata                                       23

<210> SEQ ID NO 430
<211> LENGTH: 19
<212> TYPE: RNA
<213> ORGANISM: Spodoptera frugiperda

<400> SEQUENCE: 430
cacacaucac aauggcgga                                            19

<210> SEQ ID NO 431
<211> LENGTH: 19
<212> TYPE: RNA
<213> ORGANISM: Spodoptera frugiperda

<400> SEQUENCE: 431
uccgccauug ugaugugug                                            19

<210> SEQ ID NO 432
<211> LENGTH: 23
<212> TYPE: DNA
<213> ORGANISM: Spodoptera frugiperda

<400> SEQUENCE: 432
aaggatggca tcatcggcaa gaa                                       23

<210> SEQ ID NO 433
<211> LENGTH: 19
<212> TYPE: RNA
<213> ORGANISM: Spodoptera frugiperda

<400> SEQUENCE: 433
ggauggcauc aucggcaag                                            19

<210> SEQ ID NO 434
<211> LENGTH: 19
<212> TYPE: RNA
<213> ORGANISM: Spodoptera frugiperda

<400> SEQUENCE: 434
cuugccgaug augccaucc                                            19

<210> SEQ ID NO 435
<211> LENGTH: 23
<212> TYPE: DNA
<213> ORGANISM: Spodoptera frugiperda

<400> SEQUENCE: 435
aaaggcttca tcgacaccgc gaa                                       23
```

```
<210> SEQ ID NO 436
<211> LENGTH: 19
<212> TYPE: RNA
<213> ORGANISM: Spodoptera frugiperda

<400> SEQUENCE: 436
aggcuucauc gacaccgcg                                                19

<210> SEQ ID NO 437
<211> LENGTH: 19
<212> TYPE: RNA
<213> ORGANISM: Spodoptera frugiperda

<400> SEQUENCE: 437
cgcggugucg augaagccu                                                19

<210> SEQ ID NO 438
<211> LENGTH: 23
<212> TYPE: DNA
<213> ORGANISM: Spodoptera frugiperda

<400> SEQUENCE: 438
aaacaaagta tcgcctacac cgc                                           23

<210> SEQ ID NO 439
<211> LENGTH: 19
<212> TYPE: RNA
<213> ORGANISM: Spodoptera frugiperda

<400> SEQUENCE: 439
acaaaguauc gccuacacc                                                19

<210> SEQ ID NO 440
<211> LENGTH: 19
<212> TYPE: RNA
<213> ORGANISM: Spodoptera frugiperda

<400> SEQUENCE: 440
gguguaggcg auacuuugu                                                19

<210> SEQ ID NO 441
<211> LENGTH: 23
<212> TYPE: DNA
<213> ORGANISM: Spodoptera frugiperda

<400> SEQUENCE: 441
aatagcgtcg atcttcaacg act                                           23

<210> SEQ ID NO 442
<211> LENGTH: 19
<212> TYPE: RNA
<213> ORGANISM: Spodoptera frugiperda

<400> SEQUENCE: 442
uagcgucgau cuucaacga                                                19

<210> SEQ ID NO 443
<211> LENGTH: 19
<212> TYPE: RNA
<213> ORGANISM: Spodoptera frugiperda

<400> SEQUENCE: 443
ucguugaaga ucgacgcua                                                19
```

```
<210> SEQ ID NO 444
<211> LENGTH: 23
<212> TYPE: DNA
<213> ORGANISM: Spodoptera frugiperda

<400> SEQUENCE: 444
aacgaggccg gatctcttaa gca                                              23

<210> SEQ ID NO 445
<211> LENGTH: 19
<212> TYPE: RNA
<213> ORGANISM: Spodoptera frugiperda

<400> SEQUENCE: 445
cgaggccgga ucucuuaag                                                   19

<210> SEQ ID NO 446
<211> LENGTH: 19
<212> TYPE: RNA
<213> ORGANISM: Spodoptera frugiperda

<400> SEQUENCE: 446
cuuaagagau ccggccucg                                                   19

<210> SEQ ID NO 447
<211> LENGTH: 23
<212> TYPE: DNA
<213> ORGANISM: Spodoptera frugiperda

<400> SEQUENCE: 447
aacttcacac ataactagac aaa                                              23

<210> SEQ ID NO 448
<211> LENGTH: 19
<212> TYPE: RNA
<213> ORGANISM: Spodoptera frugiperda

<400> SEQUENCE: 448
cuucacacau aacuagaca                                                   19

<210> SEQ ID NO 449
<211> LENGTH: 19
<212> TYPE: RNA
<213> ORGANISM: Spodoptera frugiperda

<400> SEQUENCE: 449
ugucuaguua ugugugaag                                                   19

<210> SEQ ID NO 450
<211> LENGTH: 23
<212> TYPE: DNA
<213> ORGANISM: Spodoptera frugiperda

<400> SEQUENCE: 450
aatgcgtggc gatttcaaac tta                                              23

<210> SEQ ID NO 451
<211> LENGTH: 19
<212> TYPE: RNA
<213> ORGANISM: Spodoptera frugiperda

<400> SEQUENCE: 451
uuagaaauua uaagcccag                                                   19
```

-continued

```
<210> SEQ ID NO 452
<211> LENGTH: 19
<212> TYPE: RNA
<213> ORGANISM: Spodoptera frugiperda

<400> SEQUENCE: 452
cugggcuuau aauuucuaa                                                      19
```